US010624900B2

(12) United States Patent
Lehmann et al.

(10) Patent No.: US 10,624,900 B2
(45) Date of Patent: Apr. 21, 2020

(54) 5-HT$_{2C}$ RECEPTOR AGONISTS AND COMPOSITIONS AND METHODS OF USE

(71) Applicant: Arena Pharmaceuticals, Inc., San Diego, CA (US)

(72) Inventors: Juerg Lehmann, San Diego, CA (US); Konrad Feichtinger, San Diego, CA (US); Albert S. Ren, San Diego, CA (US); Graeme Semple, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 16/299,880

(22) Filed: Mar. 12, 2019

(65) Prior Publication Data

US 2020/0078368 A1  Mar. 12, 2020

Related U.S. Application Data

(63) Continuation of application No. 15/748,205, filed as application No. PCT/US2016/044426 on Jul. 28, 2016, now Pat. No. 10,272,094.

(60) Provisional application No. 62/199,382, filed on Jul. 31, 2015.

(51) Int. Cl.
| | | |
|---|---|---|
| *A61K 31/55* | (2006.01) | |
| *C07D 223/32* | (2006.01) | |
| *C07D 223/16* | (2006.01) | |
| *C07D 491/052* | (2006.01) | |
| *A61P 25/08* | (2006.01) | |
| *A61P 25/32* | (2006.01) | |
| *A61P 3/10* | (2006.01) | |
| *A61P 3/04* | (2006.01) | |

(52) U.S. Cl.
CPC ............ *A61K 31/55* (2013.01); *A61P 3/04* (2018.01); *A61P 3/10* (2018.01); *A61P 25/08* (2018.01); *A61P 25/32* (2018.01); *C07D 223/16* (2013.01); *C07D 223/32* (2013.01); *C07D 491/052* (2013.01); *A61K 2121/00* (2013.01)

(58) Field of Classification Search
CPC .......... A61K 31/55; A61P 25/08; A61P 25/32; A61P 3/10; A61P 3/04; C07D 223/32; C07D 223/16; C07D 491/052
See application file for complete search history.

(56) References Cited

FOREIGN PATENT DOCUMENTS

| WO | WO 92/18005 | 10/1992 | |
|---|---|---|---|
| WO | WO 2003/086303 | 10/2003 | |
| WO | WO 03/091251 | * 11/2003 | ........... C07D 471/06 |
| WO | WO 2005/003096 | 1/2005 | |

OTHER PUBLICATIONS

Aubin et al., "Factors associated with higher body mass index, weight concern, and weight gain in a multinational cohort study of smokers intending to quit," Int. J. Environ. Res. Public Health, 2009, 6: 943-957.
Berge et al., "Pharmaceutical Salts," Journal of Pharmaceutical Sciences, 1977, 66: 1-19.
Blum et al., "Reward Deficiency Syndrome: a Biogenetic Model for the Diagnosis and Treatment of Impulsive, Addictive, and Compulsive Behaviours," Journal of Psychoactive Drugs, 2000, 32: 1-112.
Brennan et al., "Discovery of a Novel Azepine Seris of Potent and Selective 5-HT2C Agonists as Potential Treatments for Urinary Incontinence," Bioorganic & Medicinal Chemistry Letters, 2009, 19(17): 4999-5003.
Chantix (varenicline) (package insert), New York, NY: Pfizer Labs, Division of Pfizer, Inc., 2012, 13 pages.
Chiolero et al., Association of cigarettes smoked daily with obesity in a general adult population. Obesity (Silver Spring), 2007, 15: 1311-1318.
Clark et al., "The prevalence of weight concerns in a smoking abstinence clinical trial," Addict Behav, 2006, 31: 1144-1152.
Clark et al., "Weight concerns among male smokers," Addict Behav, 2004, 29: 1637-1641.
Collier, "Radiosynthesis and in-vivo evaluation of the psuedopeptide 6-opioid antagonist [$^{125}$I]-ITIPP," J. Labelled Compd. Radiopharm., 1999, 42: S264-S266.
Cummings et al., How Many Smokers Have tried to Quit?, Society for Research on Nicotine and Tobacco, Poster Session 2, Mar. 2013, POS2-65, 1 page.
Dalton et al., "Serotonin 1B and 2C Receptor Interactions in the Modulation of Feeding Behaviour in the Mouse," Psychopharmacology, 2006, 185(1): 45-57.
Di Giovanni et al., "Serotonin Involvement in the Basal Ganglia Pathophysiology: Could the 5-HT2C Receptor be a New Target for Therapeutic Strategies," Current Medicinal Chemistry, 2006, 13(25): 3069-81.

(Continued)

*Primary Examiner* — Erich A Leeser
(74) *Attorney, Agent, or Firm* — Fish & Richardson P.C.

(57) ABSTRACT

Provided in some embodiments are compounds of Formula A, as defined herein, that modulate the activity of 5-HT2C receptor. Also provided in some embodiments are methods, such as, for weight management, inducing satiety, and decreasing food intake, and for preventing and treating obesity, antipsychotic-induced weight gain, type 2 diabetes, Prader-Willi syndrome, tobacco/nicotine dependence, drug addiction, alcohol addiction, pathological gambling, reward deficiency syndrome, and sex addiction), obsessive-compulsive spectrum disorders and impulse control disorders (including nail-biting and onychophagia), sleep disorders (including insomnia, fragmented sleep architecture, and disturbances of slow-wave sleep), urinary incontinence, psychiatric disorders (including schizophrenia, anorexia nervosa, and bulimia nervosa), Alzheimer disease, sexual dysfunction, erectile dysfunction, epilepsy, movement disorders (including parkinsonism and antipsychotic-induced movement disorder), hypertension, dyslipidemia, nonalcoholic fatty liver disease, obesity-related renal disease, and sleep apnea.

25 Claims, 13 Drawing Sheets

(56) References Cited

OTHER PUBLICATIONS

Favale et al., "The Anticonvulsant Effect of Citalopram as an Indirect Evidence of Serotonergic Impairment in Human Epileptogenesis," Seizure, 2003, 12(5): 316-8.
Guillory, "Generation of Polymorphs, Hydrates, Solvates, and Amorphous Solids," Polymorphism in Pharmaceutical Solids, 1999, 95: 202-209.
Health Effects of Cigarette Smoking, Centers for Disease Prevention, www.cdc.gov/tobacco/data_statistics/fact_sheets/health_effects/effects_cig_smoking/ accessed Sep. 10, 2013, 7 pages.
Heatherton et al., "The Fagerstrom test for Nicotine Dependence: A revision of the Fagerstrom Tolerance Questionnaire," Br J Addict, 1991, 86: 1119-27.
Heidbreder et al., "Novel Pharmacotherapeutic Approaches for the Treatment of Drug Addiction and Craving," Current Opinion in Pharmacology, 2005, 5(1): 107-118.
Hellings et al., "Self-injurious behavior and serotonin in Prader-Willi syndrome," Psychopharmacology bulletin, 1994, 30(2): 245-50.
Higuchi and Stella, "Pro-drugs as Novel Delivery Systems," ACS Symposium Series, 1975, vol. 14, 129 pages.
Hughes, "The hardenign hypothesis: is the ability to quit decreasing due to increasing nicotine dependence? A review and commentary," Drug Alcohol Depend, 2011, 117: 111-117.
Hunley et al., "Scope and mechanisms of obesity-related renal disease," Current Opinion in Nephrology & Hypertension, 2010, 19(3): 227-234.
John et al., "Smoking status, cigarettes per day, and their relationship to overweight and obesity among former and current smokers in a national adult general population sample," Int. J. Obes., 2005, 29: 1289-1294.
Kinon et al., "Association Between Early and Rapid Weight Gain and Change in Weight Over One Year of Olanzapine Therapy in Patients with Schizophrenia and Related Disorders," Journal of Clinical Psychopharmacology, 2005, 25(3): 255-258.
Krishnakumar et al., "Down-regulation of Cerebellar 5-HT2C Receptors in Pilocarpine-Induced Epilepsy in Rats: Therapeutic Role of Bacopa monnieri Extract," Journal of the Neurological Sciences, 2009, 284(1-2): 124-128.
Le Bas et al., "Radioiodinated Analogs of EP 00652218 for the Exploratino of the Tachykinin NK1 Receptor by Spect," J. Labelled Compd. Radiopharm., 2001, 44: S280-S282.
Levine et al., "Smoking-related weight concerns and obesity: differences among normal weight, overweight, and obese smokers using a telephone tobacco quitline," Nicotine Tob Res., 2013, 15: 1136-1140.
Lipson et al., "5-HT2C Agonists as Therapeutics for the Treatment of Schizophrenia," Handbook of Experimental Pharmacology, 2012, 213: 147-165.
Lychkova et al., "Role of Serotonin Receptors in Regulation of Contractile Activity of Urinary Bladder in Rabbits," Urology, 2013, 81(3): 696.e13-696.e18.
Marazziti et al., "Decreased Density of the Platelet Serotonin Transporter in Pathological Gamblers," Neuropsychobiology, 2008, 57(1-2): 38-43.
Meyers et al., "Are weight concerns predictive of smoking cessation? A prospective analysis," J. Consult. Clin. Psychol., 1997, 65: 448-452.
Molgaard et al., The association between cerebrovascular disease and smoking: a case-control study. Neuroepidemiology. 1986; 5(2): 88-94.
Monti et al., "The Role of Dorsal Raphe Nucleus Serotonergic and Non-Serotonergic Neurons, and of their Receptors, in Regulating Waking and Rapid Eye Movement (REM) Sleep," Sleep medicine reviews, 2010, 14(5): 319-27.

Morabito et al., "Mice with altered serotonin 2C receptor RNA editing display characteristics of Prader-Willi syndrome," Neurobiology of Disease, 2010, 169-180.
Naughton et al., "A Review of the Role of Serotonin Receptors in Psychiatric Disorders," Human Psychopharmacology, 2000, 15(6): 397-415.
Perito et al., "Dietary Treatment of Nonalcoholic Steatohepatitis," Disclosures Curr Opin Gastroenterol, 2013, 29(2): 170-176.
Perry et al., "Prospective study of risk factors for development of non-insulin dependent diabetes in middle aged British men," BMJ, 1995, 310: 560-564.
Pomerleau et al., "Characterizing concerns about post cessation weight gain: results from a national survey of women smokers," Nicotine Tob Res., 2001, 3: 51-60.
Pomerleau et al., "Willingness of female smokers to tolerate postcessation weight gain," J Subst. Abuse, 1996, 8: 371-378.
Ravindran et al., "Obsessive-Compulsive Spectrum Disorders: a Review of the Evidence-Based Treatments," Canadian Journal of Psychiatry, 2009, 54(5): 331-43.
Reynolds et al., "The 5-HT2C Receptor and Antipsychotic-Induced Weight Gain Mechanisms and Genetics," Journal of Psychopharmacology, 2006, 20(4 Suppl), 15-18.
Rosenzweig-Lipson et al., "5-HT2C Receptor Agonists as an Innovative Approach for Psychiatric Disorders," Drug News & Perspectives, 2007, 20(9): 565-71.
Stahly, "Diversity in Single- and Multiple-Component Crystals. The Search for and Prevalence of Polymorphs and Cocrystals," Crystal Growth & Design, 2007, 7(6): 1007-1026.
Tecott et al., "Eating disorder and epilepsy in mice lacking 5-$HT_{2C}$ serotonin receptors," Nature, 1995, 374: 542-546.
Tomkins et al., "An investigation of the Role of 5-HT2C Receptors in Modifying Ethanol Self-Administration Behaviour," Pharmacology, 2002, 71(4): 735-44.
Tonnesen et al., "Higher dosage nicotine patches increase one-year smoking cessation rates: results from the European CEASE trial," Eur. Respir. J., 1999, 13: 238-246.
Vargas et al., "Effect of Lorcaserin on the Use of Concomitant Medications for Dyslipidemia, Hypertension and Type 2 Diabetes during Phase 3 Clinical Trials Assessing Weight Loss in Patients with Type 2 Diabetes," Abstracts of Papers, Obesity Society 30th, Annual Scientific Meeting, San Antonio, Texas, Sep. 20-24, 2012, 471.
Vassallo et al., "Tryptophan Availability but Normal Post-Synaptic 5-HT2C Receptor Sensitivity in Chronic Fatigue Syndrome," Psychological Medicine, 2001, 31(4): 585-91.
Veldheer et al., "Once bitten, twice shy: concern about gaining weight after smoking cessation and its association with seeking treatment," Int. J. Clin. Pract., 2014, 68: 388-395.
Waterhouse et al., "Electrophysiological Assessment of Monoamine Synaptic Function in Neuronal Circuits of Seizure Susceptible Brains," Life Sciences, 1986, 39(9): 807-18.
West, "Evaluation of the mood and physical symptoms scale (MPSS) to assess cigarette withdrawal," Psychopharmacology, 2004, 177(1-2): 195-199.
West, "Solid State Chemistry and its Applications," Wiley, New York, 1988.
World Health Organization, Fact Sheet No. 339: Tobacco. Www.who.int/mediacentre/factsheets/fs339/en/index.html, Updated Jul. 2013, Accessed Sep. 10, 2013, 4 pages.
Zhou et al., "Serotonin 2C Receptor Agonists Improve Type 2 Diabetes via Melanocortin-4 Receptor Signaling Pathways," Cell Metab., Nov. 2007, 6(5): 398-405.
Zhu et al., "Synthesis and Mode of Action of $^{125}$I- and $^{3}$H-Labeled Thieno[2,3-c]pyridine Antagonists of Cell Adhesion Molecule Expression," J. Org. Chem., 2002, 67: 943-948.
Zyban (bupropion hydrochloride) (package insert), Research Triangle Park, NC: GlaxoSmithKline, 2012, 37 pages.

* cited by examiner

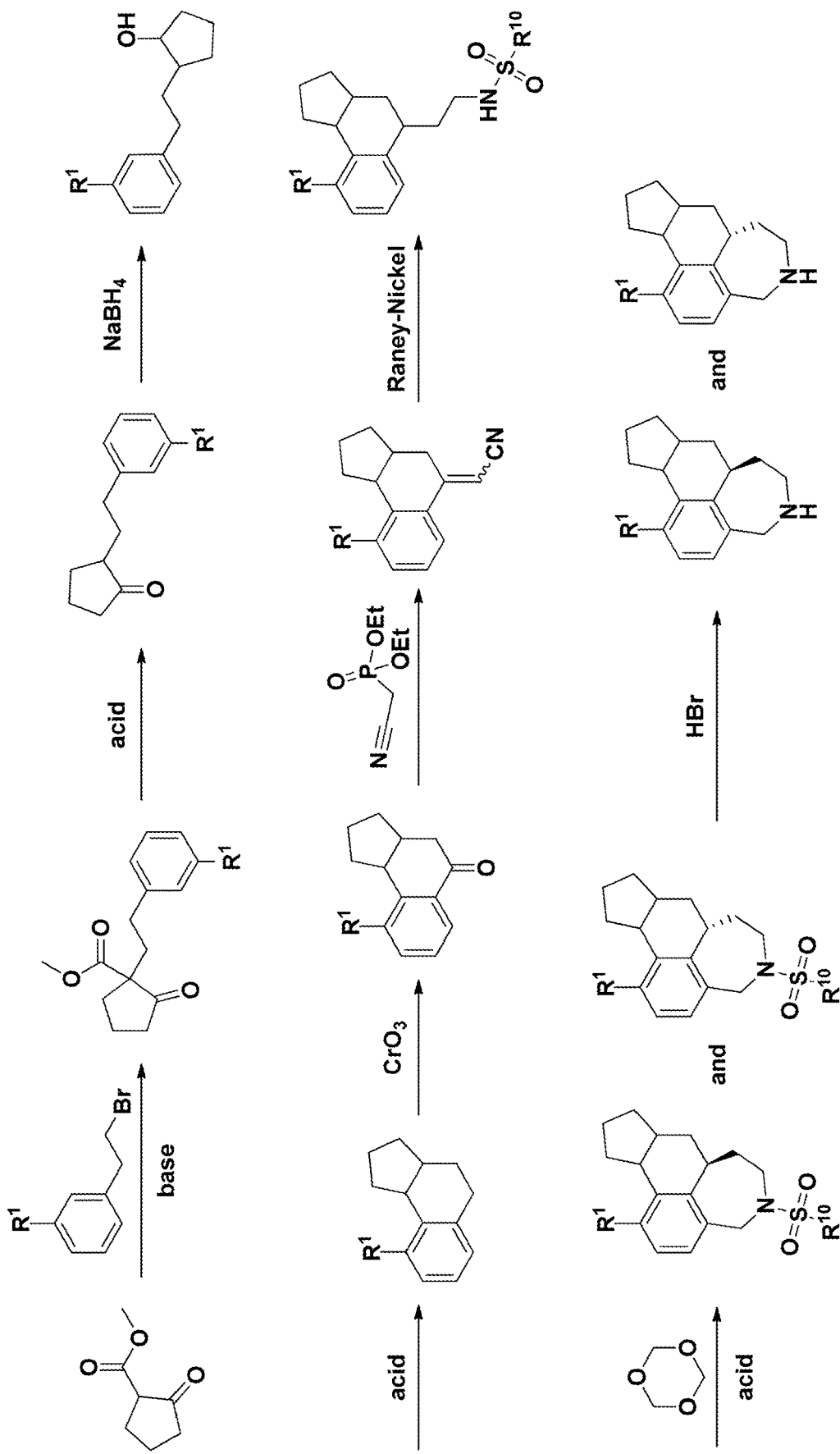

5-HT$_{2C}$ RECEPTOR AGONISTS AND COMPOSITIONS AND METHODS OF USE

Obesity is a life-threatening disorder in which there is an increased risk of morbidity and mortality arising from concomitant diseases such as type II diabetes, hypertension, stroke, cancer, and gallbladder disease.

Obesity is now a major healthcare issue in the Western World and increasingly in some third world countries. The increase in numbers of obese people is due largely to the increasing preference for high fat content foods but also the decrease in activity in most people's lives. Currently about 30% of the population of the USA is now considered obese.

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25-30 kg/m$^2$, and obesity as a BMI greater than 30 kg/m$^2$ (see table below).

| Classification Of Weight By Body Mass Index (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| ≥40 | Extreme Obesity (Class III) |

As the BMI increases there is an increased risk of death from a variety of causes that are independent of other risk factors. The most common diseases associated with obesity are cardiovascular disease (particularly hypertension), diabetes (obesity aggravates the development of diabetes), gall bladder disease (particularly cancer) and diseases of reproduction. The strength of the link between obesity and specific conditions varies. One of the strongest is the link with type 2 diabetes. Excess body fat underlies 64% of cases of diabetes in men and 77% of cases in women (Seidell, Semin Vase Med 5:3-14 (2005)). Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complications induced by obesity. It is estimated that if the entire population had an ideal weight, the risk of coronary insufficiency would decrease by 25% and the risk of cardiac insufficiency and of cerebral vascular accidents would decrease by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for diabetes and coronary heart disease and the potential value of an integrated approach to the prevention of these conditions based on the prevention of obesity (Perry, I J., et al., BMJ 310, 560-564 (1995)).

Diabetes has also been implicated in the development of kidney disease, eye diseases and nervous system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However, many patients find this difficult and need additional help from drug therapy to maintain results from these efforts.

Most currently marketed products have been unsuccessful as treatments for obesity because of a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have been launched in the USA and Europe: orlistat (Xenical™), a drug that prevents absorption of fat by the inhibition of pancreatic lipase, and sibutramine (Reductil™), a 5-HT/noradrenaline re-uptake inhibitor. However, side effects associated with these products may limit their long-term utility. Treatment with Xenical is reported to induce gastrointestinal distress in some patients, while sibutramine has been associated with raised blood pressure in some patients.

Serotonin (5-HT) neurotransmission plays an important role in numerous physiological processes both in physical and in psychiatric disorders. 5-HT has been implicated in the regulation of feeding behavior. 5-HT is believed to work by inducing a feeling of satiety, such that a subject with enhanced 5-HT stops eating earlier and fewer calories are consumed. It has been shown that a stimulatory action of 5-HT on the 5-HT$_{2C}$ receptor plays an important role in the control of eating and in the anti-obesity effect of d-fenfluramine. As the 5-HT$_{2C}$ receptor is expressed in high density in the brain (notably in the limbic structures, extrapyramidal pathways, thalamus and hypothalamus i.e. paraventricular hypothalamic nucleus and dorsomedial hypothalamic nucleus, and predominantly in the choroid plexus) and is expressed in low density or is absent in peripheral tissues, the compounds provided herein can be a more effective and safe anti-obesity agent. Also, 5-HT$_{2C}$ knockout mice are overweight with cognitive impairment and susceptibility to seizure.

It is believed that the 5-HT$_{2C}$ receptor may play a role in obsessive compulsive disorder, some forms of depression, and epilepsy. Accordingly, agonists can have anti-panic properties, and properties useful for the treatment of sexual dysfunction.

In sum, the 5-HT$_{2C}$ receptor is a receptor target for the treatment of obesity and psychiatric disorders, and it can be seen that there is a need for 5-HT$_{2C}$ agonists which safely decrease food intake and body weight.

The 5-HT$_{2C}$ receptor is one of 14 distinct serotonin receptor subtypes. Two receptors that are closely related to the 5-HT$_{2C}$ receptor are the 5-HT$_{2A}$ and 5-HT$_{2B}$ receptors, which share considerable sequence homology. It is believed that activation of central 5-HT$_{2A}$ receptors is a cause for a number of adverse central nervous system effects of nonselective serotonergic drugs including changes in perception and hallucination. Activation of 5-HT$_{2B}$ receptors located in the cardiovascular system is hypothesized to result in the heart valve disease and pulmonary hypertension associated with the use of fenfluramine and a number of other drugs that act via serotonergic mechanisms.

Lorcaserin (disclosed in PCT patent publication WO2003/086303) is an agonist of the 5-HT$_{2C}$ receptor and shows effectiveness at reducing obesity in animal models and humans. In December 2009, Arena Pharmaceuticals submitted a New Drug Application, or NDA, for lorcaserin to the US Food and Drug Administration (FDA). The NDA submission is based on an extensive data package from lorcaserin's clinical development program that includes 18 clinical trials totaling 8,576 patients. The pivotal phase 3 clinical trial program evaluated nearly 7,200 patients treated for up to two years, and showed that lorcaserin consistently produced significant weight loss with excellent tolerability. About two-thirds of patients achieved at least 5% weight loss and over one-third achieved at least 10% weight loss. On average, patients lost 17 to 18 pounds or about 8% of their weight. Secondary endpoints, including body composition, lipids, cardiovascular risk factors and glycemic parameters improved compared to placebo. In addition, heart rate and blood pressure went down. Lorcaserin did not increase the risk of cardiac valvulopathy. Lorcaserin improved quality of life, and there was no signal for depression or suicidal ideation. The only adverse event that exceeded the placebo rate by 5% was generally mild or moderate, transient headache. Based on a normal BMI of 25, patients in the first phase 3 trial lost about one-third of their excess body weight. The average weight loss was 35 pounds or 16% of body weight for the top quartile of patients in the second phase 3 trial.

As a part of the phase 3 clinical trial program, lorcaserin was evaluated in a randomized, placebo-controlled, multi-site, double-blind trial of 604 adults with poorly controlled type 2 diabetes mellitus treated with oral hyperglycemic agents ("BLOOM-DM"). Analysis of the overall study results showed significant weight loss with lorcaserin, measured as proportion of patients achieving ≥5% or ≥10% weight loss at 1 year, or as mean weight change (Diabetes 60, Suppl 1, 2011). Lorcaserin significantly improved glycemic control in the overall patient population. Accordingly, in addition to being useful for weight management, lorcaserin is also useful for the treatment of type 2 diabetes.

On Jun. 27, 2012 the FDA provisionally approved lorcaserin (BELVIQ®), contingent upon a final scheduling decision by the Drug Enforcement Administration (DEA), as an adjunct to a reduced-calorie diet and increased physical activity for chronic weight management in adult patients with an initial body mass index (BMI) of 30 kg/m$^2$ or greater (obese), or 27 kg/m$^2$ or greater (overweight) in the presence of at least one weight related comorbid condition (e.g., hypertension, dyslipidemia, type 2 diabetes). On Dec. 19, 2012 the DEA recommended that lorcaserin should be classified as a schedule 4 drug, having a low risk for abuse. The Office of the Federal Register filed for public inspection DEA's final rule placing BELVIQ into schedule 4 of the Controlled Substances Act. The scheduling designation was effective and BELVIQ was launched in the United States on Jun. 7, 2013, 30 days after publication of the DEA's final rule in the Federal Register.

Tobacco use is the leading cause of preventable illness and early death across the globe. According to the World Health Organization Fact Sheet (July 2013), 50% of all tobacco users die from a tobacco-related illness—this amounts to approximately six million people each year. It is estimated that greater than five million deaths per year result from direct tobacco use, with the remaining deaths resulting from exposure to second-hand smoke (World Health Organization website. Fact Sheet No 339: Tobacco. www.who.int/mediacentre/factsheets/fs339/en/index.html. Updated July 2013. Accessed Sep. 10, 2013). According to the Centers for Disease Control and Prevention (CDC), approximately 43.8 million adults in the United States (U.S.) are cigarette smokers. In the U.S., tobacco use is responsible for one in five deaths each year (World Health Organization website. Fact Sheet No 339: Tobacco. www.who.int/mediacentre/factsheets/fs339/en/index.html. Updated July 2013. Accessed Sep. 10, 2013). Tobacco use is directly related to cardiovascular disease, lung and other cancers, and chronic lower respiratory diseases (chronic bronchitis, emphysema, asthma, and other chronic lower respiratory diseases) (Health Effects of Cigarette Smoking. Centers for Disease Prevention website. www.cdc.gov/tobacco/data_statistics/fact_sheets/health_effects/effects_cig_smoking/Accessed Sep. 10, 2013). These have held position as the top three leading causes of death in the U.S. since 2008, when chronic lower respiratory disease replaced cerebrovascular disease, which is also directly associated with tobacco use (Molgaard C A, Bartok A, Peddecord K M, Rothrock J. *The association between cerebrovascular disease and smoking: a case-control study. Neuroepidemiology.* 1986; 5(2):88-94).

A study which surveyed the smoking behavior of 2138 US smokers over 8 years beginning in 2002 found that approximately one-third of subjects reported making a quit attempt over the previous year, approximately 85% of the original cohort made at least one quit attempt over the survey period, and the average quit rate was 3.8% for the retained cohort. Therefore the vast majority of smokers make quit attempts, but continued abstinence remains difficult to achieve (Cummings K M, Cornelius M E, Carpenter M J, et al. *Abstract: How Many Smokers Have Tried to Quit? Society for Research on Nicotine and Tobacco. Poster Session* 2. March 2013. POS2-65).

Existing smoking cessation treatments include CHANTIX (varenicline) and ZYBAN (bupropion SR). However, the prescribing information for both CHANTIX and ZYBAN include black box warnings. The CHANTIX prescribing information carries a warning for serious neuropsychiatric events, to include symptoms of agitation, hostility, depressed mood changes, behavior or thinking that are not typical for the patient, and suicidal ideation or suicidal behavior (CHANTIX (varenicline) (package insert), New York, N.Y.: Pfizer Labs, Division of Pfizer, Inc.; 2012). In addition, the warning notes that a meta-analysis found cardiovascular events were infrequent, but some were reported more frequently in individuals treated with CHANTIX; the difference was not statistically significant (CHANTIX (varenicline) (package insert), New York, N.Y.: Pfizer Labs, Division of Pfizer, Inc.; 2012). The ZYBAN prescribing information includes a similar black box warning for serious neuropsychiatric events during treatment as well as after discontinuation of treatment (ZYBAN (bupropion hydrochloride) (package insert), Research Triangle Park, N.C.: GlaxoSmithKline; 2012). Additional warnings include monitoring of individuals using antidepressants as there is an increased risk of suicidal thinking and behavior in children, adolescents and young adults, and other psychiatric disorders (ZYBAN (bupropion hydrochloride) (package insert), Research Triangle Park, N.C.: GlaxoSmithKline; 2012).

Further, weight gain is a well-recognized side effect of quitting smoking. Smoking cessation leads to weight gain in about 80% of smokers. The average weight gain in the first year after quitting is 4-5 kg, most of which is gained during the first 3 months. This amount of weight is typically viewed as a modest inconvenience compared with the health benefits of smoking cessation, but 10-20% of quitters gain more than 10 kg. Furthermore, a third of all subjects stated that they were unable to lose the excess weight after resuming smoking, lending support to the hypothesis that multiple quit attempts lead to cumulative weight gain (Veldheer S, Yingst J, Foulds G, Hrabovsky S, Berg A, Sciamanna C, Foulds J. *Once bitten, twice shy: concern about gaining weight after smoking cessation and its association with seeking treatment. Int J Clin Pract*. (2014) 68:388-395).

Given these statistics, it is perhaps not surprising that 50% of female smokers and 25% of male smokers cite fear of post-cessation weight gain (PCWG) as a major barrier to quitting, and approximately the same proportion cite weight gain as a cause of relapse in a previous quit attempt (Meyers A W, Klesges R C, Winders S E, Ward K D, Peterson B A, Eck L H. Are weight concerns predictive of smoking cessation? A prospective analysis. J Consult Clin Psychol. (1997) 65: 448-452; Clark M M, Decker P A, Offord K P, Patten C A, Vickers K S, Croghan I T, Hays J T, Hurt R D, Dale L C. Weight concerns among male smokers. Addict Behav. (2004) 29:1637-1641; Clark M M, Hurt R D, Croghan I T, Patten C A, Novotny P, Sloan J A, Dakhil S R, Croghan G A, Wos E J, Rowland K M, Bernath A, Morton R F, Thomas S P, Tschetter L K, Garneau S, Stella P J, Ebbert L P, Wender D B, Loprinzi C L. The prevalence of weight concerns in a smoking abstinence clinical trial. Addict Behav. (2006) 31:1144-1152.; Pomerleau C S, Kurth C L. Willingness of female smokers to tolerate postcessation weight gain. J Subst Abuse. (1996) 8:371-378; Pomerleau C S, Zucker A N, Stewart A J. Characterizing concerns about post cessation weight gain: results from a national survey of women smokers. Nicotine Tob Res. (2001) 3:51-60). Women, in particular, are reluctant to gain weight while quitting; about 40% state they would resume smoking if they gained any weight at all (Veldheer S, Yingst J, Foulds G, Hrabovsky S, Berg A, Sciamanna C, Foulds J. Once bitten, twice shy: concern about gaining weight after smoking cessation and its association with seeking treatment. Int J Clin Pract. (2014) 68:388-395; Pomerleau C S, Kurth CL. Willingness of female smokers to tolerate postcessation weight gain. J Subst Abuse (1996) 8:371-378; Pomerleau C S, Zucker A N, Stewart A J. Characterizing concerns about post-cessation weight gain: results from a national survey of women smokers. Nicotine Tob Res. (2001) 3:51-60; Tønnesen P, Paoletti P, Gustavsson G, Russell M A, Saracci R, Gulsvik A, Rijcken B, Sawe U. Higher dosage nicotine patches increase one-year smoking cessation rates: results from the European CEASE trial. Collaborative European Anti-Smoking Evaluation. European Respiratory Society. Eur Respir J. (1999) 13:238-246).

Light and moderate smokers are generally considered to be more motivated to quit than heavy smokers, leaving an increasingly high proportion of 'hard-core' smokers who are less likely to stop smoking (Hughes J R. *The hardening hypothesis: is the ability to quit decreasing due to increasing nicotine dependence? A review and commentary. Drug Alcohol Depend*. (2011) 117.111-117). One of the factors commonly associated with weight-gain concern (WGC) is high nicotine dependence; thus, the prospect of quitting may be even more difficult for smokers who are both highly nicotine-dependent and weight concerned. In addition, somewhat paradoxically, heavy smokers tend to have higher body weights and a higher likelihood of obesity than lighter smokers, suggesting a more complex relationship between body weight and smoking (Chiolero A, Jacot-Sadowski I, Faeh D, Paccaud F, Cornuz J. *Association of cigarettes smoked daily with obesity in a general adult population. Obesity* (Silver Spring) (2007) 15:1311-1318; John U, Hanke M, Rumpf H J, Thyrian J R. Smoking status, cigarettes per day, and their relationship to overweight and obesity among former and current smokers in a national adult general population sample. Int J Obes (Lond). (2005) 29:1289-1294). Several studies have found that overweight and obese smokers exhibit higher levels of smoking-related weight-gain concern than normal weight smokers (Aubin H-J, Berlin I, Smadja E, West R. *Factors associated with higher body mass index, weight concern, and weight gain in a multinational cohort study of smokers intending to quit. Int. J. Environ. Res. Public Health*. (2009). 6.943-957; Levine M D, Bush T, Magnusson B, Cheng, Y, Chen X. *Smoking-related weight concerns and obesity: differences among normal weight, overweight, and obese smokers using a telephone tobacco quitline. Nicotine Tob Res*. (2013) 15:1136-1140). Given the convergence of high nicotine dependence and high weight-gain concern in obese smokers, smoking cessation interventions that address post-cessation weight gain could be especially beneficial for this subpopulation.

Despite the existence of several therapies for smoking cessation, long-term success rates are low and major barriers to quitting remain. There is a significant unmet need for safe and effective therapies that address these barriers. There also remains a need for alternative compounds for the treatment of diseases and disorders related to the 5-HT$_{2C}$ receptor. The compounds described herein are 5-HT$_2$C receptor agonists that satisfy this need and provide related advantages as well. The present disclosure satisfies this need and provides related advantages as well.

SUMMARY

Provided in some embodiments are compounds of Formula A, as defined herein. Also provided in some embodiments are methods for weight management, inducing satiety, and decreasing food intake, and for preventing and treating obesity, antipsychotic-induced weight gain, type 2 diabetes, Prader-Willi syndrome, tobacco/nicotine dependence, drug addiction, alcohol addiction, pathological gambling, reward deficiency syndrome, and sex addiction), obsessive-compulsive spectrum disorders and impulse control disorders (including nail-biting and onychophagia), sleep disorders (including insomnia, fragmented sleep architecture, and disturbances of slow-wave sleep), urinary incontinence, psychiatric disorders (including schizophrenia, anorexia nervosa, and bulimia nervosa), Alzheimer disease, sexual dysfunction, erectile dysfunction, epilepsy, movement disorders (including parkinsonism and antipsychotic-induced movement disorder), hypertension, dyslipidemia, nonalcoholic fatty liver disease, obesity-related renal disease, and sleep apnea. Also provided in some embodiments are compositions comprising a compound herein, optionally in combination with a supplemental agent, and methods for reducing the frequency of smoking tobacco in an individual attempting to reduce frequency of smoking tobacco; aiding in the cessation or lessening of use of a tobacco product in an individual attempting to cease or lessen use of a tobacco product; aiding in smoking cessation and preventing associated weight gain; controlling weight gain associated with smoking cessation by an individual attempting to cease smoking tobacco; reducing weight gain associated with smoking cessation by an individual attempting to cease smoking tobacco; treating nicotine dependency, addiction and/or withdrawal in an individual attempting to treat nicotine dependency, addiction and/or withdrawal; or reducing the likelihood of relapse use of nicotine by an individual attempting to cease nicotine use comprising administering a compound herein, optionally in combination with a supplemental agent.

In one embodiment provided herein are compounds selected from compounds of Formula A and pharmaceutically acceptable salts, solvates, and hydrates thereof:

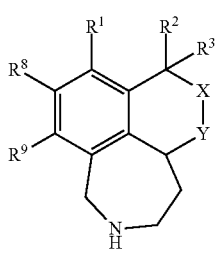

Formula A wherein:

$R^1$ is selected from: H, $C_1$-$C_6$ alkyl optionally substituted with one or more halogens, halogen, O—$C_1$-$C_6$ alkyl optionally substituted with one or more halogens, and $C_3$-$C_8$ cycloalkyl;

$R^2$ and $R^3$ are each independently H, $C_1$-$C_6$ alkyl optionally substituted with one or more halogens, or $C_3$-$C_8$ cycloalkyl; or $R^2$ and $R^3$ taken together with the carbon connecting them form a 3- to 6-membered spirocyclic carbocyclic ring;

X is O or C($R^4R^5$);

Y is O or C($R^6R^7$);

wherein if X is O, Y is (C$R^6R^7$);

$R^4$ and $R^5$ are each independently H, $C_1$-$C_6$ alkyl optionally substituted with one or more halogens, or $C_3$-$C_8$ cycloalkyl; or $R^4$ and $R^5$ taken together with the carbon connecting them form a 3- to 6-membered spirocyclic carbocyclic ring;

or $R^2$ and $R^5$ are each H and $R^3$ and $R^4$ taken together with the carbons connecting them form a 3- to 6-membered carbocyclic ring;

$R^6$ and $R^7$ are each independently H, $C_1$-$C_6$ alkyl optionally substituted with one or more halogens, or $C_3$-$C_8$ cycloalkyl; or $R^6$ and $R^7$ taken together with the carbon connecting them form a 3- to 6-membered spirocyclic carbocyclic ring;

and $R^8$ and $R^9$ are each independently H, $C_1$-$C_6$ alkyl optionally substituted with one or more halogens, or halogen.

In one embodiment provided herein are compounds selected from compounds of Formula I and pharmaceutically acceptable salts, solvates, and hydrates thereof:

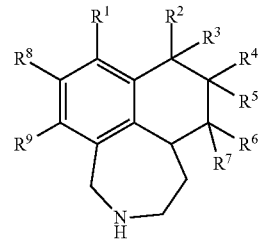

Formula I wherein:

$R^1$ is selected from: H, $C_1$-$C_6$ alkyl optionally substituted with one or more halogens, halogen, O—$C_1$-$C_6$ alkyl optionally substituted with one or more halogens, and $C_3$-$C_8$ cycloalkyl;

$R^2$ and $R^3$ are each independently H, $C_1$-$C_6$ alkyl optionally substituted with one or more halogens, or $C_3$-$C_8$ cycloalkyl; or $R^2$ and $R^3$ taken together with the carbon connecting them form a 3- to 6-membered spirocyclic carbocyclic ring;

$R^4$ and $R^5$ are each independently H, $C_1$-$C_6$ alkyl optionally substituted with one or more halogens, or $C_3$-$C_8$ cycloalkyl; or $R^4$ and $R^5$ taken together with the carbon connecting them form a 3- to 6-membered spirocyclic carbocyclic ring;

or $R^2$ and $R^5$ are each H and $R^3$ and $R^4$ taken together with the carbons connecting them form a 3- to 6-membered carbocyclic ring;

$R^6$ and $R^7$ are each independently H, $C_1$-$C_6$ alkyl optionally substituted with one or more halogens, or $C_3$-$C_8$ cycloalkyl; or $R^6$ and $R^7$ taken together with the carbon connecting them form a 3- to 6-membered spirocyclic carbocyclic ring;

and $R^8$ and $R^9$ are each independently H, $C_1$-$C_6$ alkyl optionally substituted with one or more halogens, or halogen.

Also provided are compositions comprising a compound provided herein and a pharmaceutically acceptable carrier.

Also provided are processes for preparing compositions, comprising admixing a compound provided herein and a pharmaceutically acceptable carrier.

Also provided are pharmaceutical compositions comprising a compound provided herein and a pharmaceutically acceptable carrier.

Also provided are processes for preparing pharmaceutical compositions, comprising admixing a compound provided herein a pharmaceutically acceptable carrier.

Also provided are methods for decreasing food intake in an individual in need thereof, comprising administering to said individual a therapeutically effective amount of a compound provided herein.

Also provided are methods for inducing satiety in an individual in need thereof, comprising administering to said individual a therapeutically effective amount of a compound provided herein.

Also provided are methods for the treatment of obesity in an individual in need thereof, comprising administering to said individual a therapeutically effective amount of a compound provided herein.

Also provided are methods for the prevention of obesity in an individual in need thereof, comprising administering to said individual a therapeutically effective amount of a compound provided herein.

Also provided are methods for weight management in an individual in need thereof, comprising administering to said individual a therapeutically effective amount of a compound provided herein.

Also provided are use of a compound provided herein for the manufacture of a medicament for decreasing food intake.

Also provided are use of a compound provided herein for the manufacture of a medicament for inducing satiety.

Also provided are use of a compound provided herein for the manufacture of a medicament for the treatment of obesity.

Also provided are use of a compound provided herein for the manufacture of a medicament for the prevention of obesity.

Also provided are use of a compound provided herein for the manufacture of a medicament for weight management.

Also provided are compounds for use in a method for treatment of the human or animal body by therapy.

Also provided are compounds for use in a method for decreasing food intake.

Also provided are compounds for use in a method for inducing satiety.

Also provided are compounds for use in a method for the treatment of obesity.

Also provided are compounds for use in a method for the prevention of obesity.

Also provided are compounds for use in weight management.

Provided is a method for reducing the frequency of smoking tobacco in an individual attempting to reduce frequency of smoking tobacco comprising the step of: prescribing and/or administering to the individual an effective amount of a compound provided herein.

Also provided is a method for aiding in the cessation or lessening of use of a tobacco product in an individual attempting to cease or lessen use of a tobacco product comprising the step of: prescribing and/or administering to the individual an effective amount of a compound provided herein.

Also provided is a method for aiding in smoking cessation and preventing associated weight gain in an individual attempting to cease smoking and prevent weight gain comprising the step of: prescribing and/or administering to the individual an effective amount of a compound provided herein.

Also provided is a method for controlling weight gain associated with smoking cessation by an individual attempting to cease smoking tobacco comprising the step of: prescribing and/or administering to the individual an effective amount of a compound provided herein.

Also provided is a method of treatment for nicotine dependency, addiction and/or withdrawal in an individual attempting to treat nicotine dependency, addiction and/or withdrawal comprising the step of: prescribing and/or administering to the individual an effective amount of a compound provided herein.

Also provided is a method of reducing the likelihood of relapse use of nicotine by an individual attempting to cease nicotine use comprising the step of: prescribing and/or administering to the individual an effective amount of a compound provided herein.

Also provided is a method for reducing weight gain associated with smoking cessation by an individual attempting to cease smoking tobacco comprising the step of: prescribing and/or administering to the individual an effective amount of a compound provided herein.

Also provided is a method of reducing the frequency of smoking tobacco in an individual attempting to reduce frequency of smoking tobacco, aiding in the cessation or lessening of use of a tobacco product in an individual attempting to cease or lessen use of a tobacco product, aiding in smoking cessation and preventing associated weight gain, controlling weight gain associated with smoking cessation by an individual attempting to cease smoking tobacco, reducing weight gain associated with smoking cessation by an individual attempting to cease smoking tobacco, treating nicotine dependency, addiction and/or withdrawal in an individual attempting to treat nicotine dependency, addiction and/or withdrawal, or reducing the likelihood of relapse use of nicotine by an individual attempting to cease nicotine use, comprising:

selecting an individual with an initial BMI≥27 kg/m$^2$; and prescribing and/or administering to the individual an effective amount of a compound provided herein.

Also provided is a method of reducing the frequency of smoking tobacco in an individual attempting to reduce frequency of smoking tobacco, aiding in the cessation or lessening of use of a tobacco product in an individual attempting to cease or lessen use of a tobacco product, aiding in smoking cessation and preventing associated weight gain, controlling weight gain associated with smoking cessation by an individual attempting to cease smoking tobacco, reducing weight gain associated with smoking cessation by an individual attempting to cease smoking tobacco, treating nicotine dependency, addiction and/or withdrawal in an individual attempting to treat nicotine dependency, addiction and/or withdrawal, or reducing the likelihood of relapse use of nicotine by an individual attempting to cease nicotine use, comprising:

administering a compound provided herein;

monitoring the individual for BMI during said administration; and discontinuing said administration if the BMI of the individual becomes <18.5 kg/m$^2$ during said administration.

Also provided is a method of reducing the frequency of smoking tobacco in an individual attempting to reduce frequency of smoking tobacco, aiding in the cessation or lessening of use of a tobacco product in an individual attempting to cease or lessen use of a tobacco product, aiding in smoking cessation and preventing associated weight gain, controlling weight gain associated with smoking cessation by an individual attempting to cease smoking tobacco, reducing weight gain associated with smoking cessation by an individual attempting to cease smoking tobacco, treating nicotine dependency, addiction and/or withdrawal in an individual attempting to treat nicotine dependency, addiction and/or withdrawal, or reducing the likelihood of relapse use of nicotine by an individual attempting to cease nicotine use, comprising:

administering a compound selected from compound provided herein to an individual with an initial BMI≤25 kg/m$^2$;

monitoring the individual for body weight during said administration; and discontinuing said administration if the body weight of the individual decreases by more than about 1% during said administration.

Also provided is a method of reducing the frequency of smoking tobacco in an individual attempting to reduce frequency of smoking tobacco, aiding in the cessation or lessening of use of a tobacco product in an individual attempting to cease or lessen use of a tobacco product, aiding in smoking cessation and preventing associated weight gain, controlling weight gain associated with smoking cessation by an individual attempting to cease smoking tobacco, reducing weight gain associated with smoking cessation by an individual attempting to cease smoking tobacco, treating nicotine dependency, addiction and/or withdrawal in an individual attempting to treat nicotine dependency, addiction and/or withdrawal, or reducing the likelihood of relapse use of nicotine by an individual attempting to cease nicotine use, comprising:

administering a compound provided herein to an individual;

monitoring the individual for body weight during said administration; and discontinuing said administration if the body weight of the individual decreases by more than about 1 kg during said administration.

Also provided is a composition comprising a compound provided herein and at least one supplemental agent.

Also provided is a compound provided herein for use in combination with a supplemental agent.

Also provided is a supplemental agent chosen from nicotine replacement therapies, for use in combination with a compound provided herein.

BRIEF DESCRIPTION OF THE DRAWINGS

FIG. 8 shows an example of a synthetic scheme for preparing the compounds of formula I, wherein $R^{10}$ is, for example, benzyl optionally substituted with one or more halogens, such as, 3,4-dichlorobenzyl.

DETAILED DESCRIPTION

Figure 1:
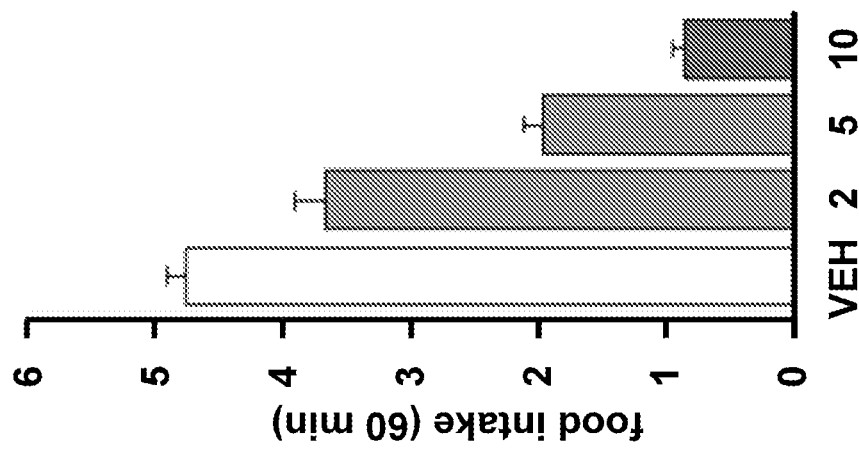
FIG. 1 shows a plot of cumulative food intake (g) over time (hours post-administration) for vehicle and for the $2^{nd}$ eluting enantiomer in example 1.1 dosed in Sprague Dawley rats (white bar: vehicle; gray bars: 2 mg/kg, 5 mg/kg, and 10 mg/kg of the $2^{nd}$ eluting enantiomer in example 1.1.
Figure 2:
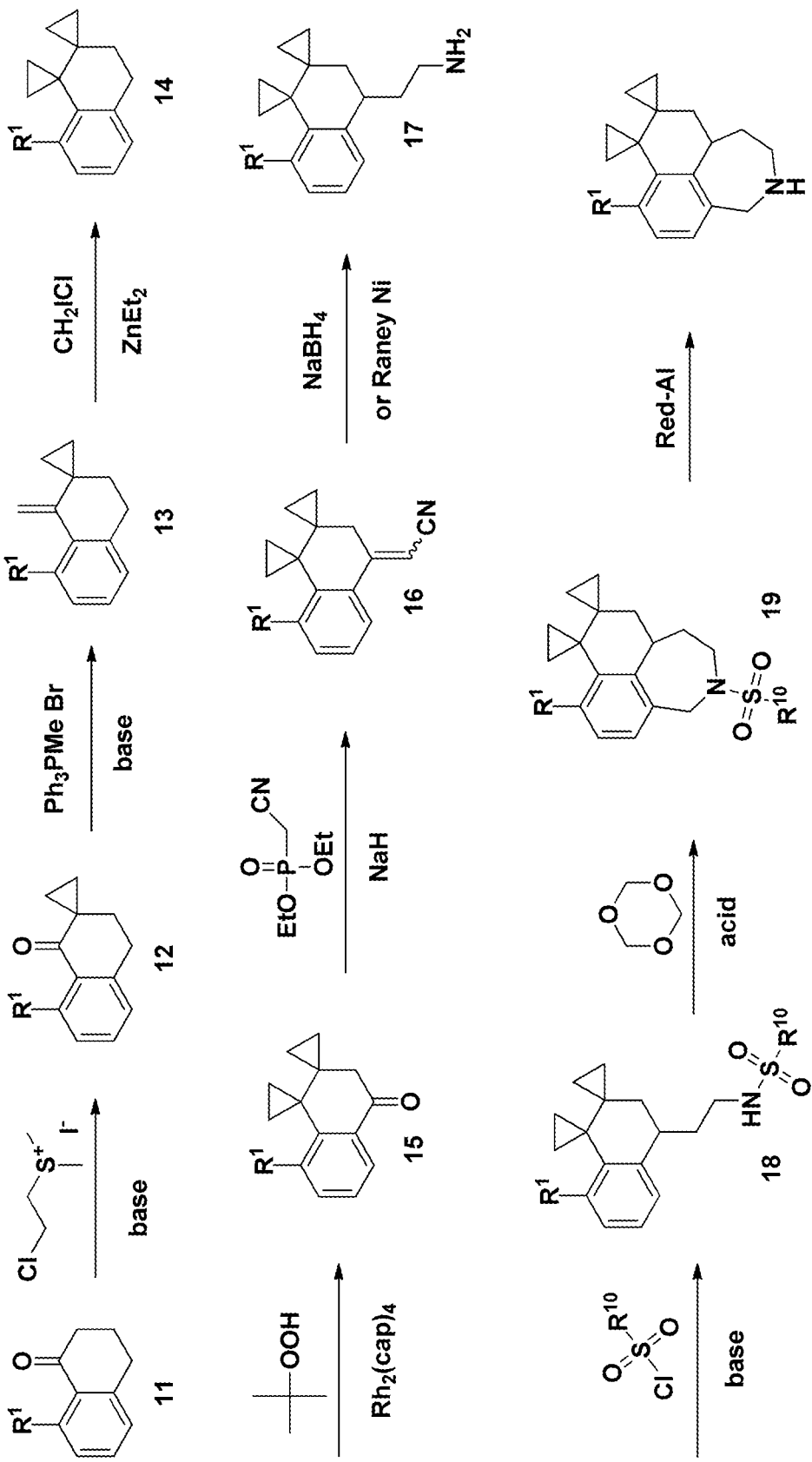
FIG. 2 shows an example of a synthetic scheme for preparing the compounds of formula I, wherein $R^1$ is, for example F or H, and $R^{10}$ is, for example, benzyl optionally substituted with one or more halogens, such as, 3,4-dichlorobenzyl.
Figure 3:
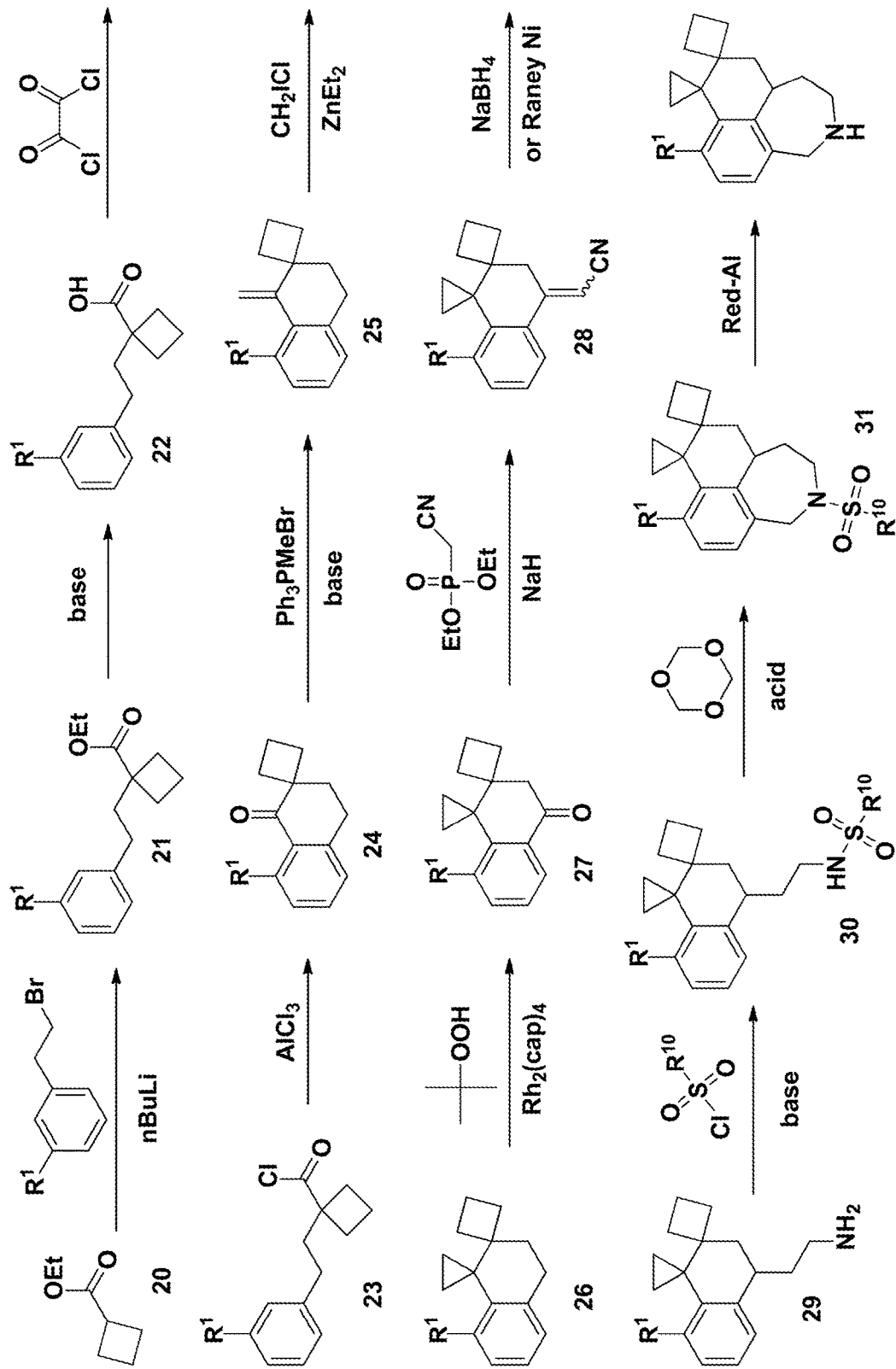
FIG. 3 shows an example of a synthetic scheme for preparing the compounds of formula I, wherein $R^1$ is, for example H, and $R^{10}$ is, for example, benzyl optionally substituted with one or more halogens, such as, 3,4-dichlorobenzyl.
Figure 4:
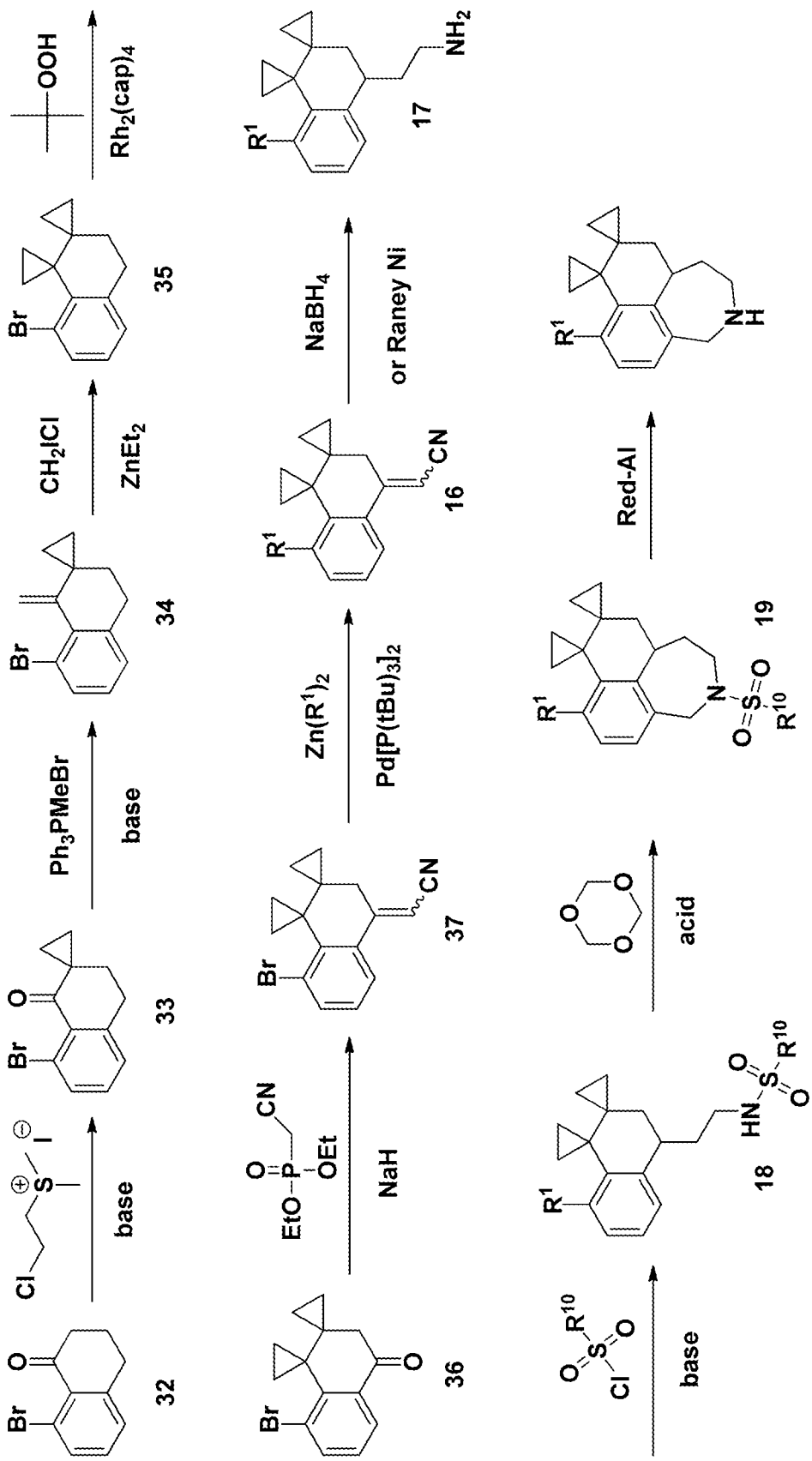
FIG. 4 shows an example of a synthetic scheme for preparing the compounds of formula I, wherein $R^1$ is, for example methyl or ethyl, and $R^{10}$ is, for example, benzyl optionally substituted with one or more halogens, such as, 3,4-dichlorobenzyl.
Figure 5:
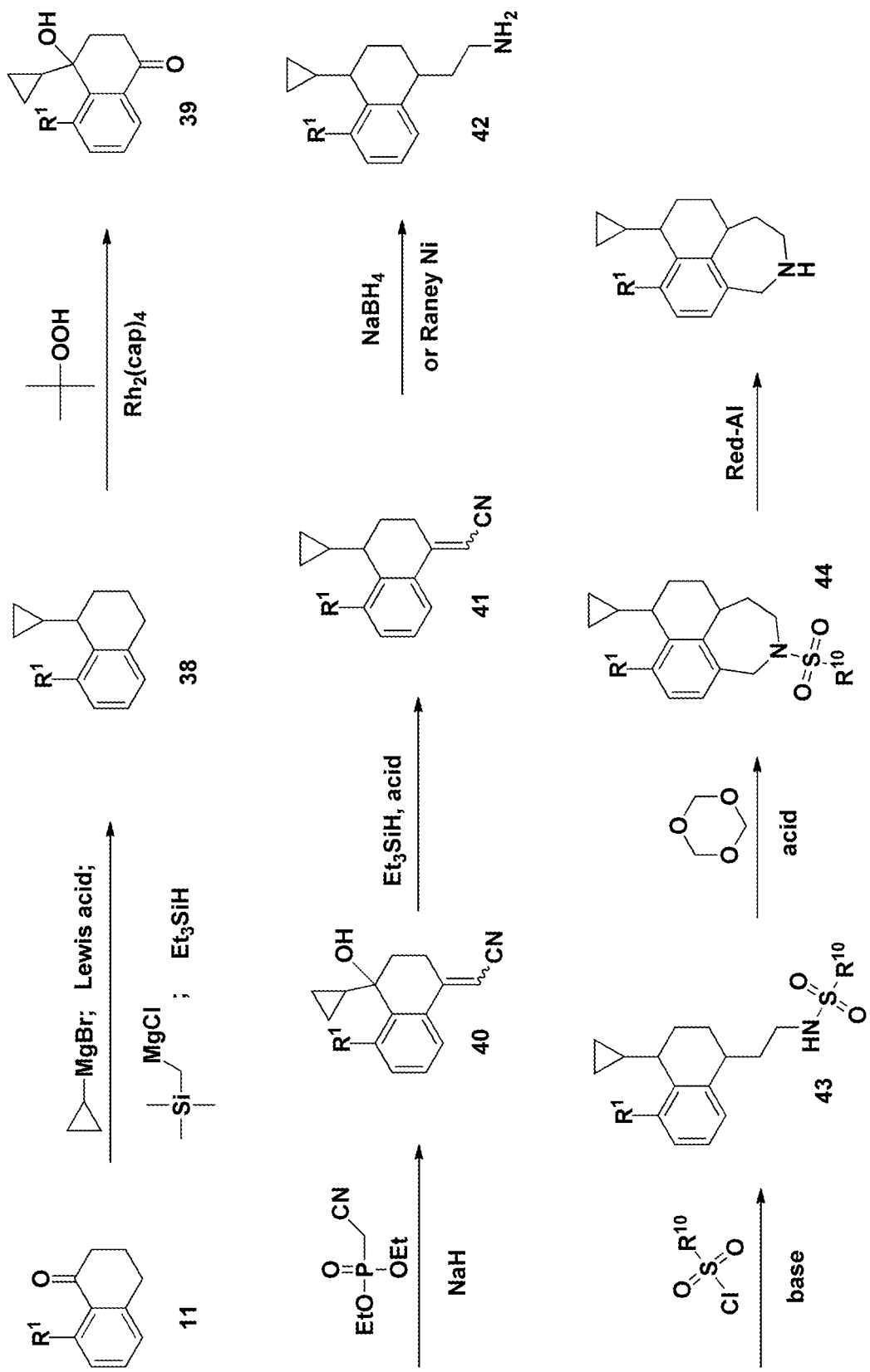
FIG. 5 shows an example of a synthetic scheme for preparing the compounds of formula I, wherein $R^1$ is, for example H, and $R^{10}$ is, for example, benzyl optionally substituted with one or more halogens, such as, 3,4-dichlorobenzyl.
Figure 6A:
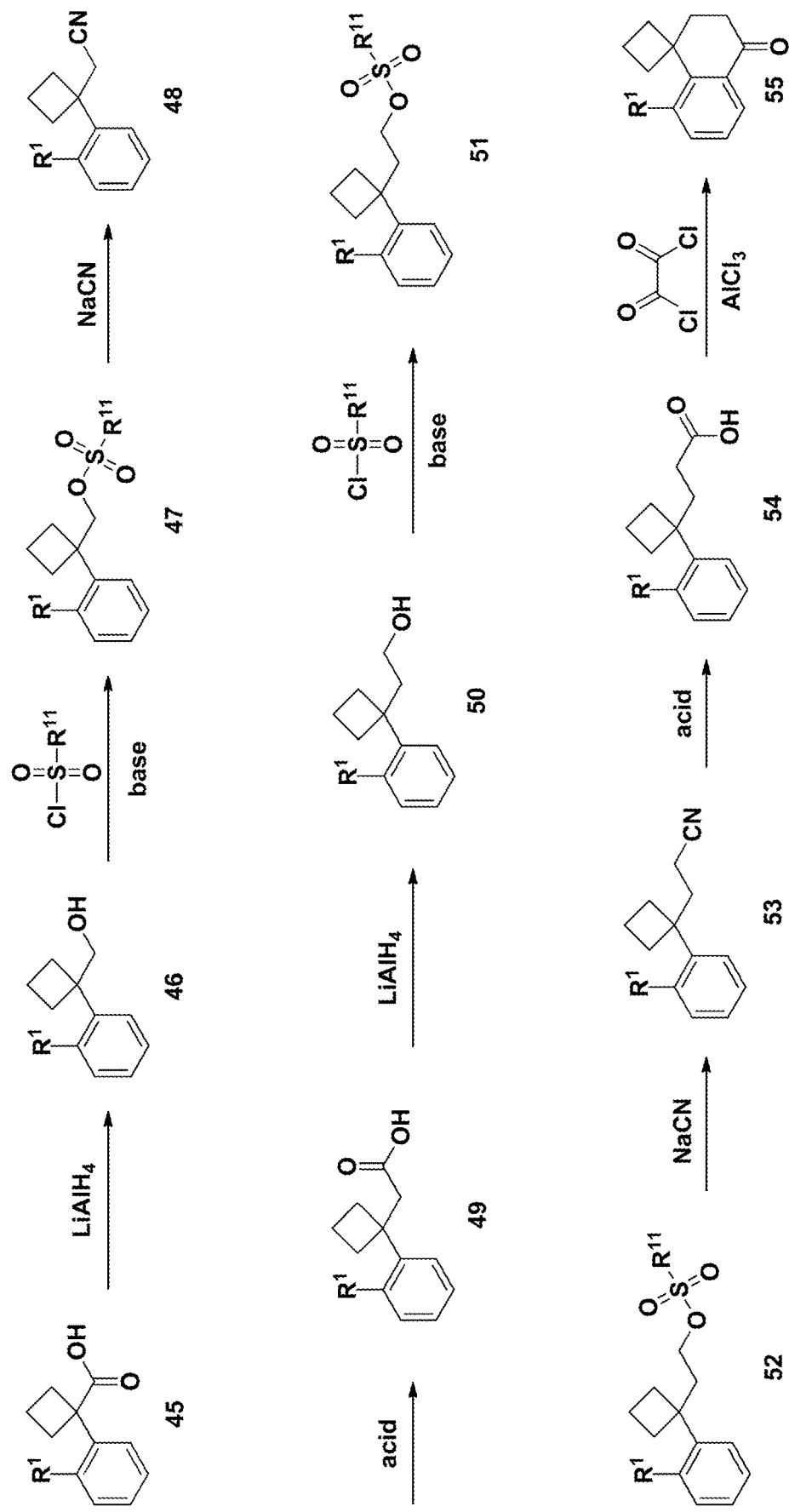
FIGS. 6A and 6B show an example of a synthetic scheme for preparing the compounds of formula I, wherein: $R^1$ is, for example H; $R^{11}$ is, for example, $C_1$-$C_6$ alkyl, such as methyl; and $R^{10}$ is, for example, benzyl optionally substituted with one or more halogens, such as, 3,4-dichlorobenzyl.
Figure 6B:
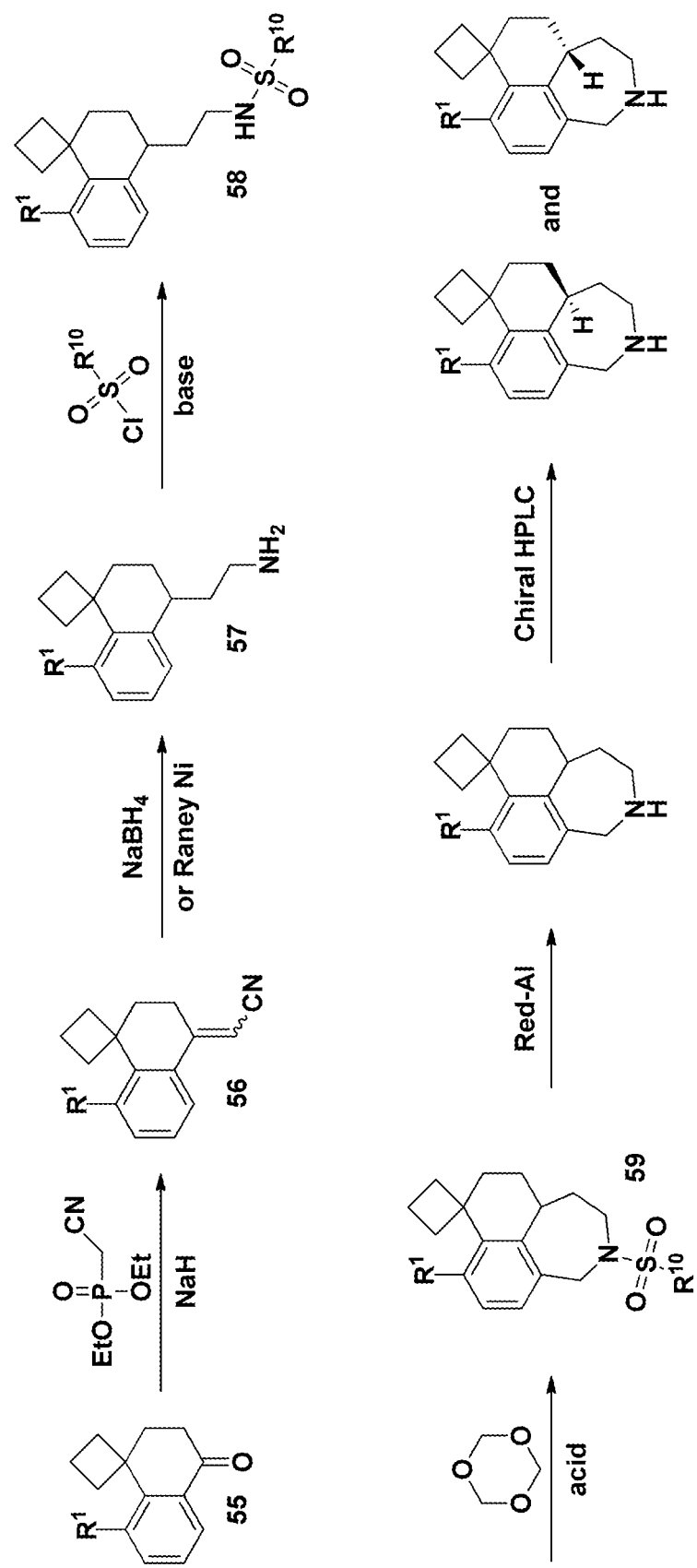
Figure 7:
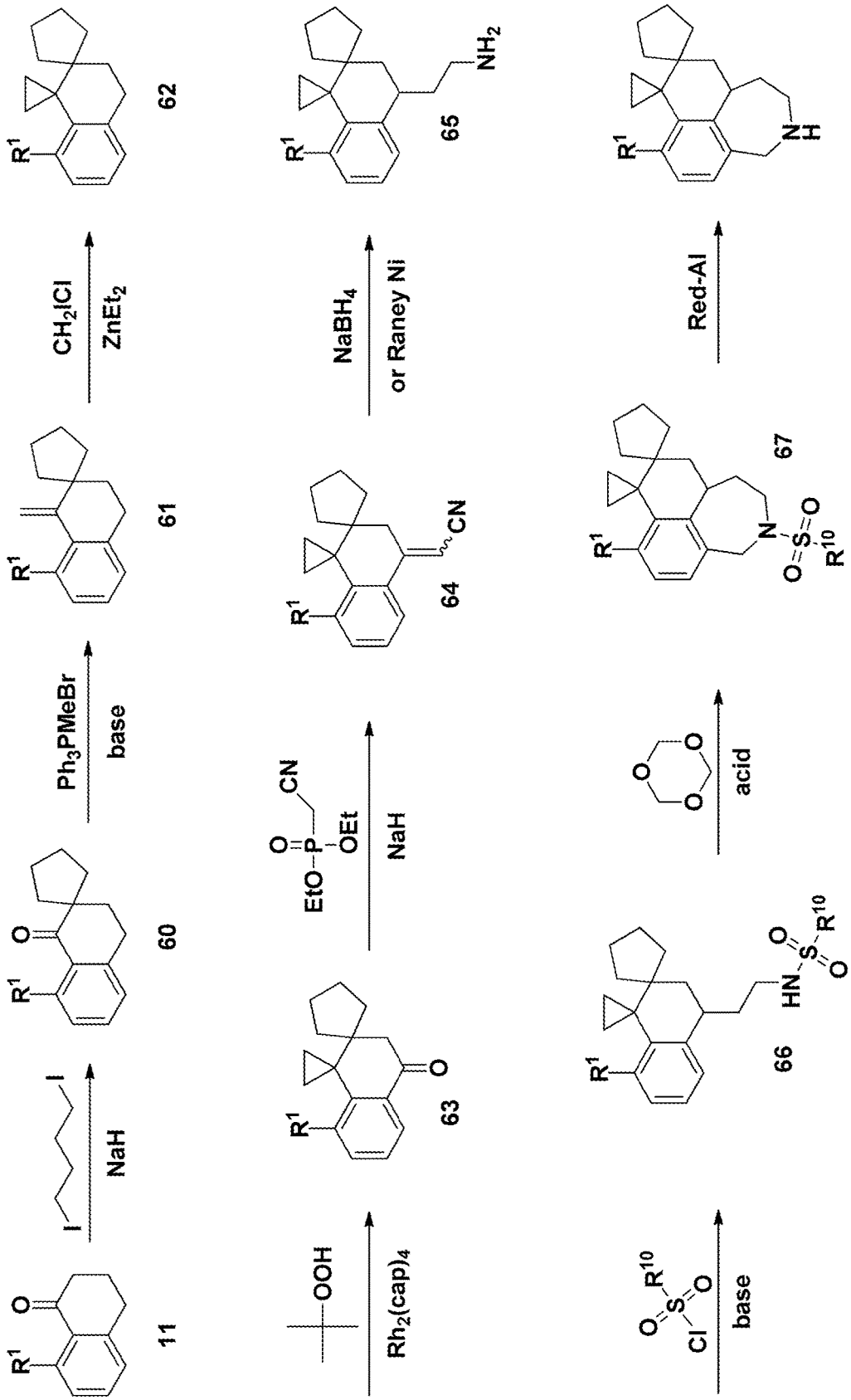
FIG. 7 shows an example of a synthetic scheme for preparing the compounds of formula I, wherein $R^1$ is, for example H, and $R^{10}$ is, for example, benzyl optionally substituted with one or more halogens, such as, 3,4-dichlorobenzyl.
Figure 9A:
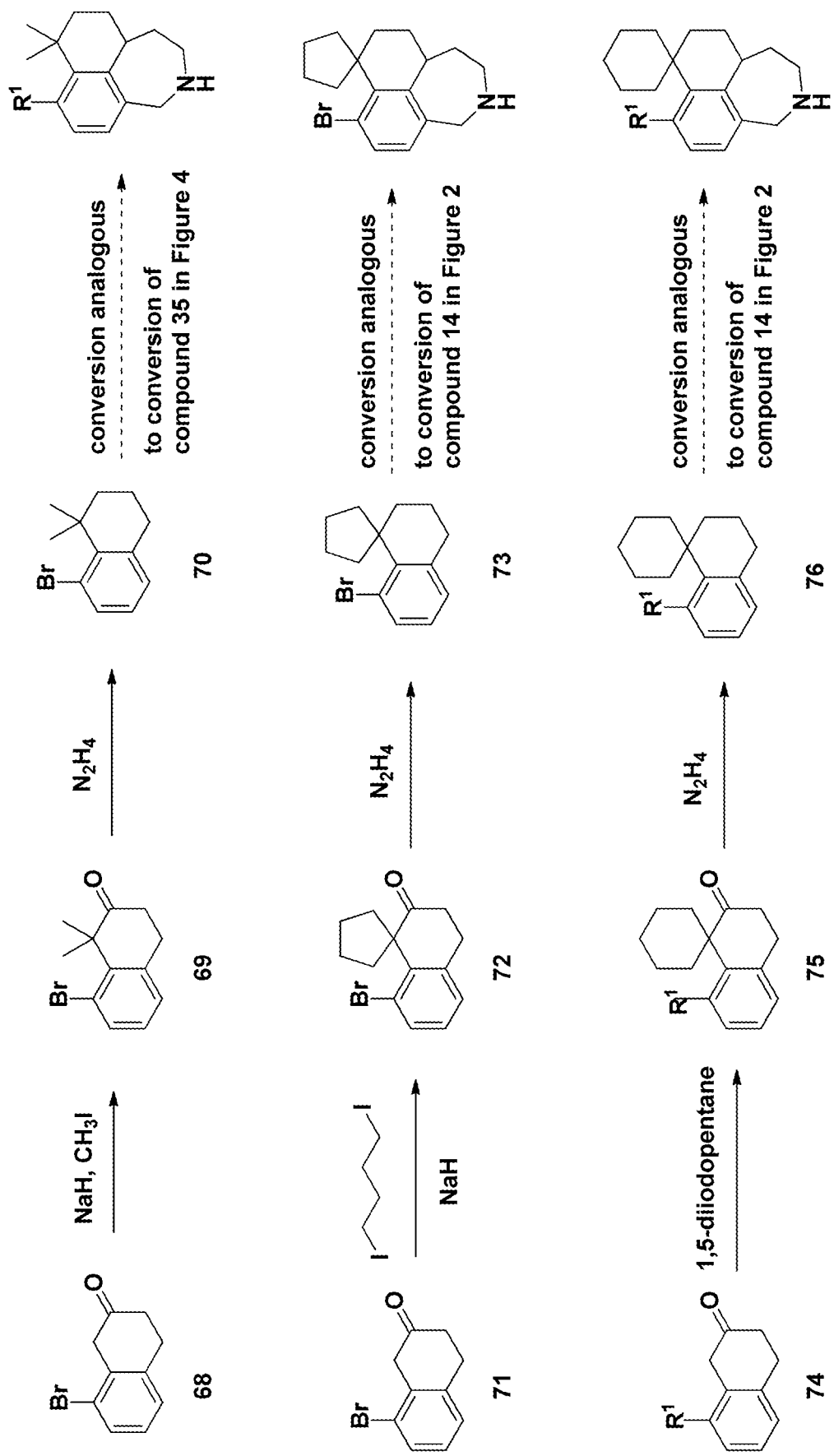
FIGS. 9A and 9B show examples of synthetic schemes for preparing the compounds of formula I.
Figure 9B:
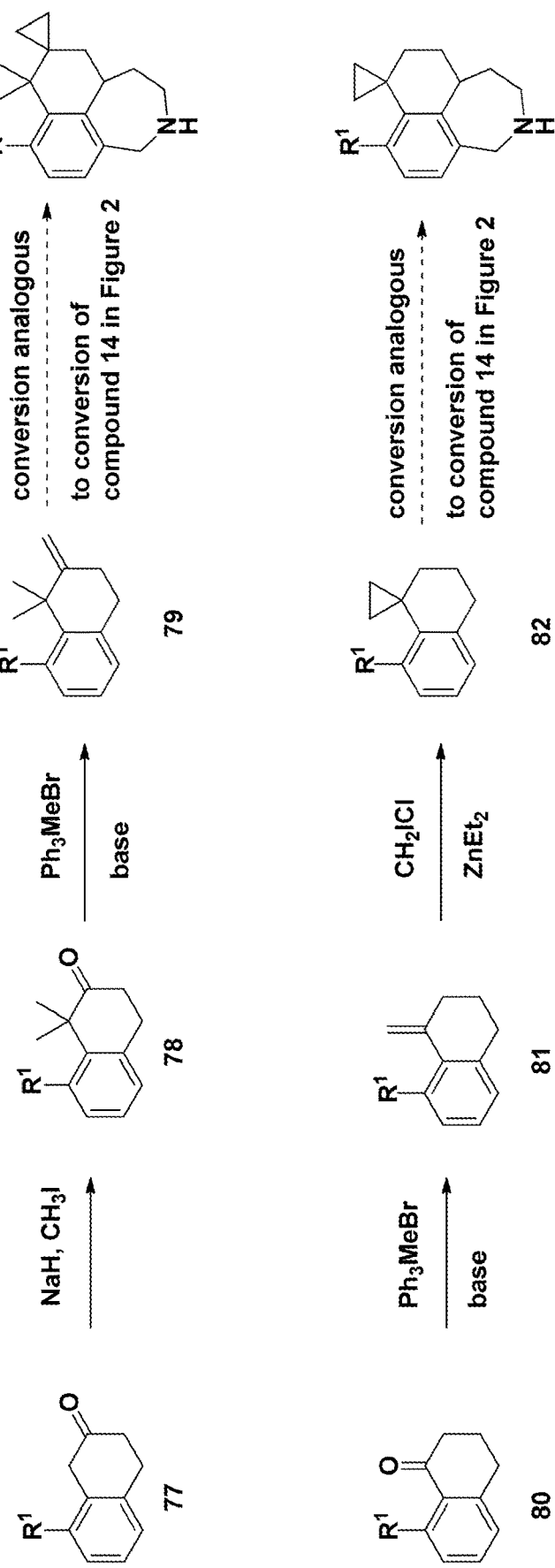
Figure 10:
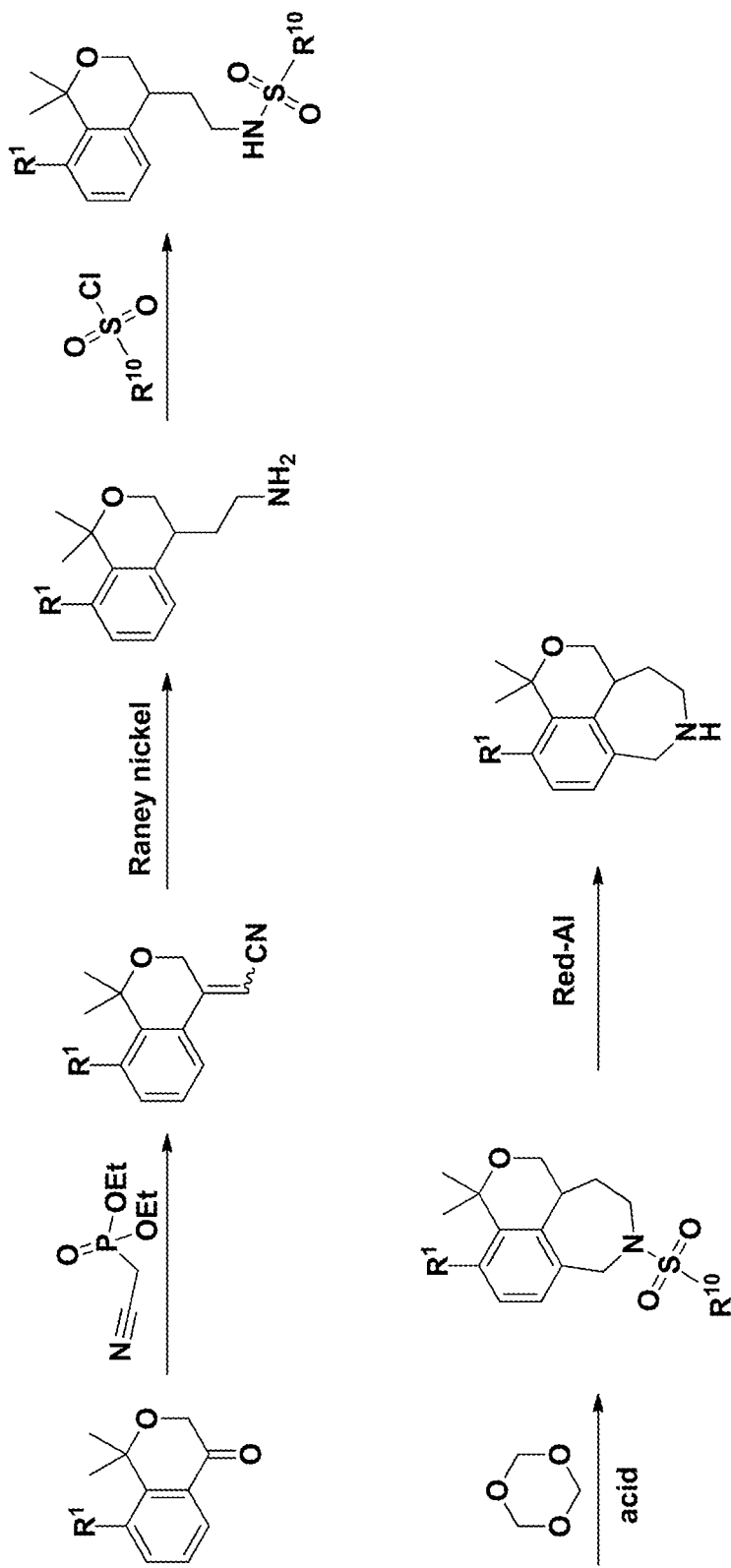
FIG. 10 shows an example of a synthetic scheme for preparing the compounds of formula A wherein X is O, and $R^{10}$ is, for example, benzyl optionally substituted with one or more halogens, such as, 3,4-dichlorobenzyl.
Figure 11:
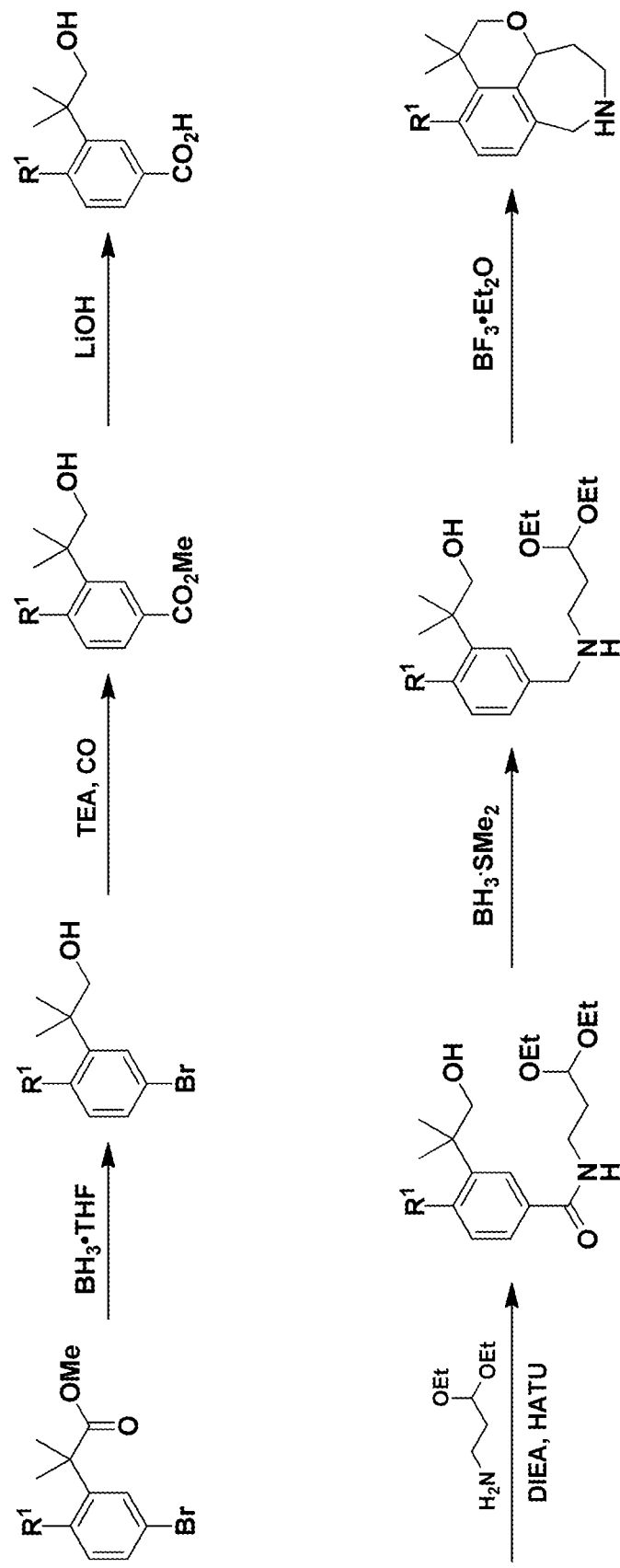
FIG. 11 shows an example of a synthetic scheme for preparing the compounds of formula A wherein Y is O.

As used in the present specification, the following words and phrases are generally intended to have the meanings as set forth below, except to the extent that the context in which they are used indicates otherwise.

As used herein, the term "agonist" refers to a moiety that interacts with and activates a receptor, such as the 5-$HT_{2C}$ serotonin receptor, and initiates a physiological or pharmacological response characteristic of that receptor.

The term "composition" refers to a compound, including but not limited to, salts, solvates, and hydrates of a compound provided herein, in combination with at least one additional component.

The phrase "pharmaceutical composition" refers to a composition comprising at least one active ingredient, such as a compound as described herein; including but not limited to, salts, solvates, and hydrates of compounds provided herein, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "individual" refers to a human. An individual can be an adult or prepubertal (a child) and can be of any gender. The individual can be a patient or other individual seeking treatment. The methods disclosed herein can also apply to non-human mammals such as livestock or pets.

As used herein, a "plurality of individuals" means more than one individual.

As used herein, "administering" means to provide a compound or other therapy, remedy or treatment. For example, a health care practitioner can directly provide a compound to an individual in the form of a sample, or can indirectly provide a compound to an individual by providing an oral or written prescription for the compound. Also, for example, an individual can obtain a compound by themselves without the involvement of a health care practitioner. Administration of the compound may or may not involve the individual actually internalizing the compound. In the case where an individual internalizes the compound, the body is transformed by the compound in some way.

As used herein, "prescribing" means to order, authorize or recommend the use of a drug or other therapy, remedy or treatment. In some embodiments, a health care practitioner can orally advise, recommend or authorize the use of a compound, dosage regimen or other treatment to an individual. In this case the health care practitioner may or may not provide a prescription for the compound, dosage regimen or treatment. Further, the health care practitioner may or may not provide the recommended compound or treatment. For example, the health care practitioner can advise the individual where to obtain the compound without providing the compound. In some embodiments, a health care practitioner can provide a prescription for the compound, dosage regimen or treatment to the individual. For example, a health care practitioner can give a written or oral prescription to an individual. A prescription can be written on paper or on electronic media such as a computer file, for example, on a hand-held computer device. For example, a health care practitioner can transform a piece of paper or electronic media with a prescription for a compound, dosage regimen or treatment. In addition, a prescription can be called in (oral) or faxed in (written) to a pharmacy or a dispensary. In some embodiments, a sample of the compound or treatment can be given to the individual. As used herein, giving a sample of a compound constitutes an implicit prescription for the compound. Different health care systems around the world use different methods for prescribing and administering compounds or treatments and these methods are encompassed by the disclosure.

A prescription can include, for example, an individual's name and/or identifying information such as date of birth. In addition, for example, a prescription can include, the medication name, medication strength, dose, frequency of administration, route of administration, number or amount to be dispensed, number of refills, physician name, and/or physician signature. Further, for example, a prescription can include a DEA number or state number.

A healthcare practitioner can include, for example, a physician, nurse, nurse practitioner, physician assistant, clinician, or other related healthcare professional who can prescribe or administer compounds (drugs) for weight management, decreasing food intake, inducing satiety, and treating or preventing obesity. In addition, a healthcare practitioner can include anyone who can recommend, prescribe, administer or prevent an individual from receiving a compound or drug including, for example, an insurance provider.

The term "prevent," "preventing," or "prevention", such as prevention of obesity, refers to the prevention of the occurrence or onset of one or more symptoms associated with a particular disorder and does not necessarily mean the complete prevention of a disorder. For example, weight gain may be prevented even if the individual gains some amount of weight. For example, the terms "prevent," "preventing," and "prevention" refer to the administration of therapy on a prophylactic or preventative basis to an individual who may ultimately manifest at least one symptom of a disease or condition but who has not yet done so. Such individuals can be identified on the basis of risk factors that are known to correlate with the subsequent occurrence of the disease. Alternatively, prevention therapy can be administered without prior identification of a risk factor, as a prophylactic measure. Delaying the onset of the at least one symptom can also be considered prevention or prophylaxis.

For example, the term "prevent," "preventing" or "prevention" may refer to prevention of weight gain associated with smoking cessation.

It is understood that when the phrase "pharmaceutically acceptable salts, solvates, and hydrates" or the phrase "pharmaceutically acceptable salt, hydrate, or solvate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate and hydrate" is used when referring to compounds described herein that are salts, it embraces pharmaceutically acceptable solvates and/or hydrates of such salts. It is also understood by a person of ordinary skill in the art that hydrates are a subgenus of solvates.

The term "prodrug" refers to an agent which must undergo chemical or enzymatic transformation to the active or parent drug after administration, so that the metabolic product or parent drug can subsequently exhibit the desired pharmacological response.

The term "treat," "treating," or "treatment" includes the administration of therapy to an individual who already manifests at least one symptom of a disease or condition or who has previously manifested at least one symptom of a disease or condition. For example, "treating" can include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically. For example, the term "treating" in reference to a disorder can mean a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder. For example, a method for treatment of obesity can result in weight loss; however, the weight loss does not need to be enough such that the individual is no longer obese. It has been shown that even modest decreases in weight or related parameters such as BMI, waist circumference and percent body fat, can result in improvement of health, for example, lower blood pressure, improved blood lipid profiles, or a reduction in sleep apnea. As another example, a method for treatment of an addiction can result in a reduction in the number, frequency, or severity of cravings, seeking behaviors, or relapses, or it can result in abstention.

In some embodiments, the term "treat," "treating" or "treatment" refers to the administration of therapy to an individual who already manifests, or who has previously manifested, at least one symptom of a disease, disorder, condition, dependence, or behavior, such as at least one symptom of a disease or condition. For example, "treating" can include any of the following with respect to a disease, disorder, condition, dependence, or behavior: alleviating, abating, ameliorating inhibiting (e.g., arresting the development), relieving, or causing regression. "Treating" can also include treating the symptoms, preventing additional symptoms, preventing the underlying physiological causes of the symptoms, or stopping the symptoms (either prophylactically and/or therapeutically) of a disease, disorder, condition, dependence, or behavior, such as the symptoms of a disease or condition.

The phrase "weight management" refers to controlling body weight and in the context of the present disclosure is directed toward weight loss and the maintenance of weight loss (also called weight maintenance herein). In addition to controlling body weight, weight management includes controlling parameters related to body weight, for example, BMI, percent body fat and waist circumference. For example, weight management for an individual who is overweight or obese can mean losing weight with the goal of keeping weight in a healthier range. Also, for example, weight management for an individual who is overweight or obese can include losing body fat or circumference around the waist with or without the loss of body weight. Maintenance of weight loss (weight maintenance) includes preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight. Therefore, weight maintenance in an individual who has lost weight can include preventing weight gain after weight loss, reducing the amount of weight gained after weight loss, controlling weight gain after weight loss or slowing the rate of weight gain after weight loss. As used herein, "weight management in an individual in need thereof" refers to a judgment made by a healthcare practitioner that an individual requires or will benefit from weight management treatment. This judgment is made based on a variety of factors that are in the realm of a healthcare practitioner's expertise, but that includes the knowledge that the individual has a condition that is treatable by the methods disclosed herein.

"Weight management" also includes preventing weight gain, controlling weight gain, reducing weight gain, maintaining weight, or inducing weight loss. Weight management also refers to controlling weight (also called weight control) and/or controlling parameters related to weight, for example, BMI, percent body fat and/or waist circumference. In addition, weight management also includes preventing an increase in BMI, reducing an increase in BMI, maintaining BMI, or reducing BMI; preventing an increase in percent body fat, reducing an increase in percent body fat, maintaining percent body fat, or reducing percent body fat; and preventing an increase in waist circumference, reducing an increase in waist circumference, maintaining waist circumference, or reducing waist circumference The phrase "decreasing food intake in an individual in need thereof" refers to a judgment made by a healthcare practitioner that an individual requires or will benefit from decreasing food intake. This judgment is made based on a variety of factors that are in the realm of a healthcare practitioner's expertise, but that includes the knowledge that the individual has a condition, for example, obesity, that is treatable by the methods disclosed herein. In some embodiments, an individual in need of decreasing food intake is an individual who is overweight. In some embodiments, an individual in need of decreasing food intake is an individual who is obese.

The term "satiety" refers to the quality or state of being fed or gratified to or beyond capacity. Satiety is a feeling that an individual has and so it is often determined by asking the individual, orally or in writing, if they feel full, sated, or satisfied at timed intervals during a meal. For example, an individual who feels sated may report feeling full, feeling a decreased or absent hunger, feeling a decreased or absent desire to eat, or feeling a lack of drive to eat. While fullness is a physical sensation, satiety is a mental feeling. An individual who feels full, sated or satisfied is more likely to stop eating and therefore inducing satiety can result in a decrease in food intake in an individual. As used herein, "inducing satiety in an individual in need thereof" refers to a judgment made by a healthcare practitioner that an individual requires or will benefit from inducing satiety. This judgment is made based on a variety of factors that are in the realm of a healthcare practitioner's expertise, but that includes the knowledge that the individual has a condition, for example, obesity, that is treatable by the methods of the disclosure.

The phrase "treatment of obesity in an individual in need thereof" refers to a judgment made by a healthcare practitioner that an individual requires or will benefit from treatment of obesity. This judgment is made based on a variety of factors that are in the realm of a healthcare practitioner's expertise, but that includes the knowledge that the individual has a condition that is treatable by the methods of the disclosure. To determine whether an individual is obese one can determine a body weight, a body mass index (BMI), a waist circumference or a body fat percentage of the individual to determine if the individual meets a body weight threshold, a BMI threshold, a waist circumference threshold or a body fat percentage threshold.

The phrase "prevention of obesity in an individual in need thereof" refers to a judgment made by a healthcare practitioner that an individual requires or will benefit from prevention of obesity. This judgment is made based on a variety of factors that are in the realm of a healthcare practitioner's expertise, but that includes the knowledge that the individual has a condition that is treatable by the methods disclosed herein. In some embodiments, an individual in need of prevention of obesity is an individual who is overweight (also called pre-obese). In some embodiments, an individual in need of prevention of obesity is an individual who has a family history of obesity. To determine whether an individual is overweight one can determine a body weight, a body mass index (BMI), a waist circumference or a body fat percentage of the individual to determine if the individual meets a body weight threshold, a BMI threshold, a waist circumference threshold or a body fat percentage threshold.

As used herein, an "adverse event" or "toxic event" is any untoward medical occurrence that may present itself during treatment. Adverse events associated with treatment may include, for example, headache, nausea, blurred vision, paresthesias, constipation, fatigue, dry mouth, dizziness, abnormal dreams, insomnia, nasopharyngitis, toothache, sinusitis, back pain, somnolence, viral gastroenteritis, seasonal allergy, or pain in an extremity. Additional possible adverse effects include, for example, gastrointestinal disorders (such as constipation, abdominal distension, and diarrhea), asthenia, chest pain, fatigue, drug hypersensitivity, fibromyalgia, temporomandibular joint syndrome, headache, dizziness, migraine, anxiety, depressed mood, irritability, suicidal ideation, bipolar disorder, depression, drug abuse, and dyspnea. In the methods disclosed herein, the term "adverse event" can be replaced by other more general terms such as "toxicity". The term "reducing the risk" of an adverse event means reducing the probability that an adverse event or toxic event could occur.

As used herein, the term "agonist" refers to a moiety that interacts with and activates a receptor, such as the 5-HT$_{2C}$ serotonin receptor, and initiates a physiological or pharmacological response characteristic of that receptor.

The phrase "immediate-release dosage form" refers to a formulation which rapidly disintegrates upon oral administration to a human or other animal releasing an active pharmaceutical ingredient (API) from the formulation. In some embodiments, the T80% of the immediate-release dosage form is less than 3 hours. In some embodiments, the T80% of the immediate-release dosage form is less than 1 hour. In some embodiments, the T80% of the immediate-release dosage form is less than 30 minutes. In some embodiments, the T80% of the immediate-release dosage form is less than 10 minutes.

The term "T80%" refers to the time needed to achieve 80% cumulative release of an API from a particular formulation comprising the API.

The phrase "modified-release dosage form" refers to any formulation that, upon oral administration to a human or other animal, releases an API after a given time (i.e., delayed release) or for a prolonged period of time (extended release), e.g., at a slower rate over an extended period of time when compared to an immediate-release dosage-form of the API (e.g., sustained release).

As used herein, "nicotine replacement therapy" (commonly abbreviated to NRT) refers to the remedial administration of nicotine to the body by means other than a tobacco product. By way of example, nicotine replacement therapy may include transdermal nicotine delivery systems, including patches and other systems that are described in the art, for example, in U.S. Pat. Nos. 4,597,961, 5,004,610, 4,946,853, and 4,920,989. Inhaled nicotine (e.g., delivery of the nicotine through pulmonary routes) is also known. Transmucosal administration (e.g., delivery of nicotine to the systemic circulation through oral drug dosage forms) is also known. Oral drug dosage forms (e.g., lozenge, capsule, gum, tablet, suppository, ointment, gel, pessary, membrane, and powder) are typically held in contact with the mucosal membrane and disintegrate and/or dissolve rapidly to allow immediate systemic absorption. It will be understood by those skilled in the art that a plurality of different treatments and means of administration can be used to treat a single individual. For example, an individual can be simultaneously treated with nicotine by transdermal administration and nicotine which is administered to the mucosa. In some embodiments, the nicotine replacement therapy is chosen from nicotine gum (e.g., NICORETTE), nicotine transdermal systems such as nicotine patches (e.g., HABITROL and NICODERM), nicotine lozenges (e.g., COMMIT), nicotine microtabs (e.g., NICORETTE Microtabs), nicotine sprays or inhalers (e.g., NICOTROL), and other nicotine replacement therapies known in the art. In some embodiments, nicotine replacement therapy includes electronic cigarettes, personal vaporizers, and electronic nicotine delivery systems.

As used herein, "combination" as used in reference to drug combinations and/or combinations of a selective 5-$HT_{2C}$ agonist with at least one supplemental agent refers to (1) a product comprised of two or more components, i.e., drug/device, biologic/device, drug/biologic, or drug/device/biologic, that are physically, chemically, or otherwise combined or mixed and produced as a single entity; (2) two or more separate products packaged together in a single package or as a unit and comprised of drug and device products, device and biological products, or biological and drug products; (3) a drug, device, or biological product packaged separately that according to its investigational plan or proposed labeling is intended for use only with an approved individually specified drug, device, or biological product where both are required to achieve the intended use, indication, or effect and where upon approval of the proposed product the labeling of the approved product would need to be changed, e.g., to reflect a change in intended use, dosage form, strength, route of administration, or significant change in dose; or (4) any investigational drug, device, or biological product packaged separately that according to its proposed labeling is for use only with another individually specified investigational drug, device, or biological product where both are required to achieve the intended use, indication, or effect. Combinations include without limitation a fixed-dose combination product (FDC) in which two or more separate drug components are combined in a single dosage form; a co-packaged product comprising two or more separate drug products in their final dosage forms, packaged together with appropriate labeling to support the combination use; and an adjunctive therapy in which a patient is maintained on a second drug product that is used together with (i.e., in adjunct to) the primary treatment, although the relative doses are not fixed, and the drugs or biologics are not necessarily given at the same time. Adjunctive therapy products may be co-packaged, and may or may not be labeled for concomitant use.

As used herein, "responder" refers to an individual who experiences continuous abstinence from tobacco use during a specified period of administration of a selective 5-$HT_{2C}$ receptor agonist. In some embodiments, "responder" refers to an individual who reports no smoking or other nicotine use from Week 9 to Week 12 of administration of a selective 5-$HT_{2C}$ receptor agonist and exhibits an end-expiratory exhaled carbon monoxide-confirmed measurement of ≤10 ppm.

As used herein, "tobacco product" refers to a product that incorporates tobacco, i.e., the agricultural product of the leaves of plants in the genus *Nicotiana*. Tobacco products can generally be divided into two types: smoked tobacco including without limitation pipe tobacco, cigarettes (including electronic cigarettes) and cigars, as well as Mu'assel, Dokha, shisha tobacco, hookah tobacco, or simply shisha; and smokeless tobacco including without limitation chewing tobacco, dipping tobacco, also known as dip, moist snuff (or snuff), American moist snuff, snus, Iqmik, Naswar, Gutka, Toombak, shammah, tobacco water, spit tobacco, creamy snuff or tobacco paste, dissolvable tobacco, and tobacco gum.

As used herein, "Fagerström test" refers to a standard test for nicotine dependence which is a test for assessing the intensity of nicotine addiction. See Heatherton, T. F., Kozlowski, L. T., Frecker, R. C., Fagerström, K. O. The Fagerström test for Nicotine Dependence: A revision of the Fagerström Tolerance Questionnaire. *Br J Addict* 1991; 86:1119-27. The test consists of a brief, self-report survey that measures nicotine dependence on a scale of 0-10, with 10 being the highest level of dependence. A score of 0-2 corresponds to very low dependence. A score of 3-4 corresponds to low dependence. A score of 5 corresponds to moderate dependence. A score of 6-7 corresponds to high dependence. A score of 8-10 corresponds to very high dependence.

Other methods may be utilized to assess the craving for nicotine, including but not limited to, the nicotine craving test specified by the Diagnostic and Statistical Manual of Mental Disorders, Revised Third Edition (DSM-III-R).

As used herein, "Mood and Physical Symptoms Scale" (MPSS) refers to a scale used to assess cigarette withdrawal symptoms (West R, *Hajek P: Evaluation of the mood and physical symptoms scale (MPSS) to assess cigarette withdrawal. Psychopharmacology* 2004, 177(1-2):195-199). The core elements of MPSS involve a 5-point rating of depressed mood, irritability, restlessness, difficulty concentrating and hunger and a 6-point rating of strength of urges to smoke and time spent with these urges.

As used herein, lorcaserin refers to (R)-8-chloro-1-methyl-2,3,4,5-tetrahydro-1H-3-benzazepine. Similarly, lorcaserin hydrochloride refers to the hydrochloric acid salt of (R)-8-chloro-1-methyl-2,3,4,5-tetrahydro-1H-3-benzazepine (see Statement on Nonproprietary Name Adopted by the USAN Council for Lorcaserin Hydrochloride).

The term "phentermine" refers to 1,1-dimethyl-2-phenyl-ethylamine, including phentermine derivatives and pharmaceutically acceptable salts thereof, such as, but not limited to, chlorphentermine (2-(4-chloro-phenyl)-1,1-dimethyl-ethylamine) and the like. In one embodiment, phentermine is in the HCl salt form of 1,1-dimethyl-2-phenyl-ethylamine.

The term "amphetamine" refers to 1-phenylpropan-2-amine and salts, solvates, and hydrates thereof.

The phrase "a substituted amphetamine" refers to a class of chemicals based on amphetamine with additional substitutions. Examples of substituted amphetamines include, but are not limited to: methamphetamine (N-methyl-1-phenyl-propan-2-amine); ephedrine (2-(methylamino)-1-phenylpropan-1-ol); cathinone (2-amino-1-phenyl-1-propanone); MDMA (3,4-methylenedioxy-N-methylamphetamine); and DOM (2,5-Dimethoxy-4-methylamphetamine); and salts, solvates, and hydrates thereof.

The term "a benzodiazepine" includes, but is not limited to alprazolam, bretazenil, bromazepam, brotizolam, chlordiazepoxide, cinolazepam, clonazepam, clorazepate, clotiazepam, cloxazolam, cyclobenzaprine, delorazepam, diazepam, estazolam, etizolam, ethyl, loflazepate, flunitrazepam, 5-(2-bromophenyl)-7-fluoro-1H-benzo[e][1,4]diazepin-2 (3H)-one, flurazepam, flutoprazepam, halazepam, ketazolam, loprazolam, lorazepam, lormetazepam, medazepam, midazolam, nimetazepam, nitrazepam, nordazepam, oxazepam, phenazepam, pinazepam, prazepam, premazepam, pyrazolam, quazepam, temazepam, tetrazepam, and triazolam and salts, solvates, and hydrates thereof.

The phrase "an atypical benzodiazepine receptor ligand" includes, but is not limited to clobazam, DMCM, flumazenil, eszopiclone, zaleplon, zolpidem, and zopiclone and salts, solvates, and hydrates thereof.

The term "marijuana" refers to a composition comprising one or more compound selected from tetrahydrocannabinol, cannabidiol, cannabinol, and tetrahydrocannabivarin and salts, solvates, and hydrates thereof.

The term "cocaine" refers to benzoylmethylecgonine and salts, solvates, and hydrates thereof.

The term "dextromethorphan" refers to (4bS,8 aR,9S)-3-methoxy-11-methyl-6,7,8,8a,9,10-hexahydro-5H-9,4b-(epiminoethano)phenanthrene and salts, solvates, and hydrates thereof.

The term "eszopiclone" refers to (S)-6-(5-chloropyridin-2-yl)-7-oxo-6,7-dihydro-5H-pyrrolo[3,4-b]pyrazin-5-yl 4-methylpiperazine-1-carboxylate and salts, solvates, and hydrates thereof.

The term "GHB" refers to 4-hydroxybutanoic acid and salts, solvates, and hydrates thereof.

The term "LSD" refers to lysergic acid diethylamide and salts, solvates, and hydrates thereof.

The term "ketamine" refers to 2-(2-chlorophenyl)-2-(methylamino)cyclohexanone and salts, solvates, and hydrates thereof.

The phrase "a monoamine reuptake inhibitor" refers to a drug that acts as a reuptake inhibitor of one or more of the three major monoamine neurotransmitters serotonin, norepinephrine, and dopamine by blocking the action of one or more of the respective monoamine transporters. Examples of monoamine reuptake inhibitors include alaproclate, citalopram, dapoxetine, escitalopram, femoxetine, fluoxetine, fluvoxamine, ifoxetine, indalpine, omiloxetine, panuramine, paroxetine, pirandamine, RTI-353, sertraline, zimelidine, desmethylcitalopram, desmethylsertraline, didesmethylcitalopram, seproxetine, cianopramine, litoxetine, lubazodone, SB-649,915, trazodone, vilazodone, vortioxetine, dextrometorphan, dimenhydrinate, diphenhydramine, mepyramine, pyrilamine, methadone, propoxyphene, mesembrine, roxindole, amedalin, tomoxetine, CP-39,332, daledalin, edivoxetine, esreboxetine, lortalamine, mazindol, nisoxetine, reboxetine, talopram, talsupram, tandamine, viloxazine, maprotiline, bupropion, ciclazindol, manifaxine, radafaxine, tapentadol, teniloxazine, ginkgo biloba, altropane, amfonelic acid, benzothiophenylcyclohexylpiperidine, DBL-583, difluoropine, 1-(2-(diphenylmethoxy)ethyl)-4-(3-phenylpropyl)piperazine, 4-{13-methyl-4,6-dioxa-11,12-diazatricyclo[7.5.0.0]tetradeca-1,3(7),8,10-tetraen-10-yl}aniline, iometopane, [(1R,2S,3S,5S)-3-(4-iodophenyl)-8-methyl-8-azabicyclo[3.2.1]octan-2-yl]-pyrrolidin-1-ylmethanone, vanoxerine, medifoxamine, *Chaenomeles speciosa*, hyperforin, adhyperforin, bupropion, pramipexole, cabergoline, venlafaxine, desvenlafaxine, duloxetine, milnacipran, levomilnacipran, bicifadine, 4-indolylarylalkylamines, 1-naphthylarylalkylamines, aminepetine, desoxypipradrol, dexmethylphenidate, difemetorex, diphenylprolinol, ethylphenidate, fencamfamine, fencamine, lefetamine, mesocarb, methylenedioxypyrovalerone, methylphenidate, nomifensine, methyl 2-cyclopentyl-2-(3,4-dichlorophenyl)acetate, oxolinic acid, pipradrol, prolintane, pyrovalerone, tametraline, 1-[1-(3-chlorophenyl)-2-(4-methylpiperazin-1-yl)ethyl]cyclohexan-1-ol, nefopam, amitifadine, EB-1020, tesofensine, NSD-788, tedatioxetine, RG7166, Lu-AA37096, Lu-AA34893, NS-2360, bicifadine, SEP-227162, SEP-225289, DOV-216,303, brasofensine, NS-2359, diclofensine, EXP-561, taxil, naphyrone, 5-APB, 6-APB, and hyperforin, and salts, solvates, and hydrates thereof.

The term "nicotine" refers to 3-(1-methylpyrrolidin-2-yl) pyridine.

The term "an opiate" includes, but is not limited to the following compounds and salts, solvates, and hydrates thereof: alfentanil, alphaprodine, anileridine, bezitramide, buprenorphine, butorphanol, dextropropoxyphene, carfentanil, codeine, diamorphine, dextromoramide, dezocine, poppy straw, dihydrocodeine, dihydroetorphine, diphenoxylate, ethylmorphine, etorphine, hydrochloride, fentanyl, hydrocodone, hydromorphone, isomethadone, levo-alphacetylmethadol, levomethorphan, levorphanol, meptazinol, metazocine, methadone, metopon, morphine, nalbuphine, opium, oripavine, oxycodone, oxymorphone, pentazocine, pethidine, phenazocine, piminodine, propoxyphene, racemethorphan, racemorphan, remifentanil, sufentanil, tapentadol, and thebaine.

For example, the term includes the following compounds and salts, solvates, and hydrates thereof: alfentanil, alphaprodine, anileridine, bezitramide, dextropropoxyphene, carfentanil, codeine, poppy straw, dihydrocodeine, dihydroetorphine, diphenoxylate, ethylmorphine, etorphine, hydrochloride, fentanyl, hydrocodone, hydromorphone, isomethadone, levo-alphacetylmethadol, levomethorphan, levorphanol, metazocine, methadone, metopon, morphine, opium, oripavine, oxycodone, oxymorphone, pethidine, phenazocine, piminodine, racemethorphan, racemorphan, remifentanil, sufentanil, tapentadol, and thebaine.

The term "PCP" refers to 1-(1-phenylcyclohexyl)piperidine and salts, solvates, and hydrates thereof.

The phrase "a substituted phenethylamine" includes, but is not limited to, the following compounds and salts, solvates, and hydrates thereof: 2-(4-bromo-2,5-dimethoxyphenyl)-N-[(2-methoxyphenyl)methyl]ethanamine, 2-(4-chloro-2,5-dimethoxyphenyl)-N-[(2-methoxyphenyl) methyl]ethanamine, 2-(4-iodo-2,5-dimethoxyphenyl)-N-[(2-methoxyphenyl)methyl]ethanamine, 4-bromo-2,5-dimethoxyphenethylamine, 1-(4-chloro-2,5-dimethoxyphenyl)-2-aminoethane, 1-(2,5-dimethoxy-4-methylphenyl)-2-aminoethane, 1-(2,5-dimethoxy-4-ethylphenyl)-2-aminoethane, 4-fluoro-2,5-dimethoxyphenethylamine, 2,5-dimethoxy-4-iodophenethylamine, 2,5-dimethoxy-4-nitrophenethylamine, 2-(2,5-dimethoxy-4-propylphenyl)

ethanamine, 2,5-dimethoxy-4-ethylthiophenethylamine, 2-[2,5-dimethoxy-4-(2-fluoroethylthio)phenyl]ethanamine, 2,5-dimethoxy-4-isopropylthiophenethylamine, 2,5-dimethoxy-4-n-propylthiophenethylamine, 2-[4-[(cyclopropylmethyl)thio]-2,5-dimethoxyphenyl]ethanamine, 2-[4-(butylthio)-2,5-dimethoxyphenyl]ethanamine, 6-hydroxydopamine, dopamine, epinephrine, mescaline, meta-octopamine, meta-tyramine, methylphenidate, n-methylphenethylamine, norepinephrine, para-octopamine, para-tyramine, phentermine, phenylephrine, salbutamol, and 3-methylphenethylamine, and salts, solvates, and hydrates thereof.

The term "psilocybin" refers to [3-(2-dimethylaminoethyl)-1H-indol-4-yl] dihydrogen phosphate, and salts, solvates, and hydrates thereof.

The phrase "an anabolic steroid" includes, but is not limited to, the following compounds and salts, solvates, and hydrates thereof: 1-androstenediol, androstenediol, 1-androstenedione, androstenedione, bolandiol, bolasterone, boldenone, boldione, calusterone, clostebol, danazol, dehydrochlormethyltestosterone, desoxymethyltestosterone, dihydrotestosterone, drostanolone, ethylestrenol, fluoxymesterone, formebolone, furazabol, gestrinone, 4-hydroxytestosterone, mestanolone, mesterolone, metenolone, methandienone, methandriol, methasterone, methyldienolone, methyl-1-testosterone, methylnortestosterone, methyltestosterone, metribolone, mibolerone, nandrolone, 19-norandrostenedione, norboletone, norclostebol, norethandrolone, oxabolone, oxandrolone, oxymesterone, oxymetholone, prasterone, prostanozol, quinbolone, stanozolol, stenbolone, 1-testosterone, testosterone, tetrahydrogestrinone, and trenbolone.

As used herein, the term "greater than" is used interchangeably with the symbol > and the term "less than" is used interchangeably with the symbol <. Likewise the term less than or equal to is used interchangeably with the symbol ≤ and the term greater than or equal to is used interchangeably with the symbol ≥.

When an integer is used in a method disclosed herein, the term "about" can be inserted before the integer. For example, the term "greater than 29 kg/m$^2$" can be substituted with "greater than about 29 kg/m$^2$".

As used in the present specification, the following abbreviations are generally intended to have the meanings as set forth below, except to the extent that the context in which they are used indicates otherwise.

| ° C. | Degrees Celsius | Kg/kg | Kilogram |
|---|---|---|---|
| A1C | Glycated hemoglobin | lbs | Pounds |
| BID | Twice a day | LDL | Low-density lipoprotein |
| BL | Baseline | M | Molar |
| BMI | Body Mass Index | m$^2$ | Square Meter |
| BP | Blood pressure | mg | Milligram |
| BPM/bpm | Beats per minute | min | Minute |
| CAR | Continuous abstinence rate | MITT | Modified intention to treat |
| CI | Confidence interval | | |
| cm | Centimeter | mmHg | Millimeters of Mercury |
| CO | Carbon monoxide | N/n | Number |
| DOI | 2,5-Dimethoxy-4-iodoamphetamine | NDA | New Drug Application |
| | | PP | Point prevalence |
| DBP | Diastolic blood pressure | ppm | parts per million |
| DEA | Drug Enforcement Administration | QD | Once a day |
| | | SAE | Serious Adverse Events |
| dL | Deciliter | SE | Standard Error |

| E$_{max}$ | Maximum possible effect | SBP | Systolic blood pressure |
|---|---|---|---|
| FDA | Food and Drug Administration | TGA | Thermogravimetric Analysis |
| g | Gram | wt | Weight |
| h | Hour | PXRD | X-ray powder diffraction |
| HDL | High-density lipoprotein | | |

Throughout this specification, unless the context requires otherwise, the word "comprise", or variations such as "comprises" or "comprising" will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all of the steps, features, compositions and compounds referred to or indicated in this specification, individually or collectively, and any and all combinations or any two or more of said steps or features unless specifically stated otherwise.

The present invention(s) is not to be limited in scope by the specific embodiments described herein, which are intended for the purpose of exemplification only. Functionally-equivalent products, compositions and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination. For example, a method that recites prescribing or administering a compound provided herein can be separated into two methods; one reciting prescribing a compound provided herein and the other reciting administering a compound provided herein. In addition, for example, a method that recites prescribing a compound provided herein and a separate method reciting administering a compound provided herein can be combined into a single method reciting prescribing and/or administering a compound provided herein. In addition, for example, a method that recites prescribing or administering a compound provided herein can be separated into two methods- one reciting prescribing a compound provided herein and the other reciting administering a compound provided herein. In addition, for example, a method that recites prescribing a compound provided herein and a separate method of the invention reciting administering a compound provided herein can be combined into a single method reciting prescribing and/or administering a compound provided herein.

Chemical Group, Moiety or Radical

The term "$C_1$-$C_6$ alkoxy" refers to a radical comprising a $C_1$-$C_6$ alkyl group attached to an oxygen atom, wherein $C_1$-$C_6$ alkyl has the same definition as found herein. Some embodiments contain 1 to 5 carbons. Some embodiments contain 1 to 4 carbons. Some embodiments contain 1 to 3 carbons. Some embodiments contain 1 to 2 carbons. Examples include, but are not limited to methoxy, ethoxy, n-propoxy, isopropoxy, n-butoxy, tert-butoxy, isobutoxy, and sec-butoxy.

The term "$C_1$-$C_6$ alkyl" refers to a straight or branched carbon radical containing 1 to 6 carbons. Some embodiments contain 1 to 5 carbons. Some embodiments contain 1 to 4 carbons. Some embodiments contain 1 to 3 carbons. Some embodiments contain 1 to 2 carbons. Examples of an alkyl group include, but are not limited to, methyl, ethyl, n-propyl, isopropyl, n-butyl, sec-butyl, isobutyl, tert-butyl, pentyl, isopentyl, t-pentyl, neopentyl, 1-methylbutyl [i.e., —CH(CH$_3$)CH$_2$CH$_2$CH$_3$], 2-methylbutyl [i.e., —CH$_2$CH (CH$_3$)CH$_2$CH$_3$], and n-hexyl.

The term "carbocyclic ring" refers to a saturated ring containing 3 to 7 carbons. Some embodiments contain 3 carbons. Some embodiments contain 5 carbons. Some embodiments contain 4 carbons. Some embodiments contain 6 carbons.

The term "$C_3$-$C_8$ cycloalkyl" refers to a saturated ring radical containing 3 to 7 carbons. Some embodiments contain 3 carbons. Some embodiments contain 5 carbons. Some embodiments contain 4 carbons. Some embodiments contain 6 carbons. Examples include cyclopropyl, cyclobutyl, cyclopentyl, and cyclohexyl.

The term "heterocyclic ring" refers to a saturated ring containing 3 to 7 atoms, one or more of which are heteroatoms. In some embodiments one, two or three of the ring atoms are heteroatoms. In some embodiments, one, two or three of the ring atoms are heteroatoms each of which is independently O, N or S.

The term "halogen" refers to a fluoro, chloro, bromo or iodo group. When referring to a group, "fluoro" and "fluorine" may be used interchangeably; "chloro" and "chlorine" may be used interchangeably; "bromo" and "bromine" may be used interchangeably; and "iodo" and "iodine" may be used interchangeably.

The number of occurrences of a given substituent in a compound may be specified by a subscript (such as "n" and the like). The subscript may be a positive integer or it may be 0, unless otherwise specified. A value of 0 for the subscript is intended to indicate that the substituent is absent.

Compounds

In one embodiment provided herein are compounds selected from compounds of Formula A and pharmaceutically acceptable salts, solvates, and hydrates thereof:

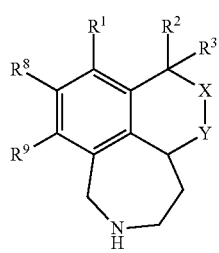

Formula A wherein:

$R^1$ is selected from: H, $C_1$-$C_6$ alkyl optionally substituted with one or more halogens, halogen, O—$C_1$-$C_6$ alkyl optionally substituted with one or more halogens, and $C_3$-$C_8$ cycloalkyl;

$R^2$ and $R^3$ are each independently H, $C_1$-$C_6$ alkyl optionally substituted with one or more halogens, or $C_3$-$C_8$ cycloalkyl; or $R^2$ and $R^3$ taken together with the carbon connecting them form a 3- to 6-membered spirocyclic carbocyclic ring;

X is O or C($R^4R^5$);
Y is O or C($R^6R^7$);
wherein if X is O, Y is (CR$^6$R$^7$);

$R^4$ and $R^5$ are each independently H, $C_1$-$C_6$ alkyl optionally substituted with one or more halogens, or $C_3$-$C_8$ cycloalkyl; or $R^4$ and $R^5$ taken together with the carbon connecting them form a 3- to 6-membered spirocyclic carbocyclic ring;

or $R^2$ and $R^5$ are each H and $R^3$ and $R^4$ taken together with the carbons connecting them form a 3- to 6-membered carbocyclic ring;

$R^6$ and $R^7$ are each independently H, $C_1$-$C_6$ alkyl optionally substituted with one or more halogens, or $C_3$-$C_8$ cycloalkyl; or $R^6$ and $R^7$ taken together with the carbon connecting them form a 3- to 6-membered spirocyclic carbocyclic ring;

and $R^8$ and $R^9$ are each independently H, $C_1$-$C_6$ alkyl optionally substituted with one or more halogens, or halogen.

In one embodiment provided herein are compounds selected from compounds of Formula I and pharmaceutically acceptable salts, solvates, and hydrates thereof:

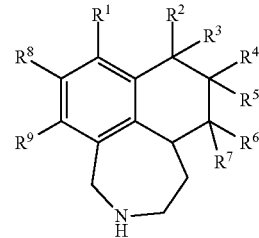

Formula I wherein:

$R^1$ is selected from: H, $C_1$-$C_6$ alkyl optionally substituted with one or more halogens, halogen, O—$C_1$-$C_6$ alkyl optionally substituted with one or more halogens, and $C_3$-$C_8$ cycloalkyl;

$R^2$ and $R^3$ are each independently H, $C_1$-$C_6$ alkyl optionally substituted with one or more halogens, or $C_3$-$C_8$ cycloalkyl; or $R^2$ and $R^3$ taken together with the carbon connecting them form a 3- to 6-membered spirocyclic carbocyclic ring;

$R^4$ and $R^5$ are each independently H, $C_1$-$C_6$ alkyl optionally substituted with one or more halogens, or $C_3$-$C_8$ cycloalkyl; or $R^4$ and $R^5$ taken together with the carbon connecting them form a 3- to 6-membered spirocyclic carbocyclic ring;

or $R^2$ and $R^5$ are each H and $R^3$ and $R^4$ taken together with the carbons connecting them form a 3- to 6-membered carbocyclic ring;

$R^6$ and R are each independently H, $C_1$-$C_6$ alkyl optionally substituted with one or more halogens, or $C_3$-$C_8$ cycloalkyl; or $R^6$ and $R^7$ taken together with the carbon connecting them form a 3- to 6-membered spirocyclic carbocyclic ring;

and $R^8$ and $R^9$ are each independently H, $C_1$-$C_6$ alkyl optionally substituted with one or more halogens, or halogen.

All combinations of the embodiments pertaining to the chemical groups represented by the variables (e.g., X, $R^1$, etc.) contained within the generic chemical formulae described herein, for example, Formula A, I, etc. are specifically embraced by the present invention(s) just as if each and every combination was individually and explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention(s) just as if each and every subcombination of chemical groups and subcombination of uses and medical indications was individually and explicitly recited herein.

In addition, some embodiments include every combination of one or more embodiments pertaining to the chemical groups represented by the variables and generic chemical formulae as described herein or every combination of one or more compounds disclosed herein together/in combination with every combination of one or more weight loss drug chosen from sodium/glucose cotransporter-2 (SGLT2) inhibitors, lipase inhibitors, monoamine reuptake inhibitors, anticonvulsants, glucose sensitizers, incretin mimetics, amylin analogs, GLP-1 analogs, Y receptor peptides, 5-$HT_{2C}$ receptor agonists, opioid receptor antagonists, appetite suppressants, anorectics, and hormones and the like, either specifically disclosed herein or specifically disclosed in any reference recited herein just as if each and every combination was individually and explicitly recited. In some embodiments, the weight loss drug is chosen from dapagliflozin, canagliflozin, ipragliflozin, tofogliflozin, empagliflozin, remogliflozin etabonate, orlistat, cetilistat, alaproclate, citalopram, dapoxetine, escitalopram, femoxetine, fluoxetine, fluvoxamine, ifoxetine, indalpine, omiloxetine, panuramine, paroxetine, pirandamine, sertraline, zimelidine, desmethylcitalopram, desmethylsertraline, didesmethylcitalopram, seproxetine, cianopramine, litoxetine, lubazodone, trazodone, vilazodone, vortioxetine, dextromethorphan, dimenhydrinate, diphenhydramine, mepyramine, pyrilamine, methadone, propoxyphene, mesembrine, roxindole, amedalin, tomoxetine, daledalin, edivoxetine, esreboxetine, lortalamine, mazindol, nisoxetine, reboxetine, talopram, talsupram, tandamine, viloxazine, maprotiline, bupropion, ciclazindol, manifaxine, radafaxine, tapentadol, teniloxazine, ginkgo biloba, altropane, difluoropine, iometopane, vanoxerine, medifoxamine, *Chaenomeles speciosa*, hyperforin, adhyperforin, bupropion, pramipexole, cabergoline, venlafaxine, desvenlafaxine, duloxetine, milnacipran, levomilnacipran, bicifadine, amineptine, desoxypipradrol, dexmethylphenidate, difemetorex, diphenylprolinol, ethylphenidate, fencamfamine, fencamine, lefetamine, mesocarb, methylenedioxypyrovalerone, methylphenidate, nomifensine, oxolinic acid, pipradrol, prolintane, pyrovalerone, tametraline, nefopam, amitifadine, tesofensine, tedatioxetine, bicifadine, brasofensine, diclofensine, taxil, naphyrone, hyperforin, topiramate, zonisamide, metformin, acarbose, rosiglitazone, pioglitazone, troglitazone, exenatide, liraglutide, taspoglutide, obinepitide, pramlintide, peptide YY, vabicaserin, naltrexone, naloxone, phentermine, diethylpropion, oxymetazoline, benfluorex, butenolide cathine, phenmetrazine, phenylpropanolamine, pyroglutamyl-histidyl-glycine, amphetamine, benzphetamine, dexmethylphenidate, dextroamphetamine, methylenedioxypyrovalerone, glucagon, lisdexamfetamine, methamphetamine, methylphenidate, phendimetrazine, phenethylamine, caffeine, bromocriptine, ephedrine, pseudoephedrine, rimonabant, surinabant, mirtazapine, Dietex®, MG Plus Protein™, insulin, and leptin and pharmaceutically acceptable salts and combinations thereof.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 to 4 substituents, a phenyl group can be substituted by 1, 2, 3, 4, or 5 substituents, a naphthyl group can be substituted by 1, 2, 3, 4, 5, 6, or 7 substituents, and the like. Likewise, "substituted with one or more substituents" refers to the substitution of a group with one substituent up to the total number of substituents physically allowed by the group. Further, when a group is substituted with more than one group they can be identical or they can be different.

Compounds provided herein can also include tautomeric forms, such as keto-enol tautomers and the like. Tautomeric forms can be in equilibrium or sterically locked into one form by appropriate substitution. It is understood that the various tautomeric forms are within the scope of the compounds provided herein.

It is understood and appreciated that compounds of Formula A, I or other formulae used throughout this disclosure may have one or more chiral centers and therefore can exist as enantiomers and/or diastereoisomers. The invention(s) are understood to extend to and embrace all such enantiomers, diastereoisomers and mixtures thereof, including but not limited to racemates. It is understood that compounds of Formula A, I or other formulae used throughout this disclosure represent all individual enantiomers and mixtures thereof, unless stated or shown otherwise.

The Group $R^1$

In some embodiments, $R^1$ is selected from: H, $C_1$-$C_6$ alkyl optionally substituted with one or more halogens, halogen, O—$C_1$-$C_6$ alkyl optionally substituted with one or more halogens, and $C_3$-$C_8$ cycloalkyl.

In some embodiments, $R^1$ is H, $C_1$-$C_6$ alkyl, halogen, O—$C_1$-$C_6$ alkyl, or $C_3$-$C_8$ cycloalkyl.

In some embodiments, $R^1$ is H, methyl, ethyl, fluorine, chlorine, bromine, methoxy, or cyclopropyl.

In some embodiments, $R^1$ is H.

In some embodiments, $R^1$ is $C_1$-$C_6$ alkyl. In some embodiments, $R^1$ is methyl. In some embodiments, $R^1$ is ethyl.

In some embodiments, $R^1$ is $C_1$-$C_6$ alkyl substituted with one or more halogens.

In some embodiments, $R^1$ is halogen. In some embodiments, $R^1$ is fluorine. In some embodiments, $R^1$ is chlorine. In some embodiments, $R^1$ is bromine. In some embodiments, $R^1$ is iodine.

In some embodiments, $R^1$ is O—$C_1$-$C_6$ alkyl. In some embodiments, $R^1$ is methoxy. In some embodiments, $R^1$ is ethoxy.

In some embodiments, $R^1$ is O—$C_1$-$C_6$ alkyl substituted with one or more halogens.

In some embodiments, $R^1$ is $C_3$-$C_8$ cycloalkyl. In some embodiments, $R^1$ is cyclopropyl. In some embodiments, $R^1$ is cyclobutyl. In some embodiments, $R^1$ is cyclopentyl. In some embodiments, $R^1$ is cyclohexyl. In some embodiments, $R^1$ is cycloheptyl. In some embodiments, $R^1$ is cyclooctyl.

The Groups $R^2$ and $R^3$

In some embodiments, $R^2$ and $R^3$ are each independently H, $C_1$-$C_6$ alkyl optionally substituted with one or more halogens, or $C_3$-$C_8$ cycloalkyl; or $R^2$ and $R^3$ taken together with the carbon connecting them form a 3- to 6-membered spirocyclic carbocyclic ring;

or $R^2$ and $R^5$ are each H and $R^3$ and $R^4$ taken together with the carbons connecting them form a 3- to 6-membered carbocyclic ring.

In some embodiments, $R^2$ and $R^3$ are each independently H, $C_1$-$C_6$ alkyl optionally substituted with one or more halogens, or $C_3$-$C_8$ cycloalkyl.

In some embodiments, $R^2$ and $R^3$ are each H.

In some embodiments, $R^2$ and $R^3$ are each $C_1$-$C_6$ alkyl. In some embodiments, $R^2$ and $R^3$ are each methyl. In some embodiments, $R^2$ and $R^3$ are each ethyl.

In some embodiments, $R^2$ and $R^3$ are each $C_1$-$C_6$ alkyl substituted with one or more halogens.

In some embodiments, $R^2$ and $R^3$ are each $C_3$-$C_8$ cycloalkyl. In some embodiments, $R^2$ and $R^3$ are each cyclopropyl.

In some embodiments, one of $R^2$ and $R^3$ is H and the other is $C_1$-$C_6$ alkyl. In some embodiments, one of $R^2$ and $R^3$ is H and the other is methyl. In some embodiments, one of $R^2$ and $R^3$ is H and the other is ethyl.

In some embodiments, one of $R^2$ and $R^3$ is H and the other is $C_3$-$C_8$ cycloalkyl. In some embodiments, one of $R^2$ and $R^3$ is H and the other is cyclopropyl.

In some embodiments, $R^2$ and $R^3$ taken together with the carbon connecting them form a 3- to 6-membered spirocyclic carbocyclic ring. In some embodiments, $R^2$ and $R^3$ taken together with the carbon connecting them form a 3-membered spirocyclic carbocyclic ring. In some embodiments, $R^2$ and $R^3$ taken together with the carbon connecting them form a 4-membered spirocyclic carbocyclic ring. In some embodiments, $R^2$ and $R^3$ taken together with the carbon connecting them form a 5-membered spirocyclic carbocyclic ring. In some embodiments, $R^2$ and $R^3$ taken together with the carbon connecting them form a 6-membered spirocyclic carbocyclic ring.

In some embodiments, $R^2$ and $R^5$ are each H and $R^3$ and $R^4$ taken together with the carbons connecting them form a 3- to 6-membered carbocyclic ring. In some embodiments, $R^2$ and $R^5$ are each H and $R^3$ and $R^4$ taken together with the carbons connecting them form a 5-membered carbocyclic ring.

The Groups X and Y

In some embodiments, X is O or $C(R^4R^5)$ and Y is O or $C(R^6R^7)$; wherein if X is O, Y is $(CR^6R^7)$.

In some embodiments, X is O or $C(R^4R^5)$ and Y is O or $C(R^6R^7)$; provided that X and Y are not both O.

In some embodiments, X is O and Y is $C(R^6R^7)$; In some embodiments, X is $C(R^4R^5)$ and Y is O.

In some embodiments, X is $C(R^4R^5)$ and Y is $C(R^6R^7)$.

The Groups $R^4$ and $R^5$

In some embodiments, $R^4$ and $R^5$ are each independently H, $C_1$-$C_6$ alkyl optionally substituted with one or more halogens, or $C_3$-$C_8$ cycloalkyl; or $R^4$ and $R^5$ taken together with the carbon connecting them form a 3- to 6-membered spirocyclic carbocyclic ring;

or $R^2$ and $R^5$ are each H and $R^3$ and $R^4$ taken together with the carbons connecting them form a 3- to 6-membered carbocyclic ring.

In some embodiments, $R^4$ and $R^5$ are each independently H, $C_1$-$C_6$ alkyl optionally substituted with one or more halogens, or $C_3$-$C_8$ cycloalkyl.

In some embodiments, $R^4$ and $R^5$ are each H.

In some embodiments, $R^4$ and $R^5$ are each $C_1$-$C_6$ alkyl. In some embodiments, $R^4$ and $R^5$ are each methyl. In some embodiments, $R^4$ and $R^5$ are each ethyl.

In some embodiments, $R^4$ and $R^5$ are each $C_1$-$C_6$ alkyl substituted with one or more halogens.

In some embodiments, $R^4$ and $R^5$ are each $C_3$-$C_8$ cycloalkyl. In some embodiments, $R^4$ and $R^5$ are each cyclopropyl.

In some embodiments, one of $R^4$ and $R^5$ is H and the other is $C_1$-$C_6$ alkyl. In some embodiments, one of $R^4$ and $R^5$ is H and the other is methyl. In some embodiments, one of $R^4$ and $R^5$ is H and the other is ethyl.

In some embodiments, one of $R^4$ and $R^5$ is H and the other is $C_3$-$C_8$ cycloalkyl. In some embodiments, one of $R^4$ and $R^5$ is H and the other is cyclopropyl.

In some embodiments, $R^4$ and $R^5$ taken together with the carbon connecting them form a 3- to 6-membered spirocyclic carbocyclic ring. In some embodiments, $R^4$ and $R^5$ taken together with the carbon connecting them form a 3-membered spirocyclic carbocyclic ring. In some embodiments, $R^4$ and $R^5$ taken together with the carbon connecting them form a 4-membered spirocyclic carbocyclic ring. In some embodiments, $R^4$ and $R^5$ taken together with the carbon connecting them form a 5-membered spirocyclic carbocyclic ring. In some embodiments, $R^4$ and $R^5$ taken together with the carbon connecting them form a 6-membered spirocyclic carbocyclic ring.

In some embodiments, $R^2$ and $R^5$ are each H and $R^3$ and $R^4$ taken together with the carbons connecting them form a 3- to 6-membered carbocyclic ring. In some embodiments, $R^2$ and $R^5$ are each H and $R^3$ and $R^4$ taken together with the carbons connecting them form a 5-membered carbocyclic ring.

The Groups $R^6$ and $R^7$

In some embodiments, $R^6$ and $R^7$ are each independently H, $C_1$-$C_6$ alkyl optionally substituted with one or more halogens, or $C_3$-$C_8$ cycloalkyl; or $R^6$ and $R^7$ taken together with the carbon connecting them form a 3- to 6-membered spirocyclic carbocyclic ring.

In some embodiments, $R^6$ and $R^7$ are each independently H, $C_1$-$C_6$ alkyl optionally substituted with one or more halogens, or $C_3$-$C_8$ cycloalkyl.

In some embodiments, $R^6$ and $R^7$ are each H.

In some embodiments, $R^6$ and $R^7$ are each $C_1$-$C_6$ alkyl. In some embodiments, $R^6$ and $R^7$ are each methyl. In some embodiments, $R^6$ and $R^7$ are each ethyl.

In some embodiments, $R^6$ and $R^7$ are each $C_1$-$C_6$ alkyl substituted with one or more halogens.

In some embodiments, $R^6$ and $R^7$ are each $C_3$-$C_8$ cycloalkyl. In some embodiments, $R^6$ and $R^7$ are each cyclopropyl.

In some embodiments, one of $R^6$ and $R^7$ is H and the other is $C_1$-$C_6$ alkyl. In some embodiments, one of $R^6$ and $R^7$ is H and the other is methyl. In some embodiments, one of $R^6$ and $R^7$ is H and the other is ethyl.

In some embodiments, one of $R^6$ and $R^7$ is H and the other is $C_3$-$C_8$ cycloalkyl. In some embodiments, one of $R^6$ and $R^7$ is H and the other is cyclopropyl.

In some embodiments, $R^6$ and $R^7$ taken together with the carbon connecting them form a 3- to 6-membered spirocyclic carbocyclic ring. In some embodiments, $R^6$ and $R^7$ taken together with the carbon connecting them form a 3-membered spirocyclic carbocyclic ring. In some embodiments, $R^6$ and $R^7$ taken together with the carbon connecting them form a 4-membered spirocyclic carbocyclic ring. In some embodiments, $R^6$ and $R^7$ taken together with the carbon connecting them form a 5-membered spirocyclic carbocyclic ring. In some embodiments, $R^6$ and $R^7$ taken together with the carbon connecting them form a 6-membered spirocyclic carbocyclic ring.

The Groups $R^8$ and $R^9$

In some embodiments, $R^8$ and $R^9$ are each independently H, $C_1$-$C_6$ alkyl optionally substituted with one or more halogens, or halogen.

In some embodiments, $R^8$ and $R^9$ are each independently H or halogen.

In some embodiments, $R^8$ and $R^9$ are each H.

In some embodiments, $R^8$ and $R^9$ are each $C_1$-$C_6$ alkyl. In some embodiments, $R^8$ and $R^9$ are each methyl. In some embodiments, $R^8$ and $R^9$ are each ethyl.

In some embodiments, $R^8$ and $R^9$ are each $C_1$-$C_6$ alkyl substituted with one or more halogens.

In some embodiments, $R^8$ and $R^9$ are each halogen. In some embodiments, $R^8$ and $R^9$ are each fluorine. In some embodiments, $R^8$ and $R^9$ are each chlorine. In some embodiments, $R^8$ and $R^9$ are each bromine. In some embodiments, $R^8$ and $R^9$ are each iodine.

In some embodiments, $R^8$ is hydrogen and $R^9$ is halogen. In some embodiments, $R^8$ is hydrogen and $R^9$ is fluorine. In some embodiments, $R^8$ is hydrogen and $R^9$ is chlorine. In some embodiments, $R^8$ is hydrogen and $R^9$ is bromine. In some embodiments, $R^8$ is hydrogen and $R^9$ is iodine.

In some embodiments, $R^9$ is hydrogen and $R^8$ is halogen. In some embodiments, $R^9$ is hydrogen and $R^8$ is fluorine. In some embodiments, $R^9$ is hydrogen and $R^8$ is chlorine. In some embodiments, $R^9$ is hydrogen and $R^8$ is bromine. In some embodiments, $R^9$ is hydrogen and $R^8$ is iodine.

In some embodiments, $R^8$ is hydrogen and $R^9$ is $C_1$-$C_6$ alkyl. In some embodiments, $R^8$ is hydrogen and $R^9$ is methyl. In some embodiments, $R^8$ is hydrogen and $R^9$ is ethyl.

In some embodiments, $R^9$ is hydrogen and $R^8$ is $C_1$-$C_6$ alkyl. In some embodiments, $R^9$ is hydrogen and $R^8$ is methyl. In some embodiments, $R^9$ is hydrogen and $R^8$ is ethyl.

Embodiments of Formula I In some embodiments, the compound of Formula I is selected from compounds of Formula Ia, and pharmaceutically acceptable salts, solvates, and hydrates thereof:

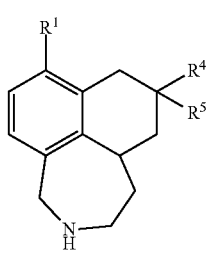

Formula Ia wherein:

$R^1$ is selected from: H, $C_1$-$C_6$ alkyl, halogen, O—$C_1$-$C_6$ alkyl, and $C_3$-$C_8$ cycloalkyl; and $R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring.

In some embodiments, the compound of Formula Ia is selected from compounds of Formula Ia-i, and pharmaceutically acceptable salts, solvates, and hydrates thereof:

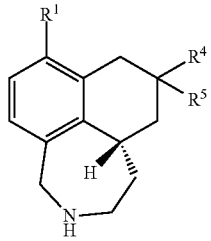

Formula Ia-i wherein:

$R^1$ is selected from: H, $C_1$-$C_6$ alkyl, halogen, O—$C_1$-$C_6$ alkyl, and $C_3$-$C_8$ cycloalkyl; and $R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring.

In some embodiments, the compound of Formula Ia is selected from compounds of Formula Ia-ii, and pharmaceutically acceptable salts, solvates, and hydrates thereof:

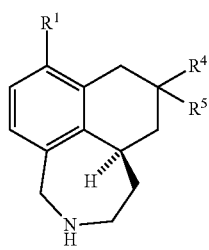

Formula Ia-ii wherein:

$R^1$ is selected from: H, $C_1$-$C_6$ alkyl, halogen, O—$C_1$-$C_6$ alkyl, and $C_3$-$C_8$ cycloalkyl; and $R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring.

In some embodiments of Formula Ia, Formula Ia-i, or Formula Ia-ii, $R^1$ is H.

In some embodiments of Formula Ia, Formula Ia-i, or Formula Ia-ii, $R^1$ is $C_1$-$C_6$ alkyl. In some embodiments of Formula Ia, Formula Ia-i, or Formula Ia-ii, $R^1$ is methyl. In some embodiments of Formula Ia, Formula Ia-i, or Formula Ia-ii, $R^1$ is ethyl.

In some embodiments of Formula Ia, Formula Ia-i, or Formula Ia-ii, $R^1$ is halogen. In some embodiments of Formula Ia, Formula Ia-i, or Formula Ia-ii, $R^1$ is fluorine. In some embodiments of Formula Ia, Formula Ia-i, or Formula Ia-ii, $R^1$ is chlorine. In some embodiments of Formula Ia, Formula Ia-i, or Formula Ia-ii, $R^1$ is bromine. In some embodiments of Formula Ia, Formula Ia-i, or Formula Ia-ii, $R^1$ is iodine.

In some embodiments of Formula Ia, Formula Ia-i, or Formula Ia-ii, $R^1$ is O—$C_1$-$C_6$ alkyl. In some embodiments of Formula Ia, Formula Ia-i, or Formula Ia-ii, $R^1$ is methoxy. In some embodiments of Formula Ia, Formula Ia-i, or Formula Ia-ii, $R^1$ is ethoxy.

In some embodiments of Formula Ia, Formula Ia-i, or Formula Ia-ii, $R^1$ is $C_3$-$C_8$ cycloalkyl. In some embodiments of Formula Ia, Formula Ia-i, or Formula Ia-ii, $R^1$ is cyclopropyl.

In some embodiments of Formula Ia, Formula Ia-i, or Formula Ia-ii, $R^4$ and $R^5$ are the same and each is H.

In some embodiments of Formula Ia, Formula Ia-i, or Formula Ia-ii, $R^4$ and $R^5$ are the same and each is methyl.

In some embodiments of Formula Ia, Formula Ia-i, or Formula Ia-ii, $R^4$ and $R^5$ taken together with the carbon connecting them form a 3-membered spirocyclic carbocyclic ring. In some embodiments of Formula Ia, Formula Ia-i, or Formula Ia-ii, $R^4$ and $R^5$ taken together with the carbon connecting them form a 4-membered spirocyclic carbocyclic ring. In some embodiments of Formula Ia, Formula Ia-i, or Formula Ia-ii, $R^4$ and $R^5$ taken together with the carbon connecting them form a 5-membered spirocyclic carbocyclic ring. In some embodiments of Formula Ia, Formula Ia-i, or Formula Ia-ii, $R^4$ and $R^5$ taken together with the carbon connecting them form a 6-membered spirocyclic carbocyclic ring.

In some embodiments, the compound of Formula I is selected from compounds of Formula Ib, and pharmaceutically acceptable salts, solvates, and hydrates thereof:

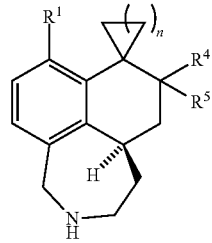

Formula Ib wherein:
$R^1$ is selected from: H, $C_1$-$C_6$ alkyl, halogen, O—$C_1$-$C_6$ alkyl, and $C_3$-$C_8$ cycloalkyl;
$R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring;
and
n is 1, 2, 3, or 4.

In some embodiments, the compound of Formula Ib is selected from compounds of Formula Ib-i, and pharmaceutically acceptable salts, solvates, and hydrates thereof:

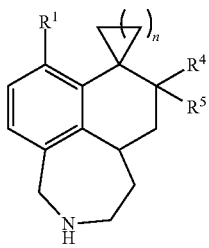

Formula Ib-i wherein:
$R^1$ is selected from: H, $C_1$-$C_6$ alkyl, halogen, O—$C_1$-$C_6$ alkyl, and $C_3$-$C_8$ cycloalkyl;

$R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring;
and
n is 1, 2, 3, or 4.

In some embodiments, the compound of Formula Ib is selected from compounds of Formula Ib-ii, and pharmaceutically acceptable salts, solvates, and hydrates thereof:

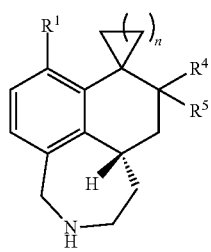

Formula Ib-ii wherein:
$R^1$ is selected from: H, $C_1$-$C_6$ alkyl, halogen, O—$C_1$-$C_6$ alkyl, and $C_3$-$C_8$ cycloalkyl;
$R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring;
and
n is 1, 2, 3, or 4.

In some embodiments of Formula Ib, Formula Ib-i, or Formula Ib-ii, $R^1$ is H.

In some embodiments of Formula Ib, Formula Ib-i, or Formula Ib-ii, $R^1$ is $C_1$-$C_6$ alkyl. In some embodiments of Formula Ib, Formula Ib-i, or Formula Ib-ii, $R^1$ is methyl. In some embodiments of Formula Ib, Formula Ib-i, or Formula Ib-ii, $R^1$ is ethyl.

In some embodiments of Formula Ib, Formula Ib-i, or Formula Ib-ii, $R^1$ is halogen. In some embodiments of Formula Ib, Formula Ib-i, or Formula Ib-ii, $R^1$ is fluorine. In some embodiments of Formula Ib, Formula Ib-i, or Formula Ib-ii, $R^1$ is chlorine. In some embodiments of Formula Ib, Formula Ib-i, or Formula Ib-ii, $R^1$ is bromine. In some embodiments of Formula Ib, Formula Ib-i, or Formula Ib-ii, $R^1$ is iodine.

In some embodiments of Formula Ib, Formula Ib-i, or Formula Ib-ii, $R^1$ is O—$C_1$-$C_6$ alkyl. In some embodiments of Formula Ib, Formula Ib-i, or Formula Ib-ii, $R^1$ is methoxy. In some embodiments of Formula Ib, Formula Ib-i, or Formula Ib-ii, $R^1$ is ethoxy.

In some embodiments of Formula Ib, Formula Ib-i, or Formula Ib-ii, $R^1$ is cyclopropyl.

In some embodiments of Formula Ib, Formula Ib-i, or Formula Ib-ii, $R^4$ and $R^5$ are the same and each is H.

In some embodiments of Formula Ib, Formula Ib-i, or Formula Ib-ii, $R^4$ and $R^5$ are the same and each is methyl.

In some embodiments of Formula Ib, Formula Ib-i, or Formula Ib-ii, $R^4$ and $R^5$ taken together with the carbon connecting them form a 3-membered spirocyclic carbocyclic ring. In some embodiments of Formula Ib, Formula Ib-i, or Formula Ib-ii, $R^4$ and $R^5$ taken together with the carbon connecting them form a 4-membered spirocyclic carbocyclic ring. In some embodiments of Formula Ib, Formula Ib-i, or Formula Ib-ii, $R^4$ and $R^5$ taken together with the carbon connecting them form a 5-membered spirocyclic carbocyclic ring. In some embodiments of Formula Ib, Formula Ib-i, or Formula Ib-ii, $R^4$ and $R^5$ taken together with the carbon connecting them form a 6-membered spirocyclic carbocyclic ring.

In some embodiments of Formula Ib, Formula Ib-i, or Formula Ib-ii, n is 1. In some embodiments of Formula Ib, Formula Ib-i, or Formula Ib-ii, n is 2. In some embodiments of Formula Ib, Formula Ib-i, or Formula Ib-ii, n is 3. In some embodiments of Formula Ib, Formula Ib-i, or Formula Ib-ii, n is 4.

In some embodiments, the compound of Formula I is selected from compounds of Formula Ic, and pharmaceutically acceptable salts, solvates, and hydrates thereof:

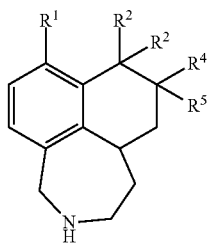

Formula Ic wherein:

$R^1$ is selected from: H, $C_1$-$C_6$ alkyl, halogen, O—$C_1$-$C_6$ alkyl, and $C_3$-$C_8$ cycloalkyl;

each $R^2$ is the same and is $C_1$-$C_6$ alkyl or $C_3$-$C_8$ cycloalkyl;

and $R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring.

In some embodiments, the compound of Formula Ic is selected from compounds of Formula Ic-i, and pharmaceutically acceptable salts, solvates, and hydrates thereof:

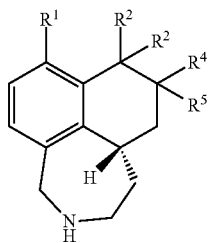

Formula Ic-i wherein:

$R^1$ is selected from: H, $C_1$-$C_6$ alkyl, halogen, O—$C_1$-$C_6$ alkyl, and $C_3$-$C_8$ cycloalkyl; each $R^2$ is the same and is $C_1$-$C_6$ alkyl or $C_3$-$C_8$ cycloalkyl;

and $R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring.

In some embodiments, the compound of Formula Ic is selected from compounds of Formula Ic-ii, and pharmaceutically acceptable salts, solvates, and hydrates thereof:

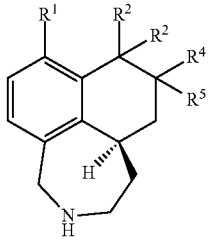

Formula Ic-ii wherein:

$R^1$ is selected from: H, $C_1$-$C_6$ alkyl, halogen, O—$C_1$-$C_6$ alkyl, and $C_3$-$C_8$ cycloalkyl;

each $R^2$ is the same and is $C_1$-$C_6$ alkyl or $C_3$-$C_8$ cycloalkyl;

and $R^4$ and $R^5$ are the same and each is H, $C_1$-$C_6$ alkyl, or $C_3$-$C_8$ cycloalkyl; or $R^4$ and $R^5$ taken together with the carbon connecting them form a 3- to 6-membered spirocyclic carbocyclic ring.

In some embodiments of Formula Ic, Formula Ic-i, or Formula Ic-ii, $R^1$ is H.

In some embodiments of Formula Ic, Formula Ic-i, or Formula Ic-ii, $R^1$ is $C_1$-$C_6$ alkyl. In some embodiments of Formula Ic, Formula Ic-i, or Formula Ic-ii, $R^1$ is methyl. In some embodiments of Formula Ic, Formula Ic-i, or Formula Ic-ii, $R^1$ is ethyl.

In some embodiments of Formula Ic, Formula Ic-i, or Formula Ic-ii, $R^1$ is halogen. In some embodiments of Formula Ic, Formula Ic-i, or Formula Ic-ii, $R^1$ is fluorine. In some embodiments of Formula Ic, Formula Ic-i, or Formula Ic-ii, $R^1$ is chlorine. In some embodiments of Formula Ic, Formula Ic-i, or Formula Ic-ii, $R^1$ is bromine. In some embodiments of Formula Ic, Formula Ic-i, or Formula Ic-ii, $R^1$ is iodine.

In some embodiments of Formula Ic, Formula Ic-i, or Formula Ic-ii, $R^1$ is O—$C_1$-$C_6$ alkyl. In some embodiments of Formula Ic, Formula Ic-i, or Formula Ic-ii, $R^1$ is methoxy. In some embodiments of Formula Ic, Formula Ic-i, or Formula Ic-ii, $R^1$ is ethoxy.

In some embodiments of Formula Ic, Formula Ic-i, or Formula Ic-ii, $R^1$ is $C_3$-$C_8$ cycloalkyl. In some embodiments of Formula Ic, Formula Ic-i, or Formula Ic-ii, $R^1$ is cyclopropyl.

In some embodiments of Formula Ic, Formula Ic-i, or Formula Ic-ii, each $R^2$ is the same and is $C_1$-$C_6$ alkyl. In some embodiments of Formula Ic, Formula Ic-i, or Formula Ic-ii, each $R^2$ is the same and is methyl. In some embodiments of Formula Ic, Formula Ic-i, or Formula Ic-ii, each $R^2$ is the same and is ethyl.

In some embodiments of Formula Ic, Formula Ic-i, or Formula Ic-ii, $R^4$ and $R^5$ are the same and each is H.

In some embodiments of Formula Ic, Formula Ic-i, or Formula Ic-ii, $R^4$ and $R^5$ are the same and each is $C_1$-$C_6$ alkyl. In some embodiments of Formula Ic, Formula Ic-i, or Formula Ic-ii, $R^4$ and $R^5$ are the same and each is methyl.

In some embodiments of Formula Ic, Formula Ic-i, or Formula Ic-ii, $R^4$ and $R^5$ taken together with the carbon connecting them form a 3- to 6-membered spirocyclic carbocyclic ring. In some embodiments of Formula Ic, Formula Ic-i, or Formula Ic-ii, $R^4$ and $R^5$ taken together with the carbon connecting them form a 3-membered spirocyclic carbocyclic ring. In some embodiments of Formula Ic, Formula Ic-i, or Formula Ic-ii, $R^4$ and $R^5$ taken together with the carbon connecting them form a 4-membered spirocyclic carbocyclic ring. In some embodiments of Formula Ic, Formula Ic-i, or Formula Ic-ii, $R^4$ and $R^5$ taken together with the carbon connecting them form a 5-membered spirocyclic carbocyclic ring. In some embodiments of Formula Ic, Formula Ic-i, or Formula Ic-ii, $R^4$ and $R^5$ taken together with the carbon connecting them form a 6-membered spirocyclic carbocyclic ring.

Some embodiments of Formula A include every combination of one or more compounds and pharmaceutically acceptable salts, solvates, and hydrates thereof selected from the following group shown in Table A.

TABLE A

| Compound No. | Chemical Structure | Chemical Name |
|---|---|---|
| 101 | 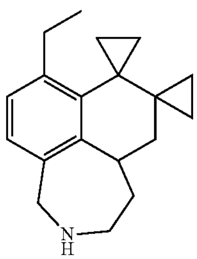 [SMILES: CCc1ccc2c3c1C1(CC1)C1(CC1)CC3CCNC2] | 8'-ethyl-2',3',4',4a',5'-pentahydro-1'H-dispiro[cyclopropane-1,6'-cyclopropane-7',1''-naphtho[1,8-cd]-azepine] |
| 102 | 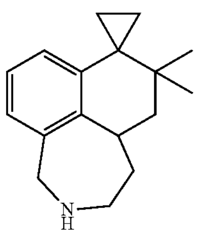 [SMILES: CC1(C)CC2CCNCc3cccc(c32)C12CC2] | 6',6'-dimethyl-2',3',4',4a',5',6'-hexahydro-1'H-spiro[cyclopropane-1,7'-naphtho[1,8-cd]azepine] |
| 103 | 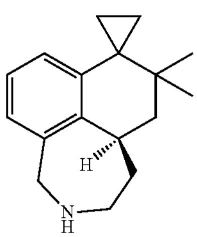 | (S)-6',6'-dimethyl-2',3',4',4a',5',6'-hexahydro-1'H-spiro[cyclopropane-1,7'-naphtho[1,8-cd]azepine] |
| 104 | 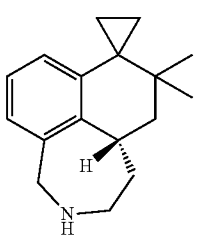 | (R)-6',6'-dimethyl-2',3'',4',4a',5',6'-hexahydro-1'H-spiro[cyclopropane-1,7'-naphtho[1,8-cd]azepine] |
| 105 | 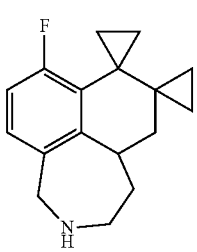 [SMILES: Fc1ccc2c3c1C1(CC1)C1(CC1)CC3CCNC2] | 8'-fluoro-2',3',4',4a',5'-pentahydro-1'H-dispiro[cyclopropane-1,6'-cyclopropane-7',1''-naphtho[1,8-cd]-azepine] |

TABLE A-continued

| Compound No. | Chemical Structure | Chemical Name |
|---|---|---|
| 106 | 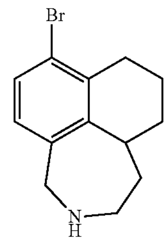 | 8-bromo-1,2,3,4,4a,5,6,7-octahydronaphtho[1,8-cd]azepine |
| 107 | 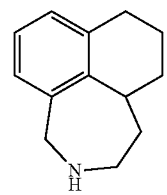 [SMILES: c1cc2c3c(c1)CNCCC3CCC2] | 1,2,3,4,4a,5,6,7-octahydronaphtho[1,8-cd]azepine |
| 108 | 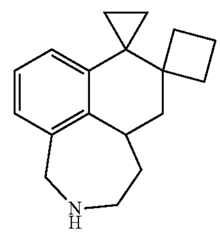 [SMILES: c1cc2c3c(c1)C1(CC1)C1(CCC1)CC3CCNC2] | 2',3',4',4a',5'-pentahydro-1'H-dispiro[cyclobutane-1,6'-cyclopropane-7',1''-naphtho[1,8-cd]-azepine] |
| 109 | 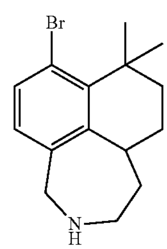 [SMILES: CC1(C)CCC2CCNCc3ccc(Br)c1c32] | 8-bromo-7,7-dimethyl-1,2,3,4,4a,5,6,7-octahydronaphtho[1,8-cd]azepine |
| 110 | 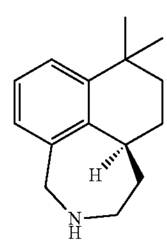 | (S)-7,7-dimethyl-1,2,3,4,4a,5,6,7-octahydronaphtho[1,8-cd]azepine |
| 111 | 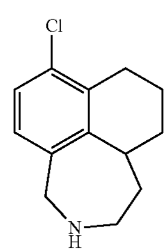 [SMILES: Clc1ccc2c3c1CCCC3CCNC2] | 8-chloro-1,2,3,4,4a,5,6,7-octahydronaphtho[1,8-cd]azepine |

TABLE A-continued

| Compound No. | Chemical Structure | Chemical Name |
|---|---|---|
| 112 | 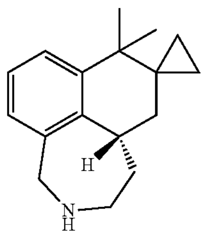 | (R)-7',7'-dimethyl-2',3',4',4a',5',7'-hexahydro-1'H-spiro[cyclopropane-1,6'-naphtho[1,8-cd]azepine] |
| 113 | 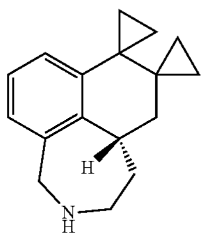 | (R)-2',3',4',4a',5'-pentahydro-1'H-dispiro[cyclopropane-1,6'-cyclopropane-7',1''-naphtho[1,8-cd]-azepine] |
| 114 | 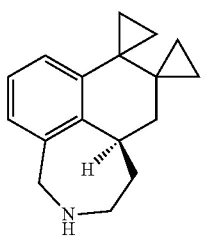 | (S)-2',3',4',4a',5'-pentahydro-1'H-dispiro[cyclopropane-1,6'-cyclopropane-7',1''-naphtho[1,8-cd]-azepine] |
| 115 | 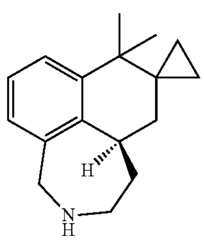 | (S)-7',7'-dimethyl-2',3',4',4a',5',7'-hexahydro-1'H-spiro[cyclopropane-1,6'-naphtho[1,8-cd]azepine] |
| 116 | 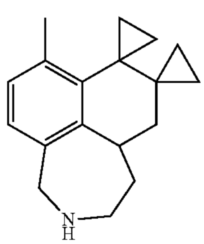 [SMILES: Cc1ccc2c3c1C1(CC1)C1(CC1)CC3CCNC2] | 8'-methyl-2',3',4',4a',5'-pentahydro-1'H-dispiro[cyclopropane-1,6'-cyclopropane-7',1''-naphtho[1,8-cd]-azepine] |
| 117 | 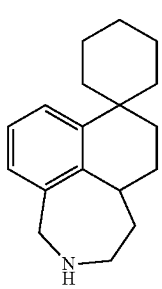 [SMILES: c1cc2c3c(c1)C1(CCCCC1)CCC3CCNC2] | 2',3',4',4a',5',6'-hexahydro-1'H-spiro[cyclohexane-1,7'-naphtho[1,8-cd]azepine] |
| 118 | | (7aR)-5,6,7,7a,8,8a,9,10,11,11a-decahydro-4H-cyclopenta[5,6]naphtho[1,8-cd]azepine |
| 119 | | 8'-fluoro-6',6'-dimethyl-2',3',4',4a',5',6'-hexahydro-1'H-spiro[cyclopropane-1,7'-naphtho[1,8-cd]azepine] |
| 120 | | 7-cyclopropyl-1,2,3,4,4a,5,6,7-octahydronaphtho[1,8-cd]azepine |
| 121 | | 7',7'-dimethyl-2',3',4',4a',5',7'-hexahydro-1'H-spiro[cyclopropane-1,6'-naphtho[1,8-cd]azepine] |
| 122 | | (R)-7,7-dimethyl-1,2,3,4,4a,5,6,7-octahydronaphtho[1,8-cd]azepine |
| 123 | | (S)-2',3',4',4a',5',6'-hexahydro-1'H-spiro[cyclopropane-1,7'-naphtho[1,8-cd]azepine] |

TABLE A-continued

| Compound No. | Chemical Name |
|---|---|
| 124 | (S)-2',3',4',4a',5',6'-hexahydro-1'H-spiro[cyclobutane-1,7'-naphtho[1,8-cd]azepine] |
| 125 | (R)-2',3',4',4a',5',6'-hexahydro-1'H-spiro[cyclobutane-1,7'-naphtho[1,8-cd]azepine] |
| 126 | 8-methoxy-1,2,3,4,4a,5,6,7-octahydronaphtho[1,8-cd]azepine |
| 127 | 8-cyclopropyl-1,2,3,4,4a,5,6,7-octahydronaphtho[1,8-cd]azepine |
| 128 | 2',3',4',4a',5',6'-hexahydro-1'H-spiro[cyclopropane-1,7'-naphtho[1,8-cd]azepine] |
| 129 | 2',3',4',4a',5'-pentahydro-1'H-dispiro[cyclopentane-1,6'-cyclopropane-7',1''-naphtho[1,8-cd]-azepine] |
| 130 | 2',3',4',4a',5'-pentahydro-1'H-dispiro[cyclopropane-1,6'-cyclopropane-7',1''-naphtho[1,8-cd]-azepine] |
| 131 | 2',3',4',4a',5',6'-hexahydro-1'H-spiro[cyclobutane-1,7'-naphtho[1,8-cd]azepine] |
| 132 | (7aS)-5,6,7,7a,8,8a,9,10,11,11a-decahydro-4H-cyclopenta[5,6]naphtho[1,8-cd]azepine |
| 133 | (R)-8'-fluoro-2',3',4',4a',5'-pentahydro-1'H-dispiro[cyclopropane-1,6'-cyclopropane-7',1''-naphtho[1,8-cd]-azepine] |
| 134 | (S)-8'-fluoro-2',3',4',4a',5'-pentahydro-1'H-dispiro[cyclopropane-1,6'-cyclopropane-7',1''-naphtho[1,8-cd]-azepine] |
| 135 | 7,7-dimethyl-1,2,3,4,4a,5,6,7-octahydronaphtho[1,8-cd]azepine |

TABLE A-continued

| Compound No. | Chemical Structure | Chemical Name |
|---|---|---|
| 136 | 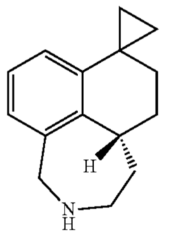 | (R)-2',3',4',4a',5',6'-hexahydro-1'H-spiro[cyclopropane-1,7'-naphtho[1,8-cd]azepine] |
| 137 | 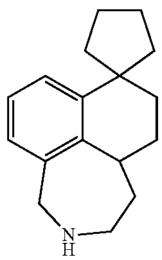 [SMILES: c1cc2c3c(c1)C1(CCCC1)CCC3CCNC2] | 2',3',4',4a',5',6'-hexahydro-1'H-spiro[cyclopentane-1,7'-naphtho[1,8-cd]azepine] |
| 138 | 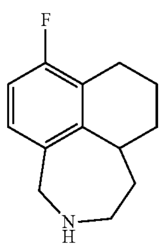 [SMILES: Fc1ccc2c3c1CCCC3CCNC2] | 8-fluoro-1,2,3,4,4a,5,6,7-octahydronaphtho[1,8-cd]azepine |
| 139 | 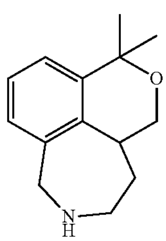 [SMILES: CC1(C)OCC2CCNCc3cccc1c32] | 1,1-dimethyl-3,3a,4,5,6,7-hexahydro-1H-isochromeno[5,4-cd]azepine |
| 140 | 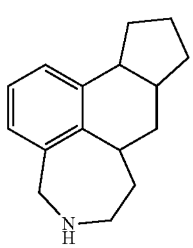 [SMILES: c1cc2c3c(c1)C1CCCC1CC3CCNC2] | 5,6,7,7a,8,8a,9,10,11,11a-decahydro-4H-cyclopenta[5,6]naphtho[1,8-cd]azepine |

In some embodiments, provided herein are intermediates disclosed in FIGS. 2-11, wherein the variables in the figures have the same definition as described herein.

Compounds of Formula A or I may be prepared, for example, as disclosed in the synthetic schemes of FIGS. 2-11 herein. Such schemes are intended to be illustrative and not intended to be limiting. The skilled artisan can readily understand and appreciate that the schemes may be modified in ways known in the art to arrive at the same or different compounds of Formula A or I. As a non-limiting example, the sulfonamide precursors of the compounds of Formula A or I shown in FIGS. 2-10 may be optionally converted to N-BOC protected compounds of Formula A or I by conducting the reaction in the presence of a protecting agent such as (BOC)$_2$O. The N-BOC protected compounds may then be deprotected to provide compounds of Formula A or I by ways known in the art.

Additionally, individual compounds and chemical genera provided herein, including, isomers, diastereoisomers and enantiomers thereof, encompass all pharmaceutically acceptable salts, solvates, and hydrates, thereof. Further, mesoisomers of individual compounds and chemical genera provided herein encompass all pharmaceutically acceptable salts, solvates and particularly hydrates, thereof.

The compounds provided herein may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention(s) embrace, each isomer, each diastereoisomer, each enantiomer and mixtures thereof of each compound and generic formulae disclosed herein just as if they were each individually disclosed with the specific stereochemical designation for each chiral carbon. Separation of the individual isomers and enantiomers (such as, by chiral HPLC, recrystallization of diastereoisomeric mixtures and the like) or selective synthesis (such as, by enantiomeric selective syntheses and the like) of the individual isomers can be accomplished by application of various methods which are well known to practitioners in the art. In some embodiments, a compound disclosed herein may exist as a stereoisomer that is substantially free of other stereoisomers. The term "substantially free of other stereoisomers" as used herein means less than 10% of other stereoisomers, such as less than 5% of other stereoisomers, such as less than 2% of other stereoisomers, such as less than 2% of other stereoisomers are present.

Also provided are compounds for use in a method for treatment of the human or animal body by therapy.

Also provided are compounds for use in a method for decreasing food intake.

Also provided are compounds for use in a method for inducing satiety.

Also provided are compounds for use in a method for the treatment of obesity.

Also provided are compounds for use in a method for the prevention of obesity.

Also provided are compounds for use in weight management.

In some embodiments, the weight management further comprises a surgical weight loss procedure.

In some embodiments, the weight management comprises weight loss.

In some embodiments, the weight management comprises maintenance of weight loss.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual in need of weight management is an obese patient with an initial body mass index ≥30 kg/m$^2$.

In some embodiments, the individual in need of weight management is an overweight patient with an initial body mass index ≥27 kg/m² in the presence of at least one weight related comorbid condition.

In some embodiments, the weight related co-morbid condition is selected from: hypertension, dyslipidemia, cardiovascular disease, glucose intolerance, and sleep apnea.

Also provided are compounds for use in the treatment of antipsychotic-induced weight gain.

Also provided are compounds for use in a method for the treatment of type 2 diabetes.

Also provided are compounds for use in a method for the treatment of type 2 diabetes in combination with one or more type 2 diabetes medications.

In some embodiments, the need for the one or more type 2 diabetes treatments is reduced.

In some embodiments, the need for the one or more type 2 diabetes treatments is eliminated.

Also provided are compounds for use in a method for the prevention of type 2 diabetes.

In some embodiments the need for other type 2 diabetes treatments is reduced.

In some embodiments the need for other type 2 diabetes treatments is eliminated.

Also provided are compounds for use in a method for the treatment of Prader-Willi syndrome.

Also provided are compounds for the treatment of addiction.

Also provided are compounds for the treatment of drug and alcohol addiction.

Also provided are compounds for the treatment of alcohol addiction.

Also provided are compounds for the treatment of drug addiction.

In some embodiments, the drug is selected from amphetamine, a substituted amphetamine, a benzodiazepine, an atypical benzodiazepine receptor ligand, marijuana, cocaine, dextromethorphan, GHB, LSD, ketamine, a monoamine reuptake inhibitor, nicotine, an opiate, PCP, a substituted phenethylamine, psilocybin, and an anabolic steroid.

In some embodiments, the drug is nicotine.
In some embodiments, the drug is amphetamine.
In some embodiments, the drug is a substituted amphetamine.
In some embodiments, the drug is methamphetamine.
In some embodiments, the drug is a benzodiazepine.
In some embodiments, the drug is an atypical benzodiazepine receptor ligand.
In some embodiments, the drug is marijuana.
In some embodiments, the drug is cocaine.
In some embodiments, the drug is dextromethorphan.
In some embodiments, the drug is GHB.
In some embodiments, the drug is LSD.
In some embodiments, the drug is ketamine.
In some embodiments, the drug is a monoamine reuptake inhibitor.
In some embodiments, the drug is an opiate.
In some embodiments, the drug is PCP.
In some embodiments, the drug is a substituted phenethylamine.
In some embodiments, the drug is psilocybin.
In some embodiments, the drug is an anabolic steroid.

Also provided are compounds for aiding smoking cessation.

Also provided are compounds for the treatment of tobacco dependence.

Also provided are compounds for the treatment of nicotine dependence.

Also provided are compounds for the treatment of alcoholism.

Also provided are compounds for use in a method for the treatment of pathological gambling.

Also provided are compounds for use in a method for the treatment of reward deficiency syndrome.

Also provided are compounds for use in a method for the treatment of sex addiction.

Also provided are compounds for use in a method for the treatment of an obsessive-compulsive spectrum disorder.

Also provided are compounds for use in a method for the treatment of an impulse control disorder.

Also provided are compounds for use in a method for the treatment of nail-biting.

Also provided are compounds for use in a method for the treatment of onychophagia.

Also provided are compounds for use in a method for the treatment of a sleep disorder.

Also provided are compounds for use in a method for the treatment of insomnia.

Also provided are compounds for use in a method for the treatment of fragmented sleep architecture.

Also provided are compounds for use in a method for the treatment of a disturbance of slow-wave sleep.

Also provided are compounds for use in a method for the treatment of urinary incontinence.

Also provided are compounds for use in a method for the treatment of a psychiatric disorder.

Also provided are compounds for use in a method for the treatment of schizophrenia.

Also provided are compounds for use in a method for the treatment of anorexia nervosa.

Also provided are compounds for use in a method for the treatment of bulimia nervosa.

Also provided are compounds for use in a method for the treatment of Alzheimer disease.

Also provided are compounds for use in a method for the treatment of sexual dysfunction.

Also provided are compounds for use in a method for the treatment of erectile dysfunction.

Also provided are compounds for use in a method for the treatment of epilepsy.

Also provided are compounds for use in a method for the treatment of a movement disorder.

Also provided are compounds for use in a method for the treatment of parkinsonism.

Also provided are compounds for use in a method for the treatment of antipsychotic-induced movement disorder.

Also provided are compounds for use in a method for the treatment of hypertension.

Also provided are compounds for use in a method for the treatment of dyslipidemia.

Also provided are compounds for use in a method for the treatment of nonalcoholic fatty liver disease.

Also provided are compounds for use in a method for the treatment of obesity-related renal disease.

Also provided are compounds for use in a method for the treatment of sleep apnea.

INDICATIONS

Weight Management

FDA approved for weight loss, BELVIQ is used along with a reduced-calorie diet and increased physical activity for chronic weight management in adults who are: obese (BMI of 30 kg/m² or greater), or overweight (BMI of 27 kg/m² or greater) with at least one weight-related medical condition (for example, high blood pressure, high cholesterol, or type 2 diabetes) (www.belviq.com).

In some embodiments, an individual in need of weight management is an individual who is overweight. In some embodiments, an individual in need of weight management is an individual who has excess visceral adiposity. In some embodiments, an individual in need of weight management is an individual who is obese. To determine whether an individual is overweight or obese one can determine a body weight, a body mass index (BMI), a waist circumference or a body fat percentage of the individual to determine if the individual meets a body weight threshold, a BMI threshold, a waist circumference threshold or a body fat percentage threshold.

Determination of body weight can be through the use of a visual estimation of body weight, the use of a weight measuring device, such as an electronic weight scale or a mechanical beam scale. In some embodiments, an individual in need of weight management is an adult male with a body weight greater than about 90 kg, greater than about 100 kg, or greater than about 110 kg. In some embodiments, an individual in need of weight management is an adult female with a body weight greater than about 80 kg, greater than about 90 kg, or greater than about 100 kg. In some embodiments, the individual is prepubertal and has a body weight greater than about 30 kg, greater than about 40 kg, or greater than about 50 kg.

Whether an individual is overweight or obese can be determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. According to the classification from the World Health Organization (W.H.O.), overweight is defined as a BMI in the range 25-30 kg/m$^2$, and obesity as a BMI greater than 30 kg/m$^2$ (see below for a detailed W.H.O. BMI classification).

The International Classification of Adult Underweight, Overweight, and Obesity According to BMI (World Health Organization)

| Classification | BMI (kg/m$^2$) | |
| --- | --- | --- |
| | Principal cut-off points | Additional cut-off points |
| Underweight | <18.50 | <18.50 |
| Severe thinness | <16.00 | <16.00 |
| Moderate thinness | 16.00-16.99 | 16.00-16.99 |
| Mild thinness | 17.00-18.49 | 17.00-18.49 |
| Normal range | 18.50-24.99 | 18.50-22.99 |
| | | 23.00-24.99 |
| Overweight | ≥25.00 | ≥25.00 |
| Pre-obese | 25.00-29.99 | 25.00-27.49 |
| | | 27.50-29.99 |
| Obese | ≥30.00 | ≥30.00 |
| Obese class I | 30.00-34.99 | 30.00-32.49 |
| | | 32.50-34.99 |
| Obese class II | 35.00-39.99 | 35.00-37.49 |
| | | 37.50-39.99 |
| Obese class III | ≥40.00 | ≥40.00 |

The healthy range of BMI, and other measures of whether one is overweight or obese, can also be dependent on genetic or racial differences. For example, since Asian populations develop negative health consequences at a lower BMI than Caucasians, some nations have redefined obesity for their populations. For example, in Japan any BMI greater than 25 is defined as obese and in China any BMI greater than 28 is defined as obese. Similarly, different threshold values for body weight, waist circumference or body fat percentage can be used for different populations of individuals. The additional cut-off points included in the table above (for example, 23, 27.5, 32.5 and 37.5) were added as points for public health action. The WHO recommends that countries should use all categories for reporting purposes with a view to facilitating international comparisons.

Determination of BMI can be through the use of a visual estimation of BMI, the use of a height measuring device such as a stadiometer or a height rod and the use of a weight measuring device, such as an electronic weight scale or a mechanical beam scale. In some embodiments, the individual in need of weight management is an adult with a BMI of greater than about 25 kg/m$^2$, greater than about 26 kg/m$^2$, greater than about 27 kg/m$^2$, greater than about 28 kg/m$^2$, greater than about 29 kg/m$^2$, greater than about 30 kg/m$^2$, greater than about 31 kg/m$^2$, greater than about 32 d kg/m$^2$, greater than about 33 kg/m$^2$, greater than about 34 kg/m$^2$, greater than about 35 kg/m$^2$, greater than about 36 kg/m$^2$, greater than about 37 kg/m$^2$, greater than about 38 kg/m$^2$, greater than about 39 kg/m$^2$, or greater than about 40 kg/m$^2$. In some embodiments, the individual is prepubertal with a BMI of greater than about 20 kg/m$^2$, greater than about 21 kg/m$^2$, greater than about 22 kg/m$^2$, greater than about 23 kg/m$^2$, greater than about 24 kg/m$^2$, greater than about 25 kg/m$^2$, greater than about 26 kg/m$^2$, greater than about 27 kg/m$^2$, greater than about 28 kg/m$^2$, greater than about 29 kg/m$^2$, greater than about 30 kg/m$^2$, greater than about 31 kg/m$^2$, greater than about 32 kg/m$^2$, greater than about 33 kg/m$^2$, greater than about 34 kg/m$^2$, or greater than about 35 kg/m$^2$.

Determination of waist circumference can be through the use of a visual estimation of waist circumference or the use of a waist circumference measuring device such as a tape measure.

Determinations of the healthy range of waist circumference and percentage body fat in an individual are dependent on gender. For example, women typically have smaller waist circumferences than men and so the waist circumference threshold for being overweight or obese is lower for a woman. In addition, women typically have a greater percentage of body fat than men and so the percentage body fat threshold for being overweight or obese for a woman is higher than for a man. Further, the healthy range of BMI and other measures of whether one is overweight or obese can be dependent on age. For example, the body weight threshold for considering whether one is overweight or obese is lower for a child (prepubertal individual) than an adult.

In some embodiments, the individual in need of weight management is an adult male with a waist circumference of greater than about 100 cm, greater than about 110 cm, greater than about 120 cm, greater than about 110 cm or an adult female with a waist circumference of greater than about 80 cm, greater than about 90 cm, or greater than about 100 cm. In some embodiments, the individual is prepubertal with a waist circumference of about of greater than about 60 cm, greater than about 70 cm, or greater than about 80 cm.

Determination of body fat percentage can be through the use of a visual estimation of body fat percentage or the use of a body fat percentage measuring device such as bioelectric impedance, computed tomography, magnetic resonance imaging, near infrared interactance, dual energy X ray absorptiometry, use of ultrasonic waves, use of body average density measurement, use of skinfold methods, or use of height and circumference methods. In some embodiments, the individual in need of weight management is an adult male with a body fat percentage of greater than about 25%, greater than about 30%, or greater than about 35% or an adult female with a body fat percentage of greater than about 30%, greater than about 35%, or greater than about 40%. In some embodiments, the individual is prepubertal with a body fat percentage of greater than about 30%, greater than about 35%, or greater than about 40%.

In some embodiments, modifying the administration of the compounds provided herein comprises prescribing or administering a weight loss drug or procedure to the individual to be used in combination with the compounds provided herein.

Antipsychotic-induced Weight Gain

Antipsychotic-induced weight gain is a serious side effect of antipsychotic medication that can lead to increased morbidity, mortality, and non-compliance in patients. The mechanisms underlying weight gain resulting from antipsychotic drugs are not fully understood, although antagonism of the 5-$HT_{2C}$ receptor is likely to contribute. Animal studies indicate that the drugs most likely to cause weight gain, clozapine and olanzapine, have direct effects on the neuropeptide Y-containing neurons of the hypothalamus; these neurons mediate the effects of the circulating anorexigenic hormone leptin on the control of food intake (*Association Between Early and Rapid Weight Gain and Change in Weight Over One Year of Olanzapine Therapy in Patients with Schizophrenia and Related Disorders*; Kinon, B. J. et al., Journal of Clinical Psychopharmacology (2005), 25(3), 255-258). Furthermore, significant overall weight gain has been found in schizophrenic or related disorder patients undergoing therapy with the 5-$HT_{2C}$-receptor antagonist, olanzapine (*The 5-$HT_{2C}$ Receptor and Antipsychotic-Induced Weight Gain-Mechanisms and Genetics*; Reynolds G. P. et al.; Journal of Psychopharmacology (2006), 20(4 Suppl), 15-8). Accordingly, 5-$HT_{2C}$-receptor agonists such as compounds provided herein are useful for treating antipsychotic-induced weight gain.

Diabetes

It is known that 5-$HT_{2C}$-receptor agonists significantly improve glucose tolerance and reduce plasma insulin in murine models of obesity and type 2 diabetes at concentrations of agonist that have no effect on ingestive behavior, energy expenditure, locomotor activity, body weight, or fat mass (*Serotonin 2C Receptor Agonists Improve Type 2 Diabetes via Melanocortin-4 Receptor Signaling Pathways*; Ligang, Z. et al., Cell Metab. 2007 Nov. 7; 6(5): 398-405).

As a part of a phase 3 clinical trial program, BELVIQ was evaluated in a randomized, placebo-controlled, multi-site, double-blind trial of 604 adults with poorly controlled type 2 diabetes mellitus treated with oral hyperglycemic agents ("BLOOM-DM"). Within the glycemic, lipid and blood pressure families, patients in the BELVIQ group achieved statistically significant improvements relative to placebo in HbA1c and fasting glucose. BELVIQ (10 mg BID) patients achieved a 0.9% reduction in HbA1c, compared to a 0.4% reduction for the placebo group (p<0.0001) and a 27.4% reduction in fasting glucose, compared to a 11.9% reduction for the placebo group (p<0.001). Among patients with type 2 diabetes, the use of medications to treat diabetes decreased in patients taking BELVIQ concurrently with mean improvement in glycemic control. In particular, mean daily doses of sulfonylureas and thiazolidinediones decreased 16-24% in the BELVIQ groups, and increased in the placebo group (*Effect of Lorcaserin on the Use of Concomitant Medications for Dyslipidemia, Hypertension and Type 2 Diabetes during Phase 3 Clinical Trials Assessing Weight Loss in Patients with Type 2 Diabetes*; Vargas, E. et al.; Abstracts of Papers, Obesity Society 30$^{th}$ Annual Scientific Meeting, San Antonio, Tex., Sep. 20-24, 2012, (2012), 471-P). In studies that excluded patients with diabetes the population was insulin resistant, as indicated by baseline homeostasis model of assessment-insulin resistance (HOMA-IR) values greater than 1.5. Mean fasting glucose was statistically significantly decreased by BELVIQ (−0.2 mg/dL) compared to placebo (+0.6 mg/dL), and BELVIQ caused a small but statistically significant decrease in HbA1c. In one study, fasting insulin decreased significantly in the BELVIQ group (−3.3 gIU/mL) relative to placebo (−1.3 gIU/mL), resulting in significant improvement in insulin resistance (indicated by HOMA-IR) in the BELVIQ group (−0.4) compared with placebo (−0.2). Accordingly the compounds provided herein are useful for the prevention and treatment of type 2 diabetes.

Prader-Willi Syndrome

Prader-Willi syndrome (PWS) is a maternally imprinted human disorder resulting from a loss of paternal gene expression on chromosome 15q11-13 that is characterized by a complex phenotype including cognitive deficits, infantile hypotonia and failure to thrive, short stature, hypogonadism and hyperphagia which can lead to morbid obesity (Goldstone, 2004; Nicholls and Knepper, 2001). There is support in the literature for the use of 5-$HT_{2C}$-receptor agonists such as compounds provided herein for treating PWS (*Mice with altered serotonin 2C receptor RNA editing display characteristics of Prader-Willi syndrome*. Morabito, M. V. et al., Neurobiology of Disease 39 2010) 169-180; and Self-injurious behavior and serotonin in Prader-Willi syndrome. Hellings, J. A. and Warnock, J. K. Psychopharmacology bulletin (1994), 30(2), 245-50).

Substance Abuse and other Addiction

Addiction is a primary, chronic disease of brain reward, motivation, memory, and related circuitry. Dysfunction in these circuits leads to characteristic biological, psychological, social, and spiritual manifestations. This is reflected in an individual pathologically pursuing reward and/or relief by substance use and other behaviors. Addiction is characterized by inability to consistently abstain, impairment in behavioral control, craving, diminished recognition of significant problems with one's behaviors and interpersonal relationships, and a dysfunctional emotional response. Like other chronic diseases, addiction often involves cycles of relapse and remission. Without treatment or engagement in recovery activities, addiction is progressive and can result in disability or premature death.

The power of external cues to trigger craving and drug use, as well as to increase the frequency of engagement in other potentially addictive behaviors, is also a characteristic of addiction, with the hippocampus being important in memory of previous euphoric or dysphoric experiences, and with the amygdala being important in having motivation concentrate on selecting behaviors associated with these past experiences. Although some believe that the difference between those who have addiction, and those who do not, is the quantity or frequency of alcohol/drug use, engagement in addictive behaviors (such as gambling or spending), or exposure to other external rewards (such as food or sex), a characteristic aspect of addiction is the qualitative way in which the individual responds to such exposures, stressors and environmental cues. A particularly pathological aspect of the way that persons with addiction pursue substance use or external rewards is that preoccupation with, obsession with and/or pursuit of rewards (e.g., alcohol and other drug use) persist despite the accumulation of adverse consequences. These manifestations can occur compulsively or impulsively, as a reflection of impaired control.

Agonists of the 5-HT$_{2C}$ receptor such as the compounds provided herein are active in rodent models of substance abuse, addiction and relapse, and there is strong support in the literature that such agonists act via modulation of dopamine function.

1. Smoking & Tobacco Use

Tobacco use can lead to tobacco/nicotine dependence and serious health problems. Cessation can significantly reduce the risk of suffering from smoking-related diseases. Tobacco/nicotine dependence is a chronic condition that often requires repeated interventions.

2. Drug addiction

There is support in the literature for the use of 5-HT$_{2C}$-receptor agonists such as compounds provided herein for treating drug addiction (*Novel Pharmacotherapeutic Approaches for the Treatment of Drug Addiction and Craving*; Heidbreder et al, Current Opinion in Pharmacology (2005), 5(1), 107-118).

3. Alcoholism

There is support in the literature for the use of 5-HT$_{2C}$-receptor agonists such as compounds provided herein for treating alcoholism (*An Investigation of the Role of 5-HT$_{2C}$ Receptors in Modifying Ethanol Self-Administration Behaviour*; Tomkins et al. Pharmacology, biochemistry, and behavior (2002), 71(4), 735-44).

4. Pathological Gambling

There is support in the literature for the use of 5-HT$_{2C}$-receptor agonists such as compounds provided herein for treating pathological gambling. Marazziti, D. et al. found that the maximum binding capacity of the platelet 5-HT transporter pathological gambling patients was significantly lower than that of healthy subjects. Pathological gambling patients showed a dysfunction at the level of the platelet 5-HT transporter that would suggest the involvement of the 5-HT system in this condition. (*Decreased Density of the Platelet Serotonin Transporter in Pathological Gamblers*; Marazziti, D. et al., Neuropsychobiology (2008), 57(1-2), 38-43.)

5. Reward Deficiency Syndrome; Sex Addiction

The dopaminergic system, and in particular the dopamine D2 receptor, has been implicated in reward mechanisms. The net effect of neurotransmitter interaction at the mesolimbic brain region induces "reward" when dopamine (DA) is released from the neuron at the nucleus accumbens and interacts with a dopamine D2 receptor. "The reward cascade" involves the release of serotonin, which in turn at the hypothalamus stimulates enkephalin, which in turn inhibits GABA at the substania nigra, which in turn fine tunes the amount of DA released at the nucleus accumbens or "reward site." It is well known that under normal conditions in the reward site DA works to maintain our normal drives. In fact, DA has become to be known as the "pleasure molecule" and/or the "antistress molecule." When DA is released into the synapse, it stimulates a number a DA receptors (D1-D5) which results in increased feelings of well-being and stress reduction. A consensus of the literature suggests that when there is a dysfunction in the brain reward cascade, which could be caused by certain genetic variants (polygenic), especially in the DA system causing a hypodopaminergic trait, the brain of that person requires a DA fix to feel good. This trait leads to multiple drug-seeking behavior. This is so because alcohol, cocaine, heroin, marijuana, nicotine, and glucose all cause activation and neuronal release of brain DA, which could heal the abnormal cravings. Certainly after ten years of study we could say with confidence that carriers of the DAD2 receptor A1 allele have compromised D2 receptors. Therefore lack of D2 receptors causes individuals to have a high risk for multiple addictive, impulsive and compulsive behavioral propensities, such as severe alcoholism, cocaine, heroin, marijuana and nicotine use, glucose bingeing, pathological gambling, sex addiction, ADHD, Tourette's Syndrome, autism, chronic violence, posttraumatic stress disorder, schizoid/avoidant cluster, conduct disorder and antisocial behavior. In order to explain the breakdown of the reward cascade due to both multiple genes and environmental stimuli (pleiotropism) and resultant aberrant behaviors, Blum united this hypodopaminergic trait under the rubric of a reward deficiency syndrome. (*Reward Deficiency Syndrome: a Biogenetic Model for the Diagnosis and Treatment of Impulsive, Addictive, and Compulsive Behaviors*; Blum K. et al.; Journal of psychoactive drugs (2000), 32 Suppl, i-iv, 1-112.) Accordingly, compounds provided herein are useful for the treatment of reward deficiency syndrome, multiple addictive, impulsive and compulsive behavioral propensities, such as severe alcoholism, cocaine, heroin, marijuana and nicotine use, glucose bingeing, pathological gambling, sex addiction, ADHD, Tourette's Syndrome, autism, chronic violence, posttraumatic stress disorder, schizoid/avoidant cluster, conduct disorder and antisocial behavior. In some embodiments, compounds provided herein are useful for the treatment of sex addiction.

Obsessive-compulsive Spectrum Disorders; Impulse Control Disorders; Onychophagia The morbidity of obsessive-compulsive spectrum disorders (OCSD), a group of conditions related to obsessive-compulsive disorder (OCD) by phenomenological and etiological similarities, is increasingly recognized. Serotonin reuptake inhibitors (SRIs) have shown benefits as first-line, short-term treatments for body dysmorphic disorder, hypochondriasis, onychophagia, and psychogenic excoriation, with some benefits in trichotillomania, pathological gambling, and compulsive buying. (*Obsessive-Compulsive Spectrum Disorders: a Review of the Evidence-Based Treatments*. Ravindran A. V., et al., Canadian journal of psychiatry, (2009), 54(5), 331-43). Furthermore, impulse control disorders such as trichotillomania (hair-pulling), pathological gambling, pyromania, kleptomania, and intermittent explosive disorder, as well as onychophagia (nail-biting), are treated by administering a serotonin reuptake inhibitor such as clomipramine, fluvoxamine, fluoxetine, zimelidine, and sertraline or their salts. Significant improvement was noted with clomipramine in a 5-week trial (*Method of Treating Trichotillomania and Onychophagia*, Swedo, S. E. et al., PCT Int. Appl. (1992), WO 9218005 A1 19921029). Accordingly, compounds provided herein are useful for the treatment of body dysmorphic disorder, hypochondriasis, onychophagia, psychogenic excoriation, trichotillomania, pathological gambling, compulsive buying, pyromania, kleptomania, and intermittent explosive disorder. In some embodiments, compounds provided herein are useful for the treatment of onychophagia.

Sleep

There is support in the literature for the use of 5-HT$_{2C}$-receptor agonists such as compounds provided herein for treating insomnia, for increasing slow-wave sleep, for sleep consolidation, and for treating fragmented sleep architecture. (*The Role of Dorsal Raphe Nucleus Serotonergic and Non-Serotonergic Neurons, and of their Receptors, in Regulating Waking and Rapid Eye Movement (REM) Sleep*; Monti, J. M.; Sleep medicine reviews (2010), 14(5), 319-27). Furthermore, 5-HT$_{2C}$-receptor knockout mice exhibit more wakefulness and less slow wave sleep than do wild-types (*Serotonin 1B and 2C Receptor Interactions in the*

*Modulation of Feeding Behaviour in the Mouse*; Dalton, G. L. et al., Psychopharmacology (2006), 185(1), 45-57). However, the 5-HT$_{2C}$-receptor agonist, m-chlorophenylpiperazine (mCPP) has been shown to decrease slow-wave sleep in humans (*Decreased Tryptophan Availability but Normal Post-Synaptic 5-HT2C Receptor Sensitivity in Chronic Fatigue Syndrome*; Vassallo, C. M. et al., Psychological medicine (2001), 31(4), 585-91).

Urinary Incontinence

The serotoninergic system has been widely implicated in the control of urinary bladder function. It has been demonstrated that preganglionic fibers and ganglionic serotoninergic neurons, expressing the 5-HT$_3$ and 5-HT$_4$ receptors, and the effector smooth muscle cells, expressing 5-HT$_1$ and 5-HT$_2$ receptors, are actively involved in the regulation of the bladder contractile activity in rabbits (*Role of Serotonin Receptors in Regulation of Contractile Activity of Urinary Bladder in Rabbits*; Lychkova, A. E. and Pavone, L. M., Urology 2013 March; 81(3):696). Furthermore, there is support in the literature for the use of 5-HT$_{2C}$-receptor agonists such as compounds provided herein for treating urinary incontinence (*Discovery of a Novel Azepine Series of Potent and Selective 5-HT$_{2C}$ Agonists as Potential Treatments for Urinary Incontinence*; Brennan et al.; Bioorganic & medicinal chemistry letters (2009), 19(17), 4999-5003).

Psychiatric Disorders

There is support in the literature for the use of 5-HT$_{2C}$-receptor agonists such as compounds provided herein for and prodrugs thereof for treating psychiatric disorders (*5-HT$_{2C}$ Receptor Agonists as an Innovative Approach for Psychiatric Disorders*; Rosenzweig-Lipson et al., Drug news & perspectives (2007), 20(9), 565-71; and Naughton et al., Human Psychopharmacology (2000), 15(6), 397-415).

1. Schizophrenia

The 5-HT$_{2C}$ receptor is a highly complex, highly regulated receptor which is widely distributed throughout the brain. The 5-HT$_{2C}$ receptor couples to multiple signal transduction pathways leading to engagement of a number of intracellular signaling molecules. Moreover, there are multiple allelic variants of the 5-HT$_{2C}$ receptor and the receptor is subject to RNA editing in the coding regions. The complexity of this receptor is further emphasized by the studies suggesting the utility of either agonists or antagonists in the treatment of schizophrenia. The preclinical profile of 5-HT$_{2C}$ agonists from a neurochemical, electrophysiological, and a behavioral perspective is indicative of antipsychotic-like efficacy without extrapyramidal symptoms or weight gain. Recently, the selective 5-HT$_{2C}$ agonist vabicaserin demonstrated clinical efficacy in a Phase II trial in schizophrenia patients without weight gain and with low extrapyramidal side effects liability. These data are highly encouraging and suggest that the compounds provided herein are useful for the treatment of psychiatric disorders, such as schizophrenia (*5-HT$_{2C}$ Agonists as Therapeutics for the Treatment of Schizophrenia*. Rosenzweig-Lipson, S. et al., Handbook of Experimental Pharmacology (2012), 213 (Novel Antischizophrenia Treatments), 147-165).

2. Eating Disorders

5-HT$_{2C}$ receptor agonists such as compounds provided herein are useful for the treatment of psychiatric symptoms and behaviors in individuals with eating disorders such as, but not limited to, anorexia nervosa and bulimia nervosa. Individuals with anorexia nervosa often demonstrate social isolation. Anorexic individuals often present symptoms of being depressed, anxious, obsession, perfectionistic traits, and rigid cognitive styles as well as sexual disinterest. Other eating disorders include, anorexia nervosa, bulimia nervosa, binge eating disorder (compulsive eating) and ED-NOS (i.e., eating disorders not otherwise specified—an official diagnosis). An individual diagnosed with ED-NOS possess atypical eating disorders including situations in which the individual meets all but a few of the criteria for a particular diagnosis. What the individual is doing with regard to food and weight is neither normal nor healthy.

Alzheimer Disease

The 5-HT$_{2C}$ receptor plays a role in Alzheimer Disease (AD). Therapeutic agents currently prescribed AD are cholinomimetic agents that act by inhibiting the enzyme acetylcholinesterase. The resulting effect is increased levels of acetylcholine, which modestly improves neuronal function and cognition in patients with AD. Although, dysfunction of cholinergic brain neurons is an early manifestation of AD, attempts to slow the progression of the disease with these agents have had only modest success, perhaps because the doses that can be administered are limited by peripheral cholinergic side effects, such as tremors, nausea, vomiting, and dry mouth. In addition, as AD progresses, these agents tend to lose their effectiveness due to continued cholinergic neuronal loss.

Therefore, there is a need for agents that have beneficial effects in AD, particularly in alleviating symptoms by improving cognition and slowing or inhibiting disease progression, without the side effects observed with current therapies. Therefore, serotonin 5-HT$_{2C}$ receptors, which are exclusively expressed in brain, are attractive targets and agonists of 5-HT$_{2C}$ receptors such as compounds provided herein are useful for the treatment of AD.

Sexual Dysfunction; Erectile dysfunction

Another disease, disorder or condition that can is associated with the function of the 5-HT$_{2C}$ receptor is erectile dysfunction (ED). Erectile dysfunction is the inability to achieve or maintain an erection sufficiently rigid for intercourse, ejaculation, or both. An estimated 20-30 million men in the United States have this condition at some time in their lives. The prevalence of the condition increases with age. Five percent of men 40 years of age report ED. This rate increases to between 15% and 25% by the age of 65, and to 55% in men over the age of 75 years.

Erectile dysfunction can result from a number of distinct problems. These include loss of desire or libido, the inability to maintain an erection, premature ejaculation, lack of emission, and inability to achieve an orgasm. Frequently, more than one of these problems presents themselves simultaneously. The conditions may be secondary to other disease states (typically chronic conditions), the result of specific disorders of the urogenital system or endocrine system, secondary to treatment with pharmacological agents (e.g. antihypertensive drugs, antidepressant drugs, antipsychotic drugs, etc.) or the result of psychiatric problems. Erectile dysfunction, when organic, is primarily due to vascular irregularities associated with atherosclerosis, diabetes, and hypertension.

There is evidence for use of a serotonin 5-HT$_{2C}$ agonist for the treatment of sexual dysfunction in males and females. The serotonin 5-HT$_{2C}$ receptor is involved with the processing and integration of sensory information, regulation of central monoaminergic systems, and modulation of neuroendocrine responses, anxiety, feeding behavior, and cerebrospinal fluid production (Tecott, L. H., et al. *Nature* 374: 542-546 (1995)). In addition, the serotonin 5-HT$_{2C}$ receptor has been implicated in the mediation of penile erections in rats, monkeys, and humans. Accordingly the compounds provided herein are useful for the treatment of sexual dysfunction and erectile dysfunction.

Seizure Disorders

Evidence suggests a role for the monoamines, norepinephrine and serotonin, in the pathophysiology of seizure disorders (*Electrophysiological Assessment of Monoamine Synaptic Function in Neuronal Circuits of Seizure Susceptible Brains*; Waterhouse, B. D.; Life Sciences (1986), 39(9), 807-18). Accordingly, 5-HT$_{2C}$ receptor agonists such as compounds provided herein, are useful for the treatment of seizure disorders.

Epilepsy is a syndrome of episodic brain dysfunction characterized by recurrent unpredictable, spontaneous seizures. Cerebellar dysfunction is a recognized complication of temporal lobe epilepsy and it is associated with seizure generation, motor deficits and memory impairment. Serotonin is known to exert a modulatory action on cerebellar function through 5-HT$_{2C}$ receptors. (*Down-regulation of Cerebellar 5-HT$_{2C}$ Receptors in Pilocarpine-Induced Epilepsy in Rats: Therapeutic Role of Bacopa monnieri Extract*; Krishnakumar, A. et al., Journal of the Neurological Sciences (2009), 284(1-2), 124-128). Mutant mice lacking functional 5-HT2C-receptors are also prone to spontaneous death from seizures (*Eating Disorder and Epilepsy in Mice Lacking 5-HT$_c$ Serotonin Receptors*; Tecott, L. H. et al., Nature. 1995 Apr. 6; 374(6522):542-6). Furthermore, in a preliminary trial of the selective serotonin reuptake inhibitor citalopram as an add on treatment in non-depressed patients with poorly controlled epilepsy, the median seizure frequency dropped by 55.6% (*The Anticonvulsant Effect of Citalopram as an Indirect Evidence of Serotonergic Impairment in Human Epileptogenesis*; Favale, E. et al., Seizure. 2003 Jul.; 12(5):316-8). Accordingly, 5-HT$_{2C}$ receptor agonists such as compounds provided herein, are useful for the treatment of epilepsy. For example, 5-HT$_{2C}$ receptor agonists such as compounds provided herein, are useful for the treatment of generalized nonconvulsive epilepsy, generalized convulsive epilepsy, petit mal status epilepticus, grand mal status epilepticus, partial epilepsy with or without impairment of consciousness, infantile spasms, or epilepsy partialis continua.

Dravet Syndrome, also known as severe myoclonic epilepsy of infancy (SMEI), is a catastrophic form of childhood epilepsy in which children are unresponsive to standard anti-epilepsy drugs. The average age of death is 4-6 years. If patients survive beyond this age they will be likely mentally retarded. Data from case studies over twenty years demonstrates that administering a low-dose of the indirectly-acting serotonin agonist fenfluramine stops patients with Dravet Syndrome fitting. Accordingly, 5-HT$_{2C}$ receptor agonists such as compounds provided herein, are useful for the treatment of Dravet Syndrome.

Movement Disorders

The basal ganglia are a highly interconnected group of subcortical nuclei in the vertebrate brain that play a critical role not only in the control of movements but also in some cognitive and behavioral functions. Several recent studies have emphasized that serotonergic pathways in the central nervous system (CNS) are intimately involved in the modulation of the basal ganglia and in the pathophysiology of human involuntary movement disorders. These observations are supported by anatomical evidence demonstrating large serotonergic innervation of the basal ganglia. In fact, serotonergic terminals have been reported to make synaptic contacts with dopamine (DA)-containing neurons and γ-aminobutyric acid (GABA)-containing neurons in the striatum, globus pallidus, subthalamus and substantia nigra. These brain areas contain the highest concentration of serotonin (5-HT), with the substantia nigra pars *reticulata* receiving the greatest input. Furthermore, in these structures a high expression of 5-HT different receptor subtypes has been revealed (*Serotonin Involvement in the Basal Ganglia Pathophysiology: Could the 5-HT$_{2C}$ Receptor be a New Target for Therapeutic Strategies*? Di Giovanni, G. et al., Current medicinal Chemistry (2006), 13(25), 3069-81). Accordingly, 5-HT$_{2C}$ receptor agonists such as compounds provided herein, are useful for the treatment of movement disorders. In some embodiments, compounds provided herein are useful for the treatment of parkisonism. In some embodiments, compounds provided herein are useful for the treatment of movement disorders associated with antipsychotic drug use.

Hypertension

In clinical trials in patients without type 2 diabetes, 2.2% of patients on BELVIQ and 1.7% of patients on placebo decreased total daily dose of antihypertensive medications, while 2.2% and 3.0%, respectively, increased total daily dose. In patients without type 2 diabetes, numerically more patients who were treated with placebo initiated dyslipidemia and hypertension therapy as compared to those treated with BELVIQ. In patients with type 2 diabetes, 8.2% on BELVIQ and 6.0% of patients on placebo decreased total daily dose of antihypertensive medications, while 6.6% and 6.3%, respectively, increased total daily dose (*Effect of Lorcaserin on the Use of Concomitant Medications for Dyslipidemia, Hypertension and Type 2 Diabetes during Phase 3 Clinical Trials Assessing Weight Loss in Patients with Type 2 Diabetes*; Vargas, E. et al.; Abstracts of Papers, Obesity Society 30$^{th}$ Annual Scientific Meeting, San Antonio, Tex., Sep. 20-24, 2012, (2012), 471-P). Accordingly, 5-HT$_{2C}$ receptor agonists such as compounds provided herein, are useful for the treatment of hypertension.

Dyslipidemia

In clinical trials in patients without type 2 diabetes, 1.3% of patients on BELVIQ and 0.7% of patients on placebo decreased the total daily dose of medications used for treatment of dyslipidemia; 2.6% and 3.4%, respectively, increased use of these medications during the trials. In patients without type 2 diabetes, numerically more patients who were treated with placebo initiated dyslipidemia and hypertension therapy as compared to those treated with BELVIQ. In patients with type 2 diabetes, 5.5% of patients on BELVIQ BID and 2.4% of patients on placebo decreased the total daily dose of medications used for treatment of dyslipidemia; 3.1% and 6.7%, respectively, increased use of these medications during the trials. (*Effect of Lorcaserin on the Use of Concomitant Medications for Dyslipidemia, Hypertension and Type 2 Diabetes during Phase 3 Clinical Trials Assessing Weight Loss in Patients with Type 2 Diabetes*; Vargas, E. et al.; Abstracts of Papers, Obesity Society 30$^{th}$ Annual Scientific Meeting, San Antonio, Tex., Sep. 20-24, 2012, (2012), 471-P). Accordingly, 5-HT$_{2C}$ receptor agonists such as compounds provided herein, are useful for the treatment of dyslipidemia.

Nonalcoholic Fatty Liver Disease

Nonalcoholic fatty liver disease encompasses a range of liver diseases. Simple steatosis, or fatty liver, is now found in up to 31% of adults and 16% of children. Of those with steatosis, approximately 5% will develop nonalcoholic steatohepatitis (NASH), in which steatosis is accompanied by inflammation and fibrosis. Up to 25% of NASH patients will progress to cirrhosis. NASH is the third leading indication for liver transplantation in the United States and will become the most common if current trends continue. Therefore, understanding its pathogenesis and treatment is of utmost importance. Overall reductions in body weight, through reduced-calorie intake and increased physical activity, are the current mainstays of NASH treatment (*Dietary Treatment of Nonalcoholic Steatohepatitis*; Perito, E. R., et al.; Disclosures Curr Opin Gastroenterol, 2013; 29(2):170-176). Accordingly, by virtue of their ability to decrease food intake and induce satiety, 5-$HT_{2C}$ receptor agonists such as compounds provided herein, are useful for the treatment of nonalcoholic fatty liver disease.

Obesity-related Renal Disease

Obesity is established as an important contributor of increased diabetes mellitus, hypertension, and cardiovascular disease, all of which can promote chronic kidney disease. Recently, there is a growing appreciation that, even in the absence of these risks, obesity itself significantly increases chronic kidney disease and accelerates its progression. (*Scope and mechanisms of obesity-related renal disease*; Hunley, T. E. et al.; Current Opinion in Nephrology & Hypertension (2010), 19(3), 227-234). Accordingly, by virtue of their ability to treat obesity, 5-$HT_{2C}$ receptor agonists such as compounds provided herein, are useful for the treatment of obesity-related kidney disease.

Catecholamine Suppression

Administering a compound provided herein to an individual causes a reduction of the individual's norepinephrine level independently of weight-loss. 5-$HT_{2C}$ receptor agonists such as compounds provided herein are useful for the treatment of disorders ameliorated by reduction of an individual's norepinephrine level, wherein said disorders include but are not limited to hypernorepinephrinemia, cardiomyopathy, cardiac hypertrophy, cardiomyocyte hypertrophy in post-myocardial infarction remodeling, elevated heart rate, vasoconstriction, acute pulmonary vasoconstriction, hypertension, heart failure, cardiac dysfunction after stroke, cardiac arrhythmia, metabolic syndrome, abnormal lipid metabolism, hyperthermia, Cushing syndrome, pheochromocytoma, epilepsy, obstructive sleep apnea, insomnia, glaucoma, osteoarthritis, rheumatoid arthritis, and asthma.

Also provided is a method for aiding in the cessation or lessening of use of a tobacco product in an individual attempting to cease or lessen use of a tobacco product comprising the step of: prescribing and/or administering to the individual an effective amount of a compound provided herein. In some embodiments, aiding in the cessation of use of a tobacco product is aiding smoking cessation, and the individual attempting to cease use of the tobacco product is an individual attempting to cease smoking.

Also provided is a method for aiding in the cessation of use of a tobacco product and the prevention of associated weight gain comprising the step of: prescribing and/or administering an effective amount of a compound provided herein to an individual attempting to cease use of the tobacco product. In some embodiments, aiding in the cessation of use of a tobacco product is aiding smoking cessation, and the individual attempting to cease use of the tobacco product is an individual attempting to cease smoking.

Also provided is a method for reducing the frequency of smoking tobacco in an individual attempting to reduce frequency of smoking tobacco comprising the step of: prescribing and/or administering to the individual an effective amount of a compound provided herein.

Also provided is a method for controlling weight gain associated with smoking cessation by an individual attempting to cease smoking tobacco comprising the step of: prescribing and/or administering to the individual an effective amount of a compound provided herein.

Also provided is a method for reducing weight gain associated with smoking cessation by an individual attempting to cease smoking tobacco comprising the step of: prescribing and/or administering to the individual an effective amount of a compound provided herein.

Also provided is a method of treatment for nicotine dependency, addiction and/or withdrawal in an individual attempting to treat nicotine dependency, addiction and/or withdrawal comprising the step of: prescribing and/or administering to the individual an effective amount of a compound provided herein.

Also provided is a method of reducing the likelihood of relapse use of nicotine by an individual attempting to cease nicotine use comprising the step of:
prescribing and/or administering to the individual an effective amount of a compound provided herein.

Methods related to nicotine addiction and smoking cessation

Also provided is a method of reducing the frequency of smoking tobacco in an individual attempting to reduce frequency of smoking tobacco, aiding in the cessation or lessening of use of a tobacco product in an individual attempting to cease or lessen use of a tobacco product, aiding in smoking cessation and preventing associated weight gain, controlling weight gain associated with smoking cessation by an individual attempting to cease smoking tobacco, reducing weight gain associated with smoking cessation by an individual attempting to cease smoking tobacco, treating nicotine dependency, addiction and/or withdrawal in an individual attempting to treat nicotine dependency, addiction and/or withdrawal, or reducing the likelihood of relapse use of nicotine by an individual attempting to cease nicotine use, comprising:

selecting an individual with an initial BMI≥27 $kg/m^2$; and prescribing and/or administering to the individual an effective amount of a compound selected from compounds provided herein, and salts, solvates, and hydrates thereof for at least one year.

Also provided is a method of reducing the frequency of smoking tobacco in an individual attempting to reduce frequency of smoking tobacco, aiding in the cessation or lessening of use of a tobacco product in an individual attempting to cease or lessen use of a tobacco product, aiding in smoking cessation and preventing associated weight gain, controlling weight gain associated with smoking cessation by an individual attempting to cease smoking tobacco, reducing weight gain associated with smoking cessation by an individual attempting to cease smoking tobacco, treating nicotine dependency, addiction and/or withdrawal in an individual attempting to treat nicotine dependency, addiction and/or withdrawal, or reducing the likelihood of relapse use of nicotine by an individual attempting to cease nicotine use, comprising:

administering a compound selected from compounds provided herein, and salts, solvates, and hydrates thereof to an individual;

monitoring the individual for BMI during said administration; and discontinuing said administration if the BMI of the individual becomes <18.5 $kg/m^2$ during said administration.

Also provided is a method of reducing the frequency of smoking tobacco in an individual attempting to reduce frequency of smoking tobacco, aiding in the cessation or lessening of use of a tobacco product in an individual attempting to cease or lessen use of a tobacco product, aiding in smoking cessation and preventing associated weight gain, controlling weight gain associated with smoking cessation by an individual attempting to cease smoking tobacco, reducing weight gain associated with smoking cessation by an individual attempting to cease smoking tobacco, treating nicotine dependency, addiction and/or withdrawal in an individual attempting to treat nicotine dependency, addiction and/or withdrawal, or reducing the likelihood of relapse use of nicotine by an individual attempting to cease nicotine use, comprising:

administering a compound selected from compounds provided herein, and salts, solvates, and hydrates thereof to an individual with an initial BMI <25 kg/m$^2$;

monitoring the individual for body weight during said administration; and discontinuing said administration if the body weight of the individual decreases by more than about 1% during said administration.

In some embodiments, administration is discontinued if the body weight of the individual decreases by more than about 2% during said administration. In some embodiments, administration is discontinued if the body weight of the individual decreases by more than about 3% during said administration. In some embodiments, administration is discontinued if the body weight of the individual decreases by more than about 4% during said administration. In some embodiments, administration is discontinued if the body weight of the individual decreases by more than about 5% during said administration.

Also provided is a method of reducing the frequency of smoking tobacco in an individual attempting to reduce frequency of smoking tobacco, aiding in the cessation or lessening of use of a tobacco product in an individual attempting to cease or lessen use of a tobacco product, aiding in smoking cessation and preventing associated weight gain, controlling weight gain associated with smoking cessation by an individual attempting to cease smoking tobacco, reducing weight gain associated with smoking cessation by an individual attempting to cease smoking tobacco, treating nicotine dependency, addiction and/or withdrawal in an individual attempting to treat nicotine dependency, addiction and/or withdrawal, or reducing the likelihood of relapse use of nicotine by an individual attempting to cease nicotine use, comprising:

administering a compound selected from compounds provided herein, and salts, solvates, and hydrates thereof to an individual;

monitoring the individual for body weight during said administration; and discontinuing said administration if the body weight of the individual decreases by more than about 1 kg during said administration.

In some embodiments, the compound is for use as an aid to smoking cessation treatment. In some embodiments, the compound is for use as an aid for cessation of cigarette smoking. In some embodiments, the compound is for use as an aid to smoking cessation treatment and the prevention of associated weight gain. In some embodiments, the compound is for use as a weight-neutral intervention for smoking cessation. In some embodiments, the weight gain occurs during smoking cessation. In some embodiments, the weight gain occurs post-smoking cessation.

Any embodiment of the invention directed to smoking cessation or the cessation or lessening of use of a tobacco product can be adapted to the cessation or lessening of use of nicotine administration from any and all sources or any individual source, including tobacco products (or specific examples thereof), tobacco replacement therapy (or specific examples thereof), and/or any electronic nicotine delivery system (e.g., electronic cigarettes or personal vaporizers). The present invention specifically embraces all such embodiments.

In some embodiments, prior to administration of the compound selected from compounds provided herein, and salts, solvates, and hydrates thereof, the individual smokes ≥10 cigarettes per day. In some embodiments, prior to administration of the compound selected from compounds provided herein, and salts, solvates, and hydrates thereof, the individual smokes 11-20 cigarettes per day. In some embodiments, prior to administration of the compound selected from compounds provided herein, and salts, solvates, and hydrates thereof, the individual smokes 21-30 cigarettes per day. In some embodiments, prior to administration of the compound selected from compounds provided herein, and salts, solvates, and hydrates thereof, the individual smokes ≥31 cigarettes per day.

In some embodiments, the individual has an initial BMI selected from one of the following: ≥24 kg/m$^2$, ≥23 kg/m$^2$, ≥22.5 kg/m$^2$, ≥22 kg/m$^2$, ≥21 kg/m$^2$, ≥20 kg/m$^2$, ≥19 kg/m$^2$, or ≥18.5 kg/m$^2$.

In some embodiments, prior to administration, the individual has an initial BMI≥23 kg/m$^2$. In some embodiments, prior to administration, the individual has an initial BMI≥22.5 kg/m$^2$. In some embodiments, prior to administration, the individual has an initial BMI≥22 kg/m$^2$. In some embodiments, prior to administration, the individual has an initial BMI≥18.5 kg/m$^2$. In some embodiments, prior to administration, the individual has an initial BMI≥18 kg/m$^2$. In some embodiments, prior to administration, the individual has an initial BMI≥17.5 kg/m$^2$. In some embodiments, prior to administration, the individual has an initial body mass index ≥25 kg/m$^2$ and at least one weight-related comorbid condition.

In some embodiments, prior to administration, the individual has an initial body mass index ≥27 kg/m$^2$. In some embodiments, prior to administration, the individual has an initial body mass index ≥27 kg/m$^2$ and at least one weight-related comorbid condition.

In some embodiments, the weight-related comorbid condition is selected from: hypertension, dyslipidemia, cardiovascular disease, glucose intolerance and sleep apnea. In some embodiments, the weight-related comorbid condition is selected from: hypertension, dyslipidemia, and type 2 diabetes.

In some embodiments, prior to administration, the individual has an initial body mass index ≥30 kg/m$^2$.

In some embodiments, the initial BMI of the individual prior to administration is 18.5 to 25 kg/m$^2$.

In some embodiments, the individual is suffering from depression prior to being administered the compound selected from compounds provided herein, and salts, solvates, and hydrates thereof.

In some embodiments, the individual is suffering from a preexisting psychiatric disease prior to being administered the compound selected from compounds provided herein, and salts, solvates, and hydrates thereof.

In some embodiments, the preexisting psychiatric disease is chosen from schizophrenia, bipolar disorder, or major depressive disorder.

In some embodiments, individuals are assessed for nicotine dependence based on the Fagerström score. In some embodiments, the individual has a score of 0, 1, or 2. In some embodiments, the individual has a score of 3 or 4. In some embodiments, the individual has a score of 5. In some embodiments, the individual has a score of 6 or 7. In some embodiments, the individual has a score of 8, 9, or 10. In some embodiments, the individual has a score ≥3. In some embodiments, the individual has a score ≥5. In some embodiments, the individual has a score ≥6. In some embodiments, the individual has a score ≥8.

In some embodiments, the individual has a Fagerström score of 0, 1, or 2 and a BMI <25 kg/m$^2$. In some embodiments, the individual has a Fagerström score of 0, 1, or 2 and a BMI≥25 kg/m$^2$ and <30 kg/m$^2$. In some embodiments, the individual has a Fagerström score of 0, 1, or 2 and a BMI≥30 kg/m$^2$.

In some embodiments, the individual has a Fagerström score of 3 or 4 and a BMI <25 kg/m$^2$. In some embodiments, the individual has a Fagerström score of 3 or 4 and a BMI≥25 kg/m$^2$ and <30 kg/m$^2$. In some embodiments, the individual has a Fagerström score of 3 or 4 and a BMI≥30 kg/m$^2$.

In some embodiments, the individual has a Fagerström score of 5 and a BMI <25 kg/m$^2$. In some embodiments, the individual has a Fagerström score of 5 and a BMI≥25 kg/m$^2$ and <30 kg/m$^2$. In some embodiments, the individual has a Fagerström score of 5 and a BMI≥30 kg/m$^2$.

In some embodiments, the individual has a Fagerström score of 6 or 7 and a BMI <25 kg/m$^2$. In some embodiments, the individual has a Fagerström score of 6 or 7 and a BMI≥25 kg/m$^2$ and <30 kg/m$^2$. In some embodiments, the individual has a Fagerström score of 6 or 7 and a BMI≥30 kg/m$^2$.

In some embodiments, the individual has a Fagerström score of 8, 9, or 10 and a BMI <25 kg/m$^2$. In some embodiments, the individual has a Fagerström score of 8, 9, or 10 and a BMI≥25 kg/m$^2$ and <30 kg/m$^2$. In some embodiments, the individual has a Fagerström score of 8, 9, or 10 and a BMI≥30 kg/m$^2$.

In some embodiments, the individual has a Fagerström score of ≥3 and a BMI <25 kg/m$^2$. In some embodiments, the individual has a Fagerström score of ≥3 and a BMI 25 kg/m$^2$ and <30 kg/m$^2$. In some embodiments, the individual has a Fagerström score of ≥3 and a BMI≥30 kg/m$^2$.

In some embodiments, the individual has a Fagerström score of ≥5 and a BMI <25 kg/m$^2$. In some embodiments, the individual has a Fagerström score of ≥5 and a BMI≥25 kg/m$^2$ and <30 kg/m$^2$. In some embodiments, the individual has a Fagerström score of ≥5 and a BMI≥30 kg/m$^2$.

In some embodiments, the individual has a Fagerström score of ≥6 and a BMI <25 kg/m$^2$. In some embodiments, the individual has a Fagerström score of ≥6 and a BMI≥25 kg/m$^2$ and <30 kg/m$^2$. In some embodiments, the individual has a Fagerström score of ≥6 and a BMI≥30 kg/m$^2$.

In some embodiments, the individual has a Fagerström score of ≥8 and a BMI <25 kg/m$^2$. In some embodiments, the individual has a Fagerström score of ≥8 and a BMI≥25 kg/m$^2$ and <30 kg/m$^2$. In some embodiments, the individual has a Fagerström score of ≥8 and a BMI≥30 kg/m$^2$.

In some embodiments, a questionnaire is used to evaluate symptoms experienced during quit, such as the urge to smoke, withdrawal, or reinforcing effects. In some embodiments, the questionnaire is selected from: the Minnesota Nicotine Withdrawal Score (MNWS), Brief Questionnaire of Smoking Urges (QSU-Brief), McNett Coping Effectiveness Questionnaire (mCEQ), Three-Factor Eating Questionnaire (TFEQ), and Food Craving Inventory (FCI).

In some embodiments, the nicotine dependency, addiction and/or withdrawal results from the use of tobacco products. In some embodiments, the nicotine dependency, addiction, and/or withdrawal results from cigarette smoking.

In some embodiments, the nicotine dependency, addiction and/or withdrawal results from the use of nicotine replacement therapies.

In some embodiments, the individual is first administered the compound selected from compounds provided herein, and salts, solvates, and hydrates thereof on the target quit day. In some embodiments, the individual is administered the compound at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 days prior to the target quit day. In some embodiments, the individual is administered the compound at least 7 days prior to the target quit day. In some embodiments, the individual is administered the compound about 7 to about 35 days prior to the target quit day. In some embodiments, the individual is administered the compound at least 14 days prior to the target quit day. In some embodiments, the individual is administered the compound about 14 to about 35 days prior to the target quit day.

In some embodiments, the individual quits smoking between days 8 and 35 of treatment. In some embodiments, the individual quits smoking between days 15 and 35 of treatment. In some embodiments, the individual quits smoking between days 22 and 35 of treatment. In some embodiments, the individual quits smoking on day 8 of treatment. In some embodiments, the individual quits smoking on day 15 of treatment. In some embodiments, the individual quits smoking on day 22 of treatment.

In some embodiments, prior to administering the compound selected from compounds provided herein, and salts, solvates, and hydrates thereof, the method further comprises the step of: instructing the individual to set a date to cease smoking tobacco. In some embodiments, administration of the compound is initiated about 7 days prior to the date set to cease smoking tobacco.

In some embodiments, after administering the compound selected from compounds provided herein, and salts, solvates, and hydrates thereof, the method further comprises the step of: instructing the individual to set a date to cease smoking tobacco. In some embodiments, the date set to cease smoking tobacco occurs after at least 7 days of administration of the compound selected from compounds provided herein, and salts, solvates, and hydrates thereof. In some embodiments, the date set to cease smoking tobacco occurs prior to 35 days of administration of the compound.

In some embodiments, the individual previously attempted to cease smoking tobacco but did not succeed in ceasing smoking tobacco. In some embodiments, the individual previously attempted to cease smoking tobacco but subsequently relapsed and resumed smoking tobacco.

In some embodiments, the administration leads to a statistically significant improvement in the ability to tolerate the cessation of smoking as measured by analysis of data from the MPSS test.

In some embodiments, the individual has abstained from nicotine use for 12 weeks prior to prescribing and/or administering the compound selected from compounds provided herein, and salts, solvates, and hydrates thereof.

In some embodiments, the individual has abstained from nicotine use for 24 weeks prior to prescribing and/or administering the compound selected from compounds provided herein, and salts, solvates, and hydrates thereof.

In some embodiments, the individual has abstained from nicotine use for 9 months prior to prescribing and/or administering the compound selected from compounds provided herein, and salts, solvates, and hydrates thereof.

In some embodiments, the individual has abstained from nicotine use for 52 weeks prior to prescribing and/or administering the compound selected from compounds provided herein, and salts, solvates, and hydrates thereof.

In some embodiments, abstinence is self-reported. In some embodiments, the self-reporting based on response to a questionnaire. In some embodiments, the questionnaire is a Nicotine Use Inventory. In some embodiments, an individual self-reports as not having smoking any cigarettes (even a puff). In some embodiments, the individual self-reports as not having used any other nicotine-containing products. In some embodiments, the individual self-reports as not having smoking any cigarettes (even a puff) and not having used any other nicotine-containing products.

In some embodiments, the duration of treatment is selected from: 12 weeks, 6 months, 9 months, 1 year, 18 months, 2 years, 3 years, 4 years, and 5 years.

In some embodiments, the compound selected from compounds provided herein, and salts, solvates, and hydrates thereof is administered for at least about 2 weeks. In some embodiments, the compound is administered for at least about 4 weeks. In some embodiments, the compound is administered for at least about 8 weeks. In some embodiments, the compound is administered for at least about 12 weeks. In some embodiments, the compound is administered for at least about 6 months.

In some embodiments, the compound is administered for at least about 1 year. In some embodiments, the compound is administered for at least about 2 years. In some embodiments, the compound is administered for between about 7 weeks to about 12 weeks. In some embodiments, the compound is administered for between about 12 weeks to about 52 weeks. In some embodiments, the compound is administered for between about 6 months to about 1 year.

In some embodiments, the individual receives treatment for a first treatment period. In some embodiments, the individual receives treatment for an additional treatment period, e.g., to increase the likelihood of long-term abstinence. In some embodiments, an individual who fails in a first treatment period is administered the compound selected from compounds provided herein, and salts, solvates, and hydrates thereof optionally in combination with a supplemental agent for a second treatment period. In some embodiments, an individual who relapses during a first treatment is administered the compound selected from compounds provided herein, and salts, solvates, and hydrates thereof optionally in combination with a supplemental agent for a second treatment period. In some embodiments, an individual who relapses following a first treatment is administered the compound selected from compounds provided herein, and salts, solvates, and hydrates thereof optionally in combination with a supplemental agent for a second treatment period. In some embodiments, the first treatment period is 12 weeks. In some embodiments, the second treatment period is 12 weeks or less. In some embodiments, the second treatment period is 12 weeks. In some embodiments, the second treatment period is more than 12 weeks. In some embodiments, the first treatment period is one year. In some embodiments, the second treatment period is one year or less. In some embodiments, the second treatment period is one year. In some embodiments, the first treatment period is longer than the second treatment period. In some embodiments, the first treatment period is shorter than the second treatment period. In some embodiments, the first treatment period and the second period are of the same length of time.

In some embodiments, the prevention or reduction of weight gain, or inducement of weight loss, is measured relative to the amount of weight gain or loss typically experienced when an individual attempts smoking cessation. In some embodiments, the prevention or reduction of weight gain, or inducement of weight loss, is measured relative the amount of weight gain or loss typically experienced when an individual attempts smoking cessation with another drug.

In some embodiments, controlling weight gain comprises preventing weight gain. In some embodiments, controlling weight gain comprises inducing weight loss. In some embodiments, controlling weight gain comprises inducing weight loss of at least about 0.5%, 1%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, or 20%. In some embodiments, the weight loss is at least 1%. In some embodiments, the weight loss is at least 1.5%. In some embodiments, the weight loss is at least about 2%. In some embodiments, the weight loss is at least 3%. In some embodiments, the weight loss is at least 4%. In some embodiments, the weight loss is at least 5%. In some embodiments, controlling weight gain comprises decreasing BMI. In some embodiments, controlling weight gain comprises decreasing in percent body fat. In some embodiments, controlling weight gain comprises decreasing waist circumference. In some embodiments, controlling weight gain comprises decreasing BMI by at least about 0.25, 0.5, 1, 1.5, 2, 2.5, 3, 3.5, 4, 4.5, 5, 6, 7, 8, 9, 10, 11, 12, 13, 14, 15, 16, 17, 18, 19, or 20 kg/m$^2$. In some embodiments, BMI is decreased by at least 1 kg/m$^2$. In some embodiments, BMI is decreased by at least 1.5 kg/m$^2$. In some embodiments, BMI is decreased by at least 2 kg/m$^2$. In some embodiments, BMI is decreased by at least 2.5 kg/m$^2$. In some embodiments, BMI is decreased by at least 5 kg/m$^2$. In some embodiments, BMI is decreased by at least 10 kg/m$^2$. In some embodiments, controlling weight gain comprises decreasing percent body fat by at least about 0.5%, 1%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, or 20%. In some embodiments, the decrease in percent body fat is at least 1%. In some embodiments, the decrease in percent body fat is at least 2.5%. In some embodiments, the decrease in percent body fat is at least 5%. In some embodiments, controlling weight gain comprises decreasing waist circumference by at least about 0.5, 1, 1.5, 2, 2.5, 3, 3.5, 4, 4.5, 5, 6, 7, 8, 9, or 10 cm. In some embodiments, the decrease in waist circumference is at least 1 cm. In some embodiments, the decrease in waist circumference is at least 2.5 cm. In some embodiments, the decrease in waist circumference is at least 5 cm. In some embodiments, controlling weight gain comprises decreasing body weight by at least about 0.5, 1, 1.5, 2, 2.5, 3, 3.5, 4, 4.5, 5, 6, 7, 8, 9, or 10 kg. In some embodiments, the decrease in body weight is at least 1 kg. In some embodiments, the decrease in body weight is at least 2.5 kg. In some embodiments, the decrease in body weight is at least 5 kg.

In some embodiments, the BMI of the individual becomes a BMI selected from one of the following: ≥18 kg/m$^2$, ≥17.5 kg/m$^2$, ≥17 kg/m$^2$, ≥16 kg/m$^2$, and ≥15 kg/m$^2$.

In some embodiments, the decrease in body weight is selected from one of the following: more than about 1.5%, more than about 2%, more than about 2.5%, more than about 3%, more than about 3.5%, more than about 4%, more than about 4.5%, and more than about 5%.

In some embodiments, the decrease in body weight is selected from one of the following: more than about 1.5 kg, more than about 2 kg, more than about 2.5 kg, more than about 3 kg, more than about 3.5 kg, more than about 4 kg, more than about 4.5 kg, and more than about 5 kg.

In some embodiments, the individual in need of treatment has a BMI selected from: ≥25 kg/m², ≥24 kg/m², ≥23 kg/m², ≥22 kg/m², ≥21 kg/m², ≥20 kg/m², ≥19 kg/m², and ≥18.5 kg/m². In some embodiments, BMI is not decreased by more than about 0.25, 0.5, 1, 1.5, 2, 2.5, 3, 3.5, 4, 4.5, 5, 6, 7, 8, 9, 10, 11, 12, 13, 14, 15, 16, 17, 18, 19, or 20 kg/m². In some embodiments, BMI is not decreased by more than 1 kg/m². In some embodiments, BMI is not decreased by more than 1.5 kg/m². In some embodiments, BMI is not decreased by more than 2 kg/m². In some embodiments, BMI is not decreased by more than 2.5 kg/m². In some embodiments, BMI is not decreased by more than 5 kg/m². In some embodiments, BMI is not decreased by more than 10 kg/m². In some embodiments, percent body fat is not decreased by more than about 0.5%, 1%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, or 20%. In some embodiments, percent body fat is not decreased by more than 1%. In some embodiments, percent body fat is not decreased by more than 2.5%. In some embodiments, percent body fat is not decreased by more than 5%. In some embodiments, waist circumference is not decreased by more than about 0.5, 1, 1.5, 2, 2.5, 3, 3.5, 4, 4.5, 5, 6, 7, 8, 9, or 10 cm. In some embodiments, waist circumference is not decreased by more than 1 cm.

In some embodiments, waist circumference is not decreased by more than 2.5 cm. In some embodiments, waist circumference is not decreased by more than 5 cm. In some embodiments, body weight is not decreased by more than about 0.5, 1, 1.5, 2, 2.5, 3, 3.5, 4, 4.5, 5, 6, 7, 8, 9, or 10 kg. In some embodiments, the decrease in body weight is not more than 1 kg. In some embodiments, the decrease in body weight is not more than 2.5 kg. In some embodiments, the decrease in body weight is not more than 5 kg.

In some embodiments, controlling weight gain comprises maintaining at least some weight loss for at least about 12 weeks, at least about 6 months, at least about 9 months, at least about one year, at least about 18 months, or at least about two years. For example, in some embodiments, an individual loses 5 kg during a first treatment and maintains at least 1 kg of that weight loss during a second treatment. In some embodiments, an individual loses 3 kg during the first 12 weeks of a treatment, and loses a total of 5 kg after one year of the treatment.

In some embodiments, use of the compound selected from compounds provided herein, and salts, solvates, and hydrates thereof is discontinued. For example, in some embodiments, use of the compound selected from compounds provided herein, and salts, solvates, and hydrates thereof is discontinued if the BMI of an individual becomes ≤ about 15 kg/m², ≤ about 15.5 kg/m², ≤ about 16 kg/m², ≤ about 16.5 kg/m², ≤ about 17 kg/m², ≤ about 17.5 kg/m², ≤ about 18 kg/m², ≤ about 18.5 kg/m², ≤ about 19 kg/m², ≤ about 19.5 kg/m²≤ about 20 kg/m², ≤ about 20.5 kg/m², ≤ about 21 kg/m², about 21.5 kg/m², ≤ about 22 kg/m², ≤ about 22.5 kg/m², or ≤ about 23 kg/m².

In some embodiments, the individual experiences one or more additional beneficial effects as a result of the administration of the compound selected from compounds provided herein, and salts, solvates, and hydrates thereof, optionally in combination with at least one supplemental agent, as described herein.

In some embodiments, the one or more additional beneficial effects are chosen from a decrease in an assessment of weight, an improvement in cardiovascular indications, and/or an improved glycemia. In some embodiments, the one or more additional beneficial effects are chosen from a decrease in an assessment of weight, an improvement in cardiovascular indications, and/or an improved lipidemia.

In some embodiments, the one or more additional beneficial effects comprise a decrease in an assessment of weight. In some embodiments, the decrease in an assessment of weight comprises weight loss. In some embodiments, the one or more beneficial effects comprises a decrease in hunger, a decrease in food cravings, or an increase in intermeal interval.

In some embodiments, the one or more additional beneficial effects comprise an improvement in one or more cardiovascular indications. In some embodiments, the improvement in one or more cardiovascular indications comprises one or more of a reduction in systolic and diastolic blood pressure (SBP and DBP, respectively), a decrease in heart rate, a decrease in total cholesterol, a decrease in LDL cholesterol, a decrease in HDL cholesterol, and/or a decrease in triglyceride levels.

In some embodiments, the one or more additional beneficial effects comprise a reduction in SBP. In some embodiments, the reduction in SBP in an individual without type 2 diabetes is at least about 2 mmHg. In some embodiments, the reduction in SBP in an individual without type 2 diabetes is between 2 and 5 mmHg. In some embodiments, reduction in SBP in an individual with type 2 diabetes is at least about 2 mmHg. In some embodiments, the reduction in SBP in an individual with type 2 diabetes is between about 2 and 5 mmHg. In some embodiments, the reduction in SBP in an individual with baseline impaired fasting glucose is at least about 1 mmHg. In some embodiments, the reduction in SBP in an individual with baseline impaired fasting glucose is between about 1 and 5 mmHg.

In some embodiments, the one or more additional beneficial effects comprise a reduction in DBP. In some embodiments, the reduction in DBP in an individual without type 2 diabetes is at least about 1 mmHg. In some embodiments, the reduction in DBP in an individual without type 2 diabetes is at least between about 1 and 5 mmHg. In some embodiments, the reduction in DBP in an individual with type 2 diabetes is at least about 1 mmHg. In some embodiments, the reduction in DBP in an individual with type 2 diabetes is between about 1 and 5 mmHg. In some embodiments, the reduction in DBP in an individual with baseline impaired fasting glucose is at least about 1 mmHg. In some embodiments, the reduction in DBP in an individual with baseline impaired fasting glucose is between about 1 and 5 mmHg.

In some embodiments, the one or more additional beneficial effects comprise a reduction in heart rate. In some embodiments, the reduction in heart rate in an individual without type 2 diabetes is at least about 2 BPM. In some embodiments, the reduction in heart rate in an individual without type 2 diabetes is between about 2 and 5 BPM. In some embodiments, the reduction in heart rate in an individual with type 2 diabetes is at least about 2 BPM. In some embodiments, the reduction in heart rate in an individual with type 2 diabetes is between about 2 and 5 BPM. In some embodiments, the reduction in heart rate in an individual with baseline impaired fasting glucose is at least about 2 BPM. In some embodiments, the reduction in heart rate in an individual with baseline impaired fasting glucose is between about 2 and 5 BPM.

In some embodiments, the improvement in lipidemia comprises a decrease in total cholesterol level. In some embodiments, the decrease in total cholesterol level in individuals without type 2 diabetes is at least about 1 mg/dL. In some embodiments, the decrease in total cholesterol level in individuals without type 2 diabetes is between about 1.5 and 2 mg/dL. In some embodiments, the decrease in total cholesterol level in individuals with type 2 diabetes is at least about 0.5 mg/dL. In some embodiments, the decrease in total cholesterol level in individuals with type 2 diabetes is between about 0.5 and 1 mg/dL. In some embodiments, the decrease in total cholesterol level in individuals with baseline impaired fasting glucose is at least about 2 mg/dL. In some embodiments, the decrease in total cholesterol level in individuals with baseline impaired fasting glucose is between about 2 and 3 mg/dL.

In some embodiments, the improvement in lipidemia comprises a decrease in LDL cholesterol level. In some embodiments, the decrease in LDL cholesterol level in individuals without type 2 diabetes is at least about 1 mg/dL. In some embodiments, the decrease in LDL cholesterol level in individuals without type 2 diabetes is between about 1 and 2 mg/dL. In some embodiments, the decrease in LDL cholesterol level in individuals with type 2 diabetes is at least about 1 mg/dL. In some embodiments, the decrease in LDL cholesterol level in individuals with type 2 diabetes is between about 1 and 1.5 mg/dL. In some embodiments, the decrease in LDL cholesterol level in individuals with baseline impaired fasting glucose is at least about 2 mg/dL. In some embodiments, the decrease in LDL cholesterol level in individuals with baseline impaired fasting glucose is between about 2 and 3 mg/dL.

In some embodiments, the improvement in lipidemia comprises a decrease in HDL cholesterol level. In some embodiments, the decrease in HDL cholesterol level in individuals without type 2 diabetes is at least about 4 mg/dL. In some embodiments, the decrease in HDL cholesterol level in individuals without type 2 diabetes is between about 3 and 6 mg/dL. In some embodiments, the decrease in HDL cholesterol level in individuals with type 2 diabetes is at least about 5 mg/dL. In some embodiments, the decrease in HDL cholesterol level in individuals with type 2 diabetes is between about 7 and 10 mg/dL. In some embodiments, the decrease in HDL cholesterol level in individuals with baseline impaired fasting glucose is at least about 2 mg/dL. In some embodiments, the decrease in HDL cholesterol level in individuals with baseline impaired fasting glucose is between about 2 and 3 mg/dL.

In some embodiments, the one or more additional beneficial effects comprise an improvement in glycemia. In some embodiments, the improvement in glycemia comprises a reduction in fasting plasma glucose and/or a reduction in glycated hemoglobin (A1C) levels. In some embodiments, the improvement in glycemia comprises a reduction in fasting plasma glucose. In some embodiments, the improvement in glycemia comprises a reduction in glycated hemoglobin (A1C) levels. In some embodiments, the improvement in glycemia comprises a decrease in triglyceride levels.

The compounds provided herein can be administered in a wide variety of dosage forms.

In some embodiments, the compound selected from compounds provided herein, and salts, solvates, and hydrates thereof is administered in a tablet suitable for oral administration.

In some embodiments, the active ingredient is formulated as an immediate-release dosage form using, e.g., techniques known in the art. In some embodiments, the active ingredient is formulated as a modified-release dosage form using, e.g., techniques known in the art. In some embodiments, the active ingredient is formulated as a sustained-release dosage form using, e.g., techniques known in the art. In some embodiments, the active ingredient is formulated as a delayed-release dosage form using, e.g., techniques known in the art.

In some embodiments, the method comprises a plurality of administrations of the modified-release dosage form, with a frequency wherein the average interval between any two sequential administrations is: at least about 24 hours; or about 24 hours.

In some embodiments, the method comprises a plurality of administrations of the modified-release dosage form, and the modified-release dosage form is administered once-a-day.

In some embodiments, the plurality of administrations is: at least about 30; at least about 180; at least about 365; or at least about 730.

COMBINATION THERAPY

A compound or a pharmaceutically acceptable salt, solvate or hydrate thereof can be administered as the sole active pharmaceutical agent (i.e., mono-therapy), or it can be used in combination with one or more weight loss drug either administered together or separately. Provided are methods for weight management, inducing satiety, decreasing food intake, aiding smoking cessation, and for preventing and treating obesity, antipsychotic-induced weight gain, type 2 diabetes, Prader-Willi syndrome, tobacco dependence, nicotine dependence, drug addiction, alcohol addiction, pathological gambling, reward deficiency syndrome, sex addiction, obsessive-compulsive spectrum disorders, impulse control disorders, nail-biting, onychophagia, sleep disorders, insomnia, fragmented sleep architecture, disturbances of slow-wave sleep, urinary incontinence, psychiatric disorders, schizophrenia, anorexia nervosa, bulimia nervosa, Alzheimer disease, sexual dysfunction, erectile dysfunction, epilepsy, movement disorder, parkinsonism, antipsychotic-induced movement disorder, hypertension, dyslipidemia, nonalcoholic fatty liver disease, obesity-related renal disease, and sleep apnea, comprising administering to an individual in need thereof a therapeutically effective amount of a compound described herein, in combination with one or more weight loss drugs as described herein.

Also provided are methods for decreasing food intake in an individual in need thereof, comprising administering to said individual a therapeutically effective amount of a compound described herein, in combination with one or more weight loss drugs as described herein.

Also provided are methods for inducing satiety in an individual in need thereof, comprising administering to said individual a therapeutically effective amount of a compound described herein, in combination with one or more weight loss drugs as described herein.

Also provided are methods for the treatment of obesity in an individual in need thereof, comprising administering to said individual a therapeutically effective amount of a compound described herein, in combination with one or more weight loss drugs as described herein.

Also provided are methods for the prevention of obesity in an individual in need thereof, comprising administering to said individual a therapeutically effective amount of a compound described herein, in combination with one or more weight loss drugs as described herein.

Also provided are methods for weight management in an individual in need thereof, comprising administering to said individual a therapeutically effective amount of a compound described herein, in combination with one or more weight loss drugs as described herein.

Also provided are methods for preventing type 2 diabetes in an individual in need thereof, comprising administering to said individual a therapeutically effective amount of a compound described herein, in combination with one or more weight loss drugs as described herein.

When a compound disclosed herein is administered as a combination therapy with a weight loss drug the compound and the weight loss drug can be formulated as separate pharmaceutical compositions given at the same time or at different times; or the compound disclosed herein and the pharmaceutical agent can be formulated together as a single unit dosage.

Provided are the compounds described herein for use in combination with a weight loss drug for use in a method of treatment of the human or animal body by therapy.

Also provided are the compounds described herein for use in combination with a weight loss drug for weight management, inducing satiety, decreasing food intake, aiding smoking cessation, and for preventing and treating obesity, antipsychotic-induced weight gain, type 2 diabetes, Prader-Willi syndrome, addiction, tobacco dependence, nicotine dependence, drug addiction, alcohol addiction, pathological gambling, reward deficiency syndrome, sex addiction, obsessive-compulsive spectrum disorders, impulse control disorders, nail-biting, onychophagia, sleep disorders, insomnia, fragmented sleep architecture, disturbances of slow-wave sleep, urinary incontinence, psychiatric disorders, schizophrenia, anorexia nervosa, bulimia nervosa, Alzheimer disease, sexual dysfunction, erectile dysfunction, epilepsy, movement disorder, parkinsonism, antipsychotic-induced movement disorder, hypertension, dyslipidemia, nonalcoholic fatty liver disease, obesity-related renal disease, and sleep apnea, comprising administering to an individual in need thereof a therapeutically effective amount of a compound described herein, in combination with one or more weight loss drugs as described herein.

Also provided are the compounds described herein for use in combination with a weight loss drug for decreasing food intake in an individual in need thereof, comprising administering to said individual a therapeutically effective amount of a compound described herein, in combination with one or more weight loss drugs as described herein.

Also provided are the compounds described herein for use in combination with a weight loss drug for inducing satiety in an individual in need thereof, comprising administering to said individual a therapeutically effective amount of a compound described herein, in combination with one or more weight loss drugs as described herein.

Also provided are the compounds described herein for use in combination with a weight loss drug for the treatment of obesity in an individual in need thereof, comprising administering to said individual a therapeutically effective amount of a compound described herein, in combination with one or more weight loss drugs as described herein.

Also provided are the compounds described herein for use in combination with a weight loss drug for the prevention of obesity in an individual in need thereof, comprising administering to said individual a therapeutically effective amount of a compound described herein, in combination with one or more weight loss drugs as described herein.

Also provided are the compounds described herein for use in combination with a weight loss drug for weight management in an individual in need thereof, comprising administering to said individual a therapeutically effective amount of a compound described herein, in combination with one or more weight loss drugs as described herein.

Also provided are the compounds described herein for use in combination with a weight loss drug for treating type 2 diabetes in an individual in need thereof, comprising administering to said individual a therapeutically effective amount of a compound described herein, in combination with one or more weight loss drugs as described herein.

Also provided are the compounds described herein for use in combination with a weight loss drug for preventing type 2 diabetes in an individual in need thereof, comprising administering to said individual a therapeutically effective amount of a compound described herein, in combination with one or more weight loss drugs as described herein.

In some embodiments, the compound described herein and the weight loss drug are administered simultaneously.

In some embodiments, the compound described herein and the weight loss drug are administered separately.

In some embodiments, the compound described herein and the weight loss drug are administered sequentially.

In some embodiments, the weight loss drug chosen from sodium/glucose cotransporter-2 (SGLT2) inhibitors, lipase inhibitors, monoamine reuptake inhibitors, anticonvulsants, glucose sensitizers, incretin mimetics, amylin analogs, GLP-1 analogs, Y receptor peptides, $5\text{-HT}_{2C}$ receptor agonists, opioid receptor antagonists, appetite suppressants, anorectics, and hormones and the like, either specifically disclosed herein or specifically disclosed in any reference recited herein just as if each and every combination was individually and explicitly recited. In some embodiments, the weight loss drug is chosen from dapagliflozin, canagliflozin, ipragliflozin, tofogliflozin, empagliflozin, remogliflozin etabonate, orlistat, cetilistat, alaproclate, citalopram, dapoxetine, escitalopram, femoxetine, fluoxetine, fluvoxamine, ifoxetine, indalpine, omiloxetine, panuramine, paroxetine, pirandamine, sertraline, zimelidine, desmethylcitalopram, desmethylsertraline, didesmethylcitalopram, seproxetine, cianopramine, litoxetine, lubazodone, trazodone, vilazodone, vortioxetine, dextromethorphan, dimenhydrinate, diphenhydramine, mepyramine, pyrilamine, methadone, propoxyphene, mesembrine, roxindole, amedalin, tomoxetine, daledalin, edivoxetine, esreboxetine, lortalamine, mazindol, nisoxetine, reboxetine, talopram, talsupram, tandamine, viloxazine, maprotiline, bupropion, ciclazindol, manifaxine, radafaxine, tapentadol, teniloxazine, ginkgo biloba, altropane, difluoropine, iometopane, vanoxerine, medifoxamine, *Chaenomeles speciosa*, hyperforin, adhyperforin, bupropion, pramipexole, cabergoline, venlafaxine, desvenlafaxine, duloxetine, milnacipran, levomilnacipran, bicifadine, amineptine, desoxypipradrol, dexmethylphenidate, difemetorex, diphenylprolinol, ethylphenidate, fencamfamine, fencamine, lefetamine, mesocarb, methylenedioxypyrovalerone, methylphenidate, nomifensine, oxolinic acid, pipradrol, prolintane, pyrovalerone, tametraline, nefopam, amitifadine, tesofensine, tedatioxetine, bicifadine, brasofensine, diclofensine, taxil, naphyrone, hyperforin, topiramate, zonisamide, metformin, rosiglitazone, pioglitazone, troglitazone, exenatide, liraglutide, taspoglutide, obinepitide, pramlintide, peptide YY, vabicaserin, naltrexone, naloxone, phentermine, diethylpropion, oxymetazoline, benfluorex, butenolide cathine, phenmetrazine, phenylpropanolamine, pyroglutamyl-histidyl-glycine, amphetamine, benzphetamine, dexmethylphenidate, dextroamphetamine, methylenedioxypyrovalerone, glucagon, lisdexamfetamine, methamphetamine, methylphenidate, phendimetrazine, phenethylamine, caffeine, bromocriptine, ephedrine, pseudoephedrine, rimonabant, surinabant, mirtazapine, Dietex®, MG Plus Protein™, insulin, and leptin and pharmaceutically acceptable salts and combinations thereof. In some embodiments, the weight loss drug is phentermine.

In some embodiments, the weight management further comprises a surgical weight loss procedure.

In some embodiments, the weight management further comprises a reduced-calorie diet.

In some embodiments, the weight management further comprises a program of regular exercise.

In some embodiments, the individual has an initial body mass index ≥25 kg/m².

In some embodiments, the individual has an initial body mass index ≥27 kg/m².

In some embodiments, the individual has at least one weight related comorbid condition.

In some embodiments, the weight related comorbid condition is selected from: hypertension, dyslipidemia, cardiovascular disease, glucose intolerance and sleep apnea.

In some embodiments, the weight related comorbid condition is selected from: hypertension, dyslipidemia, and type 2 diabetes.

In some embodiments, the individual has an initial body mass index ≥30 kg/m².

Also provided are methods for treating type 2 diabetes in an individual in need thereof, comprising administering to said individual a therapeutically effective amount of a compound described herein, in combination with one or more weight loss drugs as described herein.

REPRESENTATIVE METHODS

Provided are methods for decreasing food intake in an individual in need thereof, comprising administering to said individual a therapeutically effective amount of a compound provided herein.

Also provided are methods for inducing satiety in an individual in need thereof, comprising administering to said individual a therapeutically effective amount of a compound provided herein.

Also provided are methods for the treatment of obesity in an individual in need thereof, comprising administering to said individual a therapeutically effective amount of a compound provided herein.

Also provided are methods for the prevention of obesity in an individual in need thereof, comprising administering to said individual a therapeutically effective amount of a compound provided herein.

Also provided are methods for weight management in an individual in need thereof, comprising administering to said individual a therapeutically effective amount of a compound provided herein.

In some embodiments, the weight management further comprises a surgical weight loss procedure.

In some embodiments, the weight management further comprises a surgical weight loss procedure.

In some embodiments, the weight management comprises weight loss.

In some embodiments, the weight management comprises maintenance of weight loss.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual in need of weight management is an obese patient with an initial body mass index ≥30 kg/m².

In some embodiments, the individual in need of weight management is an overweight patient with an initial body mass index ≥27 kg/m² in the presence of at least one weight related comorbid condition.

In some embodiments, the weight related co-morbid condition is selected from: hypertension, dyslipidemia, cardiovascular disease, glucose intolerance and sleep apnea.

Also provided are methods for the treatment of antipsychotic-induced weight gain in an individual in need thereof, comprising administering to said individual a therapeutically effective amount of a compound provided herein.

Also provided are methods for the treatment of type 2 diabetes in an individual in need thereof, comprising administering to said individual a therapeutically effective amount of a compound provided herein.

Also provided are methods for the treatment of type 2 diabetes in an individual in need thereof, comprising administering to said individual a therapeutically effective amount of a compound provided herein combination with one or more type 2 diabetes medications.

In some embodiments, the need for the one or more type 2 diabetes treatments is reduced.

In some embodiments, the need for the one or more type 2 diabetes treatments is eliminated.

Also provided are methods for the prevention of type 2 diabetes in an individual in need thereof, comprising administering to said individual a therapeutically effective amount of a compound provided herein.

Also provided are methods for the treatment of Prader-Willi syndrome in an individual in need thereof, comprising administering to said individual a therapeutically effective amount of a compound provided herein.

Also provided are methods for the treatment of addiction in an individual in need thereof, comprising administering to said individual a therapeutically effective amount of a compound provided herein.

Also provided are methods for the treatment of drug and alcohol addiction in an individual in need thereof, comprising administering to said individual a therapeutically effective amount of a compound provided herein.

Also provided are methods for the treatment of alcohol addiction in an individual in need thereof, comprising administering to said individual a therapeutically effective amount of a compound provided herein.

Also provided are methods for the treatment of drug addiction in an individual in need thereof, comprising administering to said individual a therapeutically effective amount of a compound provided herein.

In some embodiments, the drug is selected from amphetamine, a substituted amphetamine, a benzodiazepine, an atypical benzodiazepine receptor ligand, marijuana, cocaine, dextromethorphan, GHB, LSD, ketamine, a monoamine reuptake inhibitor, nicotine, an opiate, PCP, a substituted phenethylamine, psilocybin, and an anabolic steroid.

In some embodiments, the drug is nicotine.

In some embodiments, the drug is amphetamine.

In some embodiments, the drug is a substituted amphetamine.

In some embodiments, the drug is methamphetamine.

In some embodiments, the drug is a benzodiazepine.

In some embodiments, the drug is an atypical benzodiazepine receptor ligand.

In some embodiments, the drug is marijuana.

In some embodiments, the drug is cocaine.

In some embodiments, the drug is dextromethorphan.

In some embodiments, the drug is eszopiclone.

In some embodiments, the drug is GHB.

In some embodiments, the drug is LSD.

In some embodiments, the drug is ketamine.

In some embodiments, the drug is a monoamine reuptake inhibitor.

In some embodiments, the drug is an opiate.

In some embodiments, the drug is PCP.

In some embodiments, the drug is a substituted phenethylamine.

In some embodiments, the drug is psilocybin.

In some embodiments, the drug is an anabolic steroid.

In some embodiments, the drug is zolpidem.

Also provided are methods for aiding smoking cessation in an individual in need thereof, comprising administering to said individual a therapeutically effective amount of a compound provided herein.

Also provided are methods for the treatment of tobacco dependence in an individual in need thereof, comprising administering to said individual a therapeutically effective amount of a compound provided herein.

Also provided are methods for the treatment of nicotine dependence in an individual in need thereof, comprising administering to said individual a therapeutically effective amount of a compound provided herein.

Also provided are methods for the treatment of alcoholism in an individual in need thereof, comprising administering to said individual a therapeutically effective amount of a compound provided herein.

Also provided are methods for the treatment of pathological gambling in an individual in need thereof, comprising administering to said individual a therapeutically effective amount of a compound provided herein.

Also provided are methods for the treatment of reward deficiency syndrome in an individual in need thereof, comprising administering to said individual a therapeutically effective amount of a compound provided herein.

Also provided are methods for the treatment of sex addiction in an individual in need thereof, comprising administering to said individual a therapeutically effective amount of a compound provided herein.

Also provided are methods for the treatment of an obsessive-compulsive spectrum disorder in an individual in need thereof, comprising administering to said individual a therapeutically effective amount of a compound provided herein.

Also provided are methods for the treatment of an impulse control disorder in an individual in need thereof, comprising administering to said individual a therapeutically effective amount of a compound provided herein.

Also provided are methods for the treatment of nail-biting in an individual in need thereof, comprising administering to said individual a therapeutically effective amount of a compound provided herein.

Also provided are methods for the treatment of onychophagia in an individual in need thereof, comprising administering to said individual a therapeutically effective amount of a compound provided herein.

Also provided are methods for the treatment of a sleep disorder in an individual in need thereof, comprising administering to said individual a therapeutically effective amount of a compound provided herein.

Also provided are methods for the treatment of insomnia in an individual in need thereof, comprising administering to said individual a therapeutically effective amount of a compound provided herein.

Also provided are methods for the treatment of fragmented sleep architecture in an individual in need thereof, comprising administering to said individual a therapeutically effective amount of a compound provided herein.

Also provided are methods for the treatment of disturbances of slow-wave sleep in an individual in need thereof, comprising administering to said individual a therapeutically effective amount of a compound provided herein.

Also provided are methods for the treatment of urinary incontinence in an individual in need thereof, comprising administering to said individual a therapeutically effective amount of a compound provided herein.

Also provided are methods for the treatment of a psychiatric disorder in an individual in need thereof, comprising administering to said individual a therapeutically effective amount of a compound provided herein.

Also provided are methods for the treatment of schizophrenia in an individual in need thereof, comprising administering to said individual a therapeutically effective amount of a compound provided herein.

Also provided are methods for the treatment of anorexia nervosa in an individual in need thereof, comprising administering to said individual a therapeutically effective amount of a compound provided herein.

Also provided are methods for the treatment of bulimia nervosa in an individual in need thereof, comprising administering to said individual a therapeutically effective amount of a compound provided herein.

Also provided are methods for the treatment of Alzheimer disease in an individual in need thereof, comprising administering to said individual a therapeutically effective amount of a compound provided herein.

Also provided are methods for the treatment of sexual dysfunction in an individual in need thereof, comprising administering to said individual a therapeutically effective amount of a compound provided herein.

Also provided are methods for the treatment of erectile dysfunction in an individual in need thereof, comprising administering to said individual a therapeutically effective amount of a compound provided herein.

Also provided are methods for the treatment of a seizure disorder in an individual in need thereof, comprising administering to said individual a therapeutically effective amount of a compound provided herein.

Also provided are methods for the treatment of epilepsy in an individual in need thereof, comprising administering to said individual a therapeutically effective amount of a compound provided herein.

Also provided are methods for the treatment of Dravet syndrome in an individual in need thereof, comprising administering to said individual a therapeutically effective amount of a compound provided herein.

Also provided are methods for the treatment of a movement disorder in an individual in need thereof, comprising administering to said individual a therapeutically effective amount of a compound provided herein.

Also provided are methods for the treatment of parkinsonism in an individual in need thereof, comprising administering to said individual a therapeutically effective amount of a compound provided herein.

Also provided are methods for the treatment of antipsychotic-induced movement disorder in an individual in need thereof, comprising administering to said individual a therapeutically effective amount of a compound provided herein.

Also provided are methods for the treatment of hypertension in an individual in need thereof, comprising administering to said individual a therapeutically effective amount of a compound provided herein.

Also provided are methods for the treatment of dyslipidemia in an individual in need thereof, comprising administering to said individual a therapeutically effective amount of a compound provided herein.

Also provided are methods for the treatment of nonalcoholic fatty liver disease in an individual in need thereof, comprising administering to said individual a therapeutically effective amount of a compound provided herein.

Also provided are methods for the treatment of obesity-related renal disease in an individual in need thereof, comprising administering to said individual a therapeutically effective amount of a compound provided herein.

Also provided are methods for the treatment of sleep apnea in an individual in need thereof, comprising administering to said individual a therapeutically effective amount of a compound provided herein.

Also provided are uses of a compound provided herein for the manufacture of a medicament for decreasing food intake.

Also provided are uses of a compound provided herein for the manufacture of a medicament for inducing satiety of a compound provided herein.

Also provided are uses of a compound provided herein for the manufacture of a medicament for the treatment of obesity.

Also provided are uses of a compound provided herein for the manufacture of a medicament for the prevention of obesity.

Also provided are uses of a compound provided herein for the manufacture of a medicament for weight management.

In some embodiments, the weight management further comprises a surgical weight loss procedure.

In some embodiments, the weight management comprises weight loss.

In some embodiments, the weight management comprises maintenance of weight loss.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual in need of weight management is an obese patient with an initial body mass index $\geq 30$ kg/m$^2$.

In some embodiments, the individual in need of weight management is an overweight patient with an initial body mass index $\geq 27$ kg/m$^2$ in the presence of at least one weight related comorbid condition.

In some embodiments, the weight related co-morbid condition is selected from: hypertension, dyslipidemia, cardiovascular disease, glucose intolerance and sleep apnea.

Also provided are uses of a compound provided herein for the manufacture of a medicament for the treatment of antipsychotic-induced weight gain.

Also provided are uses of a compound provided herein for the manufacture of a medicament for the treatment of type 2 diabetes.

Also provided are uses of a compound provided herein for the manufacture of a medicament for the treatment of type 2 diabetes in combination with one or more type 2 diabetes medications.

In some embodiments, the need for the one or more type 2 diabetes treatments is reduced.

In some embodiments, the need for the one or more type 2 diabetes treatments is eliminated.

Also provided are uses of a compound provided herein for the manufacture of a medicament for the prevention of type 2 diabetes.

Also provided are uses of a compound provided herein for the manufacture of a medicament for the treatment of Prader-Willi syndrome.

Also provided are uses of a compound provided herein for the manufacture of a medicament for the treatment of addiction.

Also provided are uses of a compound provided herein for the manufacture of a medicament for the treatment of drug and alcohol addiction.

Also provided are uses of a compound provided herein for the manufacture of a medicament for the treatment of alcohol addiction.

Also provided are uses of a compound provided herein for the manufacture of a medicament for the treatment of drug addiction.

In some embodiments, the drug is selected from amphetamine, a substituted amphetamine, a benzodiazepine, an atypical benzodiazepine receptor ligand, marijuana, cocaine, dextromethorphan, GHB, LSD, ketamine, a monoamine reuptake inhibitor, nicotine, an opiate, PCP, a substituted phenethylamine, psilocybin, and an anabolic steroid.

In some embodiments, the drug is nicotine.

In some embodiments, the drug is amphetamine.

In some embodiments, the drug is a substituted amphetamine.

In some embodiments, the drug is methamphetamine.

In some embodiments, the drug is a benzodiazepine.

In some embodiments, the drug is an atypical benzodiazepine receptor ligand.

In some embodiments, the drug is marijuana.

In some embodiments, the drug is cocaine.

In some embodiments, the drug is dextromethorphan.

In some embodiments, the drug is eszopiclone.

In some embodiments, the drug is GHB.

In some embodiments, the drug is LSD.

In some embodiments, the drug is ketamine.

In some embodiments, the drug is a monoamine reuptake inhibitor.

In some embodiments, the drug is an opiate.

In some embodiments, the drug is PCP.

In some embodiments, the drug is a substituted phenethylamine.

In some embodiments, the drug is psilocybin.

In some embodiments, the drug is an anabolic steroid.

In some embodiments, the drug is zolpidem.

Also provided are uses of a compound provided herein for the manufacture of a medicament for aiding smoking cessation.

Also provided are uses of a compound provided herein for the manufacture of a medicament for the treatment of tobacco dependence.

Also provided are uses of a compound provided herein for the manufacture of a medicament for the treatment of nicotine dependence.

Also provided are uses of a compound provided herein for the manufacture of a medicament for the treatment of alcoholism.

Also provided are uses of a compound provided herein for the manufacture of a medicament for the treatment of pathological gambling.

Also provided are uses of a compound provided herein for the manufacture of a medicament for the treatment of reward deficiency syndrome.

Also provided are uses of a compound provided herein for the manufacture of a medicament for the treatment of sex addiction.

Also provided are uses of a compound provided herein for the manufacture of a medicament for the treatment of an obsessive-compulsive spectrum disorder.

Also provided are uses of a compound provided herein for the manufacture of a medicament for the treatment of an impulse control disorder.

Also provided are uses of a compound provided herein for the manufacture of a medicament for the treatment of nail-biting.

Also provided are uses of a compound provided herein for the manufacture of a medicament for the treatment of onychophagia.

Also provided are uses of a compound provided herein for the manufacture of a medicament for the treatment of a sleep disorder.

Also provided are uses of a compound provided herein for the manufacture of a medicament for the treatment of insomnia.

Also provided are uses of a compound provided herein for the manufacture of a medicament for the treatment of fragmented sleep architecture.

Also provided are uses of a compound provided herein for the manufacture of a medicament for the treatment of disturbances of slow-wave sleep.

Also provided are uses of a compound provided herein for the manufacture of a medicament for the treatment of urinary incontinence.

Also provided are uses of a compound provided herein for the manufacture of a medicament for the treatment of a psychiatric disorder.

Also provided are uses of a compound provided herein for the manufacture of a medicament for the treatment of schizophrenia.

Also provided are uses of a compound provided herein for the manufacture of a medicament for the treatment of anorexia nervosa.

Also provided are uses of a compound provided herein for the manufacture of a medicament for the treatment of bulimia nervosa.

Also provided are uses of a compound provided herein for the manufacture of a medicament for the treatment of Alzheimer disease.

Also provided are uses of a compound provided herein for the manufacture of a medicament for the treatment of sexual dysfunction.

Also provided are uses of a compound provided herein for the manufacture of a medicament for the treatment of erectile dysfunction.

Also provided are uses of a compound provided herein for the manufacture of a medicament for the treatment of a seizure disorder.

Also provided are uses of a compound provided herein for the manufacture of a medicament for the treatment of epilepsy.

Also provided are uses of a compound provided herein for the manufacture of a medicament for the treatment of Dravet syndrome.

Also provided are uses of a compound provided herein for the manufacture of a medicament for the treatment of a movement disorder.

Also provided are uses of a compound provided herein for the manufacture of a medicament for the treatment of parkinsonism.

Also provided are uses of a compound provided herein for the manufacture of a medicament for the treatment of antipsychotic-induced movement disorder.

Also provided are uses of a compound provided herein for the manufacture of a medicament for the treatment of hypertension.

Also provided are uses of a compound provided herein for the manufacture of a medicament for the treatment of dyslipidemia.

Also provided are uses of a compound provided herein for the manufacture of a medicament for the treatment of nonalcoholic fatty liver disease.

Also provided are uses of a compound provided herein for the manufacture of a medicament for the treatment of obesity-related renal disease.

Also provided are uses of a compound provided herein for the manufacture of a medicament for the treatment of sleep apnea.

In some embodiments, the individual is also being prescribed and/or administered a supplemental agent.

Also provided is a composition comprising a compound selected from compounds provided herein, and salts, solvates, and hydrates thereof and at least one supplemental agent.

As used herein, "supplemental agent" refers to an additional therapeutic agent which complements the activity of the 5-HT$_{2C}$ agonists described herein as it relates to methods for reducing the frequency of smoking tobacco in an individual attempting to reduce frequency of smoking tobacco; aiding in the cessation or lessening of use of a tobacco product in an individual attempting to cease or lessen use of a tobacco product; aiding in smoking cessation and preventing associated weight gain; controlling weight gain associated with smoking cessation by an individual attempting to cease smoking tobacco; reducing weight gain associated with smoking cessation by an individual attempting to cease smoking tobacco; treating nicotine dependency, addiction and/or withdrawal in an individual attempting to treat nicotine dependency, addiction and/or withdrawal; or reducing the likelihood of relapse use of nicotine by an individual attempting to cease nicotine use. In some embodiments, the "supplemental agent" is not phentermine.

Supplemental agents include nicotine replacement therapies, antidepressants and anxiolytics such as selective serotonin reuptake inhibitors, e.g., citalopram, escitalopram, fluoxetine, paroxetine, sertraline, and the like. Serotonin and norepinephrine reuptake inhibitors, such as duloxetine, venlafaxine, and the like may also be used. Norepinephrine and dopamine reuptake inhibitors such as bupropion may also be used. Tetracyclic antidepressants such as mirtazapine; combined reuptake inhibitors and receptor blockers such as trazodone, nefazodone, maprotiline; tricyclic antidepressants, such as amitriptyline, amoxapine, desipramine, doxepin, imipramine, nortriptyline, protriptyline and trimipramine; monoamine oxidase inhibitors, such as phenelzine, tranylcypromine, isocarboxazid, selegiline; benzodiazepines such as lorazepam, clonazepam, alprazolam, and diazepam; serotonin 1A receptor agonists such as buspirone, aripiprazole, quetiapine, tandospirone and bifeprunox; and a beta-adrenergic receptor blocker, such as propranolol may also be used. Other supplemental agents include other pharmacologic agents such as UTP, amiloride, antibiotics, bronchodilators, anti-inflammatory agents, and mucolytics (e.g., n-acetyl-cysteine).

In some embodiments, the supplemental agent is chosen from nicotine replacement therapies.

In some embodiments, the nicotine replacement therapy is chosen from nicotine gum, nicotine transdermal systems, nicotine lozenges, nicotine microtabs, and nicotine sprays or inhalers. In some embodiments, the supplemental agent is an electronic cigarette.

In some embodiments, the supplemental agent is nicotine gum, and the composition is a composition comprising a compound selected from compounds provided herein, and salts, solvates, and hydrates thereof and nicotine gum.

In some embodiments, the supplemental agent is a nicotine transdermal system, and the composition is a composition comprising a compound selected from compounds provided herein, and salts, solvates, and hydrates thereof and a nicotine transdermal system.

In some embodiments, the supplemental agent is nicotine lozenges, and the composition is a composition comprising a compound selected from compounds provided herein, and salts, solvates, and hydrates thereof and nicotine lozenges.

In some embodiments, the supplemental agent is nicotine microtabs, and the composition is a composition comprising a compound selected from compounds provided herein, and salts, solvates, and hydrates thereof and nicotine microtabs.

In some embodiments, the supplemental agent is nicotine sprays or inhalers, and the composition is a composition comprising a compound selected from compounds provided herein, and salts, solvates, and hydrates thereof and nicotine sprays or inhalers.

In some embodiments, the supplemental agent is an electronic cigarette, and the composition is a composition comprising a compound selected from compounds provided herein, and salts, solvates, and hydrates thereof and an electronic cigarette.

In some embodiments, the supplemental agent is chosen from antidepressants, and the composition is a composition comprising a compound selected from compounds provided herein, and salts, solvates, and hydrates thereof and a supplemental agent chosen from antidepressants.

In some embodiments, the supplemental agent is an antidepressant, and the composition is a composition comprising a compound selected from compounds provided herein, and salts, solvates, and hydrates thereof and an antidepressant.

In some embodiments, the compound selected from compounds provided herein, and salts, solvates, and hydrates thereof and the antidepressant are formulated as a fixed dose combination product.

In some embodiments, the compound selected from compounds provided herein, and salts, solvates, and hydrates thereof and the antidepressant are formulated as a co-packaged product.

In some embodiments, the compound selected from compounds provided herein, and salts, solvates, and hydrates thereof and the antidepressant are formulated for adjunctive therapy.

In some embodiments, the supplemental agent is nortriptyline, and the composition is a composition comprising a compound selected from compounds provided herein, and salts, solvates, and hydrates thereof and nortriptyline.

In some embodiments, the compound selected from compounds provided herein, and salts, solvates, and hydrates thereof and the nortriptyline are formulated as a fixed dose combination product.

In some embodiments, the compound selected from compounds provided herein, and salts, solvates, and hydrates thereof and the nortriptyline are formulated as a co-packaged product.

In some embodiments, the compound selected from compounds provided herein, and salts, solvates, and hydrates thereof and the nortriptyline are formulated for adjunctive therapy.

In some embodiments, the supplemental agent is nortriptyline, and the composition is a composition comprising a compound selected from compounds provided herein, and salts, solvates, and hydrates thereof and bupropion.

In some embodiments, the compound selected from compounds provided herein, and salts, solvates, and hydrates thereof and the bupropion are formulated as a fixed dose combination product.

In some embodiments, the compound selected from compounds provided herein, and salts, solvates, and hydrates thereof and the bupropion are formulated as a co-packaged product.

In some embodiments, the compound selected from compounds provided herein, and salts, solvates, and hydrates thereof and the bupropion are formulated for adjunctive therapy.

In some embodiments, the supplemental agent is nortriptyline, and the composition is a composition comprising a compound selected from compounds provided herein, and salts, solvates, and hydrates thereof and clonidine.

In some embodiments, the compound selected from compounds provided herein, and salts, solvates, and hydrates thereof and the clonidine are formulated as a fixed dose combination product.

In some embodiments, the compound selected from compounds provided herein, and salts, solvates, and hydrates thereof and the clonidine are formulated as a co-packaged product.

In some embodiments, the compound selected from compounds provided herein, and salts, solvates, and hydrates thereof and the clonidine are formulated for adjunctive therapy.

In some embodiments, the supplemental agent is nortriptyline, and the composition is a composition comprising a compound selected from compounds provided herein, and salts, solvates, and hydrates thereof and varenicline.

In some embodiments, the compound selected from compounds provided herein, and salts, solvates, and hydrates thereof and the varenicline are formulated as a fixed dose combination product.

In some embodiments, the compound selected from compounds provided herein, and salts, solvates, and hydrates thereof and the varenicline are formulated as a co-packaged product.

In some embodiments, the compound selected from compounds provided herein, and salts, solvates, and hydrates thereof and the varenicline are formulated for adjunctive therapy.

In some embodiments, the individual has previously undergone treatment with a supplemental agent. In some embodiments, the individual was refractory to the previous treatment with the supplemental agent.

In some embodiments, the individual has previously undergone treatment with a nicotine replacement therapy. In some embodiments, the individual was refractory to the previous treatment with the nicotine replacement therapy.

Also provided is a composition comprising a compound selected from compounds provided herein, and salts, solvates, and hydrates thereof and at least one supplemental agent for: reducing the frequency of smoking tobacco in an individual attempting to reduce frequency of smoking tobacco;

aiding in the cessation or lessening of use of a tobacco product in an individual attempting to cease or lessen use of a tobacco product;
aiding in smoking cessation and preventing associated weight gain;
controlling weight gain associated with smoking cessation by an individual attempting to cease smoking tobacco;
reducing weight gain associated with smoking cessation by an individual attempting to cease smoking tobacco;
treating nicotine dependency, addiction and/or withdrawal in an individual attempting to treat nicotine dependency, addiction and/or withdrawal; or
reducing the likelihood of relapse use of nicotine by an individual attempting to cease nicotine use.

Also provided is a composition comprising a compound selected from compounds provided herein, and salts, solvates, and hydrates thereof and at least one supplemental agent for use as a medicament for:
reducing the frequency of smoking tobacco in an individual attempting to reduce frequency of smoking tobacco;
aiding in the cessation or lessening of use of a tobacco product in an individual attempting to cease or lessen use of a tobacco product;
aiding in smoking cessation and preventing associated weight gain;
controlling weight gain associated with smoking cessation by an individual attempting to cease smoking tobacco;
reducing weight gain associated with smoking cessation by an individual attempting to cease smoking tobacco;
treating nicotine dependency, addiction and/or withdrawal in an individual attempting to treat nicotine dependency, addiction and/or withdrawal; or
reducing the likelihood of relapse use of nicotine by an individual attempting to cease nicotine use.

Also provided is a composition comprising a compound selected from compounds provided herein, and salts, solvates, and hydrates thereof and at least one supplemental agent in the manufacture of a medicament for: reducing the frequency of smoking tobacco in an individual attempting to reduce frequency of smoking tobacco; aiding in the cessation or lessening of use of a tobacco product in an individual attempting to cease or lessen use of a tobacco product; aiding in smoking cessation and preventing associated weight gain; controlling weight gain associated with smoking cessation by an individual attempting to cease smoking tobacco; reducing weight gain associated with smoking cessation by an individual attempting to cease smoking tobacco; treating nicotine dependency, addiction and/or withdrawal in an individual attempting to treat nicotine dependency, addiction and/or withdrawal; or reducing the likelihood of relapse use of nicotine by an individual attempting to cease nicotine use.

Also provided is a unit dosage form of a composition comprising a compound selected from compounds provided herein, and salts, solvates, and hydrates thereof and at least one supplemental agent.

Also provided is a compound selected from compounds provided herein, and salts, solvates, and hydrates thereof for use in combination with a supplemental agent, for: reducing the frequency of smoking tobacco in an individual attempting to reduce frequency of smoking tobacco; aiding in the cessation or lessening of use of a tobacco product in an individual attempting to cease or lessen use of a tobacco product; aiding in smoking cessation and preventing associated weight gain; controlling weight gain associated with smoking cessation by an individual attempting to cease smoking tobacco; reducing weight gain associated with smoking cessation by an individual attempting to cease smoking tobacco; treating nicotine dependency, addiction and/or withdrawal in an individual attempting to treat nicotine dependency, addiction and/or withdrawal; or reducing the likelihood of relapse use of nicotine by an individual attempting to cease nicotine use.

Also provided is a supplemental agent chosen from nicotine replacement therapies, for use in combination with a compound selected from compounds provided herein, and salts, solvates, and hydrates thereof.

Also provided is a supplemental agent for use in combination with a compound selected from compounds provided herein, and salts, solvates, and hydrates thereof for: reducing the frequency of smoking tobacco in an individual attempting to reduce frequency of smoking tobacco; aiding in the cessation or lessening of use of a tobacco product in an individual attempting to cease or lessen use of a tobacco product; aiding in smoking cessation and preventing associated weight gain; controlling weight gain associated with smoking cessation by an individual attempting to cease smoking tobacco; reducing weight gain associated with smoking cessation by an individual attempting to cease smoking tobacco; treating nicotine dependency, addiction and/or withdrawal in an individual attempting to treat nicotine dependency, addiction and/or withdrawal; or reducing the likelihood of relapse use of nicotine by an individual attempting to cease nicotine use.

In some embodiments, the compound is formulated as an immediate-release dosage form and the supplemental agent is also formulated as an immediate-release dosage form. In some embodiments, the 5-HT$_C$ agonist is formulated as an immediate-release dosage form and the supplemental agent is formulated as a modified-release dosage form. In some embodiments, the compound is formulated as a modified-release dosage form and the supplemental agent is formulated as an immediate-release dosage form. In some embodiments, the compound selected from compounds provided herein, and salts, solvates, and hydrates thereof is formulated as a modified-release dosage form and the supplemental agent is also formulated as a modified-release dosage form.

The compound selected from compounds provided herein, and salts, solvates, and hydrates thereof may be administered sequentially or concurrently with the one or more other supplemental agents identified herein. The amounts of formulation and pharmacologic agent depend, for example, on what type of pharmacologic agent(s) are used, and the scheduling and routes of administration Supplemental agents may be delivered concomitantly with the compounds selected from compounds provided herein, and salts, solvates, and hydrates thereof, or may be administered independently. Supplemental agent delivery may be via any suitable method known in the art including orally, inhalation, injection, etc.

In some embodiments, the methods described herein further comprise the step of: providing the individual with educational materials and/or counseling. In some embodiments, the counseling relates to smoking cessation. In some embodiments, the counseling relates to weight management, including without limitation counseling regarding diet and exercise. In some embodiments, the counseling relates to both smoking cessation and weight management, including without limitation counseling regarding diet and exercise.

In some embodiments, the methods described herein further comprise the step of: providing the individual with biochemical feedback; acupuncture; hypnosis; behavioral intervention; support services; and/or psychosocial treatment.

It will be apparent to those skilled in the art that the dosage forms described herein may comprise, as the active component, either a compound described herein, a pharmaceutically acceptable salt of a compound described herein, a solvate or hydrate of a compound described herein, or a solvate or hydrate of a pharmaceutically acceptable salt of a compound described herein. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present disclosure pertains to methods of administering hydrates and solvates of compounds described herein and/or their pharmaceutically acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

PSUEDOPOLYMORPHISM

Polymorphism is the ability of a substance to exist as two or more crystalline phases that have different arrangements and/or conformations of the molecules in the crystal lattice. Polymorphs show the same properties in the liquid or gaseous state but they may behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

Recently, polymorph screens of 245 compounds revealed that about 90% of them exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, Crystal Growth & Design (2007), 7(6), 1007-1026.)

ISOTOPES

The present disclosure includes all isotopes of atoms occurring in the present salts and crystalline forms thereof. Isotopes include those atoms having the same atomic number but different mass numbers. One aspect of the present invention includes every combination of one or more atoms in the present salts and crystalline forms thereof that is replaced with an atom having the same atomic number but a different mass number. One such example is the replacement of an atom that is the most naturally abundant isotope, such as $^1H$ or $^{12}C$, found in one the present salts and crystalline forms thereof, with a different atom that is not the most naturally abundant isotope, such as $^2H$ or $^3H$ (replacing $^1H$), or $^{11}C$, $^{13}C$, or $^{14}C$ (replacing $^{12}C$). A salt wherein such a replacement has taken place is commonly referred to as being isotopically-labeled. Isotopic-labeling of the present salts and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include $^{11}C$, $^{13}C$, and $^{14}C$. Isotopes of nitrogen include $^{13}N$ and $^{15}N$. Isotopes of oxygen include $^{15}O$, $^{17}O$, and $^{18}O$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present salts and crystalline forms thereof, wherein the naturally occurring distribution of the isotopes in the composition is perturbed. Another aspect of the present invention includes compositions and pharmaceutical compositions comprising salts and crystalline forms thereof as described herein wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Improving absorption, distribution, metabolism, excretion and toxicity (ADMET) properties while maintaining a desired pharmacological profile is a major challenge in drug development. Structural changes to improve ADMET properties often alter the pharmacology of a lead compound. While the effects of deuterium substitution on ADMET properties are unpredictable, in select cases deuterium can improve a compound's ADMET properties with minimal perturbation of its pharmacology. Two examples where deuterium has enabled improvements in therapeutic entities are: CTP-347 and CTP-354. CTP-347 is a deuterated version of paroxetine with a reduced liability for mechanism-based inactivation of CYP2D6 that is observed clinically with paroxetine. CTP-354 is a deuterated version of a promising preclinical gamma-aminobutyric acid A receptor (GABAA) modulator (L-838417) that was not developed due to poor pharmacokinetic (PK) properties. In both cases, deuterium substitution resulted in improved ADMET profiles that provide the potential for improved safety, efficacy, and/or tolerability without significantly altering the biochemical potency and selectivity versus the all-hydrogen compounds. Provided are deuterium substituted compounds of the present invention with improved ADMET profiles and substantially similar biochemical potency and selectivity versus the corresponding all-hydrogen compounds.

OTHER UTILITIES

Provided are radio-labeled compounds provided herein useful not only in radio-imaging but also in assays, both in vitro and in vivo, for localizing and quantitating 5-HT$_{2C}$ receptors in tissue samples, including human, and for identifying 5-HT$_{2C}$ receptor ligands by inhibition binding of a radio-labeled compound. Also provided are novel 5-HT$_{2C}$ receptor assays of which comprise such radio-labeled compounds.

Certain isotopically-labeled compounds provided herein are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds provided herein can generally be prepared by following procedures analogous to those disclosed in the Drawings and Examples infra, by substituting an isotopically labeled reagent for a non-isotopically labeled reagent. Other synthetic methods that are useful are discussed infra.

Synthetic methods for incorporating radio-isotopes into organic compounds are applicable to compounds provided herein and are well known in the art. These synthetic methods, for example, incorporating activity levels of tritium into target molecules, include the following:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl (3H) products by treating appropriate precursors with high specific activity methyl iodide (3H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [e.g. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled compound disclosed herein can be used in a screening assay to identify/evaluate compounds. In general terms, a newly synthesized or identified compound (i.e., test compound) can be evaluated for its ability to reduce binding of a radio-labeled compound to a 5-HT$_{2C}$ receptor. The ability of a test compound to compete with a radio-labeled compound disclosed herein for the binding to a 5-HT$_{2C}$ receptor directly correlates to its binding affinity.

Certain labeled compounds provided herein bind to certain 5-HT$_{2C}$ receptors. In one embodiment the labeled compound has an IC$_{50}$ less than about 500 µM. In one embodiment the labeled compound has an IC$_{50}$ less than about 100 µM. In one embodiment the labeled compound has an IC$_{50}$ less than about 10 µM. In one embodiment the labeled compound has an IC$_{50}$ less than about 1 µM. In one embodiment the labeled compound has an IC$_{50}$ less than about 0.1 µM. In one embodiment the labeled compound has an IC$_{50}$ less than about 0.01 µM. In one embodiment the labeled compound has an IC$_{50}$ less than about 0.005 µM.

Other uses of the disclosed receptors and methods will become apparent to those skilled in the art based upon, inter alia, a review of this disclosure.

COMPOSITIONS AND FORMULATIONS

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants can be used in tablets and capsules for oral administration. Liquid preparations for oral administration can be in the form of solutions, emulsions, aqueous or oily suspensions and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives and flavorings and colorants can be added to the liquid preparations. Parenteral dosage forms can be prepared by dissolving the compound provided herein in a suitable liquid vehicle and filter sterilizing the solution before filling and sealing an appropriate vial or ampule. These are just a few examples of the many appropriate methods well known in the art for preparing dosage forms.

A compound provided herein can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.).

While it is possible that, for use in the prophylaxis or treatment, a compound provided herein can, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds provided herein, together with a conventional adjuvant, carrier, or diluent, can thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof can comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds provided herein can be used as active ingredients in pharmaceutical compositions, specifically as 5-$HT_{2C}$ receptor modulators. The term "active ingredient", defined in the context of a "pharmaceutical composition"," refers to a component of a pharmaceutical composition that provides the primary pharmacological effect, as opposed to an "inactive ingredient" which would generally be recognized as providing no pharmaceutical benefit.

The dose when using the compounds provided herein can vary within wide limits and as is customary and is known to the physician, it is to be tailored to the individual conditions in each individual case. It depends, for example, on the nature and severity of the illness to be treated, on the condition of the individual, such as a patient, on the compound employed, on whether an acute or chronic disease state is treated, or prophylaxis conducted, or on whether further active compounds are administered in addition to the compounds provided herein. Representative doses include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the healthcare provider it may be necessary to deviate upward or downward from the doses described herein.

All dosage amounts disclosed herein are calculated with respect to the active moiety, i.e., the molecule or ion that gives the intended pharmacologic or physiologic action.

The amount of active ingredient, or an active salt or derivative thereof, required for use in treatment will vary not only with the particular salt selected but also with the route of administration, the nature of the condition being treated and the age and condition of the individual and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the individual, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis conducted or whether further active compounds are administered in addition to the compounds provided herein such as part of a drug combination. The dosage regimen for treating a disease condition with the compounds and/or compositions provided herein is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods disclosed herein.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds provided herein can be administered in a wide variety of oral and parenteral dosage forms.

For preparing pharmaceutical compositions from the compounds provided herein, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" refers to the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds provided herein may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds provided herein may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds provided herein or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds provided herein as an aerosol can be prepared by processes well known to the person skilled in the art. For their preparation, for example, solutions or dispersions of the compounds provided herein in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds provided herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds provided herein which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1,N^2$-dibenzylethane-1,2-diamine), chloroprocaine (2-(diethylamino)ethyl 4-(chloroamino)benzoate), choline, diethanolamine, ethylenediamine, meglumine ((2R,3R,4R,5S)-6-(methylamino)hexane-1,2,3,4,5-pentaol), procaine (2-(diethylamino)ethyl 4-aminobenzoate), and the like. Certain pharmaceutically acceptable salts are listed in Berge, et al., *Journal of Pharmaceutical Sciences*, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds provided herein may form solvates with standard low molecular weight solvents using methods known to the skilled artisan.

Compounds provided herein can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds provided herein containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987.

Some embodiments include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the 5-$HT_{2C}$ receptor modulators are utilized as active ingredients in pharmaceutical compositions, these are not intended for use in humans only, but in non-human mammals as well. Recent advances in the area of animal health-care mandate that consideration be given for the use of active agents, such as 5-$HT_{2C}$ receptor modulators, for the treatment of a 5-$HT_{2C}$ receptor-associated disease or disorder in companionship animals (e.g., cats, dogs, etc.) and in livestock animals (e.g., horses, cows, etc.) Those of ordinary skill in the art are readily credited with understanding the utility of such compounds in such settings.

As will be recognized, the steps of the methods provided herein need not be performed any particular number of times or in any particular sequence. Additional objects, advantages and novel features of the invention(s) will become apparent to those skilled in the art upon examination of the following examples thereof, which are intended to be illustrative and not intended to be limiting.

EXAMPLES

The compounds disclosed herein and their syntheses are further illustrated by the following examples. The following examples are provided to further define the invention without, however, limiting the invention to the particulars of these examples. The compounds described herein, supra and infra, are named according to ChemBioDraw Ultra 12.0.2.1076, except for compounds 101, 105, 108, 113, 114, 116, 129, 130, 133, and 134, in table A, for which ChemBioDraw Ultra 12.0.2.1076 did not generate a chemical name. In certain instances common names are used and it is understood that these common names would be recognized by those skilled in the art.

Chemistry: Proton nuclear magnetic resonance ($^1$H NMR) spectra were recorded on a Bruker Avance III-400 equipped with a 5 mm BBFO probe. Chemical shifts are given in parts per million (ppm) with the residual solvent signal used as reference. NMR abbreviations are used as follows: s=singlet, d=doublet, dd=doublet of doublets, t=triplet, q=quartet, m=multiplet, bs=broad singlet, sxt=sextet. Microwave irradiations were carried out using a Smith Synthesizer™ or an Emrys Optimizer™ (Biotage). Thin-layer chromatography (TLC) was performed on silica gel 60 $F_{254}$ (Merck), preparatory thin-layer chromatography (prep TLC) was performed on PK6F silica gel 60 Å 1 mm plates (Whatman) and column chromatography was carried out on a silica gel column using Kieselgel 60, 0.063-0.200 mm (Merck). Evaporation was done under reduced pressure on a Büchi rotary evaporator. Celite® 545 was used for filtration of palladium.

LCMS spec: HPLC-Agilent 1200; pumps: G1312A; DAD:G1315B; Autosampler: G1367B; Mass spectrometer-Agilent G1956A; ionization source: ESI; Drying Gas Flow: 10 L/min; Nebulizer Pressure: 40 psig; Drying Gas Temperature: 350° C.; Capillary Voltage: 2500 V) Software: Agilent Chemstation Rev.B.04.03.

Example 1: Syntheses of Compounds of Table A

Example 1.1: Preparation of 8'-fluoro-2',3',4',4a',5'-pentahydro-1'H-dispiro[cyclopropane-1,6'-cyclopropane-7',1''-naphtho[1,8-cd]-azepine] (Compound 105)

Step A: Preparation of N-(8-oxo-5,6,7,8-tetrahydronaphthalen-1-yl)acetamide

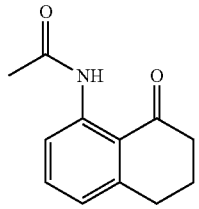

To a solution of 5,6,7,8-tetrahydronaphthalen-1-amine (10.6 g, 72.0 mmol) in CH$_2$Cl$_2$ (82 mL), acetic anhydride (10.2 mL, 108 mmol), and triethylamine (20.4 mL, 146.3 mmol) were added. After stirring at room temperature for 1 hour, the mixture was diluted with CH$_2$Cl$_2$ and acidified with saturated NH$_4$Cl solution. The aqueous layer was extracted with CH$_2$Cl$_2$. Organic layers were dried over MgSO$_4$, filtered and concentrated. The amide was used without further purification. The resulting amide in acetone (918 mL) and 1.48M aqueous magnesium sulfate (57.1 mL, 84.7 mmol) at 0° C. was treated with potassium permanganate (34.3 g, 217 mmol). The mixture was allowed to stir at 0° C. for 2 hours. Acetone was removed with residue extracted with CH$_2$Cl$_2$/water. Organic layers were washed with brine, dried over MgSO$_4$, filtered and concentrated. The residue was purified by biotage column chromatography (SiO$_2$, hexane/AcOEt gradient) to give N-(8-oxo-5,6,7,8-tetrahydronaphthalen-1-yl)acetamide (12.9 g, 64%). LCMS m/z=204.2 [M+1]$^+$; $^1$H NMR (400 MHz, CDCl$_3$) δ 2.07-2.11 (m, 2H), 2.22 (s, 3H), 2.70 (t, J=13.1 Hz, 2H), 2.97 (t, J=12.2 Hz, 2H), 6.91-6.93 (m, 1H), 7.44 (t, J=16.0 Hz, 1H), 8.60 (d, J=8.5 Hz, 1H), 12.1 (s, 1H).

Step B: Preparation of 8-amino-3,4-dihydronaphthalen-1(2H)-one

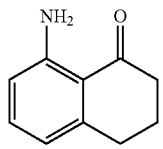

A mixture of N-(8-oxo-5,6,7,8-tetrahydronaphthalen-1-yl)acetamide (12.9 g, 63.5 mmol) in 6M HCl (437 mL, 2.62 mol) was heated at 90° C. for 3 hours. The mixture was cooled to room temperature and was neutralized with sodium bicarbonate by adding in small portions followed by addition of 2N NaOH until the mixture was at pH 8. The aqueous layer was extracted with AcOEt and washed with brine. Organic layers were combined, dried, filtered, and concentrated to give 8-amino-3,4-dihydronaphthalen-1(2H)-one (9.1 g, 89%). LCMS m/z=162.0 [M+1]$^+$. $^1$H NMR (400 MHz, CDCl$_3$) δ 2.02-2.06 (m, 2H), 2.61-2.64 (m, 2H), 2.87 (t, J=12.2 Hz, 2H), 6.44 (br s, 2H), 6.44-6.48 (m, 2H), 7.13-7.16 (m, 1H).

Step C: Preparation of 8-fluoro-3,4-dihydronaphthalen-1(2H)-one

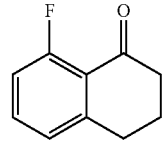

To a solution of 8-amino-3,4-dihydronaphthalen-1(2H)-one (9.1 g, 56.5 mmol) in CH$_2$Cl$_2$ (415 mL) at 0° C. boron trifluoride etherate (12.0 g, 84.7 mmol) was added. The mixture was stirred for 10 min and treated with a solution of tert-butyl nitrite (7.04 g, 68.3 mmol) in CH$_2$Cl$_2$ (50 mL) dropwise. The reaction was vigorously stirred at 0° C. for 1 hour. The solution was cooled in dry-ice bath, diluted in pentane (415 mL), and stirred for 10 min. The agitation was stopped, allowing the solid to settle, and the solvent was removed. This operation was repeated once, and the solid was dried under vacuum. The solid was heated in heptane at 100° C. for 2 hours. The reaction was cooled to room temperature, dissolved in CH$_2$Cl$_2$, and washed with water and brine. The organic layers were combined, dried over MgSO$_4$, filtered, and concentrated. The residue was purified by biotage column chromatography (SiO$_2$, hexane/AcOEt gradient) to give 8-fluoro-3,4-dihydronaphthalen-1(2H)-one (4.92 g, 53%). LCMS m/z=165.2 [M+1]$^+$; $^1$H NMR (400 MHz, CDCl$_3$) δ 2.09-2.13 (m, 2H), 2.64-2.67 (m, 2H), 2.97 (t, J=12.2 Hz, 2H), 6.95-6.99 (m, 1H), 7.04 (d, J=7.6 Hz, 1H), 7.38-7.43 (m, 1H).

Step D: Preparation of (2-chloroethyl)dimethylsulfonium iodide

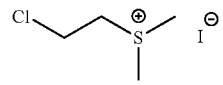

A mixture of (2-chloroethyl)(methyl)sulfane (4.1 mL, 45.2 mmol) and iodomethane (8.5 mL, 136.2 mmol) was stirred at room temperature for 4.5 days. To the dark brown residue, acetone (ca. 50 mL) was added and stirred for a while (ca. 1 h). Solid was filtered off, washed with acetone (3×), and dried under high vacuum to give (2-chloroethyl)dimethylsulfonium iodide (8.63 g, 76%) as an off-white solid. $^1$H NMR (400 MHz, DMSO-d$_6$) δ 2.97 (s, 6H), 3.79 (t, J=6.4 Hz, 2H), 4.13 (t, J=6.4 Hz, 2H).

Step E: Preparation of 8'-fluoro-3',4'-dihydro-1'H-spiro[cyclopropane-1,2'-naphthalen]-1'-one

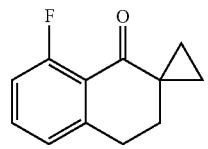

To a solution of 8-fluoro-3,4-dihydronaphthalen-1(2H)-one (1.34 g, 7.754 mmol) in 55 mL tBuOH, 1 M potassium 2-methylpropan-2-olate in THF (25 mL, 25.00 mmol) was added. After stirring at room temperature for 45 min, (2-chloroethyl)dimethylsulfonium iodide (2.2 g, 8.711 mmol) was added. After stirring at room temperature overnight, the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give 8'-fluoro-3',4'-dihydro-1'H-spiro[cyclopropane-1,2'-naphthalen]-1'-one (1.00 g, 68%) as a yellow-orange oil that solidified after a while. LCMS m/z=191.4 $[M+1]^+$. $^1$H NMR (400 MHz, $CDCl_3$) δ 0.81-0.84 (m, 2H), 1.43-1.45 (m, 2H), 1.65 (t, J=6.2 Hz, 2H), 2.92 (t, J=6.2 Hz, 2H), 6.96-7.01 (m, 1H), 7.04-7.06 (d, J=7.4 Hz, 1H), 7.38-7.43 (m, 1H).

Step F: Preparation of 8'-fluoro-1'-methylene-3',4'-dihydro-1'H-spiro[cyclopropane-1,2'-naphthalene]

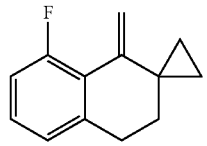

To a suspension of methyltriphenylphosphonium bromide (4.67 g, 8.958 mmol) in 35 mL toluene, 1 M potassium 2-methylpropan-2-olate in THF (13.5 mL, 13.50 mmol) was added. After stirring at 110° C. (oil bath) for 40 min, a solution of 8'-fluoro-3',4'-dihydro-1'H-spiro[cyclopropane-1,2'-naphthalen]-1'-one (1.66 g, 8.727 mmol) in 10 mL toluene was added. The mixture was stirred at 110° C. for 15 min, cooled in an ice/water-bath, and extracted with water and $CH_2Cl_2$. Organic phases were dried over $MgSO_4$, filtered, and concentrated. The residue was purified by biotage column chromatography ($SiO_2$, hexanes) to give 8'-fluoro-1'-methylene-3',4'-dihydro-1'H-spiro[cyclopropane-1,2'-naphthalene] (1.47 g, 90%) as a colorless liquid. $^1$H NMR (400 MHz, $CDCl_3$) δ 0.60-0.63 (m, 2H), 0.83-0.85 (m, 2H), 1.65 (t, J=6.4 Hz, 2H), 2.92 (t, J=6.4 Hz, 2H), 5.10 (d, J=3.6 Hz, 1H), 5.72 (s, 1H), 6.87-6.94 (m, 2H), 7.07-7.12 (m, 1H).

Step G: Preparation of Compound 14 of FIG. 2, where $R^1$=F

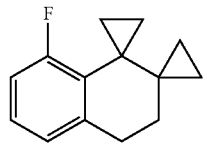

To an ice-cooled solution of 8'-fluoro-1'-methylene-3',4'-dihydro-1'H-spiro [cyclopropane-1,2'-naphthalene] (1.47 g, 7.809 mmol) and chloroiodomethane (3.4 mL, 46.84 mmol) in 53 mL DCE, 1 M diethylzinc in hexanes (39 mL, 39.00 mmol) was added over ca. 10 min. After stirring at 0° C. for 2.5 h, suspension was quenched by the addition of 1 M $NH_4Cl$ and extracted with water and $CH_2Cl_2$. Combined organic phases were dried over $MgSO_4$, filtered, and concentrated. The residue was purified by biotage column chromatography ($SiO_2$, hexanes) to give the title compound for this step (1.44 g, 91%) as a colorless liquid. $^1$H NMR (400 MHz, $CDCl_3$) δ 0.20-0.23 (m, 2H), 0.34-0.36 (m, 2H), 0.48-0.51 (m, 2H), 1.37-1.39 (m, 2H), 1.67 (t, J=6.3 Hz, 2H), 2.94-2.97 (t, J=6.3 Hz, 2H), 6.71-6.76 (m, 1H), 6.89-6.91 (m, 1H), 6.96-7.01 (m, 1H).

Step H: Preparation of Compound 15 of FIG. 2, where $R^1$=F

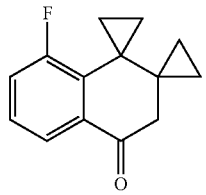

To a solution of the product of Step G (1.43 g, 7.070 mmol) in 30 mL DCE, sodium bicarbonate (312 mg, 3.714 mmol), dirhodium caprolactamate ($Rh_2(cap)_4$) (99.3 mg, 0.152 mmol), and 5.5 M 2-hydroperoxy-2-methylpropane in decane (8 mL, 44.00 mmol) were added. After stirring at 40° C. (oil bath) for 3 h, more $Rh_2(cap)_4$ (93 mg) was added. After stirring over-the-weekend, more $Rh_2(cap)_4$ (89 mg) and 5.5 M 2-hydroperoxy-2-methylpropane in decane (8 mL) were added. After stirring for another 3 h at 40° C., the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give the title compound for this step (85% pure, 1.34 g, 75%) as a colorless liquid. LCMS m/z=217.4 $[M+1]^+$. $^1$H NMR (400 MHz, $CDCl_3$) δ 0.26-0.46 (m, 4H), 0.59-0.65 (m, 2H), 1.47-1.49 (m, 2H), 2.59 (s, 2H), 7.10-7.15 (m, 1H), 7.19-7.24 (m, 1H), 7.89-7.91 (m, 1H).

Step I: Preparation of Compound 16 of FIG. 2, where $R^1$=F

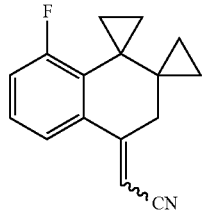 [SMILES: N#CC=C1CC2(CC2)C2(CC2)c2c(F)cccc21]

To a suspension of 60% sodium hydride dispersion (85% pure, 660 mg, 16.50 mmol) in 50 mL THF, a solution of diethyl (cyanomethyl)phosphonate (2.9 g, 16.37 mmol) in 20 mL THF was added slowly (over ca. 5 min). After stirring at room temperature for 5 min, a solution of the product of Step H (1.34 g, 5.267 mmol) in 40 mL THF was added. After stirring at 60° C. (oil bath) for 1 h, the mixture was partly concentrated and residue was extracted with $CH_2Cl_2$ and water. Organic phases were dried over $MgSO_4$, filtered, and concentrated. The residue was purified by biotage column chromatography ($SiO_2$, hexane/AcOEt gradient) to give the title compound for this step (1.14 g, 91%) as a colorless oil (E:Z isomer=56:44). LCMS m/z=240.1 $[M+1]^+$. $^1$H NMR (400 MHz, CDCl$_3$) δ 0.05-0.10 (m, 2H), 0.26-0.29 (m, 1H), 0.36-0.46 (m, 3H), 0.59-0.66 (m, 2H), 2.40 (d, 1.1H), 2.72 (s, 0.9H), 5.17 (s, 0.56H), 5.71 (s, 0.44H), 6.96-7.04 (m, 1H), 7.10-7.22 (m, 1H), 7.32-7.34 (m, 0.44H), 7.96-7.98 (m, 0.56H).

Step J: Preparation of Compound 17 of FIG. 2, where R$^1$=F

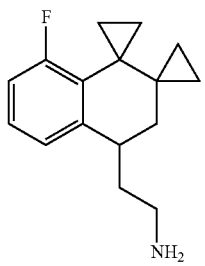 [SMILES: NCCC1CC2(CC2)C2(CC2)c2c(F)cccc21]

To a mixture of the product of Step I (1.13 g, 4.722 mmol) and cobalt(II) chloride hexahydrate (3.4 g, 14.29 mmol) in 30 mL MeOH, sodium tetrahydroborate (3 g, 79 mmol) was added in small portions over 7 h. After stirring at room temperature overnight, the mixture was extracted with water and CH$_2$Cl$_2$. Phases were filtered through celite and washed with CH$_2$Cl$_2$. Phases of filtrate were separated and aqueous layer was extracted three more times with CH$_2$Cl$_2$. Combined organic phases were dried over MgSO$_4$, filtered, and concentrated. The residue was purified by biotage column chromatography (SiO$_2$, hexane/AcOEt gradient first and then CH$_2$Cl$_2$/MeOH/7M NH$_3$ in MeOH 80:18:2) to give the title compound for this step (80% pure, 725 mg, 50%). LCMS m/z=246.0 [M+1]$^+$.

Step K: Preparation of Compound 18 of FIG. 2, where R$^1$=F and R$^{10}$ is 3,4-dichlorobenzyl

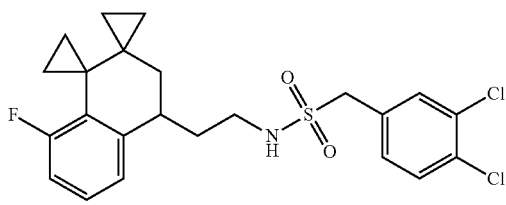 [SMILES: O=S(=O)(Cc1ccc(Cl)c(Cl)c1)NCCC1CC2(CC2)C2(CC2)c2c(F)cccc21]

To an ice-cooled solution of the product of Step J (80% pure, 720 mg, 2.142 mmol) and N-ethyl-N-isopropylpropan-2-amine (0.663 mL, 3.806 mmol) in 20 mL CH$_2$Cl$_2$, a solution of (3,4-dichlorophenyl)methanesulfonyl chloride (840 mg, 3.237 mmol) in 10 mL CH$_2$Cl$_2$ was added slowly by a syringe pump (over ca. 15 min). After stirring under ice-cooling for 0.5 h, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (995 mg, 99%). LCMS m/z=466.4 [M−1]$^+$. H NMR (400 MHz, CDCl$_3$) δ 0.15-0.20 (m, 1H), 0.23-0.30 (m, 2H), 0.41-0.53 (m, 3H), 1.34-1.41 (m, 2H), 1.58-1.72 (m, 2H), 1.90-2.07 (m, 2H), 3.04-3.11 (m, 3H), 4.05-4.08 (m, 1H), 4.18 (s, 2H), 6.75-6.80 (m, 1H), 6.92-6.94 (m, 1H), 7.02-7.08 (m, 1H), 7.22-7.25 (m, 1H), 7.45-7.49 (m, 2H).

Step L: Preparation of Compound 19 of FIG. 2, where R$^1$=F and R$^{10}$ is 3,4-dichlorobenzyl

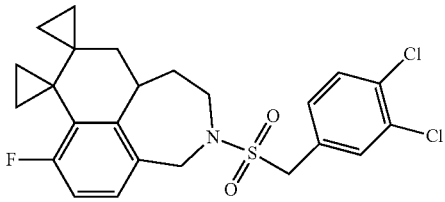 [SMILES: O=S(=O)(Cc1ccc(Cl)c(Cl)c1)N1CCC2CC3(CC3)C3(CC3)c3c(F)ccc(c32)C1]

To a solution of the product of Step K (992 mg, 2.118 mmol) in 22 mL DCE, acetic anhydride (0.200 mL, 2.118 mmol), 1,3,5-trioxane (407 mg, 4.518 mmol), and methanesulfonic acid (0.87 mL, 13.42 mmol) were added. After stirring at room temperature for 5 min, the mixture was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (885 mg, 87%) as a white solid. $^1$H NMR (400 MHz, CDCl$_3$) 0.08-0.14 (m, 1H), 0.15-0.19 (m, 1H), 0.23-0.34 (m, 1H), 0.38-0.47 (m, 2H), 0.55-0.61 (m, 1H), 1.31-10.36 (m, 1H), 1.42-1.62 (m, 4H), 2.08-2.13 (m, 1H), 3.21-3.30 (m, 2H), 3.82-4.00 (m, 3H), 4.21-4.25 (m, 1H), 4.57-4.61 (m, 1H), 6.74-6.80 (m, 1H), 6.92-6.99 (m, 2H), 7.05-7.06 (m, 1H), 7.33-7.35 (m, 1H).

Step M: Preparation of 8'-fluoro-2',3',4',4a',5'-pentahydro-1'H-dispiro[cyclopropane-1,6'-cyclopropane-7',1''-naphtho[1,8-cd]-azepine] (Compound 105)

To a solution of the product of Step K (883 mg, 1.838 mmol) in 10 mL toluene, 60% bis(2-methoxyethoxy)aluminum(III) sodium hydride in toluene (10 mL, 30.75 mmol) was added. After stirring at 80° C. (oil bath) for 2 h, mixture cooled in an ice/water-bath, and quenched by the slow addition of 2 M NH$_4$Cl. The mixture was extracted with 1 M NaOH and CH$_2$Cl$_2$. Organic phases were concentrated and residue was purified by biotage (SiO$_2$, hexane/AcOEt gradient first and then AcOEt/7M NH$_3$ in MeOH 10:1) to give the title compound for this example 1.1 (92% pure, 326 mg, 63%). LCMS m/z=258.2 [M+1]$^+$. $^1$H NMR (400 MHz, CDCl$_3$) δ 0.145-0.24 (m, 2H), 0.33-0.52 (m, 4H), 1.36-1.40 (m, 1H), 1.45-1.50 (m, 1H), 1.57-1.73 (m, 4H), 1.94-1.99 (m, 1H), 3.05-3.12 (m, 1H), 3.31-3.37 (m, 2H), 3.86 (d, J=14.5 Hz, 1H), 3.97 (d, J=14.5 Hz, 1H), 6.64-6.69 (m, 1H), 6.86-6.89 (m, 1H).

Step N: Resolution of Compound 105 into Enantiomers 134 and 133

Compound 105 was resolved to give two enantiomers by normal phase preparative chiral HPLC under the following conditions:
Column: Normal phase semi preparative CHIRALPAK®IF column, 5 m (particle size), 250×20 mm (L×ID)
Eluent: Acetonitrile with 0.1% triethylamine
Gradient: Isocratic
Flow: 10 mL/min
Detector: UV 225 nm
Retention Times: 1$^{st}$ enantiomer: 26.1 min; 2$^{nd}$ enantiomer: 28.7 min Fractions containing single enantiomer were concentrated and residue was re-purified by HPLC (CH$_3$CN/H$_2$O gradient+0.1% TFA (trifluoroacetic acid) to give the corresponding enantiomer as a TFA salt. LCMS m/z=258.4 [M+1]$^+$. $^1$H NMR (400 MHz, CD$_3$OD) δ 0.25-0.29 (m, 2H), 0.40-0.46 (m, 2H), 0.51-0.61 (m, 2H), 1.35-1.40 (m, 1H), 1.43-1.47 (m, 1H), 1.69-1.74 (m, 1H), 1.99-2.08 (m, 3H), 3.37-3.53 (m, 3H), 4.26 (dd, J$_1$=14.1 Hz, J$_2$=0.7 Hz, 1H), 4.43 (d, J=14.1 Hz, 1H), 6.83-6.89 (m, 1H), 7.17-7.20 (m, 1H).

Example 1.2: Preparation of 6',6'-dimethyl-2',3',4',4a',5',6'-hexahydro-1'H-spiro[cyclopropane-1,7'-naphtho[1,8-cd]azepine] (Compound 102)

Step A: Preparation of 2,2-dimethyl-3,4-dihydronaphthalen-1(2H)-one

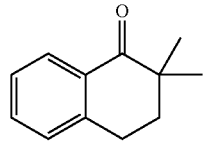

To a suspension of 60% sodium hydride dispersion (4 g, 100.0 mmol) in 180 mL THF, a solution of 3,4-dihydronaphthalen-1(2H)-one (5.1 g, 34.89 mmol) in 20 mL THF was added slowly. After stirring at room temperature for 10 min, flask was placed into an ice/water-bath and iodomethane (6.5 mL, 104.2 mmol) was added. The mixture was allowed to slowly warm to room temperature. After stirring overnight, the mixture was quenched by the slow addition of water, partly concentrated, an extracted with water and AcOEt. Organic phase was dried over MgSO$_4$, filtered, and concentrated. The residue was purified by biotage column chromatography (SiO$_2$, hexane/AcOEt gradient) to give 2,2-dimethyl-3,4-dihydronaphthalen-1(2H)-one (5.5 g, 91%) as a colorless liquid. $^1$H NMR (400 MHz, CDCl$_3$) δ 1.22 (s, 6H), 1.99 (t, J=6.4 Hz, 2H), 2.99 (t, J=6.4 Hz, 2H), 7.20-7.23 (m, 1H), 7.28-7.32 (m, 1H), 7.43-7.47 (m, 1H), 8.04 (dd, J$_1$=8.0 Hz, J$_2$=1.3 Hz, 1H).

Step B: Preparation of 2,2-dimethyl-1-methylene-1,2,3,4-tetrahydronaphthalene

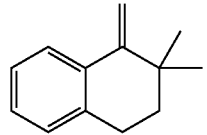

To a suspension of methyltriphenylphosphonium bromide (5.1 g, 14.28 mmol) in 20 mL toluene, 1 M potassium 2-methylpropan-2-olate in THF (17.2 mL, 17.20 mmol) was added. After stirring at 120° C. (oil bath) for 40 min, a solution of 2,2-dimethyl-3,4-dihydronaphthalen-1(2H)-one (1.1 g, 6.313 mmol) in 3 mL toluene was added. The mixture was stirred at 120° C. for 10 min, allowed to cool to room temperature, and extracted with water and AcOEt. Organic phase was dried over MgSO$_4$, filtered, and concentrated. The residue was purified by biotage column chromatography (SiO$_2$, hexane/AcOEt gradient) to give 2,2-dimethyl-1-methylene-1,2,3,4-tetrahydronaphthalene (927 mg, 85%) as a colorless liquid. $^1$H NMR (400 MHz, CDCl$_3$) δ 1.22 (s, 6H), 1.68 (t, J=6.6 Hz, 2H), 2.86 (t, J=6.6 Hz, 2H), 5.07 (s, 1H), 5.44 (s, 1H), 7.08-7.19 (m, 3H), 7.58-7.60 (m, 1H).

Step C: Preparation of 2',2'-dimethyl-3',4'-dihydro-2'H-spiro[cyclopropane-1,1'-naphthalene]

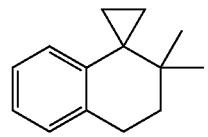

To an ice-cooled solution of 2,2-dimethyl-1-methylene-1,2,3,4-tetrahydronaphthalene (822 mg, 4.772 mmol) and chloroiodomethane (2.1 mL, 28.93 mmol) in 30 mL DCE, 1 M diethylzinc in hexanes (24 mL, 24.00 mmol) was added slowly (over ca. 5 min). The mixture was allowed to warm to room temperature. After 2 h, suspension was quenched by the slow addition of 1 M NH$_4$Cl and ice, and extracted with water and CH$_2$Cl$_2$ (3×). Combined organic phases were dried over MgSO$_4$, filtered, and concentrated. The residue was purified by biotage column chromatography (SiO$_2$, hexane/AcOEt gradient) to give 2',2'-dimethyl-3',4'-dihydro-2'H-spiro[cyclopropane-1,1'-naphthalene] (848 mg, 95%) as a colorless liquid. $^1$H NMR (400 MHz, CDCl$_3$) δ 0.74-0.77 (m, 2H), 0.84 (s, 6H), 0.99-1.02 (m, 2H), 1.69 (t, J=6.7 Hz, 2H), 2.90 (t, J=6.7 Hz, 2H), 6.71 (d, J=7.8 Hz, 1H), 7.01-7.10 (m, 3H).

Step D: Preparation of 2',2'-dimethyl-2'H-spiro[cyclopropane-1,1'-naphthalen]-4'(3'H)-one

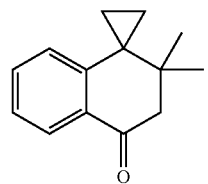

To a solution of 2',2'-dimethyl-3',4'-dihydro-2'H-spiro[cyclopropane-1,1'-naphthalene] (822 mg, 4.412 mmol) in 16 mL DCE, Rh$_2$(cap)$_4$ (18.8 mg, 44.42 µmol), sodium bicarbonate (190 mg, 2.262 mmol), and 5.5 M 2-hydroperoxy-2-methylpropane in decane (4 mL, 22.00 mmol) were added. After stirring at 40° C. (oil bath) for 3 h, more Rh$_2$(cap)$_4$ (18.6 mg) and 5.5 M 2-hydroperoxy-2-methylpropane (4 mL) were added. After stirring at 40° C. overnight, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give 2',2'-dimethyl-2'H-spiro[cyclopropane-1,1'-naphthalen]-4'(3'H)-one (643 mg, 73%) as a colorless oil that solidified after a while. $^1$H NMR (400 MHz, CDCl$_3$) δ 0.92-0.95 (m, 8H), 1.18-1.21 (m, 2H), 2.63 (s, 2H), 6.88 (d, J=7.9 Hz, 1H), 7.22-7.26 (m, 1H), 7.44-7.49 (m, 1H), 8.01 (dd, J$_1$=7.9 Hz, J$_2$=1.4 Hz, 1H).

Step E: Preparation of (E, Z)-2-(2',2'-dimethyl-2'H-spiro[cyclopropane-1,1'-naphthalen]-4'(3'H)-ylidene)acetonitrile

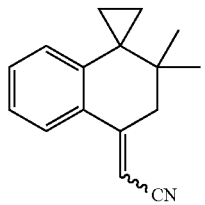 [SMILES: CC1(C)CC(=CC#N)c2ccccc2C12CC2]

To a suspension of 60% sodium hydride dispersion (255 mg, 6.38 mmol) in 20 mL THF, a solution of diethyl (cyanomethyl)phosphonate (1.11 g, 6.266 mmol) in 5 mL THF was added (over ca. 10 min). Reaction flask was put into an ice/water-bath and a solution of 2',2'-dimethyl-2'H-spiro[cyclopropane-1,1'-naphthalen]-4'(3'H)-one (631 mg, 3.151 mmol) in 5 mL THF was added. The mixture was allowed to warm to room temperature. After 2 h, the mixture was continued to be stirred at 60° C. (oil bath). After stirring over-the-weekend, the mixture was extracted with water and AcOEt. Organic phases were dried over MgSO₄, filtered, and concentrated. The residue was purified by HPLC (CH₃CN/H₂O gradient+0.1% TFA). Fractions containing the product were partly concentrated. The residue was extracted with 1 M NaHCO₃ and CH₂Cl₂. Organic phases were dried over MgSO4, filtered, and concentrated to give (E, Z)-2-(2',2'-dimethyl-2'H-spiro[cyclopropane-1,1'-naphthalen]-4'(3'H)-ylidene)acetonitrile (399 mg, 57%) as an oil (E:Z=64:36). $^1$H NMR (400 MHz, CDCl₃) δ 0.84-0.87 (m, 2H), 0.90 (s, 6H), 1.11-1.15 (m, 2H), 2.46 (d, J=1.3 Hz, 0.72H), 2.78 (d, J=1.2 Hz, 1.28H), 5.23-5.24 (m, 0.36H), 5.77-5.78 (m, 0.64), 6.75-6.80 (m, 1H), 7.13-7.17 (m, 0.64H), 7.20-7.24 (m, 0.36H), 7.30-7.36 (m, 1H), 7.52 (dd, $J_1$=7.9 Hz, $J_2$=1.3 Hz, 0.64H), 8.28 (dd, $J_1$=7.9 Hz, $J_2$=1.3 Hz, 0.36H).

Step F: Preparation of tert-butyl (2-(2',2'-dimethyl-3',4'-dihydro-2'H-spiro[cyclopropane-1,1'-naphthalen]-4'-yl)ethyl)carbamate

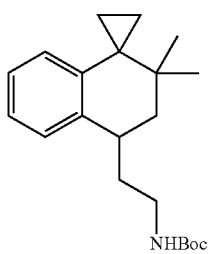 [SMILES: CC(C)(C)OC(=O)NCCC1CC(C)(C)C2(CC2)c2ccccc21]

To a solution of 2-(2',2'-dimethyl-2'H-spiro[cyclopropane-1,1'-naphthalen]-4'(3'H)-ylidene)acetonitrile (342 mg, 1.531 mmol) in 30 mL MeOH, cobalt(II) chloride hexahydrate (1.1 g, 4.623 mmol) were added. After stirring at room temperature for 5 min, sodium tetrahydroborate (289 mg, 7.639 mmol) was added in small portions over ca. 0.5 h (slightly exothermic). After stirring at room temperature for 2 h, more cobalt(II) chloride hexahydrate (1.1 g) and MeOH (ca. 20 mL) were added and another ca. 2 g of sodium tetrahydroborate was added in small portions over the course of ca. 5 h. Then, di-tert-butyl dicarbonate di-tert-butyl dicarbonate (670 mg, 3.070 mmol) was added and mixture was stirred at room temperature. After 1 h, the mixture was extracted with water and AcOEt. Organic phases were dried over MgSO₄, filtered, and concentrated. The residue was purified by biotage column chromatography (SiO₂, hexane/AcOEt gradient) to give tert-butyl (2-(2',2'-dimethyl-3',4'-dihydro-2'H-spiro[cyclopropane-1,1'-naphthalen]-4'-yl)ethyl)carbamate (335 mg, 66%) as a viscous oil. LCMS m/z=330.4 [M+1]⁺. $^1$H NMR (400 MHz, CDCl₃) δ 0.48-0.52 (m, 1H), 0.74 (s, 3H), 0.86-0.91 (m, 4H), 0.99-1.04 (m, 2H), 1.40-1.55 (m, 11H), 1.70-1.81 (m, 2H), 2.11-2.20 (m, 1H), 2.99-3.07 (m, 1H), 3.20-3.26 (m, 1H), 4.48-4.53 (m, 1H), 6.74-6.76 (m, 1H), 7.07-7.10 (m, 2H), 7.23-7.26 (m, 1H).

Step G: Preparation of tert-butyl (2-(2',2'-dimethyl-3',4'-dihydro-2'H-spiro[cyclopropane-1,1'-naphthalen]-4'-yl)ethyl)carbamate

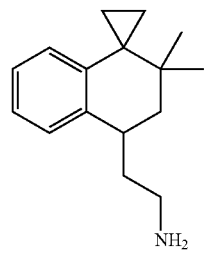 [SMILES: CC1(C)CC(CCN)c2ccccc2C12CC2]

To a solution of tert-butyl (2-(2',2'-dimethyl-3',4'-dihydro-2'H-spiro[cyclopropane-1,1'-naphthalen]-4'-yl)ethyl)carbamate (333 mg, 1.011 mmol) in 10 mL DCM, TFA (2.34 mL, 30.56 mmol) was added. After stirring at room temperature for 1 h, solution was concentrated and dried under high vacuum to give 2-(2',2'-dimethyl-3',4'-dihydro-2'H-spiro[cyclopropane-1,1'-naphthalen]-4'-yl)ethanamine 2,2,2-trifluoroacetate (347 mg, 100%) as a tanned solid. LCMS m/z=230.6 [M+1]⁺. $^1$H NMR (400 MHz, CD₃OD) δ 0.42-0.47 (m, 1H), 0.78 (s, 3H), 0.90-0.98 (m, 4H), 1.05-1.10 (m, 2H), 1.52-1.58 (m, 1H), 1.77-1.81 (m, 1H), 1.94-2.04 (m, 1H), 2.21-2.29 (m, 1H), 2.86-3.02 (m, 2H), 3.13-3.20 (m, 1H), 6.79-6.83 (m, 1H), 7.08-7.12 (m, 2H), 7.25-7.29 (m, 1H).

Step H: Preparation of tert-butyl (2-(2',2'-dimethyl-3',4'-dihydro-2'H-spiro[cyclopropane-1,1'-naphthalen]-4'-yl)ethyl)carbamate

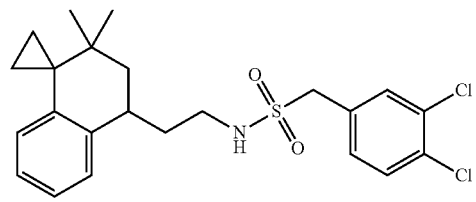 [SMILES: CC1(C)CC(CCNS(=O)(=O)Cc2ccc(Cl)c(Cl)c2)c2ccccc2C12CC2]

To an ice-cooled solution of (3,4-dichlorophenyl)methanesulfonyl chloride (393 mg, 1.514 mmol) and triethylamine (0.563 mL, 3.984 mmol) in 10 mL DCM, a solution of (3,4-dichlorophenyl)methanesulfonyl chloride (393 mg, 1.514 mmol) in 5 mL DCM was added slowly (over ca. 15 min). After 0.5 h, solution was allowed to warm to room temperature. After stirring at room temperature for 3 h, more triethylamine (0.1 mL) and (3,4-dichlorophenyl)methanesulfonyl chloride (60 mg) dissolved in 1 mL DCM were added at 0° C. The mixture was stirred for an additional 1 hour at room temperature and then, extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give 1-(3,4-dichlorophenyl)-N-(2-(2',2'-dimethyl-3',4'-dihydro-2'H-spiro[cyclopropane-1,1'-naphthalen]-4'-yl)ethyl)methanesulfonamide (297 mg, 66%). LCMS m/z=450.4 [M−1]$^+$. $^1$H NMR (400 MHz, CDCl$_3$) δ 0.45-0.51 (m, 1H), 0.74 (s, 3H), 0.86-0.95 (m, 4H), 1.01-1.07 (m, 2H), 1.42-1.48 (m, 1H), 1.64-1.69 (m, 1H), 1.80-1.90 (m, 1H), 2.08-2.16 (m, 1H), 3.00-3.14 (m, 3H), 4.04-4.07 (m, 1H), 4.17 (s, 2H), 6.74-6.78 (m, 1H), 7.08-7.13 (m, 2H), 7.23 (dd, J$_1$=8.1 Hz, J$_2$=2.0 Hz, 1H), 7.45 (d, J=8.2 Hz, 1H), 7.49 (d, J=2.0 Hz, 1H).

Step I: Preparation of 2'-((3,4-dichlorobenzyl)sulfonyl)-6',6'-dimethyl-2',3',4',4a',5',6'-hexahydro-1'H-spiro[cyclopropane-1,7'-naphtho[1,8-cd]azepine]

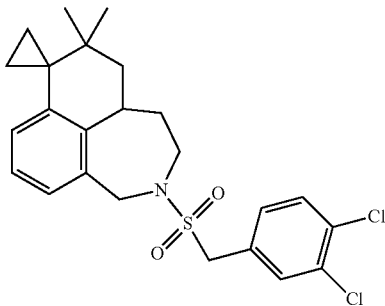 [SMILES: CC1(C)CC2CCN(S(=O)(=O)Cc3ccc(Cl)c(Cl)c3)Cc3cccc(c32)C12CC2]

To a solution of acetic anhydride (20.9 μl, 0.222 mmol), methanesulfonic acid (89 μl, 1.371 mmol), and 1,3,5-trioxane (29.2 mg, 0.324 mmol) in 3 mL DCE, a solution of 1-(3,4-dichlorophenyl)-N-(2-(2',2'-dimethyl-3',4'-dihydro-2'H-spiro[cyclopropane-1,1'-naphthalen]-4'-yl)ethyl)methanesulfonamide (91 mg, 0.201 mmol) in 1 mL DCE was added. After stirring at room temperature for 1 h, solution was diluted with CH$_2$Cl$_2$ and extracted with 1 M NaHCO$_3$. Organic phase was dried over MgSO$_4$, filtered, and concentrated. The residue was purified by biotage column chromatography (SiO$_2$, hexane/AcOEt gradient) to give 2'-((3,4-dichlorobenzyl)sulfonyl)-6',6'-dimethyl-2',3',4',4a',5',6'-hexahydro-1'H-spiro[cyclopropane-1,7'-naphtho[1,8-cd]azepine] (28.3 mg, 30%) as a white solid. H NMR (400 MHz, CDCl$_3$) δ 0.62-0.67 (m, 1H), 0.74 (s, 3H), 0.86 (s, 3H), 0.88-1.02 (m, 2H), 1.07-1.12 (m, 1H), 1.18-1.28 (m, 1H), 1.51-1.67 (m, 3H), 3.17-3.33 (m, 2H), 3.88-3.99 (m, 3H), 4.16 (d, J=15.7 Hz, 1H), 4.64 (dd, J$_1$=15.4 Hz, J$_2$=1.8 Hz, 1H), 6.75 (dd, J$_1$=8.0 Hz, J$_2$=1.1 Hz, 1H), 6.92 (dd, J$_1$=8.2 Hz, J$_2$=2.0 Hz, 1H), 7.01 (dd, J$_1$=7.2 Hz, J$_2$=1.2 Hz, 1H), 7.07-7.11 (m, 2H), 7.30 (d, J=8.2 Hz, 1H).

Step J: Preparation of 6',6'-dimethyl-2',3',4',4a',5',6'-hexahydro-1'H-spiro[cyclopropane-1,7'-naphtho[1,8-cd]azepine] (Compound 102)

To a solution of 2'-((3,4-dichlorobenzyl)sulfonyl)-6',6'-dimethyl-2',3',4',4a',5',6'-hexahydro-1'H-spiro[cyclopropane-1,7'-naphtho[1,8-cd]azepine] (52.3 mg, 0.113 mmol) in 2 mL toluene, 60% Red-Al in toluene (1.1 mL, 3.382 mmol) was added. After stirring at room temperature for 4 h, solution was quenched by the careful addition of ice. The mixture was concentrated, CH$_3$CN was added, solids were filtered off, and filtrate was partly concentrated. The residue was purified by HPLC (CH$_3$CN/H$_2$O gradient+0.1% TFA) to give 6',6'-dimethyl-2',3',4',4a',5',6'-hexahydro-1'H-spiro[cyclopropane-1,7'-naphtho[1,8-cd]azepine] 2,2,2-trifluoroacetate (20.1 mg, 50%). LCMS m/z=242.4 [M+1]$^+$. $^1$H NMR (400 MHz, CD$_3$OD) δ 0.52-0.57 (m, 1H), 0.79 (s, 3H), 0.90 (s, 3H), 0.95-1.01 (m, 1H), 1.03-1.09 (m, 1H), 1.12-1.16 (m, 1H), 1.61-1.78 (m, 2H), 1.92-2.03 (m, 2H), 3.38-3.46 (m, 2H), 3.51-3.57 (m, 1H), 4.24-4.37 (m, 2H), 6.85-6.90 (m, 1H), 7.13-7.17 (m, 2H).

Step K: Resolution of 6',6'-dimethyl-2',3',4',4a',5',6'-hexahydro-1'H-spiro[cyclopropane-1,7'-naphtho[1,8-cd]azepine] (Compound 102) into Enantiomers 103 and 104

Compound 102 was resolved to give two enantiomers by normal phase preparative chiral HPLC under the following conditions:
Column: Normal phase semi preparative CHIRALPAK®IF column, 5 m (particle size), 250×20 mm (L×ID)
Eluent: hexanes/EtOH 100:5+0.1% triethylamine
Gradient: Isocratic
Flow: 10 mL/min
Detector: UV 254 nm
Retention Times: 1st enantiomer: 30.3 min; 2nd enantiomer: 32.7 min Example 1.3: Preparation of 1,2,3,4,4a,5,6,7-octahydronaphtho[1,8-cd]azepine (Compound 107)

Step A: Preparation of 2-(3,4-dihydronaphthalen-1(2H)-ylidene)acetonitrile

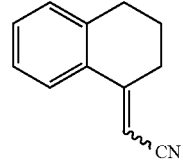 [SMILES: N#CC=C1CCCc2ccccc21]

To a suspension of 60% sodium hydride dispersion (0.83 g, 20.75 mmol) in 50 mL THF, a solution of diethyl (cyanomethyl)phosphonate (3.65 g, 20.61 mmol) in 15 mL THF was added (over ca. 5 min). The mixture was placed into an ice/water-bath and a solution of 3,4-dihydronaphthalen-1(2H)-one (2.13 g, 14.57 mmol) in 15 mL THF was added. The mixture was allowed to warm to room temperature and stirred overnight. The mixture was quenched by the dropwise addition of water and extracted with water and AcOEt. Organic phases were concentrated and residue was purified by HPLC (CH$_3$CN/H$_2$O gradient+0.1% TFA). Fractions containing the product were partly concentrated and residue extracted with 1 M NaHCO$_3$ and CH$_2$Cl$_2$. Organic phases were dried over MgSO$_4$, filtered, and concentrated to give 2-(3,4-dihydronaphthalen-1(2H)-ylidene)acetonitrile (1.63 g, 66%) as an oil (E:Z=75:25). $^1$H NMR (400 MHz, CDCl$_3$) δ 1.92-2.00 (m, 2H), 2.59-2.62 (m, 0.5H), 2.86-2.92

(m, 3.5H), 5.27-5.28 (m, 0.25H), 5.73-5.74 (m, 0.75H), 7.18-7.36 (m, 3H), 7.56 (d, J=8.0 Hz, 0.75H), 8.30 (dd, J₁=7.8 Hz, J₂=0.96 Hz, 0.25H).

Step B: Preparation of 2-(1,2,3,4-tetrahydronaphthalen-1-yl)ethanamine

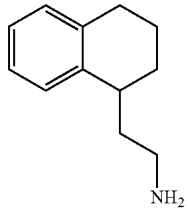 [SMILES: NCCC1CCCc2ccccc21]

To an undetermined amount of raney nickel (slurry in water; washed three times with MeOH), a solution of 2-(3,4-dihydronaphthalen-1(2H)-ylidene)acetonitrile (1.62 g, 9.573 mmol) in ca. 80 mL MeOH and 7 M ammonia in MeOH (15 mL, 105.0 mmol) were added. The mixture was shaken on a Parr-shaker under ca. 60 psi hydrogen pressure over-the-weekend. Raney nickel was filtered off through celite, washed with additional MeOH, and concentrated to give 2-(1,2,3,4-tetrahydronaphthalen-1-yl)ethanamine (86% pure, 1.71 g, 88%). LCMS m/z=176.6 [M+1]⁺. ¹H NMR (400 MHz, CDCl₃) δ 1.65-1.90 (m, 6H), 2.70-2.97 (m, 5H), 7.04-7.17 (m, 4H).

Step C: Preparation of 1-(3,4-dichlorophenyl)-N-(2-(1,2,3,4-tetrahydronaphthalen-1-yl)ethyl)methanesulfonamide

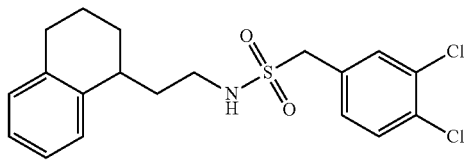 [SMILES: O=S(=O)(Cc1ccc(Cl)c(Cl)c1)NCCC1CCCc2ccccc21]

To a solution of 2-(1,2,3,4-tetrahydronaphthalen-1-yl)ethanamine (86% pure, 1.6 g, 7.851 mmol) and triethylamine (1.91 mL, 13.72 mmol) in 70 mL CH₂Cl₂, a solution of (3,4-dichlorophenyl)methanesulfonyl chloride (2.4 g, 9.247 mmol) in 20 mL CH₂Cl₂ was added (over ca. 5 min). After stirring at room temperature for 2 h, the mixture was extracted with 1 M NaHCO₃ and CH₂Cl₂. Combined organic phases were dried over MgSO₄, filtered, and concentrated. The residue was purified by biotage column chromatography (SiO₂, hexane/AcOEt gradient) to give 1-(3,4-dichlorophenyl)-N-(2-(1,2,3,4-tetrahydronaphthalen-1-yl)ethyl)methanesulfonamide (2.7 g, 86%). LCMS m/z=396.3 [M−1]⁺. ¹H NMR (400 MHz, CDCl₃) δ 1.55-1.62 (m, 1H), 1.68-1.93 (m, 5H), 2.73-2.87 (m, 3H), 3.08-3.13 (m, 2H), 4.08-4.13 (m, 1H), 4.18 (s, 2H), 7.05-7.15 (m, 4H), 7.23 (dd, J₁=8.3 Hz, J₂=2.1 Hz, 1H), 7.45 (d, J=8.2 Hz, 1H), 7.49 (d, J=2.1 Hz, 1H).

Step D: Preparation of 2-((3,4-dichlorobenzyl)sulfonyl)-1,2,3,4,4a,5,6,7-octahydronaphtho[1,8-cd]azepine

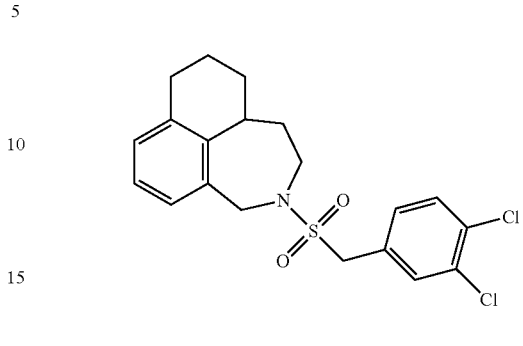

To a solution of 1-(3,4-dichlorophenyl)-N-(2-(1,2,3,4-tetrahydronaphthalen-1-yl)ethyl)methanesulfonamide (110 mg, 0.276 mmol) in 2 mL DCE, 1,3,5-trioxane (42 mg, 0.466 mmol), acetic anhydride (26.1 μL, 0.276 mmol), and methanesulfonic acid (112 μL, 1.725 mmol) were added. After stirring at room temperature for 15 min, solution was extracted with CH₂Cl₂ and 1 M NaHCO₃. Combined organic phases were dried over MgSO₄, filtered, and concentrated. The residue was purified by biotage column chromatography (SiO₂, hexane/AcOEt gradient) to give 2-((3,4-dichlorobenzyl)sulfonyl)-1,2,3,4,4a,5,6,7-octahydronaphtho[1,8-cd]azepine (86.1 mg, 76%) as a white solid. ¹H NMR (400 MHz, CDCl₃) δ 1.08-1.18 (m, 1H), 1.49-1.55 (m, 1H), 1.59-1.72 (m, 3H), 1.91-1.99 (m, 1H), 2.70-2.86 (m, 2H), 3.05-3.11 (m, 1H), 3.26-3.33 (m, 1H), 3.77-3.84 (m, 2H), 3.92 (d, J=13.0 Hz, 1H), 4.29 (d, J=15.3 Hz, 1H), 4.62 (dd, J₁=15.3 Hz, J₂=1.5 Hz, 1H), 6.82 (d, J=2.0 Hz, 1H), 6.92 (dd, J₁=8.3 Hz, J₂=2.0 Hz, 1H), 7.07-7.13 (m, 3H), 7.31 (d, J=8.2 Hz, 1H).

Step E: Preparation of tert-butyl 3,4,4a,5,6,7-hexahydronaphtho[1,8-cd]azepine-2(1H)-carboxylate

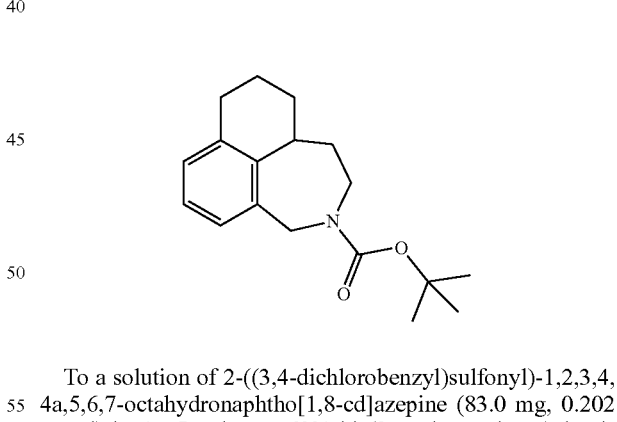

To a solution of 2-((3,4-dichlorobenzyl)sulfonyl)-1,2,3,4,4a,5,6,7-octahydronaphtho[1,8-cd]azepine (83.0 mg, 0.202 mmol) in 4 mL toluene, 60% bis(2-methoxyethoxy)aluminum(III) sodium hydride in toluene (2 mL, 6.15 mmol) was added. After stirring at room temperature overnight, solution was continued to be stirred at 80° C. After 5.5 h, vial was put in an ice/water-bath and quenched by the slow addition of ca. 1 mL EtOH. After stirring under ice-cooling for 10 min, (BOC)₂O (150 mg, 0.687 mmol) was added. After stirring for another 30 min, the mixture was extracted with water and AcOEt. Organic phases were dried over MgSO₄, filtered, and concentrated. The residue was purified by biotage column chromatography (SiO₂, hexane/AcOEt gradient) to give tert-butyl 3,4,4a,5,6,7-hexahydronaphtho[1,8-cd]

azepine-2(1H)-carboxylate (30.2 mg, 0.105 mmol, 52%). LCMS m/z=288.4 [M+1]⁺. ¹H NMR (400 MHz, CDCl₃) δ 1.42 (s, 9H), 1.64-1.81 (m, 5H), 1.95-2.04 (m, 1H), 2.73-2.77 (m, 2H), 3.06-3.12 (m, 1H), 3.20-3.42 (m, 1H), 3.66-3.73 (m, 0.33H), 4.07-4.26 (m, 1.77H), 4.54-4.65 (m, 1H), 6.99-7.14 (m, 3H).

Step F: Preparation of 1,2,3,4,4a,5,6,7-octahydronaphtho[1,8-cd]azepine (Compound 107)

To a solution of tert-butyl 3,4,4a,5,6,7-hexahydronaphtho[1,8-cd]azepine-2(1H)-carboxylate (10 mg, 34.80 μmol) in 0.35 mL CH₂Cl₂, TFA (80 μl, 1.045 mmol) was added. After stirring at room temperature for 2 h, solution was concentrated and residue was purified by HPLC (CH₃CN/H₂O gradient+0.1% TFA) to give 1,2,3,4,4a,5,6,7-octahydronaphtho[1,8-cd]azepine 2,2,2-trifluoroacetate (9.5 mg, 91%). LCMS m/z=188.4 [M+1]⁺. ¹H NMR (400 MHz, CD₃OD) δ 1.69-1.91 (m, 4H), 1.94-2.00 (m, 1H), 2.04-2.13 (m, 1H), 2.72-2.84 (m, 2H), 3.24-3.30 (m, 1H), 3.36-3.49 (m, 2H), 4.23 (dd, J₁=14.0 Hz, J₂=0.4 Hz, 1H), 4.42 (d, J=14.0 Hz, 1H), 7.11-7.19 (m, 3H).

Example 1.4: Preparation of 8-bromo-1,2,3,4,4a,5,6,7-octahydronaphtho[1,8-cd]azepine (Compound 106)

Step A: Preparation of 2-(5-bromo-3,4-dihydronaphthalen-1(2H)-ylidene)acetonitrile

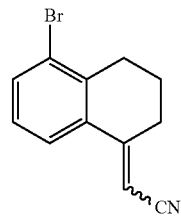

To a suspension of 60% sodium hydride dispersion (0.5 g, 12.50 mmol) in 50 mL THF, a solution of diethyl (cyanomethyl)phosphonate (2.2 g, 12.42 mmol) in 15 mL THF was added slowly. After stirring at room temperature for 5 min, a solution of 5-bromo-3,4-dihydronaphthalen-1(2H)-one (2.0 g, 8.886 mmol) in 20 mL THF was added. After stirring at room temperature for 4 h, the mixture was extracted with AcOEt and water. Organic phase was dried over MgSO₄, filtered, and concentrated. The residue was purified by biotage column chromatography (SiO₂, hexane/AcOEt gradient) to give 2-(5-bromo-3,4-dihydronaphthalen-1(2H)-ylidene)acetonitrile (2.18 g, 99%) (E:Z=61:39). H NMR (400 MHz, CDCl₃) δ 1.96-2.05 (m, 2H), 2.53-2.56 (m, 0.61H), 2.84-2.92 (m, 3.39H), 5.32-5.33 (m, 0.39H), 5.71-5.72 (5, 0.61H), 7.08-7.18 (m, 1H), 7.50 (d, J=8.0 Hz, 0.61H), 7.60-7.64 (m, 1H), 8.16-8.18 (m, 0.39H), Step B: Preparation of tert-butyl (2-(5-bromo-1,2,3,4-tetrahydronaphthalen-1-yl)ethyl)carbamate

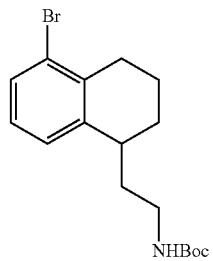 [SMILES: CC(C)(C)OC(=O)NCCC1CCCc2c(Br)cccc21]

To a mixture of 2-(5-bromo-3,4-dihydronaphthalen-1(2H)-ylidene)acetonitrile (1.04 g, 4.192 mmol) and cobalt (II) chloride hexahydrate (4.09 g, 17.19 mmol) in 80 mL MeOH, sodium tetrahydroborate (2 g, 52.86 mmol) was added in small portions over ca. 3 h. After stirring at room temperature overnight, di-tert-butyl dicarbonate (1.8 g, 8.248 mmol) was added. After stirring at room temperature for 1.5 h, the mixture was partly concentrated and residue was extracted with water and AcOEt. Organic phase was dried over MgSO₄, filtered, and concentrated. The residue was purified by biotage column chromatography (SiO₂, hexane/AcOEt gradient) to give tert-butyl (2-(5-bromo-1,2,3,4-tetrahydronaphthalen-1-yl)ethyl)carbamate (934 mg, 63%) ¹H NMR (400 MHz, CDCl₃) δ 1.45 (s, 9H), 1.68-1.88 (m, 6H), 2.62-2.91 (m, 3H), 3.14-3.30 (m, 2H), (br s, 1H), 6.96-7.00 (m, 1H), 7.09 (d, J=7.6 Hz, 1H), 7.38 (dd, J₁=7.8 Hz, J₂=1.0 Hz, 1H).

Step C: Preparation of N-(2-(5-bromo-1,2,3,4-tetrahydronaphthalen-1-yl)ethyl)-1-(3,4-dichlorophenyl)methanesulfonamide

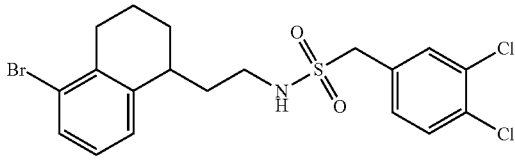 [SMILES: O=S(=O)(Cc1ccc(Cl)c(Cl)c1)NCCC1CCCc2c(Br)cccc21]

To a solution of tert-butyl (2-(5-bromo-1,2,3,4-tetrahydronaphthalen-1-yl)ethyl)carbamate (928 mg, 2.619 mmol) in 26 mL CH₂Cl₂, TFA (6.05 mL, 79.01 mmol) was added. After stirring at room temperature for 0.5 h, solution was concentrated and dried under high vacuum. The residue was dissolved in 20 mL CH₂Cl₂ and triethylamine (1.83 mL, 13.13 mmol). And then, a solution of (3,4-dichlorophenyl)methanesulfonyl chloride (780 mg, 3.005 mmol) in 6 mL CH₂Cl₂ was added. After stirring at room temperature for 1 h, solution was extracted with water and CH₂Cl₂. Organic phase was dried over MgSO₄, filtered, and concentrated. The residue was purified by biotage column chromatography (SiO₂, hexane/AcOEt gradient) to give N-(2-(5-bromo-1,2,3,4-tetrahydronaphthalen-1-yl)ethyl)-1-(3,4-dichlorophenyl)methanesulfonamide (690 mg, 55%). LCMS m/z=476.3 [M−1]. ¹H NMR (400 MHz, CDCl₃) δ 1.56-1.66 (m, 1H), 1.70-1.87 (m, 5H), 2.65-2.87 (m, 3H), 3.03-3.19 (m, 2H), 4.09-4.14 (m, 1H), 4.18-4.20 (m, 2H), 6.97-7.03 (m, 2H), 7.24 (dd, $J_1$=8.3 Hz, $J_2$=2.0 Hz, 1H), 7.40 (dd, $J_1$=7.0 Hz, $J_2$=2.0 Hz, 1H), 7.44-7.49 (m, 2H).

Step D: Preparation of 8-bromo-2-((3,4-dichlorobenzyl)sulfonyl)-1,2,3,4,4a,5,6,7-octahydronaphtho[1,8-cd]azepine

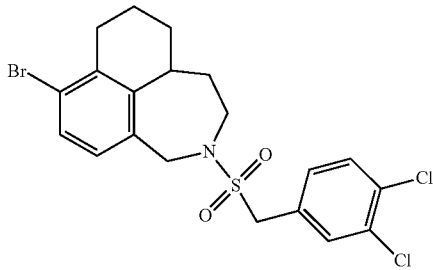 [SMILES: O=S(=O)(Cc1ccc(Cl)c(Cl)c1)N1CCC2CCCc3c(Br)ccc(c32)C1]

To a solution of N-(2-(5-bromo-1,2,3,4-tetrahydronaphthalen-1-yl)ethyl)-1-(3,4-dichlorophenyl)methanesulfonamide (612 mg, 1.282 mmol) in 13 mL DCE, 1,3,5-trioxane (340 mg, 3.775 mmol), acetic anhydride (0.121 mL, 1.282 mmol), methanesulfonic acid (515 µl, 7.931 mmol) were added. After stirring at room temperature for 15 min, solution was extracted with 1 M $NaHCO_3$ and $CH_2Cl_2$. Organic phases were dried over $MgSO_4$, filtered, and concentrated. The residue was purified by biotage column chromatography ($SiO_2$, hexane/AcOEt gradient) to give 8-bromo-2-((3,4-dichlorobenzyl)sulfonyl)-1,2,3,4,4a,5,6,7-octahydronaphtho[1,8-cd]azepine (484 mg, 77%) as a white solid. $^1$H NMR (400 MHz, $CDCl_3$) δ 1.17-1.28 (m, 1H), 1.52-1.59 (m, 1H), 1.62-1.70 (m, 2H), 1.73-1.81 (m, 1H), 1.84-1.90 (m, 1H), 2.61-2.69 (m, 1H), 2.84-2.91 (m, 1H), 3.06-3.12 (m, 1H), 3.25-3.32 (m, 1H), 3.73-3.79 (m, 1H), 3.86 (d, J=14.0 Hz, 1H), 3.88 (d, J=14.0 Hz, 1H), 4.24 (d, J=15.3 Hz, 1H), 4.55 (dd, $J_1$=15.3 Hz, J2=1.4 Hz, 1H), 6.91-6.94 (m, 2H), 6.99 (dd, $J_1$=8.3 Hz, $J_2$=2.1 Hz, 1H), 7.34 (d, J=8.2 Hz, 1H), 7.42 (d, J=7.9 Hz, 1H).

Step E: Preparation tert-butyl 8-bromo-3,4,4a,5,6,7-hexahydronaphtho[1,8-cd]azepine-2(1H)-carboxylate

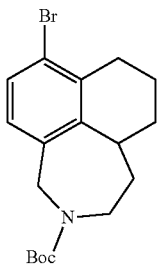 [SMILES: CC(C)(C)OC(=O)N1CCC2CCCc3c(Br)ccc(c32)C1]

A mixture of 8-bromo-2-((3,4-dichlorobenzyl)sulfonyl)-1,2,3,4,4a,5,6,7-octahydronaphtho[1,8-cd]azepine (429 mg, 0.877 mmol), phenol (181 mg, 1.923 mmol), and 48% hydrogen bromide in water (10 mL, 88.4 mmol) in 10 mL AcOH (in a high pressure vessel) was stirred at 120° C. (oil bath) for 2 d. The mixture was concentrated and residue was purified by HPLC ($CH_3CN/H_2O$ gradient+0.1% TFA). Fractions containing the product were concentrated and dried under high vacuum. The residue was dissolved in 7 mL $CH_2Cl_2$ and triethylamine (0.122 mL, 0.877 mmol) and $(BOC)_2O$ (380 mg, 1.741 mmol) was added. After stirring at room temperature for 1 h, solution was concentrated and residue was purified by biotage column chromatography ($SiO_2$, hexane/AcOEt gradient) to give tert-butyl 8-bromo-3,4,4a,5,6,7-hexahydronaphtho[1,8-cd]azepine-2(1H)-carboxylate (271 mg, 84%) as a colorless viscous oil. LCMS m/z=366.5 [M+1]$^+$. $^1$H NMR (400 MHz, $CDCl_3$) δ 1.42 (s, 9H), 1.66-1.79 (m, 5H), 1.87-1.95 (m, 1H), 2.62-2.70 (m, 1H), 2.77-2.86 (m, 1H), 3.06-3.14 (m, 1H), 3.21-3.29 (m, 0.65H), 3.35-3.44 (m, 0.35H), 3.66-3.74 (m, 0.35H), 4.05-4.22 (m, 1.65H), 4.51-4.62 (m, 1H), 6.90-7.03 (m, 1H), 7.33-7.38 (m, 1H).

Step F: Preparation of 8-bromo-1,2,3,4,4a,5,6,7-octahydronaphtho[1,8-cd]azepine (Compound 106)

To a solution of tert-butyl 8-bromo-3,4,4a,5,6,7-hexahydronaphtho[1,8-cd]azepine-2(1H)-carboxylate (5 mg, 13.65 µmol) in 0.2 mL $CH_2Cl_2$, TFA (29 µl, 0.379 mmol) was added. After stirring at room temperature overnight, solution was concentrated and dried under high vacuum to give 8-bromo-1,2,3,4,4a,5,6,7-octahydronaphtho[1,8-cd]azepine 2,2,2-trifluoroacetate (5.2 mg, 100%). LCMS m/z=266.0 [M+1]$^+$. $^1$H NMR (400 MHz, $CD_3OD$) δ 1.72-2.07 (m, 6H), 2.67-2.75 (m, 1H), 2.79-2.86 (m, 1H), 3.30-3.35 (m, 1H), 3.41-3.44 (m, 2H), 4.24 (d, J=14.2 Hz, 1H), 4.43 (d, J=14.2 Hz, 1H), 7.12 (d, J=8.0 Hz, 1H), 7.48 (d, J=8.0 Hz, 1H).

Example 1.5: Preparation of 8-cyclopropyl-1,2,3,4,4a,5,6,7-octahydronaphtho[1,8-cd]azepine (Compound 127)

A mixture of tert-butyl 8-bromo-3,4,4a,5,6,7-hexahydronaphtho[1,8-cd]azepine-2(1H)-carboxylate (36 mg, 98.28 µmol), bis(tri-t-butylphosphine)palladium (10 mg, 19.57 µmol), and 0.5 M cyclopropylzinc(II) bromide in THF (1 mL, 0.500 mmol) was stirred at 80° C. (oil bath) overnight. The mixture was extracted with water and AcOEt. Organic phase was concentrated and residue was purified by HPLC ($CH_3CN/H_2O$ gradient+0.1% TFA). Fractions containing the product were concentrated. The residue was dissolved in 1 mL $CH_2Cl_2$ and TFA (226 µl, 2.951 mmol) was added. After stirring at room temperature for 1 h, the mixture was concentrated and dried under high vacuum to give 8-cyclopropyl-1,2,3,4,4a,5,6,7-octahydronaphtho[1,8-cd]azepine 2,2,2-trifluoroacetate (29.3 mg, 87%). LCMS m/z=228.4 [M+1]$^+$. $^1$H NMR (400 MHz, $CD_3OD$) δ 0.51-0.63 (m, 2H), 0.88-0.99 (m, 2H), 1.72-2.08 (m, 7H), 2.80-2.97 (m, 2H), 3.25-3.45 (m, 3H), 4.18 (d, J=14.0 Hz, 1H), 4.41 (d, J=14.0 Hz, 1H), 6.90 (d, J=7.7 Hz, 1H), 7.10 (d, J=7.7 Hz, 1H).

Example 1.6: Preparation of 8-fluoro-1,2,3,4,4a,5,6,7-octahydronaphtho[1,8-cd]azepine (Compound 138)

A solution of tert-butyl 8-bromo-3,4,4a,5,6,7-hexahydronaphtho[1,8-cd]azepine-2(1H)-carboxylate (39 mg, 0.106 mmol) in 1 mL THF was cooled in a dry-ice/acetone-bath and 2 M butyllithium in hexane (0.1 mL, 0.200 mmol) was added. After stirring at −78° C. for 0.5 h, a solution of N-fluoro-N-(phenylsulfonyl)benzenesulfonamide (50 mg, 0.159 mmol) in 0.2 mL THF was added. The mixture was allowed to warm to room temperature. After stirring for 2 h, the mixture was quenched by the slow addition of water and extracted with water and AcOEt. Organic phase was concentrated and residue was purified by HPLC (CH₃CN/H₂O gradient+0.1% TFA) to give an inseparable mixture of desired Boc-product and de-bromination side product (major). The residue was dissolved in 1 mL DCM and TFA (250 µl, 3.265 mmol) was added. After stirring at room temperature for 1 h, the mixture was concentrated and residue was purified by HPLC (CH₃CN/H₂O gradient+0.1% TFA) to give 8-fluoro-1,2,3,4,4a,5,6,7-octahydronaphtho[1,8-cd]azepine 2,2,2-trifluoroacetate (4.1 mg, 12%). LCMS m/z=206.9 [M+1]⁺. ¹H NMR (400 MHz, CD₃OD) δ 1.72-2.10 (m, 6H), 2.64-2.79 (m, 2H), 3.25-3.49 (m, 3H), 4.25 (d, J=14.1 Hz, 1H), 4.42 (d, J=14.1 Hz, 1H), 6.91-6.95 (m, 1H), 7.21-7.24 (m, 1H).

Example 1.7: Preparation of 8-chloro-1,2,3,4,4a,5,6,7-octahydronaphtho[1,8-cd]azepine (Compound 111)

To a solution of tert-butyl 8-bromo-3,4,4a,5,6,7-hexahydronaphtho[1,8-cd]azepine-2(1H)-carboxylate (38 mg, 0.104 mmol) in 1 mL THF in a dry-ice/acetone-bath, 2 M butyllithium in hexane (0.1 mL, 0.200 mmol) was added. After stirring at −78° C. for 1 h, a solution of perchloroethane (52 mg, 0.220 mmol) in 0.2 mL THF was added. The mixture was allowed to warm to room temperature. After 1 h, the mixture was quenched with water and extracted with water and CH₂Cl₂. Organic phases were concentrated and residue was purified by HPLC (CH₃CN/H₂O gradient+0.1% TFA). Fractions containing Boc-product were concentrated. The residue was dissolved in 1 mL CH₂Cl₂ and 2,2,2-trifluoroacetic acid (300 µl, 3.918 mmol) was added. After stirring overnight, the mixture was concentrated and residue was dried under high vacuum to give 8-chloro-1,2,3,4,4a,5,6,7-octahydronaphtho[1,8-cd]azepine 2,2,2-trifluoroacetate (3.3 mg, 10%).

LCMS m/z=222.4 [M+1]⁺. ¹H NMR (400 MHz, CD₃OD) δ 1.29-1.39 (m, 1H), 1.72-2.07 (m, 6H), 2.69-2.88 (m, 2H), 3.39-3.47 (m, 2H), 4.25 (d, J=14.2 Hz, 1H), 4.45 (d, J=14.2 Hz, 1H), 7.20 (d, J=8.1 Hz, 1H), 7.28 (d, J=8.1 Hz, 1H).

Example 1.8: Preparation 7,7-dimethyl-1,2,3,4,4a,5,6,7-octahydronaphtho[1,8-cd]azepine (Compound 135)

Step A: Preparation of 2-(5-bromo-3,4-dihydronaphthalen-1(2H)-ylidene)acetonitrile

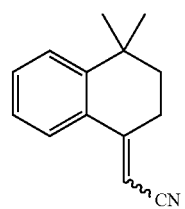

To a suspension of 60% sodium hydride dispersion (0.18 g, 4.500 mmol) in 10 mL THF, a solution of diethyl (cyanomethyl)phosphonate (0.8 g, 4.516 mmol) in 5 mL THF was added slowly. After stirring at room temperature for 5 min, a solution of 4,4-dimethyl-3,4-dihydronaphthalen-1(2H)-one (525 mg, 3.013 mmol) in 5 mL THF was added. After stirring at room temperature overnight, the mixture was extracted with AcOEt and water. Organic phase was dried over MgSO₄, filtered, and concentrated. The residue was purified by biotage column chromatography (SiO₂, hexane/AcOEt gradient) to give 2-(4,4-dimethyl-3,4-dihydronaphthalen-1(2H)-ylidene)acetonitrile (480 mg, 81%) (E:Z=67:33). ¹H NMR (400 MHz, CDCl₃) δ 1.31 (S, 1.98H), 1.32 (s, 4.02H), 1.79-1.84 (m, 2H), 2.60-2.63 (m, 0.66), 2.91-2.95 (m, 1.34H), 5.26-5.27 (m, 0.33H), 5.68-5.69 (m, 0.67H), 7.18-7.22 (m, 0.67H), 7.24-7.29 (m, 0.33H), 7.36-7.42 (m, 2H), 7.49-7.51 (m, 0.67H), 8.15-8.17 (m, 0.33H).

Step B: Preparation of 2-(4,4-dimethyl-1,2,3,4-tetrahydronaphthalen-1-yl)ethanamine To an undetermined amount of raney nickel (slurry in water; washed three times with MeOH), a solution of 2-(4,4-dimethyl-3,4-dihydronaphthalen-1(2H)-ylidene)acetonitrile (477 mg, 2.418 mmol) in ca. 20 mL MeOH and 7 M ammonia in MeOH (5 mL, 35.00 mmol) were added. The mixture was shaken on a Parr-shaker under ca. 60 psi hydrogen pressure overnight. Raney nickel was filtered off through celite, washed with additional MeOH, and concentrated to give 2-(4,4-dimethyl-1,2,3,4-tetrahydronaphthalen-1-yl)ethanamine (84% pure, 504 mg, 86%). LCMS m/z=204.4 [M+1]⁺.

Step C: Preparation of 1-(3,4-dichlorophenyl)-N-(2-(4,4-dimethyl-1,2,3,4-tetrahydronaphthalen-1-yl)ethyl)methanesulfonamide To a solution of 2-(4,4-dimethyl-1,2,3,4-tetrahydronaphthalen-1-yl)ethanamine (84% pure, 501 mg, 2.070 mmol) and triethylamine (0.61 mL, 4.377 mmol) in 20 mL CH₂Cl₂, a solution of (3,4-dichlorophenyl)methanesulfonyl chloride (780 mg, 3.005 mmol) in 10 mL CH₂Cl₂ was added. After stirring at room temperature for 0.5 h, the mixture was extracted with CH₂Cl₂ and water. Organic phases were dried over MgSO₄, filtered, and concentrated. The residue was purified by biotage column chromatography (SiO₂, hexane/AcOEt gradient) to give 1-(3,4-dichlorophenyl)-N-(2-(4,4-dimethyl-1,2,3,4-tetrahydronaphthalen-1-yl)ethyl)methanesulfonamide (70% pure, 710 mg, 56%). LCMS m/z=424.3 [M−1]⁺. ¹H NMR (400 MHz, CDCl₃) δ 1.21 (s, 3H), 1.24 (s, 3H), 1.53-1.62 (m, 2H), 1.68-1.95 (m, 4H), 2.77-2.83 (m, 1H), 3.09-3.14 (m, 2H), 4.09-4.19 (m, 3H), 7.01-7.04 (m, 1H), 7.08-7.25 (m, 4H), 7.45-7.50 (m, 2H).

Step D: Preparation of 2-((3,4-dichlorobenzyl)sulfonyl)-7,7-dimethyl-1,2,3,4,4a,5,6,7-octahydronaphtho[1,8-cd]azepine

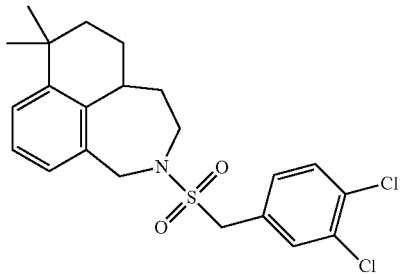 [SMILES: CC1(C)CCC2CCN(S(=O)(=O)Cc3ccc(Cl)c(Cl)c3)Cc3cccc1c32]

To a solution of 1-(3,4-dichlorophenyl)-N-(2-(4,4-dimethyl-1,2,3,4-tetrahydronaphthalen-1-yl)ethyl)methanesulfonamide (70% pure, 705 mg, 1.157 mmol) in 10 mL DCE, 1,3,5-trioxane (177 mg, 1.965 mmol), acetic anhydride (0.11 mL, 1.164 mmol), and methanesulfonic acid (0.5 mL, 7.700 mmol) were added. After stirring at room temperature for 10 min, the mixture was extracted with water and $CH_2Cl_2$. Organic phases were dried over $MgSO_4$, filtered, and concentrated. The residue was purified by biotage column chromatography ($SiO_2$, hexane/AcOEt gradient). Fractions containing the product were concentrated and residue was re-purified by HPLC ($CH_3CN/H_2O$ gradient+0.1% TFA). Fractions containing the product were concentrated and residue was extracted with $CH_2Cl_2$ and 1 M $NaHCO_3$. Organic phases were dried over $MgSO_4$, filtered, and concentrated to give 2-((3,4-dichlorobenzyl)sulfonyl)-7,7-dimethyl-12,3,4,4a,5,6,7-octahydronaphtho[1,8-cd]azepine (325 mg, 64%) as a white solid. H NMR (400 MHz, $CDCl_3$) δ 1.25 (s, 3H), 1.33 (s, 3H), 1.43-1.69 (m, 5H), 2.03-2.11 (m, 1H), 3.08-3.14 (m, 1H), 3.29-3.36 (m, 1H), 3.69-3.75 (m, 1H), 3.8-3.92 (m, 2H), 4.30 (d, J=15.0 Hz, 1H), 4.54 (dd, $J_1$=15.0 Hz, $J_2$=1.3 Hz, 1H), 6.87 (dd, $J_1$=8.2 Hz, $J_2$=2.0 Hz, 1H), 7.02 (dd, $J_1$=7.3 Hz, $J_2$=1.2 Hz, 1H), 7.13-7.17 (m, 1H), 7.28 (d, J=2.1 Hz, 1H), 7.32 (d, J=8.2 Hz, 1H), 7.37 (dd, $J_1$=8.0 Hz, $J_2$=1.2 Hz, 1H).

Step E: Preparation 7,7-dimethyl-1,2,3,4,4a,5,6,7-octahydronaphtho[1,8-cd]azepine (Compound 135)

A mixture of 2-((3,4-dichlorobenzyl)sulfonyl)-7,7-dimethyl-1,2,3,4,4a,5,6,7-octahydronaphtho[1,8-cd]azepine (194 mg, 0.443 mmol), phenol (85 mg, 0.903 mmol), and 48% hydrogen bromide in water (4 mL, 35.36 mmol) in 4 mL acetic acid was stirred at 120° C. (oil bath). After 22 h, the mixture was concentrated and residue was purified by HPLC ($CH_3CN/H_2O$ gradient+0.1% TFA). Fractions containing the product were concentrated. The residue was dissolved in 5 mL DCM and triethylamine (310 μl, 2.224 mmol) and $(BOC)_2O$ (0.2 g, 0.916 mmol) were added. After stirring at room temperature for 0.5 h, solution was concentrated and residue was purified by biotage column chromatography ($SiO_2$, hexane/AcOEt gradient). Fractions containing the desired product were concentrated. The residue was dissolved in 5 mL $CH_2Cl_2$ and TFA (1 mL, 13.06 mmol) was added. After stirring at room temperature for 1 h, the mixture was concentrated and dried under high vacuum to give 7,7-dimethyl-1,2,3,4,4a,5,6,7-octahydronaphtho[1,8-cd]azepine 2,2,2-trifluoroacetate (83 mg, 57%). LCMS m/z=216.4 [M+1]$^+$. $^1$H NMR (400 MHz, $CD_3OD$) δ 1.28 (s, 3H), 1.32 (s, 3H), 1.57-1.63 (m, 1H), 1.69-1.78 (m, 2H), 1.85-2.02 (m, 2H), 2.11-2.20 (m, 1H), 3.25-3.33 (m, 1H), 3.39-3.43 (m, 2H), 4.22 (d, J=14.1 Hz, 1H), 4.46 (d, J=14.1 Hz, 1H), 7.15-7.23 (m, 2H), 7.49 (dd, $J_1$=7.8 Hz, $J_2$=1.4 Hz, 1H).

Step F: Resolution of Compound 135 into Enantiomers 110 and 122

Compound 135 was resolved to give two enantiomers by normal phase preparative chiral HPLC under the following conditions:
Column: Normal phase semi preparative CHIRALPAK®IF column, 5 m (particle size), 250×20 mm (L×ID)
Eluent: hexanes/EtOH 100:5+0.1% triethylamine
Gradient: Isocratic
Flow: 10 mL/min
Detector: UV 254 nm
Retention Times: 1$^{st}$ enantiomer: 25.8 min; 2$^{nd}$ enantiomer: 31.8 min Example 1.9: Preparation of 2',3',4',4a',5',6'-hexahydro-1'H-spiro[cyclopropane-1,7'-naphtho[1,8-cd]azepine] (Compound 128)

Step A: Preparation of 1-methylene-1,2,3,4-tetrahydronaphthalene

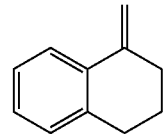

To a suspension of methyltriphenylphosphonium bromide (5.03 g, 14.08 mmol) in 20 mL toluene, potassium 2-methylpropan-2-olate (15 mL, 15.00 mmol) was added. After stirring at 120° C. (oil bath) for 40 min, a solution of 3,4-dihydronaphthalen-1(2H)-one (1.01 g, 6.909 mmol) in 3 mL toluene was added. The mixture was stirred at 120° C. for 10 min, allowed to cool to room temperature, and extracted with water and AcOEt. Organic phase was dried over $MgSO_4$, filtered, and concentrated. The residue was purified by biotage column chromatography ($SiO_2$, hexane/AcOEt gradient) to give 1-methylene-1,2,3,4-tetrahydronaphthalene (931 mg, 93%) as a colorless liquid. $^1$H NMR (400 MHz, $CDCl_3$) δ 1.85 (m, 2H), 2.52-2.56 (m, 2H), 2.84 (t, J=6.3 Hz, 2H), 4.93-4.95 (m, 1H), 5.46-5.48 (m, 1H), 7.08-7.18 (m, 3H), 7.62-7.66 (m, 1H).

Step B: Preparation of 3',4'-dihydro-2'H-spiro[cyclopropane-1,1'-naphthalene]

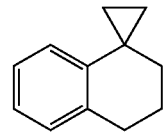 [SMILES: c1ccc2c(c1)CCCC21CC1]

To a solution of 1-methylene-1,2,3,4-tetrahydronaphthalene (904 mg, 6.269 mmol) in 40 mL DCE, chloroiodomethane (5 g, 28.35 mmol) was added. Flask was placed into an ice/water-bath and 1 M diethylzinc in hexanes (25 mL, 25.00 mmol) was added over ca. 5 min. After stirring under ice-cooling for 1.5 h, the mixture was quenched by the slow addition of 1 M NH$_4$Cl. The mixture was extracted with CH$_2$Cl$_2$ and water. Organic phases were dried over MgSO$_4$, filtered, and concentrated. The residue was purified by biotage column chromatography (SiO$_2$, hexane/AcOEt gradient) to give 3',4'-dihydro-2'H-spiro[cyclopropane-1,1'-naphthalene] (894 mg, 90%) as a colorless oil. $^1$H NMR (400 MHz, CDCl$_3$) δ 0.76-0.79 (m, 2H), 0.94-0.97 (m, 2H), 1.65-1.68 (m, 2H), 1.87-1.93 (m, 2H), 2.88 (t, J=6.3 Hz, 2H), 6.65 (d, J=7.6 Hz, 1H), 7.00-7.09 (m, 3H).

Step C: Preparation of 2'H-spiro[cyclopropane-1,1'-naphthalen]-4'(3'H)-one

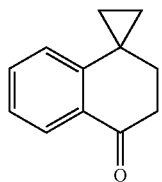 [SMILES: O=C1CCC2(CC2)c2ccccc21]

To a mixture of 3',4'-dihydro-2'H-spiro[cyclopropane-1,1'-naphthalene] (861 mg, 5.441 mmol), sodium bicarbonate (460 mg, 5.476 mmol), and Rh$_2$(cap)$_4$ (29.6 mg, 69.94 µmol) in 20 mL DCE, 5.5 M 2-hydroperoxy-2-methylpropane in decane (5 mL, 27.50 mmol) was added. The mixture was stirred at 40° C. (oil bath). After 3 h, more Rh$_2$(cap)$_4$ (25 mg) was added. After stirring overnight, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give 2'H-spiro[cyclopropane-1,1'-naphthalen]-4'(3'H)-one (718 mg, 77%) as a colorless oil. $^1$H NMR (400 MHz, CDCl$_3$) δ 0.97-1.00 (m, 2H), 1.09-1.11 (m, 2H), 1.97-2.00 (m, 2H), 2.76-2.79 (m, 2H), 6.82 (dd, J$_1$=8.0 Hz, J$_2$=0.64 Hz, 1H), 7.23-7.27 (m, 1H), 7.43-7.47 (m, 1H), 8.03 (dd, J$_1$=7.8 Hz, J$_2$=1.3 Hz, 1H).

Step D: Preparation of 2-(2'H-spiro[cyclopropane-1,1'-naphthalen]-4'(3'H)-ylidene)acetonitrile

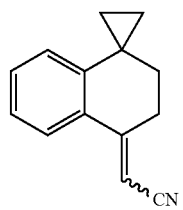 [SMILES: N#CC=C1CCC2(CC2)c2ccccc21]

To a suspension of 60% sodium hydride dispersion (270 mg, 6.75 mmol) in 15 mL THF, a solution of diethyl (cyanomethyl)phosphonate (1.1 g, 6.210 mmol) in 6 mL THF was added slowly. After stirring at room temperature for 5 min, a solution of 2'H-spiro[cyclopropane-1,1'-naphthalen]-4'(3'H)-one (710 mg, 4.123 mmol) in 6 mL THF was added. After stirring at room temperature overnight, the mixture was extracted with AcOEt and water. Organic phase was dried over MgSO$_4$, filtered, and concentrated. The residue was purified by biotage column chromatography (SiO$_2$, hexane/AcOEt gradient) to give 2-(2'H-spiro[cyclopropane-1,1'-naphthalen]-4'(3'H)-ylidene)acetonitrile (628 mg, 78%) (E:Z=68:32). $^1$H NMR (400 MHz, CDCl$_3$) δ 0.90-0.93 (m, 2H), 1.03-1.06 (m, 2H), 1.80-1.86 (m, 2H), 2.65-2.69 (m, 0.64H), 2.96-3.00 (m, 1.36H), 5.27-5.28 (m, 0.32H), 5.72-5.73 (m, 0.68H), 6.71-6.78 (m, 1H), 7.13-7.23 (m, 1H), 7.29-7.35 (m, 1H), 7.53 (dd, J$_1$=8.0 Hz, J$_2$=1.2 Hz, 0.68H), 8.21 (dd, J$_1$=7.9 Hz, J$_2$=1.2 Hz, 0.32H).

Step E: Preparation of tert-butyl (2-(5-bromo-1,2,3,4-tetrahydronaphthalen-1-yl)ethyl)carbamate

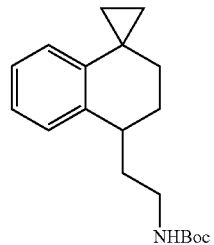 [SMILES: CC(C)(C)OC(=O)NCCC1CCC2(CC2)c2ccccc21]

To a mixture of 2-(2'H-spiro[cyclopropane-1,1'-naphthalen]-4'(3'H)-ylidene)acetonitrile (626 mg, 3.206 mmol) and cobalt(II) chloride hexahydrate (3.05 g, 12.82 mmol) in 60 mL MeOH, sodium tetrahydroborate (1.5 g, 39.65 mmol) was added in small portions over 2 h. After stirring at room temperature overnight, di-tert-butyl dicarbonate (1.4 g, 6.415 mmol) was added. After stirring at room temperature for 1 h, the mixture was partly concentrated and residue was extracted with water and AcOEt. Organic phases were dried over MgSO$_4$, filtered, and concentrated. The residue was purified by biotage column chromatography (SiO$_2$, hexane/AcOEt gradient) to give tert-butyl (2-(3',4'-dihydro-2'H-spiro[cyclopropane-1,1'-naphthalen]-4'-yl)ethyl)carbamate (647 mg, 67%). $^1$H NMR (400 MHz, CDCl$_3$) δ 0.77-0.86 (m, 3H), 1.03.1.10 (m, 1H), 1.34-1.38 (m, 1H), 1.45 (s, 9H), 1.76-2.05 (m, 5H), 2.90-2.95 (m, 1H), 3.17-3.33 (m, 2H), 4.52 (br s, 1H), 6.64-6.66 (m, 1H), 7.04-7.12 (m, 3H).

Step F: Preparation of 1-(3,4-dichlorophenyl)-N-(2-(3',4'-dihydro-2'H-spiro[cyclopropane-1,1'-naphthalen]-4'-yl)ethyl)methanesulfonamide

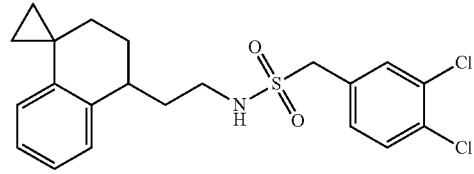 [SMILES: O=S(=O)(Cc1ccc(Cl)c(Cl)c1)NCCC1CCC2(CC2)c2ccccc21]

To a solution of tert-butyl (2-(3',4'-dihydro-2'H-spiro[cyclopropane-1,1'-naphthalen]-4'-yl)ethyl)carbamate (649 mg, 2.153 mmol) in 20 mL CH$_2$Cl$_2$, TFA (5 mL, 65.29 mmol) was added. After stirring at room temperature for 0.5 h, the mixture was concentrated and dried under high vacuum. The residue was dissolved in 15 mL CH$_2$Cl$_2$ and triethylamine (1.5 mL, 10.76 mmol). The mixture was cooled in an ice/water-bath and a solution of (3,4-dichlorophenyl)methanesulfonyl chloride (837 mg, 3.225 mmol) dissolved in 5 mL $CH_2Cl_2$ was added slowly. The mixture was allowed to warm to room temperature and after 30 min, extracted with water and $CH_2Cl_2$. Organic phases were dried over $MgSO_4$, filtered, and concentrated. The residue was purified by biotage column chromatography ($SiO_2$, hexane/AcOEt gradient) to give 1-(3,4-dichlorophenyl)-N-(2-(3',4'-dihydro-2'H-spiro[cyclopropane-1,1'-naphthalen]-4'-yl)ethyl)methanesulfonamide (694 mg, 76%). LCMS m/z=422.3 [M−1]$^+$. $^1$H NMR (400 MHz, $CDCl_3$) δ 0.78-0.87 (m, 3H), 1.05-1.08 (m, 1H), 1.36-1.42 (m, 1H), 1.67-1.42 (m, 1H), 1.79-2.03 (m, 4H), 2.89-2.95 (m, 1H), 3.09-3.17 (m, 2H), 4.09-4.13 (m, 1H), 4.19 (s, 2H), 6.65-6.67 (m, 1H), 7.02-7.12 (m, 3H), 7.24 (dd, $J_1$=8.2 Hz, $J_2$=2.1 Hz, 1H), 7.45 (d, J=8.2 Hz, 1H), 7.49 (d, J=2.0 Hz, 1H).

Step G: Preparation of 2'-((3,4-dichlorobenzyl)sulfonyl)-2',3',4',4a',5',6'-hexahydro-1'H-spiro[cyclopropane-1,7'-naphtho[1,8-cd]azepine]

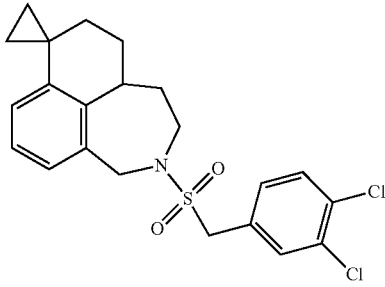 [SMILES: O=S(=O)(Cc1ccc(Cl)c(Cl)c1)N1CCC2CCC3(CC3)c3cccc(c32)C1]

To a solution of 1-(3,4-dichlorophenyl)-N-(2-(3',4'-dihydro-2'H-spiro[cyclopropane-1,1'-naphthalen]-4'-yl)ethyl)methanesulfonamide (674 mg, 1.588 mmol) in 17 mL DCE, acetic anhydride (0.152 mL, 1.608 mmol), 1,3,5-trioxane (352 mg, 3.908 mmol), and methanesulfonic acid (0.64 mL, 9.856 mmol) were added. After stirring at room temperature for 10 min, the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give 2'-((3,4-dichlorobenzyl)sulfonyl)-2',3',4',4a',5',6'-hexahydro-1'H-spiro[cyclopropane-1,7'-naphtho[1,8-cd]azepine] (310 mg, 45%) as a white solid. $^1$H NMR (400 MHz, $CDCl_3$) δ 0.79-0.92 (m, 3H), 1.19-1.32 (m, 3H), 1.50-1.56 (m, 1H), 1.70-1.76 (m, 1H), 1.84-1.91 (m, 1H), 2.06-2.15 (m, 1H), 3.17-3.23 (m, 1H), 3.29-3.36 (m, 1H), 3.75-3.83 (m, 2H), 3.92 (d, J=14.0 Hz, 1H), 4.35 (d, J=15.3 Hz, 1H), 4.61 (dd, $J_1$=15.3 Hz, $J_2$=1.2 Hz, 1H), 6.72-6.77 (m, 2H), 7.00-7.03 (m, 2H), 7.09-7.13 (m, 1H), 7.31 (d, J=8.2 Hz, 1H).

Step H: Preparation of 2',3',4',4a',5',6'-hexahydro-1'H-spiro[cyclopropane-1,7'-naphtho[1,8-cd]azepine] (Compound 128)

To a solution of 2'-((3,4-dichlorobenzyl)sulfonyl)-2',3',4',4a',5',6'-hexahydro-1'H-spiro[cyclopropane-1,7'-naphtho[1,8-cd]azepine] (249 mg, 0.571 mmol) in 10 mL toluene, 60% bis(2-methoxyethoxy)aluminum(III) sodium hydride in toluene (5 mL, 15.37 mmol) was added. After stirring at room temperature for 5 h, solution was continued to be stirred at 80° C. (oil bath). After stirring at 80° C. overnight, vial was put in an ice-water bath and quenched by the slow addition of EtOH. After stirring under ice-cooling for 10 min, $(BOC)_2O$ (0.5 g, 2.291 mmol) was added. The mixture was allowed to warm to room temperature. After 1 h, the mixture was extracted with 1 M NaOH and $CH_2Cl_2$. Organic phases were dried over $MgSO_4$, filtered, and concentrated. The residue was purified by biotage column chromatography ($SiO_2$, hexane/AcOEt gradient). Fractions containing BOC-protected product were concentrated. The residue was dissolved in 6 mL $CH_2Cl_2$ and TFA (1.3 mL, 16.98 mmol) was added. After stirring at room temperature for 1 h, the mixture was concentrated and dried under high vacuum to give 2',3',4',4a',5',6'-hexahydro-1'H-spiro[cyclopropane-1,7'-naphtho[1,8-cd]azepine] 2,2,2-trifluoroacetate (125 mg, 67%). LCMS m/z=214.2 [M+1]$^+$. $^1$H NMR (400 MHz, $CD_3OD$) δ 0.84-0.90 (m, 3H), 1.07-1.14 (m, 1H), 1.38-1.45 (m, 1H), 1.83-2.02 (m, 4H), 2.18-2.21 (m, 1H), 3.36-3.45 (m, 3H), 4.23 (d, J=14.1 Hz, 1H), 4.48 (d, J=14.1 Hz, 1H), 6.81-6.86 (m, 1H), 7.11-7.16 (m, 2H).

Step I: Resolution of Compound 128 into Enantiomers 123 and 136

Compound 128 was resolved to give two enantiomers by normal phase preparative chiral HPLC under the following conditions:
Column: Normal phase semi preparative CHIRALPAK®IF column, 5 m (particle size), 250×20 mm (L×ID)
Eluent: hexanes/EtOH 100:5+0.1% triethylamine
Gradient: Isocratic
Flow: 10 mL/min
Detector: UV 254 nm
Retention Times: 1$^{st}$ enantiomer: 32.9 min; 2$^{nd}$ enantiomer: 38.7 min Example 1.10: Preparation of 8-bromo-7,7-dimethyl-1,2,3,4,4a,5,6,7-octahydronaphtho[1,8-cd]azepine (Compound 109)

Step A: Preparation of 8-bromo-1,1-dimethyl-3,4-dihydronaphthalen-2(1H)-one

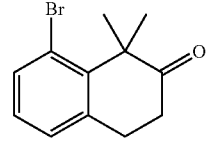

To a suspension of 60% sodium hydride dispersion (0.4 g, 10.00 mmol) in 25 mL THF, a solution of 8-bromo-3,4-dihydronaphthalen-2(1H)-one (1 g, 4.443 mmol) in 5 mL THF was added slowly (over ca. 5 min). After stirring at room temperature for 10 min, iodomethane (0.56 mL, 8.976 mmol) was added. After stirring at room temperature for 2 h, the mixture was extracted with water and AcOEt. Organic phase was dried over $MgSO_4$, filtered, and concentrated. The residue was purified by biotage column chromatography ($SiO_2$, hexane/AcOEt gradient) to give 8-bromo-1,1-dimethyl-3,4-dihydronaphthalen-2(1H)-one (791 mg, 70%) as a colorless oil. $^1$H NMR (400 MHz, $CDCl_3$) δ 1.72 (s, 6H), 2.72-2.76 (m, 2H), 3.06 (t, J=7.0 Hz, 2H), 6.99 (m, 1H), 7.09-7.11 (m, 1H), 7.52-7.54 (m, 1H).

Step B: Preparation of 8-bromo-1,1-dimethyl-1,2,3,4-tetrahydronaphthalene

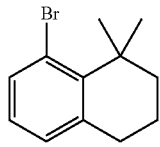

A mixture of 8-bromo-1,1-dimethyl-3,4-dihydronaphthalen-2(1H)-one (786 mg, 3.105 mmol), potassium hydroxide (1.7 g, 30.30 mmol), and hydrazine (1.19 mL, 37.91 mmol) in 25 mL ethyleneglycol (in a high pressure vial) was stirred at 205° C. (oil bath). After 2 h, the mixture was allowed to cool to room temperature and was extracted with water and AcOEt. Organic phase was dried over $MgSO_4$, filtered, and concentrated. The residue was purified by biotage column chromatography ($SiO_2$, hexane/AcOEt gradient) to give 8-bromo-1,1-dimethyl-1,2,3,4-tetrahydronaphthalene (573 mg, 77%) as a colorless oil. $^1$H NMR (400 MHz, $CDCl_3$) δ 1.55 (s, 6H), 1.69-1.76 (m, 4H), 2.80 (t, J=5.8 Hz, 2H), 6.85-6.89 (m, 1H), 6.99-7.01 (m, 1H), 7.39-7.41 (m, 1H).

Step C: Preparation of 5-bromo-4,4-dimethyl-3,4-dihydronaphthalen-1(2H)-one

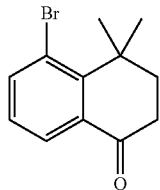

To a mixture of 8-bromo-1,1-dimethyl-1,2,3,4-tetrahydronaphthalene (560 mg, 2.342 mmol), sodium bicarbonate (106 mg, 1.262 mmol), and $Rh_2(cap)_4$ (16.4 mg, 38.75 μmol) in 10 mL DCE, 5.5 M 2-hydroperoxy-2-methylpropane in decane (2.2 mL, 12.10 mmol) was added. The mixture was stirred at 40° C. (oil bath). After 3 h, more $Rh_2(cap)_4$ (11.4 mg) was added. After stirring overnight, the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give 5-bromo-4,4-dimethyl-3,4-dihydronaphthalen-1(2H)-one (488 mg, 82%) as a colorless oil. LCMS m/z=255.6 $[M+1]^+$. $^1$H NMR (400 MHz, $CDCl_3$) δ 1.66 (s, 6H), 2.02-2.05 (m, 2H), 2.66-2.70 (m, 2H), 7.12-7.16 (m, 1H), 7.77 (dd, $J_1$=7.8 Hz, $J_2$=1.5 Hz, 1H), 8.06 (dd, $J_1$=7.7 Hz, $J_2$=1.6 Hz, 1H).

Step D: Preparation of give 2-(5-bromo-4,4-dimethyl-3,4-dihydronaphthalen-1(2H)-ylidene)acetonitrile

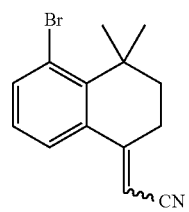 [SMILES: CC1(C)CCC(=CC#N)c2cccc(Br)c21]

To a suspension of 60% sodium hydride dispersion (120 mg, 3.000 mmol) in 4 mL THF, a solution of 5-bromo-4,4-dimethyl-3,4-dihydronaphthalen-1(2H)-one (482 mg, 1.904 mmol) in 8 mL THF was added slowly. After stirring at room temperature for 5 min, a solution of 5-bromo-4,4-dimethyl-3,4-dihydronaphthalen-1(2H)-one (482 mg, 1.904 mmol) in 4 mL THF was added. After stirring at room temperature for 3 h, the mixture was extracted with AcOEt and water. Organic phase was dried over $MgSO_4$, filtered, and concentrated. The residue was purified by biotage column chromatography ($SiO_2$, hexane/AcOEt gradient) to give 2-(5-bromo-4,4-dimethyl-3,4-dihydronaphthalen-1(2H)-ylidene)acetonitrile (473 mg, 90%) (E:Z=56:44). LCMS m/z=276.5 $[M+1]^+$. $^1$H NMR (400 MHz, $CDCl_3$) δ 1.59 (s, 2.6H), 1.60 (s, 3.4H), 1.86-1.92 (m, 2H), 2.48-2.52 (m, 1H), 2.80-2.83 (m, 1H), 5.25-5.26 (m, 0.44H), 5.58-5.59 (m, 0.56H), 7.02-7.13 (m, 1H), 7.44 (dd, $J_1$=7.9 Hz, $J_2$=1.4 Hz, 0.56H), 7.65-7.69 (m, 1H), 8.02 (dd, $J_1$=7.8 Hz, $J_2$=1.4 Hz, 0.44H).

Step E: Preparation of tert-butyl (2-(5-bromo-4,4-dimethyl-1,2,3,4-tetrahydronaphthalen-1-yl)ethyl)carbamate

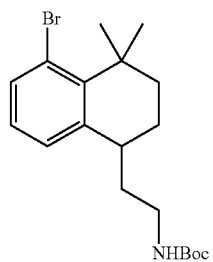 [SMILES: CC(C)(C)OC(=O)NCCC1CCC(C)(C)c2c(Br)cccc21]

To a mixture of 2-(5-bromo-4,4-dimethyl-3,4-dihydronaphthalen-1(2H)-ylidene)acetonitrile (502 mg, 1.818 mmol) and cobalt(II) chloride hexahydrate (1.77 g, 7.439 mmol) in 40 mL MeOH, sodium tetrahydroborate (990 mg, 26.17 mmol) was added in small portions over ca. 3 h. After stirring at room temperature overnight, di-tert-butyl dicarbonate (1 g, 4.582 mmol) was added. After stirring at room temperature for 1 h, the mixture was partly concentrated and residue was extracted with water and AcOEt. Organic phases were dried over MgSO4, filtered, and concentrated. The residue was purified by biotage column chromatography ($SiO_2$, hexane/AcOEt gradient) to give tert-butyl (2-(5-bromo-4,4-dimethyl-1,2,3,4-tetrahydronaphthalen-1-yl)ethyl)carbamate (175 mg, 25%). H NMR (400 MHz, $CDCl_3$) δ 1.45 (s, 9H), 1.49 (s, 3H), 1.57-1.65 (m, 2H), 1.60 (s, 3H), 1.74-1.92 (m, 4H), 2.82-2.88 (m, 1H), 3.16-3.27 (m, 2H), 4.51 (br s, 1H), 6.90-6.94 (m, 1H), 7.07 (d, J=7.4 Hz, 1H), 7.42 (dd, $J_1$=7.8 Hz, $J_2$=1.4 Hz, 1H).

Step F: Preparation of N-(2-(5-bromo-4,4-dimethyl-1,2,3,4-tetrahydronaphthalen-1-yl)ethyl)-1-(3,4-dichlorophenyl)methanesulfonamide

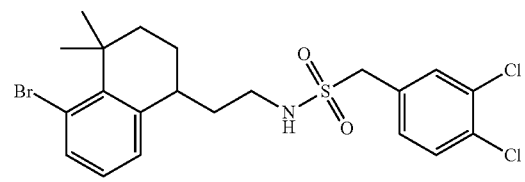 [SMILES: CC1(C)CCC(CCNS(=O)(=O)Cc2ccc(Cl)c(Cl)c2)c2cccc(Br)c21]

To a solution of tert-butyl (2-(5-bromo-4,4-dimethyl-1,2,3,4-tetrahydronaphthalen-1-yl)ethyl)carbamate (174 mg, 0.455 mmol) in 5 mL CH$_2$Cl$_2$, 2,2,2-trifluoroacetic acid (1.1 mL, 14.36 mmol) was added. After stirring at room temperature for 1 h, solution was concentrated and dried under high vacuum. The residue was dissolved in 5 mL CH$_2$Cl$_2$ and triethylamine (320 μL, 2.299 mmol). The mixture was cooled in an ice-water bath and a solution of (3,4-dichlorophenyl)methanesulfonyl chloride (177 mg, 0.682 mmol) in 2 mL CH$_2$Cl$_2$ was added. The mixture was allowed to warm to room temperature. After stirring at room temperature for 1 h, more (3,4-dichlorophenyl)methanesulfonyl chloride (100 mg) was added. After stirring at room temperature for another 1 h, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give N-(2-(5-bromo-4,4-dimethyl-1,2,3,4-tetrahydronaphthalen-1-yl)ethyl)-1-(3,4-dichlorophenyl)methanesulfonamide (168 mg, 73%). LCMS m/z=506.3 [M−1]$^+$. $^1$H NMR (400 MHz, CDCl$_3$) δ 1.49 (s, 3H), 1.53-1.59 (m, 2H), 1.60 (s, 3H), 1.74-1.89 (m, 4H), 2.82-2.88 (m, 1H), 3.04-3.13 (m, 2H), 4.05-4.09 (m, 1H), 4.20 (s, 2H), 6.91-6.95 (m, 1H), 6.99-7.02 (m, 1H), 7.24-7.26 (m, 1H), 7.43-7.50 (m, 3H).

Step G: Preparation of 8-bromo-7,7-dimethyl-1,2,3,4,4a,5,6,7-octahydronaphtho[1,8-cd]azepine (Compound 109)

To a solution of N-(2-(5-bromo-4,4-dimethyl-1,2,3,4-tetrahydronaphthalen-1-yl)ethyl)-1-(3,4-dichlorophenyl)methanesulfonamide (43.1 mg, 85.30 μmol) in 1 mL DCE, acetic anhydride (8.1 μL, 85.69 μmol), 1,3,5-trioxane (19 mg, 0.211 mmol), and methanesulfonic acid (35 μL, 0.539 mmol) were added. After stirring at room temperature for 20 min, the mixture was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give 8-bromo-2-((3,4-dichlorobenzyl)sulfonyl)-7,7-dimethyl-1,2,3,4,4a,5,6,7-octahydronaphtho[1,8-cd]azepine (not pure). The residue was dissolved in 0.5 mL AcOH and phenol (8.1 mg, 86.07 μmol) and 48% hydrogen bromide (0.5 mL, 9.208 mmol) were added. The mixture was stirred at 120° C. for 2 h and then purified by HPLC (CH$_3$CN/H$_2$O gradient+0.1% TFA) to give 8-bromo-7,7-dimethyl-1,2,3,4,4a,5,6,7-octahydronaphtho[1,8-cd]azepine 2,2,2-trifluoroacetate (1.5 mg, 4.3%). LCMS m/z=296.2 [M+1]$^+$. $^1$H NMR (400 MHz, CD$_3$OD) δ 1.54 (s, 3H), 1.62 (s, 3H), 1.63-2.11 (m, 6H), 3.30-3.46 (m, 3H), 4.23 (d, J=14.1H, 1H), 4.45 (d, J=14.1 Hz, 1H), 7.08 (d, J=8.0 Hz, 1H), 7.53 (d, J=8.0 Hz, 1H).

Example 1.11: Preparation of 2',3',4',4a',5',6'-hexahydro-1'H-spiro[cyclopentane-1,7'-naphtho[1,8-cd]azepine] (Compound 137)

Step A: Preparation of 8'-bromo-3',4'-dihydro-2'H-spiro[cyclopentane-1,1'-naphthalen]-2'-one

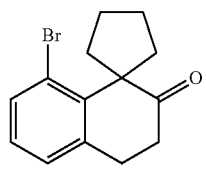 [SMILES: O=C1CCc2cccc(Br)c2C12CCCC2]

To a suspension of 60% sodium hydride dispersion (365 mg, 9.13 mmol) in 20 mL THF, a solution of 8-bromo-3,4-dihydronaphthalen-2(1H)-one (932 mg, 4.141 mmol) in 20 mL THF was added slowly (over ca. 5 min). After stirring at room temperature for 5 min, 1,4-diiodobutane (0.545 mL, 4.145 mmol) was added. After stirring at room temperature overnight, the mixture was extracted with water and AcOEt. Organic phase was dried over MgSO$_4$, filtered, and concentrated. The residue was purified by biotage column chromatography (SiO$_2$, hexane/AcOEt gradient) to give 8'-bromo-3',4'-dihydro-2'H-spiro[cyclopentane-1,1'-naphthalen]-2'-one (810 mg, 70%) as an off-white solid. LCMS m/z=281.4 [M+1]$^+$. $^1$H NMR (400 MHz, CDCl$_3$) δ 1.79-1.91 (m, 2H), 2.04-2.15 (m, 4H), 2.48-2.57 (m, 2H), 2.76-2.80 (m, 2H), 3.07 (t, J=6.9 Hz, 2H), 6.98-7.02 (m, 1H), 7.08-7.10 (m, 1H), 7.53-7.55 (m, 1H).

Step B: Preparation of 8-bromo-1,1-dimethyl-1,2,3,4-tetrahydronaphthalene

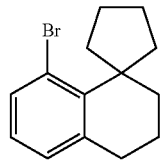 [SMILES: Brc1cccc2c1C1(CCCC1)CCC2]

A mixture of 8'-bromo-3',4'-dihydro-2'H-spiro[cyclopentane-1,1'-naphthalen]-2'-one (800 mg, 2.866 mmol), potassium hydroxide (1.45 g, 25.84 mmol), and hydrazine (1.081 mL, 34.44 mmol) in 20 mL ethylene glycol (in a high pressure vessel) was stirred at 205° C. (oil bath). After 2 h, the mixture was extracted with water and AcOEt. Organic phase was dried over MgSO$_4$, filtered, and concentrated. The residue was dried over MgSO$_4$, filtered, and concentrated. The residue was purified by biotage column chromatography (SiO$_2$, hexane/AcOEt gradient) to give 8'-bromo-3',4'-dihydro-2'H-spiro[cyclopentane-1,1'-naphthalene] (370 mg, 49%). $^1$H NMR (400 MHz, CDCl$_3$) δ 1.53-1.60 (m, 2H), 1.65-1.86 (m, 6H), 2.01-2.11 (m, 2H), 2.58-2.65 (m, 2H), 2.81 (t, J=6.2 Hz, 2H), 6.86-6.90 (m, 1H), 7.00-7.03 (m, 1H), 7.42-7.44 (m, 1H).

Step C: Preparation of 8'-bromo-2'H-spiro[cyclopentane-1,1'-naphthalen]-4'(3'H)-one

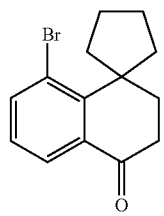 [SMILES: O=C1CCC2(CCCC2)c2c(Br)cccc21]

To a mixture of 8'-bromo-3',4'-dihydro-2'H-spiro[cyclopentane-1,1'-naphthalene] (365 mg, 1.376 mmol), sodium bicarbonate (130 mg, 1.547 mmol), and Rh$_2$(cap)$_4$ (17.6 mg, 41.59 μmol) in 10 mL DCE, 5.5 M 2-hydroperoxy-2-methylpropane in decane (1.4 mL, 7.700 mmol) was added. The mixture was stirred at 40° C. (oil bath). After 3 h, more Rh$_2$(cap)$_4$ (12.3 mg) was added. After stirring overnight, the mixture was extracted with water and CH₂Cl₂. Organic phases were dried over MgSO₄, filtered, and concentrated. The residue was purified by biotage column chromatography (SiO₂, hexane/AcOEt gradient) to give 8'-bromo-2'H-spiro[cyclopentane-1,1'-naphthalen]-4'(3'H)-one (280 mg, 73%) as a colorless oil. LCMS m/z=281.2 [M+1]⁺. ¹H NMR (4 00 MHz, CDCl₃) δ 1.73-1.92 (m, 4H), 2.04-2.19 (m, 4H), 2.60-2.67 (m, 4H), 7.11-7.15 (m, 1H), 7.79 (dd, J₁=7.8 Hz, J₂=1.5 Hz, 1H), 8.05 (dd, J₁=7.7 Hz, J₂=1.6 Hz, 1H).

Step D: Preparation of 2-(8'-bromo-2'H-spiro[cyclopentane-1,1'-naphthalen]-4'(3'H)-ylidene)acetonitrile

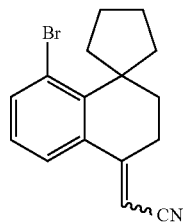 [SMILES: N#CC=C1CCC2(CCCC2)c2c(Br)cccc21]

To a suspension of 60% sodium hydride dispersion (68 mg, 1.700 mmol) in 3 mL THF, a solution of diethyl (cyanomethyl)phosphonate (280 mg, 1.581 mmol) in 3 mL THF was added slowly. After stirring at room temperature for 5 min, a solution of 8'-bromo-2'H-spiro[cyclopentane-1,1'-naphthalen]-4'(3'H)-one (284 mg, 1.017 mmol) in 4 mL THF was added. After stirring at room temperature for 5 h, the mixture was extracted with CH₂Cl₂ and water. Organic phases was dried over MgSO₄, filtered, and concentrated. The residue was purified by biotage column chromatography (SiO₂, hexane/AcOEt gradient) to give 2-(8'-bromo-2'H-spiro[cyclopentane-1,1'-naphthalen]-4'(3'H)-ylidene)acetonitrile (295 mg, 96%) (E:Z=60:40). ¹H NMR (400 MHz, CDCl₃) δ 1.57-1.66 (m, 2H), 1.79-1.95 (m, 4H), 2.05-2.17 (m, 2H), 2.43-2.47 (m, 1H), 2.60-2.70 (m, 2H), 2.75-2.78 (m, 1H), 5.25-5.26 (m, 0.4H), 5.60-5.61 (m, 0.6H), 7.01-7.12 (m, 1H), 7.44 (dd, J₁=7.9 Hz, J₂=1.4H, 0.6H), 7.67-7.71 (m, 1H), 8.04 (dd, J₁=7.8 Hz, J₂=1.4 Hz, 0.4H).

Step E: Preparation of 1-(3,4-dichlorophenyl)-N-(2-(3',4'-dihydro-2'H-spiro[cyclopentane-1,1'-naphthalen]-4'-yl)ethyl)methanesulfonamide

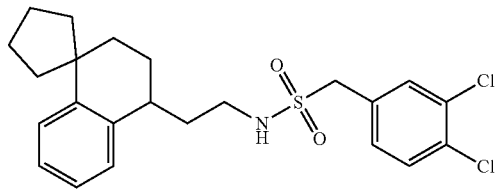 [SMILES: O=S(=O)(Cc1ccc(Cl)c(Cl)c1)NCCC1CCC2(CCCC2)c2ccccc21]

To an undetermined amount of raney nickel (slurry in water; washed three times with MeOH), a solution of 2-(8'-bromo-2'H-spiro[cyclopentane-1,1'-naphthalen]-4'(3'H)-ylidene)acetonitrile (295 mg, 0.976 mmol) in ca.10 mL MeOH and 7 M ammonia in MeOH (2 mL, 14.00 mmol) were added. The mixture was shaken on a Parr-shaker under ca. 60 psi hydrogen pressure overnight. Raney nickel was filtered off through celite, washed with additional MeOH, concentrated and dried under high vacuum. The residue was dissolved in 7 mL CH₂Cl₂ and triethylamine (0.272 mL, 1.954 mmol) and a solution of (3,4-dichlorophenyl)methanesulfonyl chloride (380 mg, 1.464 mmol) in 3 mL CH₂Cl₂ was added. After stirring at room temperature for 0.5 h, the mixture was extracted with water and CH₂Cl₂. Organic phases were dried over MgSO₄, filtered, and concentrated. The residue was purified by biotage column chromatography (SiO₂, hexane/AcOEt gradient) to give 1-(3,4-dichlorophenyl)-N-(2-(3',4'-dihydro-2'H-spiro[cyclopentane-1,1'-naphthalen]-4'-yl)ethyl)methanesulfonamide (180 mg, 41%) as an oil. LCMS m/z=450.4 [M-1]⁺. ¹H NMR (400 MHz, CDCl₃) δ 1.56-2.02 (m, 14H), 2.77-2.83 (m, 1H), 3.09-3.15 (m, 2H), 4.05-4.09 (m, 1H), 4.19 (s, 2H), 7.00-7.02 (m, 1H), 7.07-7.11 (m, 1H), 7.14-7.19 (m, 1H), 7.23-7.29 (m, 2H), 7.45-7.50 (m, 2H).

Step F: Preparation of 2'-((3,4-dichlorobenzyl)sulfonyl)-2',3',4',4a',5',6'-hexahydro-1'H-spiro[cyclopropane-1,7'-naphtho[1,8-cd]azepine]

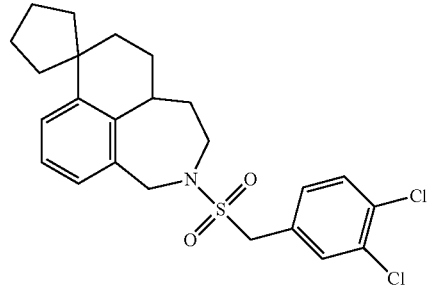 [SMILES: O=S(=O)(Cc1ccc(Cl)c(Cl)c1)N1CCC2CCC3(CCCC3)c3cccc(c32)C1]

To a solution of 1-(3,4-dichlorophenyl)-N-(2-(3',4'-dihydro-2'H-spiro[cyclopentane-1,1'-naphthalen]-4'-yl)ethyl)methanesulfonamide (175 mg, 0.387 mmol) in 4 mL DCE, 1,3,5-trioxane (100 mg, 1.110 mmol), acetic anhydride (37 µl, 0.391 mmol), and methanesulfonic acid (166 µl, 2.560 mmol) were added. After stirring at room temperature for 15 min, the mixture was extracted with 1 M NaHCO₃ and CH₂Cl₂. Organic phases were dried over MgSO₄, filtered, and concentrated. The residue was purified by biotage column chromatography (SiO₂, hexane/AcOEt gradient). Fractions containing (mainly pure) product were concentrated to give 2'-((3,4-dichlorobenzyl)sulfonyl)-2',3',4',4a',5',6'-hexahydro-1'H-spiro[cyclopentane-1,7'-naphtho[1,8-cd]azepine] (108 mg, 60%) as a white solid. ¹H NMR (400 MHz, CDCl₃) δ 1.34-1.44 (m, 1H), 1.56-1.44 (m, 4H), 1.68-1.90-m, 7H), 1.97-2.11 (m, 2H), 3.06-3.11 (m, 1H), 3.28-3.35 (m, 1H), 3.70-3.75 (m, 1H), 3.85-3.93 (m, 2H), 4.31 (d, J=15.1H, 1H), 4.57 (dd, J₁=15.1 Hz, J₂=1.3 Hz, 1H), 6.76 (dd, J₁=8.2H, J₂=2.0 Hz, 1H), 7.02 (dd, J₁=7.5 Hz, J₂=1.2 Hz, 1H), 7.14-7.18 (m, 1H), 7.25-7.33 (m, 3H).

Step G: Preparation of 2',3',4',4a',5',6'-hexahydro-1'H-spiro[cyclopentane-1,7'-naphtho[1,8-cd]azepine] (Compound 137)

A mixture of 2'-((3,4-dichlorobenzyl)sulfonyl)-2',3',4',4a',5',6'-hexahydro-1'H-spiro[cyclopentane-1,7'-naphtho[1,8-cd]azepine] (105 mg, 0.226 mmol), phenol (50 mg, 0.531 mmol), and 48% hydrogen bromide in water (2 mL, 36.83 mmol) in 2 mL acetic acid was stirred at 120° C. (oil bath). After 1 d, the mixture was concentrated and residue was purified by HPLC (CH₃CN/H₂O gradient+0.1% TFA). Fractions containing the product were concentrated. The residue was dissolved in 2 mL CH$_2$Cl$_2$ and triethylamine (160 µL, 1.148 mmol) and di-tert-butyl dicarbonate (140 mg, 0.641 mmol) were added. After stirring at room temperature for 0.5 h, solution was concentrated and residue was purified by biotage column chromatography (SiO$_2$, hexane/AcOEt gradient). Fractions containing desired product were concentrated. The residue was dissolved in 2 mL CH$_2$Cl$_2$ and TFA (1 mL, 13.06 mmol) was added. After stirring at room temperature for 1 h, the mixture was concentrated and dried under high vacuum to give 2',3',4',4a',5',6'-hexahydro-1'H-spiro[cyclopentane-1,7'-naphtho[1,8-cd]azepine] 2,2,2-trifluoroacetate (50.0 mg, 62%). LCMS m/z=242.2 [M+1]$^+$. $^1$H NMR (400 MHz, CD$_3$OD) δ 1.65-2.15 (m, 14H), 3.24-3.33 (m, 1H), 3.39-3.44 (m, 2H), 4.23 (d, J=14.1 Hz, 1H), 4.46 (d, J=14.1 Hz, 1H), 7.14-7.24 (m, 2H), 7.41-7.43 (m, 1H).

Example 1.12: Preparation of 2',3',4',4a',5',6'-hexahydro-1'H-spiro[cyclohexane-1,7'-naphtho[1,8-cd]azepine] (Compound 117)

Step A: Preparation of 3',4'-dihydro-2'H-spiro[cyclohexane-1,1'-naphthalen]-2'-one

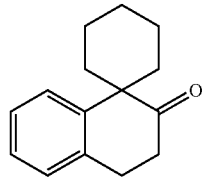 [SMILES: O=C1CCc2ccccc2C12CCCCC2]

To a suspension of 60% sodium hydride dispersion (1.2 g, 30.00 mmol) in 70 mL THF, a solution of 3,4-dihydronaphthalen-2(1H)-one (2.0 g, 13.68 mmol) in 30 mL THF was added (over ca. 5 min). After stirring at room temperature for 10 min, 1,5-diiodopentane (2.04 mL, 13.71 mmol) was added. After stirring at room temperature overnight, the mixture was partly concentrated and residue was extracted with water and AcOEt. Organic phase was dried over MgSO$_4$, filtered, and concentrated. The residue was purified by biotage column chromatography (SiO$_2$, hexane/AcOEt gradient) to give 3',4'-dihydro-2'H-spiro[cyclohexane-1,1'-naphthalen]-2'-one (2.24 g, 76%) as a colorless oil. $^1$H NMR (400 MHz, CDCl$_3$) δ 1.27-1.39 (m, 1H), 1.62-1.79 (m, 7H), 2.10-2.17 (m, 2H), 2.70 (t, J=7.1 Hz, 2H), 3.19 (t, J=7.2 Hz, 2H), 7.12 (m, 2H), 7.22-7.27 (m, 1H), 7.38-7.40 (m, 1H).

Step B: Preparation of 3',4'-dihydro-2'H-spiro[cyclohexane-1,1'-naphthalene

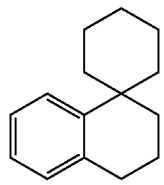 [SMILES: c1ccc2c(c1)CCCC21CCCCC1]

A mixture of 3',4'-dihydro-2'H-spiro[cyclohexane-1,1'-naphthalen]-2'-one (1.05 g, 4.900 mmol), potassium hydroxide (2.58 g, 45.98 mmol), and hydrazine (1.85 mL, 58.94 mmol) in 50 mL ethylene glycol (in a high pressure vessel) was stirred at 205° C. (oil bath). After stirring overnight, the mixture was extracted with water and AcOEt. Organic phases were dried over MgSO$_4$, filtered, and concentrated. The residue was dried over MgSO$_4$, filtered, and concentrated. The residue was purified by biotage column chromatography (SiO$_2$, hexane/AcOEt gradient) to give 3',4'-dihydro-2'H-spiro[cyclohexane-1,1'-naphthalene] (555 mg, 57%) as a colorless oil. $^1$H NMR (400 MHz, CDCl$_3$) δ 1.26-1.35 (m, 1H), 1.48-1.84 (m, 13H), 2.75 (t, J=6.4 Hz, 2H), 7.02-7.08 (m, 2H), 7.14 (m, 1H), 7.41 (d, J=7.9 Hz, 1H).

Step C: Preparation of 2'H-spiro[cyclohexane-1,1'-naphthalen]-4'(3'H)-one

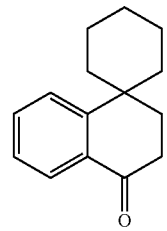 [SMILES: O=C1CCC2(CCCCC2)c2ccccc21]

To a mixture of 3',4'-dihydro-2'H-spiro[cyclohexane-1,1'-naphthalene] (550 mg, 2.746 mmol), sodium bicarbonate (283 mg, 3.369 mmol), and Rh$_2$(cap)$_4$ (25.2 mg, 59.55 µmol) in 20 mL DCE, 5.5 M 2-hydroperoxy-2-methylpropane in decane (0.247 g, 2.746 mmol) was added. The mixture was stirred at 40° C. (oil bath). After 3 h, more Rh$_2$(cap)$_4$ (20 mg) was added. After stirring overnight, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give 2'H-spiro[cyclohexane-1,1'-naphthalen]-4'(3'H)-one (485 mg, 82%) as a colorless oil. LCMS m/z=215.0 [M+1]$^+$. $^1$H NMR (4 00 MHz, CDCl$_3$) δ 1.24-1.83 (m, 10H), 2.16-2.19 (m, 2H), 2.63-2.67 (m, 2H), 7.27-7.31 (m, 1H), 7.52-7.57 (m, 2H), 8.01-8.04 (m, 1H).

Step D: Preparation of 2-(2'H-spiro[cyclohexane-1,1'-naphthalen]-4'(3'H)-ylidene)acetonitrile

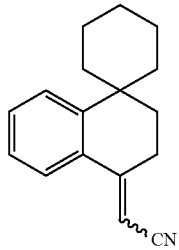 [SMILES: N#CC=C1CCC2(CCCCC2)c2ccccc21]

To a suspension of 60% sodium hydride dispersion (2.500 µL, 6.251 mmol) in 10 mL THF, a diethyl (cyanomethyl) phosphonate (610 mg, 3.444 mmol) in 5 mL THF was added slowly. After stirring at room temperature for 5 min, a solution of 2'H-spiro[cyclohexane-1,1'-naphthalen]-4'(3'H)-one (484 mg, 2.258 mmol) in 5 mL THF was added. After stirring at room temperature for 5 h, the mixture was extracted with CH$_2$Cl$_2$ and water. Organic phases was dried over MgSO$_4$, filtered, and concentrated. The residue was purified by biotage column chromatography (SiO$_2$, hexane/AcOEt gradient) to give 2-(2'H-spiro[cyclohexane-1,1'-naphthalen]-4'(3'H)-ylidene)acetonitrile (376 mg, 70%) (E:Z=63:37). $^1$H NMR (400 MHz, CDCl$_3$) δ 1.25-1.80 (m, 10H), 1.93-1.97 (m, 2H), 2.53-2.57 (m, 0.74), 2.84-2.88 (m, 1.26H), 5.25-5.26 (m, 0.37H), 5.65-5.66 (m, 0.63H), 7.19-7.29 (m, 1H), 7.38-7.44 (m, 1H), 7.47-7.50 (m, 1.63H), 8.11 (dd, J$_1$=7.9 Hz, J$_2$=1.3 Hz, 0.37H).

Step E: Preparation of 1-(3,4-dichlorophenyl)-N-(2-(3',4'-dihydro-2'H-spiro[cyclohexane-1,1'-naphthalen]-4'-yl)ethyl)methanesulfonamide

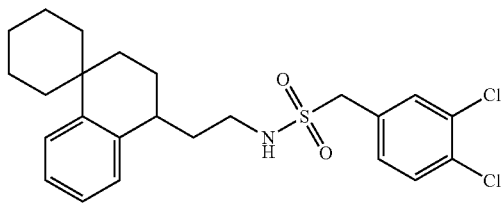 [SMILES: O=S(=O)(Cc1ccc(Cl)c(Cl)c1)NCCC1CCC2(CCCCC2)c2ccccc21]

To an undetermined amount of raney nickel (slurry in water; washed three times with MeOH), a solution of 2-(2'H-spiro[cyclohexane-1,1'-naphthalen]-4'(3'H)-ylidene)acetonitrile (374 mg, 1.576 mmol) in ca. 20 mL MeOH and 7 M ammonia in MeOH (3 mL, 21.00 mmol) were added. The mixture was shaken on a Parr-shaker under ca. 60 psi hydrogen pressure overnight. Raney nickel was filtered off through celite, washed with additional MeOH, concentrated and dried under high vacuum. The residue was dissolved in 10 mL CH$_2$Cl$_2$ and triethylamine (0.440 mL, 3.161 mmol) and a solution of (3,4-dichlorophenyl)methanesulfonyl chloride (640 mg, 2.466 mmol) in 6 mL CH$_2$Cl$_2$ was added slowly. After stirring at room temperature for 0.5 h, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give 1-(3,4-dichlorophenyl)-N-(2-(3',4'-dihydro-2'H-spiro[cyclohexane-1,1'-naphthalen]-4'-yl)ethyl)methanesulfonamide (294 mg, 40.0%). LCMS m/z=464.5 [M−1]$^+$. $^1$H NMR (400 MHz, CDCl$_3$) δ 1.23-1.69 (m, 10H), 1.74-1.95 (m, 6H), 2.74-2.81 (m, 1H), 3.09-3.15 (m, 2H), 4.02-4.05 (m, 1H), 4.19 (s, 2H), 7.00-7.03 (m, 1H), 7.08-7.12 (m, 1H), 7.16-7.21 (m, 1H), 7.23-2.26 (m, 1H), 7.41-7.50 (m, 3H).

Step F: Preparation of 2'-((3,4-dichlorobenzyl)sulfonyl)-2',3',4',4a',5',6'-hexahydro-1'H-spiro[cyclopropane-1,7'-naphtho[1,8-cd]azepine]

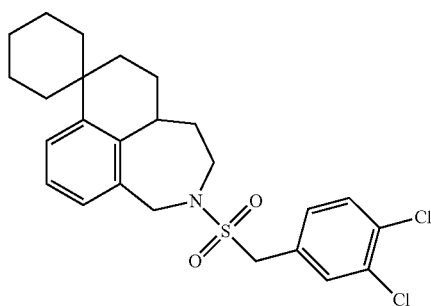 [SMILES: O=S(=O)(Cc1ccc(Cl)c(Cl)c1)N1CCC2CCC3(CCCCC3)c3cccc(c32)C1]

To a solution of 1-(3,4-dichlorophenyl)-N-(2-(3',4'-dihydro-2'H-spiro[cyclohexane-1,1'-naphthalen]-4'-yl)ethyl)methanesulfonamide (290 mg, 0.622 mmol) in 6 mL DCE, 1,3,5-trioxane (138 mg, 1.532 mmol), acetic anhydride (59 μl, 0.624 mmol), and methanesulfonic acid (265 μl, 4.086 mmol) were added. After stirring at room temperature for 15 min, the mixture was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient). Fractions containing the product were concentrated to give 2'-((3,4-dichlorobenzyl)sulfonyl)-2',3',4',4a',5',6'-hexahydro-1'H-spiro[cyclohexane-1,7'-naphtho[1,8-cd]azepine] (251 mg, 84%). $^1$H NMR (400 MHz, CDCl$_3$) δ 1.24-1.67 (m, 12H), 1.75-1.80 (m, 1H), 1.85-2.00 (m, 3H), 3.06-3.12 (m, 1H), 3.30-3.37 (m, 1H), 3.71-3.76 (m, 1H), 3.81 (d, J=15.0 Hz, 1H), 3.89 (d. J=15.0 Hz, 1H), 4.32 (d, J=15.0 Hz, 1H), 4.54 (dd, J$_1$=15.0 Hz, J$_2$=1.1 Hz, 1H), 6.87 (dd, J$_1$=8.2 Hz, J$_2$=2.1 Hz, 1H), 7.02 (dd, J$_1$=7.2H, J$_2$=1.0 Hz, 1H), 7.15-7.19 (m, 1H), 7.28-7.32 (m, 2H), 7.45 (d, J=8.2 Hz, 1H).

Step G: Preparation of 2',3',4',4a',5',6'-hexahydro-1'H-spiro[cyclohexane-1,7'-naphtho[1,8-cd]azepine] (Compound 117)

A mixture of 2'-((3,4-dichlorobenzyl)sulfonyl)-2',3',4',4a',5',6'-hexahydro-1'H-spiro[cyclohexane-1,7'-naphtho[1,8-cd]azepine] (245 mg, 0.512 mmol), phenol (108 mg, 1.148 mmol), and 48% hydrogen bromide in water (3 mL, 55.25 mmol) in 3 mL acetic acid was stirred at 120° C. (oil bath) (in a closed microwave vial). After 1 d, the mixture was concentrated and residue was purified by HPLC (CH$_3$CN/H$_2$O gradient+0.1% TFA). Fractions containing the product were concentrated. The residue was dissolved in 5 mL CH$_2$Cl$_2$ and triethylamine (0.4 mL, 2.870 mmol) and di-tert-butyl dicarbonate (250 mg, 1.145 mmol) were added. After stirring at room temperature for 0.5 h, solution was concentrated and residue was purified by biotage column chromatography (SiO$_2$, hexane/AcOEt gradient). Fractions containing desired product were concentrated. The residue was dissolved in 5 mL CH$_2$Cl$_2$ and 2,2,2-trifluoroacetic acid (1.2 mL, 15.67 mmol) was added. After stirring at room temperature for 1 h, the mixture was concentrated and dried under high vacuum to give 2',3',4',4a',5',6'-hexahydro-1'H-spiro[cyclohexane-1,7'-naphtho[1,8-cd]azepine] 2,2,2-trifluoroacetate (98 mg, 52%). LCMS m/z=242.2 [M+1]$^+$. $^1$H NMR (400 MHz, CD$_3$OD) δ 1.29-1.42 (m, 1H), 1.48-1.82 (m, 10H), 1.85-2.08 (m, 5H), 3.23-3.29 (m, 1H), 3.39-3.42 (m, 2H), 4.23 (d, J=14.1 Hz, 1H), 4.47 (d, J=14.1 Hz, 1H), 7.16 (dd, J$_1$=7.4 Hz, J$_2$=1.3 Hz, 1H), 7.21-7.25 (m, 1H), 7.57 (dd, J$_1$=8.0 Hz, J$_2$=1.0 Hz, 1H).

Example 1.13: Preparation of 7',7'-dimethyl-2',3',4',4a',5',7'-hexahydro-1'H-spiro[cyclopropane-1,6'-naphtho[1,8-cd]azepine] (Compound 121)

Step A: Preparation of 1,1-dimethyl-3,4-dihydronaphthalen-2(1H)-one

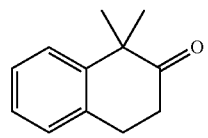

To a suspension of 60% sodium hydride dispersion (640 mg, 16.00 mmol) in 20 mL THF, a solution of 3,4-dihydronaphthalen-2(1H)-one (1.03 g, 7.046 mmol) in 10 mL THF was added (over ca. 5 min). After stirring at room temperature for 20 min, iodomethane (0.880 mL, 14.10 mmol) was added. After stirring at room temperature for 50 min, the mixture was extracted with water and AcOEt. Organic phases were dried over MgSO$_4$, filtered, and concentrated. The residue was purified by biotage column chromatography (SiO$_2$, hexane/AcOEt gradient) to give 1,1-dimethyl-3,4-dihydronaphthalen-2(1H)-one (991 mg, 81%) as a colorless oil. $^1$H NMR (400 MHz, CDCl$_3$) δ 1.44 (s, 6H), 2.67-2.71 (m, 2H), 3.10 (t, J=6.6 Hz, 2H), 7.15-7.22 (m, 2H), 7.24-7.29 (m, 1H), 7.33-7.36 (m, 1H).

Step B: Preparation of 1,1-dimethyl-2-methylene-1,2,3,4-tetrahydronaphthalene

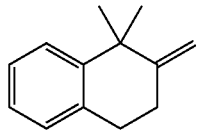

To a suspension of methyltriphenylphosphonium bromide (4.61 g, 12.91 mmol) in 20 mL toluene, 1 M potassium 2-methylpropan-2-olate in THF (17 mL, 17.00 mmol) was added. After stirring at 120° C. (oil bath) for 40 min, a solution of 1,1-dimethyl-3,4-dihydronaphthalen-2(1H)-one (984 mg, 5.647 mmol) in 3 mL toluene was added. The mixture was stirred at 120° C. for 10 min, allowed to cool to room temperature, and extracted with water and CH$_2$Cl$_2$. Organic phases were dried over MgSO$_4$, filtered, and concentrated. The residue was purified by biotage column chromatography (SiO$_2$, hexanes) to give 1,1-dimethyl-2-methylene-1,2,3,4-tetrahydronaphthalene (867 mg, 89%) as a colorless liquid. $^1$H NMR (400 MHz, CDCl$_3$) δ 1.46 (s, 6H), 2.53 (dt, J$_1$=6.5 Hz, J$_2$=1.0 Hz, 2H), 2.85 (t, J=6.5 Hz, 2H), 4.85-4.86 (m, 1H), 4.91-4.92 (m, 1H), 7.03-7.10 (m, 2H), 7.16 (m, 1H), 7.36-7.38 (m, 1H).

Step C: Preparation of 1',1'-dimethyl-3',4'-dihydro-1'H-spiro[cyclopropane-1,2'-naphthalene]

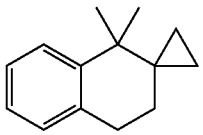

To a solution of 1,1-dimethyl-2-methylene-1,2,3,4-tetrahydronaphthalene (1.03 g, 5.979 mmol) in 20 mL DCE, chloroiodomethane (2.7 mL, 37.20 mmol) was added. Flask was placed into an ice/water-bath and 1 M diethylzinc in hexane (30 mL, 30.00 mmol) was added over ca. 5 min. After stirring under ice-cooling for 1 h, the mixture was allowed to warm to room temperature. After stirring for two more hours, the mixture was placed into an ice/water bath and quenched by the slow addition of 1 M NH$_4$Cl. The mixture was extracted with CH$_2$Cl$_2$ and 1 M NH$_4$Cl. Organic phases were dried over MgSO$_4$, filtered, and concentrated. The residue was purified by biotage column chromatography (SiO$_2$, hexane) to 1',1'-dimethyl-3',4'-dihydro-1'H-spiro[cyclopropane-1,2'-naphthalene] (83% pure, 0.987 g, 74%) as a colorless oil. $^1$H NMR (400 MHz, CDCl$_3$) δ 0.23-0.25 (m, 2H), 0.62-0.65 (m, 2H), 1.14 (s, 6H), 1.60 (t, J=6.3 Hz, 2H), 2.82 (t, J=6.3 Hz, 2H), 7.05-7.18 (m, 3H), 7.32 (d, J=7.7 Hz, 1H).

Step D: Preparation of 1',1'-dimethyl-1'H-spiro[cyclopropane-1,2'-naphthalen]-4'(3'H)-one

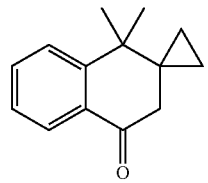

To a solution of 1',1'-dimethyl-3',4'-dihydro-1'H-spiro[cyclopropane-1,2'-naphthalene] (83% pure. 977 mg, 4.353 mmol) in 20 mL DCE, sodium bicarbonate (240 mg, 2.857 mmol), Rh$_2$(cap)$_4$ (27.1 mg, 41.41 µmol), and 5.5 M 2-hydroperoxy-2-methylpropane in decane (5 mL, 27.50 mmol) were added. After stirring at 40° C. (oil bath) for 3 h, more Rh$_2$(cap)$_4$ (23.2 mg) was added. After stirring at 40° C. overnight, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give 1',1'-dimethyl-1'H-spiro[cyclopropane-1,2'-naphthalen]-4'(3'H)-one (626 mg, 72%). $^1$H NMR (400 MHz, CDCl$_3$) δ 0.30-0.33 (m, 2H), 0.71-0.74 (m, 2H), 1.25 (s, 6H), 2.56 (s, 2H), 7.29-7.33 (m, 1H), 7.43-7.46 (m, 1H), 7.51-7.55 (m, 1H), 8.02-8.04 (m, 1H).

Step E: Preparation of 2-(1',1'-dimethyl-1'H-spiro[cyclopropane-1,2'-naphthalen]-4'(3'H)-ylidene)acetonitrile

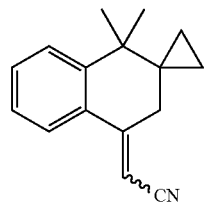 [SMILES: CC1(C)c2ccccc2C(=CC#N)CC12CC2]

To a suspension of 60% sodium hydride dispersion (196 mg, 4.900 mmol) in 10 mL THF, a solution of diethyl (cyanomethyl)phosphonate (843 mg, 4.759 mmol) in 10 mL THF was added slowly. After stirring at room temperature for 5 min, a solution of 1',1'-dimethyl-1'H-spiro[cyclopropane-1,2'-naphthalen]-4'(3'H)-one (622 mg, 3.106 mmol) in 10 mL THF was added. After stirring at room temperature over the weekend, the mixture was extracted with CH$_2$Cl$_2$ and water. Organic phases was dried over MgSO$_4$, filtered, and concentrated. The residue was purified by biotage column chromatography (SiO$_2$, hexane/AcOEt gradient) to give 2-(1',1'-dimethyl-1'H-spiro[cyclopropane-1,2'-naphthalen]-4'(3'H)-ylidene)acetonitrile (265 mg, 38%) (E:Z=61:39). $^1$H NMR (400 MHz, CDCl$_3$) 0.28-0.31 (m, 1.22H), 0.37-0.39 (m, 0.78H), 0.68-0.73 (m, 2H), 1.17 (s, 3.7H), 1.18 (s, 2.3H), 2.32 (d, J=0.8 Hz, 1.22H), 2.68 (d, J=0.9 Hz, 0.78H), 5.12-5.13 (m, 0.61H), 5.65-5.66 (m, 0.39H), 7.19-7.29 (m, 1H), 7.37-7.43 (m, 2H), 7.48-7.50 (m, 0.39H), 8.14-8.16 (m, 0.61H).

Step F: Preparation of 2-(1',1'-dimethyl-3',4'-dihydro-1'H-spiro[cyclopropane-1,2'-naphthalen]-4'-yl)ethanamine

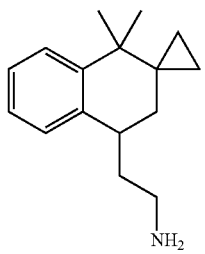 [SMILES: CC1(C)c2ccccc2C(CCN)CC12CC2]

To a mixture of 2-(1',1'-dimethyl-1'H-spiro[cyclopropane-1,2'-naphthalen]-4'(3'H)-ylidene)acetonitrile (262 mg, 1.173 mmol) and cobalt(II) chloride hexahydrate (647 mg, 2.719 mmol) in 20 mL MeOH, sodium tetrahydroborate (1.08 g, 28.55 mmol) was added in small portions over ca. 6 h. After stirring at room temperature overnight, di-tert-butyl dicarbonate (510 mg, 2.337 mmol) was added. After stirring at room temperature for 0.5 h, the mixture was partly concentrated and residue was extracted with water and CH$_2$Cl$_2$. Organic phases were dried over MgSO$_4$, filtered, and concentrated. The residue was purified by biotage column chromatography (SiO$_2$, hexane/AcOEt gradient). Fractions containing Boc-protected product were concentrated. The residue was dissolved in 8 mL CH$_2$Cl$_2$ and TFA (2.7 mL, 35.26 mmol) was added. After stirring at room temperature for 1 h, solution was concentrated and dried under high vacuum to give 2-(1',1'-dimethyl-3',4'-dihydro-1'H-spiro[cyclopropane-1,2'-naphthalen]-4'-yl)ethanamine 2,2,2-trifluoroacetate (304 mg, 76%). LCMS m/z=230.6 [M+1]$^+$. $^1$H NMR (400 MHz, CD$_3$OD) δ 0.21-0.27 (m, 1H), 0.36-0.41 (m, 1H), 0.58-0.62 (m, 1H), 0.78-0.81 (m, 1H), 1.09 (s, 3H), 1.18 (s, 3H), 1.60-1.65 (m, 1H), 1.70-1.74 (m, 1H), 2.01-2.16 (m, 2H), 2.95-3.03 (m, 3H), 7.09-7.19 (m, 3H), 7.38 (dd, J$_1$=7.9 Hz, J$_2$=1.6 Hz, 1H).

Step G: Preparation of 1-(3,4-dichlorophenyl)-N-(2-(1',1'-dimethyl-3',4'-dihydro-1'H-spiro[cyclopropane-1,2'-naphthalen]-4'-yl)ethyl)methanesulfonamide

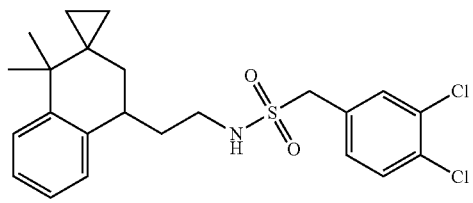 [SMILES: CC1(C)c2ccccc2C(CCNS(=O)(=O)Cc2ccc(Cl)c(Cl)c2)CC12CC2]

To a solution of 2-(1',1'-dimethyl-3',4'-dihydro-1'H-spiro[cyclopropane-1,2'-naphthalen]-4'-yl)ethanamine 2,2,2-trifluoroacetate (296 mg, 0.862 mmol) and triethylamine (0.6 mL, 4.305 mmol) in 5 mL CH$_2$Cl$_2$, a solution of (3,4-dichlorophenyl)methanesulfonyl chloride (360 mg, 1.387 mmol) in 4 mE CH$_2$Cl$_2$ was added slowly. After stirring at room temperature for 0.5 h, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient). Fractions containing product were concentrated and residue was re-purified by HPLC (CH$_3$CN/H$_2$O gradient+ 0.1% TFA). Fractions containing product were partly concentrated and residue was extracted with 1 M NaHCO$_3$ and CH$_2$Cl$_2$. Organic phases were dried over MgSO$_4$, filtered, and concentrated to give 1-(3,4-dichlorophenyl)-N-(2-(1',1'-dimethyl-3',4'-dihydro-1'H-spiro[cyclopropane-1,2'-naphthalen]-4'-yl)ethyl)methanesulfonamide (199 mg, 51%). LCMS m/z=450.1 [M-1]$^+$. $^1$H NMR (400 MHz, CDCl$_3$) δ 0.16 (m, 1H), 0.29-0.33 (m, 1H), 0.54-0.59 (m, 1H), 0.71 (m, 1H), 1.07 (s, 3H), 1.17 (s, 3H), 1.51-1.62 (m, 2H), 1.87-2.03 (m, 2H), 2.89-2.96 (m, 1H), 3.03-3.12 (m, 2H), 4.03-4.06 (m, 1H), 4.18 (s, 2H), 7.08-7.21 (m, 3H), 7.22-7.25 (m, 1H), 7.35 (dd, J$_1$=7.8 Hz, J$_1$=1.5 Hz, 1H), 7.45-7.49 (m, 2H).

Step H: Preparation of 2'-((3,4-dichlorobenzyl)sulfonyl)-7',7'-dimethyl-2',3',4',4a',5',7'-hexahydro-1'H-spiro[cyclopropane-1,6'-naphtho[1,8-cd]azepine]

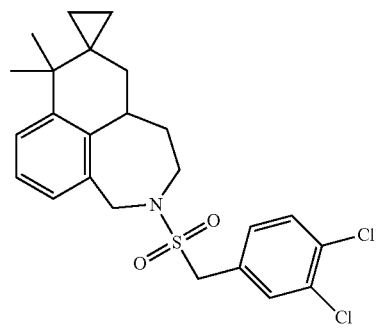 [SMILES: CC1(C)c2cccc3c2C(CCN(S(=O)(=O)Cc2ccc(Cl)c(Cl)c2)C3)CC12CC2]

To a solution of 1-(3,4-dichlorophenyl)-N-(2-(1',1'-dimethyl-3',4'-dihydro-1'H-spiro[cyclopropane-1,2'-naphthalen]-4'-yl)ethyl)methanesulfonamide (196 mg, 0.433 mmol) in 4 mL DCE, 1,3,5-trioxane (111 mg, 1.232 mmol), acetic anhydride (41 μl, 0.434 mmol), and methanesulfonic acid (185 μl, 2.853 mmol) were added. After stirring at room temperature for 10 min, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give 2'-((3,4-dichlorobenzyl)sulfonyl)-7',7'-dimethyl-2',3',4',4a',5',7'-hexahydro-1'H-spiro[cyclopropane-1, 6'-naphtho[1,8-cd]azepine] (141 mg, 70%) as a white solid. $^1$H NMR (400 MHz, CDCl$_3$) 0.16-0.21 (m, 1H), 0.27-0.32 (m, 1H), 0.48-0.53 (m, 1H), 0.68-0.71 (m, 1H), 1.13 (s, 3H), 1.15 (s, 3H), 1.37-1.65 (m, 4H), 1.97-2.04 (m, 1H), 3.12-3.17 (m, 1H), 3.23-3.31 (m, 1H), 3.81-3.86 (m, 1H), 3.90 (s, 2H), 4.27 (d, J=15.2 Hz, 1H), 4.60 (dd, J$_1$=15.2 Hz, J$_2$=1.5 Hz, 1H), 6.82 (dd, J$_1$=8.3 Hz, J$_2$=2.1 Hz, 1H), 7.05 (dd, J$_1$=7.2 Hz, J$_2$=1.3 Hz, 1H), 7.14-7.18 (m, 1H), 7.28-7.31 (m, 2H), 7.38 (dd, J$_1$=8.0 Hz, J$_2$=1.2 Hz, 1H).

Step I: Preparation of 7',7'-dimethyl-2',3',4',4a',5',7'-hexahydro-1'H-spiro[cyclopropane-1,6'-naphtho[1,8-cd]azepine] (Compound 121)

To a solution of 2'-((3,4-dichlorobenzyl)sulfonyl)-7',7'-dimethyl-2',3',4',4a',5',7'-hexahydro-1'H-spiro[cyclopropane-1,6'-naphtho[1,8-cd]azepine] (70.7 mg, 0.152 mmol) in 2 mL toluene, 60% bis(2-methoxyethoxy)aluminum(III) sodium hydride in toluene (1.3 mL, 3.997 mmol) was added. After stirring at room temperature for 1.5 h, solution was continued to be stirred at 80° C. (oil bath). After stirring overnight, the mixture was cooled in an ice/water-bath, quenched by the slow addition of water, concentrated, and residue was purified by HPLC (CH$_3$CN/H$_2$O gradient+0.1% TFA) to give 7',7'-dimethyl-2',3',4',4a',5',7'-hexahydro-1'H-spiro[cyclopropane-1,6'-naphtho[1,8-cd]azepine] 2,2,2-trifluoroacetate (39.7 mg, 73%). LCMS m/z=242.4 [M+1]$^+$. $^1$H NMR (400 MHz, CD$_3$OD) δ 0.25-0.29 (m, 1H), 0.38-0.43 (m, 1H), 0.54-0.58 (m, 1H), 0.72-0.77 (m, 1H), 1.15 (s, 3H), 1.16 (s, 3H), 1.55-1.60 (m, 1H), 1.91-2.08 (m, 3H), 3.30-3.43 (m, 2H), 3.47-3.51 (m, 1H), 4.25 (dd, J$_1$=14.1 Hz, J$_2$=0.8 Hz, 1H), 4.43 (d, J=14.1 Hz, 1H), 7.17-7.24 (m, 2H), 7.50 (dd, =7.8 Hz, J2=1.6 Hz, 1H).

Step J: Resolution of Compound 121 into Enantiomers 115 and 112

Compound 121 was resolved to give two enantiomers by normal phase preparative chiral HPLC under the following conditions:
Column: Normal phase semi preparative CHIRALPAK®IF column, 5 m (particle size), 250×20 mm (L×ID)
Eluent: hexanes/EtOH 100:5+0.1% triethylamine
Gradient: Isocratic
Flow: 10 mL/min
Detector: UV 254 nm
Retention Times: 1$^{st}$ enantiomer: 28.9 min; 2$^{nd}$ enantiomer: 35.6 min Example 1.14: Preparation of 2',3',4',4a',5'-pentahydro-1'H-dispiro[cyclopropane-1,6'-cyclopropane-7',1''-naphtho[1,8-cd]-azepine] (Compound 130)

Step A: Preparation of 3',4'-dihydro-1'H-spiro[cyclopropane-1,2'-naphthalen]-1'-one

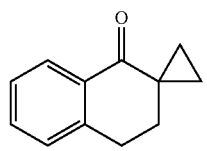

To a solution of 3,4-dihydronaphthalen-1(2H)-one (3.0 g, 20.52 mmol) in 200 mL tBuOH, 1 M potassium 2-methylpropan-2-olate in THF (62 mL, 62.00 mmol) was added. After stirring at room temperature for 0.5 h, (2-chloroethyl) dimethylsulfonium iodide (5.19 g, 20.55 mmol) was added. After stirring at room temperature over-the-weekend, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give 3',4'-dihydro-1'H-spiro[cyclopropane-1,2'-naphthalen]-1'-one (2.49 g, 71%). LCMS m/z=191.4 [M+1]$^+$. $^1$H NMR (400 MHz, CDCl$_3$) 0.81-0.84 (m, 2H), 1.39-1.42 (m, 2H), 1.97-2.00 (m, 2H), 3.01 (t, J=6.2 Hz, 2H), 7.25-7.33 (m, 2H), 7.44-7.48 (m, 1H), 8.00 (dd, J$_1$=7.8 Hz, J$_2$=1.1 Hz, 1H).

Step B: Preparation of 8'-fluoro-1'-methylene-3',4'-dihydro-1'H-spiro[cyclopropane-1,2'-naphthalene]

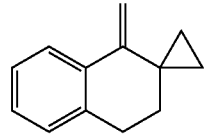

To a suspension of methyltriphenylphosphonium bromide (8.8 g, 24.63 mmol) in 60 mL toluene, 1 M potassium 2-methylpropan-2-olate in THF (44 mL, 44.00 mmol) was added. After stirring at 110° C. (oil bath) for 50 min, a solution of 3',4'-dihydro-1'H-spiro[cyclopropane-1,2'-naphthalen]-1'-one (2.489 g, 14.45 mmol) in 10 mL toluene was added. The mixture was stirred at 110° C. for 10 min, allowed to cool to room temperature, and extracted with water and CH$_2$Cl$_2$. Organic phases were dried over MgSO$_4$, filtered, and concentrated. The residue was purified by biotage column chromatography (SiO$_2$, hexanes) to give 1'-methylene-3',4'-dihydro-1'H-spiro[cyclopropane-1,2'-naphthalene] (2.01 g, 82%) as a colorless liquid. $^1$H NMR (400 MHz, CDCl$_3$) δ 0.63-0.66 (m, 2H), 0.81-0.84 (m, 2H), 1.63-1.66 (m, 2H), 2.90 (t, J=6.2 Hz, 2H), 4.73 (s, 1H), 5.41 (s, 1H), 7.12-7.20 (m, 3H), 7.64-7.66 (m, 1H).

Step C: Preparation of Compound 14 of FIG. 2, where R$^1$=H

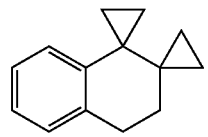 [SMILES: c1ccc2c(c1)CCC1(CC1)C21CC1]

To an ice-cooled solution of 2'-methylene-3',4'-dihydro-2'H-spiro[cyclopropane-1,1'-naphthalene] (2.0 g, 11.75 mmol) and chloroiodomethane (5.1 mL, 70.26 mmol) in 75 mL DCE, 1 M diethylzinc in hexanes (59 mL, 59.00 mmol) was added over ca. 10 min. The mixture was allowed to warm to room temperature (slight exotherm observed). After 1 h, suspension was quenched by the addition of 1 M NH$_4$Cl and extracted with water and CH$_2$Cl$_2$. Combined organic phases were dried over MgSO$_4$, filtered, and concentrated. The residue was purified by biotage column chromatography (SiO$_2$, hexane/AcOEt gradient) to give the title compound for this step (1.57 g, 73%) as a colorless liquid. $^1$H NMR (400 MHz, CDCl$_3$) δ 0.23-0.26 (m, 2H), 0.29-0.32 (m, 2H), 0.66-0.69 (m, 2H), 0.78-0.81 (m, 2H), 1.70-1.72 (m, 2H), 2.97 (t, J=6.3 Hz, 2H), 6.66-6.69 (m, 1H), 7.03-7.11 (m, 3H).

Step D: Preparation of Compound 15 of FIG. 2, where R$^1$=H

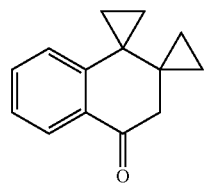 [SMILES: O=C1CC2(CC2)C2(CC2)c2ccccc21]

To a solution of the product of Step C (1.557 g, 8.449 mmol) in 40 mL DCE, sodium bicarbonate (365 mg, 4.345 mmol), Rh$_2$(cap)$_4$ (132 mg, 0.202 mmol), and 5.5 M 2-hydroperoxy-2-methylpropane in decane (10 mL, 55.00 mmol) were added. After stirring at 40° C. (oil bath) for 3 h, more Rh$_2$(cap)$_4$ (125 mg) and 5.5 M 2-hydroperoxy-2-methylpropane in decane (10 mL) were added. After stirring at 40° C. overnight, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (1.15 g, 69%) as a colorless liquid. H NMR (400 MHz, CDCl$_3$) 0.34-0.42 (m, 4H), 0.86-0.89 (m, 2H), 0.96-0.99 (m, 2H), 2.63 (s, 2H), 6.85 (dd, J$_1$=8.0 Hz, J$_2$=0.4 Hz, 1H), 7.25-7.29 (m, 1H), 7.43-7.48 (m, 1H), 8.08 (dd, J$_1$=7.8 Hz, J$_2$=1.4 Hz, 1H).

Step E: Preparation of Compound 16 of FIG. 2, where R$^1$=H

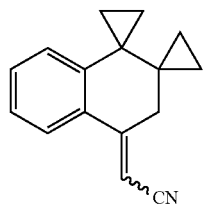 [SMILES: N#CC=C1CC2(CC2)C2(CC2)c2ccccc21]

To a suspension of 60% sodium hydride dispersion (570 mg, 14.25 mmol) in 20 mL THF, a solution of diethyl (cyanomethyl)phosphonate (2.52 g, 14.23 mmol) in 40 mL THF was added slowly (over ca. 5 min). After stirring at room temperature for 5 min, a solution of the product of Step D (1.15 g, 5.800 mmol) in 20 mL THF was added. After stirring at 60° C. (oil bath) for 2 h, the mixture was extracted with CH$_2$Cl$_2$ and water+brine. Organic phases were dried over MgSO$_4$, filtered, and concentrated. The residue was purified by biotage column chromatography (SiO$_2$, hexane/AcOEt gradient) to give the title compound for this step (1.18 g, 92%) as a colorless oil (E:Z=59:41). $^1$H NMR (400 MHz, CDCl$_3$) δ 0.29-0.41 (m, 4H), 0.78-0.91 (m, 4H), 2.43 (d, J=0.9 Hz, 1.18H), 2.77 (d, J=0.9 Hz, 0.82H), 5.15-5.16 (m, 0.59H), 5.72-5.73 (m, 0.41H), 6.73-6.78 (m, 1H), 7.15-7.26 (m, 1H), 7.30-7.35 (m, 1H), 7.54 (dd, J$_1$=8.0 Hz, J$_2$=1.3 Hz, 0.41H), 8.23 (dd, J$_1$=7.9 Hz, J$_2$=1.2 Hz, 0.59H).

Step F: Preparation of Compound 17 of FIG. 2, where R$^1$=H, Boc-protected

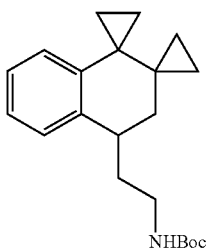 [SMILES: CC(C)(C)OC(=O)NCCC1CC2(CC2)C2(CC2)c2ccccc21]

To a mixture of the product of Step E (1.18 g, 5.332 mmol) and cobalt(II) chloride hexahydrate (6.9 g, 29.00 mmol) in 160 mL MeOH, sodium tetrahydroborate (5 g, 132.2 mmol) was added in small portions over 5 h. After stirring at room temperature overnight, di-tert-butyl dicarbonate (3.3 g, 15.12 mmol) was added. After stirring at room temperature for 1 h, the mixture was partly concentrated and residue was extracted with water+brine and CH$_2$Cl$_2$. Part of the organic layer was separated and the rest was filtered through celite (and washed with additional CH$_2$Cl$_2$). Filtrate was extracted three more times with CH$_2$Cl$_2$. Combined organic phases were dried over MgSO$_4$, filtered, and concentrated. The residue was purified by biotage column chromatography (SiO$_2$, hexane/AcOEt gradient) to give the title compound for this step (1.07 g, 61%) as a viscous oil the solidified while drying under high vacuum. LCMS m/z=328.6 [M+1]$^+$. $^1$H NMR (400 MHz, CDCl$_3$) δ 0.18-0.24 (m, 2H), 0.32-0.41 (m, 2H), 0.62-0.69 (m, 2H), 0.75-0.85 (m, 2H), 1.45 (s, 9H), 1.70-1.75 (m, 1H), 1.79-1.84 (m, 1H), 1.87-1.96 (m, 1H), 2.01-2.09 (m, 1H), 3.03-3.10 (m, 1H), 3.19-3.26 (m, 2H), 4.50 (br s, 1H), 6.67-6.71 (m, 1H), 7.07-7.22 (m, 2H), 7.19-7.22 (m, 1H).

Step G: Preparation of Compound 18 of FIG. 2, where R$^1$=H and R$^{10}$ is 3,4-dichlorobenzyl

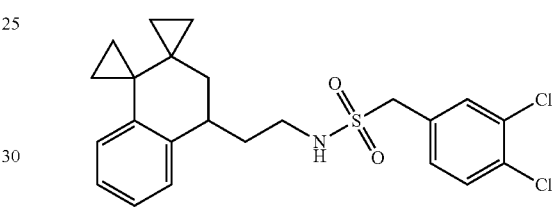

To an ice-cooled solution of the product of Step F (1.07 g, 3.268 mmol) in 33 mL CH$_2$Cl$_2$, TFA (7.5 mL, 97.94 mmol) was added. The mixture was allowed to warm to room temperature. After 0.5 h, solution was concentrated and dried under high vacuum. The residue was dissolved in 40 mL DCM and DIEA (2.17 mL, 12.46 mmol), cooled in an ice/water-bath, and a solution of (3,4-dichlorophenyl)methanesulfonyl chloride (1.73 g, 6.666 mmol) in 10 mL CH$_2$Cl$_2$ was added (over ca. 5 min). After stirring at 0° C. for 1 h, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (1.23 g, 84%). LCMS m/z=448.4 [M−1]$^+$. $^1$H NMR (400 MHz, CDCl$_3$) δ 0.17-0.32 (m, 3H), 0.37-0.42 (m, 1H), 0.62-0.70 (m, 2H), 0.76-0.82 (m, 2H), 1.63-1.68 (m, 1H), 1.72-1.77 (m, 1H), 1.94-2.08 (m, 2H), 3.05-3.14 (m, 3H), 4.04-4.07 (m, 1H), 4.18 (s, 2H), 6.69-6.71 (m, 1H), 7.08-7.15 (m, 3H), 7.24 (dd, J$_1$=8.2 Hz, J$_2$=2.1 Hz, 1H), 7.45-7.49 (m, 2H).

Step H: Preparation of Compound 19 of FIG. 2, where R$^1$=H and R$^{10}$ is 3,4-dichlorobenzyl

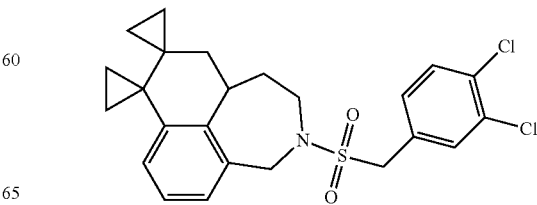

To a solution of the product of Step G (1.226 g, 2.722 mmol) in 30 mL DCE, 1,3,5-trioxane (583 mg, 6.472 mmol), acetic anhydride (0.257 mL, 2.722 mmol), and methanesulfonic acid (1.16 mL, 17.89 mmol) were added. After stirring at room temperature for 10 min, the mixture was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (435 mg, 35%) as a white solid. $^1$H NMR (400 MHz, CDCl$_3$) 0.10-0.177 (m, 2H), 0.29-0.33 (m, 1H), 0.39-0.43 (m, 1H), 0.60-0.65 (m, 1H), 0.74-0.77 (m, 2H), 0.95-0.99 (m, 1H), 1.36-1.58 (m, 3H), 2.16-2.21 (m, 1H), 3.25-3.32 (m, 2H), 3.84-3.96 (m, 3H), 4.32 (d, J=15.4 Hz, 1H), 4.66 (dd, J$_1$=15.4 Hz, J$_2$=1.5 Hz, 1H), 6.74 (dd, J$_1$=8.0 Hz, J$_2$=1.1 Hz, 1H), 6.79 (dd, J$_1$=8.3 Hz, J$_2$=2.0 Hz, 1H), 7.01-7.06 (m, 2H), 7.10-7.14 (m, 1H), 7.28 (d, J=8.2 Hz, 1H).

Step I: Preparation of Compound 130, Boc-protected

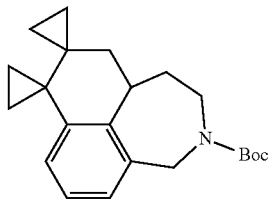 [SMILES: CC(C)(C)OC(=O)N1CCC2CC3(CC3)C3(CC3)c3cccc(c32)C1]

To a solution of the product of Step H (430 mg, 0.930 mmol) in 10 mL toluene, 60% bis(2-methoxyethoxy)aluminum(III) sodium hydride in toluene (5 mL, 15.37 mmol) was added. The mixture was warmed to 80° C. (oil bath). After 3 h, more 60% bis(2-methoxyethoxy)aluminum(III) sodium hydride in toluene (5 mL) was added and continued to be stirred at 80° C. After another 2 h, the mixture was cooled in an ice/water-bath and quenched by the dropwise addition of 1 M NH$_4$Cl. The mixture was diluted with additional toluene (ca. 20 mL) and (BOC)$_2$O (1.5 g, 6.873 mmol) was added. The mixture was allowed to warm to room temperature. After 1 h, 2 M NH$_4$Cl (ca. 100 mL), followed by 1 M NaOH (ca. 100 mL) were added. After stirring for a while (ca. 0.5 h), the mixture was extracted with CH$_2$Cl$_2$ (3×). Combined organic phases were dried over MgSO$_4$, filtered, and concentrated. The residue was purified by biotage column chromatography (SiO$_2$, hexane/AcOEt gradient) to give the title compound for this step (234 mg, 74%) as colorless, viscous oil. LCMS m/z=340.2 [M+1]$^+$. $^1$H NMR (400 MHz, CDCl$_3$) δ 0.15-0.19 (m, 2H), 0.36-0.40 (m, 2H), 0.58-0.63 (m, 1H), 0.67-0.78 (m, 2H), 0.86-0.91 (m, 1H), 1.42 (s, 9H), 1.55-1.75 (m, 2H), 1.88-2.01 (m, 1H), 2.06-2.16 (m, 1H), 3.17-3.37 (m, 2H), 4.15-4.26 (m, 2H), 4.59-4.71 (m, 1H), 6.64 (d, J=8.2 Hz, 1H), 6.99-7.14 (m, 2H).

Step J: Preparation of 2',3',4',4a',5'-pentahydro-1'H-dispiro[cyclopropane-1,6'-cyclopropane-7',1"-naphtho[1,8-cd]-azepine] (Compound 130)

To an ice-cooled solution of the product of Step I (231 mg, 0.680 mmol) in 7 mL CH$_2$Cl$_2$, TFA (1.58 mL, 20.63 mmol) was added. Solution was allowed to warm to room temperature. After 0.5 h, solution was concentrated. The residue was dissolved in CH$_2$Cl$_2$ (ca. 10 mL) and 1.25 M hydrogen chloride in EtOH (1 mL, 1.250 mmol) was added. The mixture was concentrated and dried under the high vacuum to give the title compound for this example 1.14 (188 mg, 100%) as a white solid. LCMS m/z=240.2 [M+1]$^+$. $^1$H NMR (400 MHz, CD$_3$OD) δ 0.20-0.30 (m, 2H), 0.38-0.46 (m, 2H), 0.67-0.84 (m, 3H), 0.89-0.94 (m, 1H), 1.69-1.74 (m, 1H), 1.98-2.16 (m, 3H), 3.38-3.54 (m, 3H), 4.26 (d, J$_1$=14.1 Hz, J$_2$=0.8 Hz, 1H), 4.45 (d, J=14.1 Hz, 1H), 6.83-6.87 (m, 1H), 7.12-7.17 (m, 2H).

Step K: Resolution of Compound 130 into Enantiomers 114 and 113

Compound 130 was resolved to give two enantiomers by normal phase preparative chiral HPLC under the following conditions:
Column: Normal phase semi preparative CHIRALPAK®IF column, 5 m (particle size), 250×20 mm (L×ID)
Eluent: hexanes/EtOH 100:5+0.1% triethylamine
Gradient: Isocratic
Flow: 10 mL/min
Detector: UV 254 nm
Retention Times: 1$^{st}$ enantiomer: 35.3 min; 2$^{nd}$ enantiomer: 39.8 min Example 1.15: 2',3',4',4a',5',6'-hexahydro-1'H-spiro[cyclobutane-1,7'-naphtho[1,8-cd]azepine](Compound 131)

Step A: Preparation of (1-phenylcyclobutyl)methanol

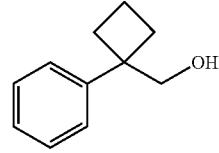 [SMILES: OCC1(c2ccccc2)CCC1]

To a stirred solution of 1-phenylcyclobutanecarboxylic acid (2.51 g, 14.24 mmol) in 50 mL THF at 60° C. (oil bath), 2 M lithium aluminum hydride in THF (20 mL, 40.00 mmol) was added slowly by an additional funnel (over ca. 45 min). After stirring for at 60° C. for 1 h, the mixture was cooled in an ice/water-bath and quenched by the drop wise addition of 1 M NaOH. Solids were filtered, washed with additional THF, and filtrate was partly concentrated. The residue was extracted with brine and CH$_2$Cl$_2$. Combined organic phases were dried over MgSO$_4$, filtered, and concentrated to give (1-phenylcyclobutyl)methanol (2.09 g, 90) as a white solid. $^1$H NMR (400 MHz, CDCl$_3$) δ 1.19 (t, J=6.6 Hz, 1H), 1.85-1.93 (m, 1H), 2.05-2.14 (m, 1H), 2.21-2.27 (m, 2H), 2.31-2.38 (m, 2H), 3.75 (d, J=6.6 Hz, 2H), 7.14-7.16 (m, 2H), 7.19-7.23 (m, 1H), 7.31-7.36 (m, 2H).

Step B: Preparation of (1-phenylcyclobutyl)methyl methanesulfonate

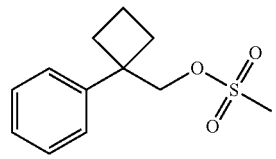 [SMILES: CS(=O)(=O)OCC1(c2ccccc2)CCC1]

To an ice-cooled solution of (1-phenylcyclobutyl)methanol (2.09 g, 12.88 mmol) and triethylamine (3.6 mL, 25.83 mmol) in 100 mL CH$_2$Cl$_2$, methanesulfonyl chloride (1.5 mL, 19.30 mmol) was added slowly (over ca. 10 min). After stirring under ice-cooling for 0.5 h, the mixture was allowed to warm to room temperature. After stirring at room temperature for 3 h, solution was extracted with 1 M HCl. Organic phase was dried over MgSO$_4$, filtered, and concentrated to give (1-phenylcyclobutyl)methyl methanesulfonate (90% pure, 3.4 g, 99%). H NMR (400 MHz, CDCl$_3$) δ 1.87-1.97 (m, 1H), 2.07-2.18 (m, 1H), 2.31-2.37 (m, 2H), 2.42-2.49 (m, 2H), 2.61 (s, 3H), 4.34 (s, 2H), 7.16-7.19 (m, 2H), 7.20-7.25 (m, 7.4 Hz, 1H), 7.31-7.35 (m, 2H).

Step C: Preparation of
2-(1-phenylcyclobutyl)acetonitrile

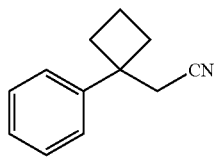 [SMILES: N#CCC1(c2ccccc2)CCC1]

To a solution of (1-phenylcyclobutyl)methyl methanesulfonate (90% pure, 3.39 g, 12.70 mmol) in 100 mL DMF, cyanosodium (7.2 g, 146.9 mmol) was added. After stirring at 70° C. (oil bath) overnight, the mixture was extracted with water and AcOEt. Combined organic phases were dried over MgSO$_4$, filtered, and concentrated. The residue was purified by biotage column chromatography (SiO$_2$, hexane/AcOEt gradient) to give 2-(1-phenylcyclobutyl)acetonitrile (2.05 g, 94%) as a colorless liquid. $^1$H NMR (400 MHz, CDCl$_3$) δ 1.89-1.98 (m, 1H), 2.09-2.21 (m, 1H), 2.28-2.35 (m, 2H), 2.50-2.57 (m, 2H), 2.74 (s, 2H), 7.19-7.22 (m, 2H), 7.24-7.26 (m, 1H), 7.33-7.38 (m, 2H).

Step D: Preparation of 2-(1-phenylcyclobutyl)acetic acid

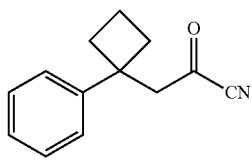 [SMILES: N#CC(=O)CC1(c2ccccc2)CCC1]

A mixture of 2-(1-phenylcyclobutyl)acetonitrile (1.92 g, 11.21 mmol) and concentrated hydrogen chloride (200 mL, 2.400 mol) was stirred at 100° C. (oil bath) for 2.5 days. The mixture was partly concentrated (to about 50 mL) and residue was extracted with CH$_2$Cl$_2$ (3×). Organic phases were dried over MgSO$_4$, filtered, and concentrated to give 2-(1-phenylcyclobutyl)acetic acid (2.07 g, 97%) as a tanned solid. LCMS m/z=189.4 [M−1]$^+$. $^1$H NMR (400 MHz, DMSO-d$_6$) δ 1.71-1.81 (m, 1H), 1.99-2.10 (m, 1H), 2.30-2.35 (m, 4H), 2.71 (s, 2H), 7.12-7.16 (m, 1H), 7.18-7.20 (m, 2H), 7.25-7.29 (m, 2H), 11.78 (s, 1H).

Step E: Preparation of
2-(1-phenylcyclobutyl)ethanol

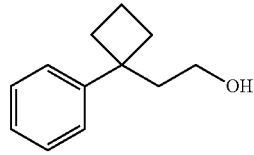 [SMILES: OCCC1(c2ccccc2)CCC1]

To a stirred solution of 2-(1-phenylcyclobutyl)acetic acid (2.06 g, 10.83 mmol) in 50 mL THF at 60° C. (oil bath), 2 M lithium aluminum hydride in THF (15 mL, 30.00 mmol) was added slowly by an additional funnel (over ca. 20 min). After stirring at 60° C. for 0.5 h, the mixture was cooled in an ice/water-bath and quenched by the drop wise addition of 1 M NaOH (ca. 30 mL). Solids were filtered, washed with additional THF, and filtrate was partly concentrated. The residue was extracted with water and CH$_2$Cl$_2$. Combined organic phases were dried over MgSO$_4$, filtered, and concentrated to give 2-(1-phenylcyclobutyl)ethanol (1.93 g, 98%). H NMR (400 MHz, CDCl$_3$) δ 0.89 (t, J=5.6 Hz, 1H), 1.79-1.89 (m, 1H), 2.06-2.15 (m, 3H), 2.16-2.23 (m, 2H), 2.35-2.43 (m, 2H), 3.42-3.47 (m, 2H), 7.12-7.19 (m, 3H), 7.28-7.32 (m, 2H).

Step F: Preparation of 2-(1-phenylcyclobutyl)ethyl methanesulfonate

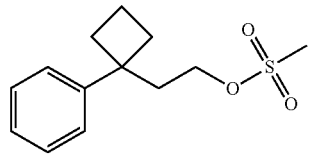 [SMILES: CS(=O)(=O)OCCC1(c2ccccc2)CCC1]

To an ice-cooled solution of 2-(1-phenylcyclobutyl)ethanol (1.92 g, 10.89 mmol) and triethylamine (3 mL, 21.52 mmol) in 50 mL CH$_2$Cl$_2$, methanesulfonyl chloride (1.3 mL, 16.73 mmol) was added slowly (over ca. 10 min). After stirring under ice-cooling for 0.5 h, the mixture was allowed to warm to room temperature. After stirring at room temperature for 3 h, solution was extracted with 1 M HCl. Organic phase was dried over MgSO$_4$, filtered, and concentrated to give 2-(1-phenylcyclobutyl)ethyl methanesulfonate (89% pure, 3.1 g, 100%). $^1$H NMR (400 MHz, CDCl$_3$) δ 1.83-1.91 (m, 1H), 2.05-2.16 (m, 1H), 2.19-2.25 (m, 2H), 2.28 (t, J=7.4 Hz, 2H), 2.39-2.47 (m, 2H), 2.86 (s, 3H), 3.96 (t, J=7.4 Hz, 2H), 7.11-7.14 (m, 2H), 7.17-7.21 (m, 1H), 7.29-7.34 (m, 2H).

Step G: Preparation of
3-(1-phenylcyclobutyl)propanenitrile

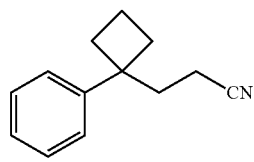 [SMILES: N#CCCC1(c2ccccc2)CCC1]

A mixture of 2-(1-phenylcyclobutyl)ethyl methanesulfonate (89% pure, 3.09 g, 10.81 mmol) and cyanosodium (6 g, 122.4 mmol) in 100 mL DMF, was stirred at 70° C. (oil bath) overnight. The mixture was extracted with water and AcOEt. Combined organic phases were dried over MgSO$_4$, filtered, and concentrated. The residue was purified by biotage column chromatography (SiO$_2$, hexane/AcOEt gradient) to give 3-(1-phenylcyclobutyl)propanenitrile (1.71 g, 85%) as a colorless liquid. $^1$H NMR (400 MHz, CDCl$_3$) δ 1.83-1.92 (m, 1H), 1.95-1.99 (m, 2H), 2.03-2.13 (m, 1H), 2.14-2.21 (m, 4H), 2.38-2.46 (m, 2H), 7.08-7.11 (m, 2H), 7.19-7.26 (m, 1H), 7.30-7.35 (m, 2H).

Step H: Preparation of 3-(1-phenylcyclobutyl)propanoic acid

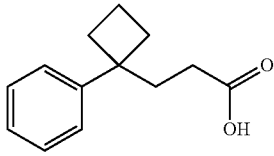 [SMILES: O=C(O)CCC1(c2ccccc2)CCC1]

A mixture of 3-(1-phenylcyclobutyl)propanenitrile (1.7 g, 9.176 mmol) and concentrated hydrogen chloride (200 mL, 2.400 mol) was stirred at 100° C. (oil bath). After 2.5 days, the mixture was allowed to cool to room temperature and extracted with CH$_2$Cl$_2$ (3×). Organic phases were dried over MgSO$_4$, filtered, concentrated, and dried under high vacuum to give 3-(1-phenylcyclobutyl)propanoic acid (1.83 g, 98%) as a white solid. LCMS m/z=203.8 [M−1]$^+$. $^1$H NMR (400 MHz, DMSO-d$_6$) δ 1.71-1.80 (m, 1H), 1.83-1.87 (m, 2H), 1.97-2.14 (m, 5H), 2.21-2.29 (m, 2H), 7.09-7.12 (m, 2H), 7.14-7.19 (m, 1H), 7.28-7.33 (m, 2H), 11.93 (s, 1H).

Step I: Preparation of 2'H-spiro[cyclobutane-1,1'-naphthalen]-4'(3'H)-one

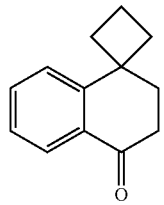 [SMILES: O=C1CCC2(CCC2)c2ccccc21]

To a solution of 3-(1-phenylcyclobutyl)propanoic acid (1.83 g, 8.959 mmol) in 100 mL CH$_2$Cl$_2$, oxalyl chloride (1.565 mL, 17.94 mmol) was added. Solution was stirred at room temperature (bubbling observed). After stirring overnight, solution was concentrated and dried under high vacuum. The residue was dissolved in 100 mL DCE and AlCl$_3$ (2.57 g, 19.27 mmol) was added. The mixture was stirred at 80° C. (oil bath) for 4 h, poured onto ice, and extracted with water and CH$_2$Cl$_2$. Organic phases were dried over MgSO$_4$, filtered, and concentrated. The residue was purified by biotage column chromatography (SiO$_2$, hexanes/AcOEt gradient) to give 2'H-spiro[cyclobutane-1,1'-naphthalen]-4'(3'H)-one (910 mg, 55%) as a colorless oil. LCMS m/z=187.0 [M+1]$^+$. $^1$H NMR (400 MHz, CDCl$_3$) δ 2.08-2.23 (m, 4H), 2.29 (t, J=6.2 Hz, 2H), 2.37-2.44 (m, 2H), 2.66-2.69 (m, 2H), 7.29-7.33 (m, 1H), 7.57-7.61 (m, 1H), 7.67 (dd, J$_1$=7.8 Hz, J$_2$=1.0 Hz, 1H), 8.0 (dd, J$_1$=7.4 Hz, J$_2$=1.2 Hz, 1H).

Step J: Preparation of 2-(2'H-spiro[cyclobutane-1,1'-naphthalen]-4'(3'H)-ylidene)acetonitrile

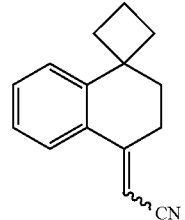 [SMILES: N#CC=C1CCC2(CCC2)c2ccccc21]

To a suspension of 60% sodium hydride dispersion (450 mg, 11.25 mmol) in 20 mL THF, a solution of diethyl (cyanomethyl)phosphonate (1.71 g, 9.653 mmol) in 10 mL THF was added slowly (over ca. 10 min). After stirring at room temperature for 5 min, a solution of 2'H-spiro[cyclobutane-1,1'-naphthalen]-4'(3'H)-one (905 mg, 4.859 mmol) in 5 mL THF was added. After stirring at room temperature for 5 days, the mixture was extracted with CH$_2$Cl$_2$ and water+brine. Organic phase was dried over MgSO$_4$, filtered, and concentrated. The residue was purified by biotage column chromatography (SiO$_2$, hexane/AcOEt gradient) to give 2-(2'H-spiro[cyclobutane-1,1'-naphthalen]-4'(3'H)-ylidene)acetonitrile (980 mg, 96%) (E:Z=70:30). $^1$H NMR (400 MHz, CDCl$_3$) δ 2.02-2.15 (m, 6H), 2.33-2.41 (m, 2H), 2.54-2.58 (m, 0.6H), 2.85-2.89 (m, 1.4H), 5.26 (t, J=1.4 Hz, 0.3H), 5.67 (t, J=1.3 Hz, 0.7H), 7.19-7.23 (m, 0.7H), 7.28-7.29 (m, 0.3H), 7.43-7.51 (m, 1.7H), 7.67 (dd, J$_1$=8.0 Hz, J$_2$=1.0 Hz, 1H), 8.18 (dd, J$_1$=7.9 Hz, J$_2$=1.2 Hz, 0.3H).

Step K: Preparation of 1-(3,4-dichlorophenyl)-N-(2-(3',4'-dihydro-2'H-spiro[cyclobutane-1,1'-naphthalen]-4'-yl)ethyl)methanesulfonamide

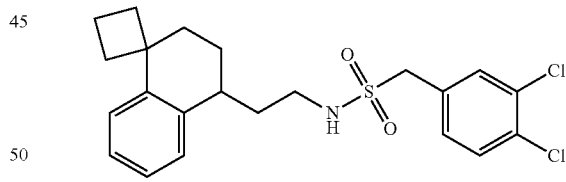

To an undetermined amount of raney nickel (slurry in water; washed three times with MeOH), a solution of 2-(2'H-spiro[cyclobutane-1,1'-naphthalen]-4'(3'H)-ylidene) acetonitrile (972 mg, 4.644 mmol) in ca. 50 mL MeOH and 7 M ammonia in MeOH (7 mL, 49.00 mmol) were added. The mixture was shaken on a Parr-shaker under ca. 60 psi hydrogen pressure for 2 days. Raney nickel was filtered off through celite, washed with additional MeOH, concentrated and dried under high vacuum. The residue was dissolved in 20 mL CH$_2$Cl$_2$, triethylamine (1.29 mL, 9.255 mmol) and a solution of (3,4-dichlorophenyl)methanesulfonyl chloride (1.77 g, 6.820 mmol) in 8 mL CH$_2$Cl$_2$ was added slowly. After stirring at room temperature for 1 h, the mixture was extracted with water and CH$_2$Cl$_2$. Organic phases were dried over MgSO$_4$, filtered, and concentrated. The residue was purified by biotage column chromatography (SiO₂, hexane/AcOEt gradient). Fractions containing product were concentrated and residue was re-purified by HPLC (CH₃CN/H₂O gradient+0.1% TFA). Fractions containing product were partly concentrated and residue was extracted with 1 M NaHCO₃ and CH₂Cl₂. Organic phases were dried over MgSO₄, filtered, and concentrated to give 1-(3,4-dichlorophenyl)-N-(2-(3',4'-dihydro-2'H-spiro[cyclobutane-1,1'-naphthalen]-4'-yl)ethyl)methanesulfonamide (886 mg, 44%). LCMS m/z=436.5 [M−1]⁺. ¹H NMR (400 MHz, CDCl₃) δ 1.50-1.57 (m, 1H), 1.72-1.93 (m, 5H), 1.95-2.15 (m, 4H), 2.21-2.29 (m, 1H), 2.40-2.49 (m, 1H), 2.76-2.82 (m, 1H), 3.07-3.13 (m, 2H), 4.08 (t, J=6.1 Hz, 1H), 4.18 (s, 2H), 7.02 (d, J=7.8 Hz, 1H), 7.10-7.15 (m, 1H), 7.22-7.25 (m, 2H), 7.45 (d, J=8.3 Hz, 1H), 7.49 (d, J=2.1 Hz, 1H), 7.61 (dd, J₁=7.8 Hz, J₂=1.2 Hz, 1H).

Step L: Preparation of 2'-((3,4-dichlorobenzyl)sulfonyl)-2',3',4',4a',5',6'-hexahydro-1'H-spiro[cyclobutane-1,7'-naphtho[1,8-cd]azepine]

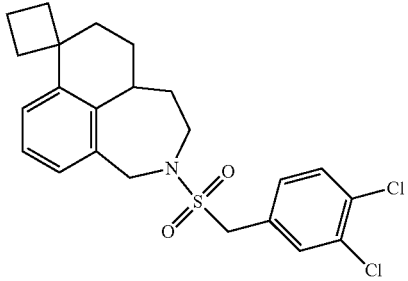 [SMILES: O=S(=O)(Cc1ccc(Cl)c(Cl)c1)N1CCC2CCC3(CCC3)c3cccc(c32)C1]

To a solution of 1-(3,4-dichlorophenyl)-N-(2-(3',4'-dihydro-2'H-spiro[cyclobutane-1,1'-naphthalen]-4'-yl)ethyl)methanesulfonamide (888 mg, 2.025 mmol) in 20 mL DCE, 1,3,5-trioxane (314 mg, 3.486 mmol), acetic anhydride (0.2 mL, 2.116 mmol), and methanesulfonic acid (0.85 mL, 13.11 mmol) were added. After stirring at room temperature for 10 min, the mixture was extracted with water and CH₂Cl₂. Organic phases were dried over MgSO₄, filtered, and concentrated. The residue was purified by biotage column chromatography (SiO₂, hexane/AcOEt gradient) to give 2'-((3,4-dichlorobenzyl)sulfonyl)-2',3',4',4a',5',6'-hexahydro-1'H-spiro[cyclobutane-1,7'-naphtho[1,8-cd]azepine] (595 mg, 65%) as a white solid. ¹H NMR (400 MHz, CDCl₃) δ 1.18-1.28 (m, 1H), 1.52-1.61 (m, 2H), 1.73-1.80 (m, 1H), 1.89-1.98 (m, 2H), 2.01-2.24 (m, 5H), 2.53-2.61 (m, 1H), 3.01-3.08 (m, 1H), 3.26-3.33 (m, 1H), 3.72-3.78 (m, 1H), 3.84 (d, J=14.2 Hz, 1H), 3.92 (d, J=14.2 Hz, 1H), 4.29 (d, J=15.0 Hz, 1H), 4.59 (dd, J₁=15.0 Hz, J₂=1.2 Hz, 1H), 6.71 (dd, J₁=8.2 Hz, J₂=2.0 Hz, 1H), 7.06 (dd, J₁=7.3 Hz, J₂=1.2 Hz, 1H), 7.12 (d, J=2.0 Hz, 1H), 7.22-7.26 (m, 2H), 7.68 (dd, J₁=8.2 Hz, J₂=1.0 Hz, 1H).

Step M: Preparation of 2',3',4',4a',5',6'-hexahydro-1'H-spiro[cyclobutane-1,7'-naphtho[1,8-cd]azepine] (Compound 131)

A mixture of 2'-((3,4-dichlorobenzyl)sulfonyl)-2',3',4',4a',5',6'-hexahydro-1'H-spiro[cyclobutane-1,7'-naphtho[1,8-cd]azepine] (102 mg, 0.226 mmol), phenol (51 mg, 0.542 mmol), and 48% hydrogen bromide in water (2 mL, 36.81 mmol) in 2 mL AcOH (in a sealed microwave vial) was stirred at 120° C. (oil bath) overnight. The mixture was partly concentrated and residue was purified by HPLC (CH₃CN/H₂O gradient+0.1% TFA) to give 2',3',4',4a',5',6'-hexahydro-1'H-spiro[cyclobutane-1,7'-naphtho[1,8-cd]azepine] 2,2,2-trifluoroacetate (51.0 mg, 66%). LCMS m/z=228.4 [M+1]⁺. ¹H NMR (400 MHz, CD₃OD) δ 1.66-1.73 (m, 1H), 1.78-1.89 (m, 1H), 1.91-2.19 (m, 8H), 2.25-2.33 (m, 1H), 2.41-2.50 (m, 1H), 3.21-3.27 (m, 1H), 3.38-3.42 (m, 2H), 3.98 (s, 0.5H), 4.23 (d, J=14.2 Hz, 1H), 4.43 (d, J=14.2 Hz, 1H), 7.18 (dd, J₁=7.4 Hz, J₂=1.2 Hz, 1H), 7.29 (t, J=7.8 Hz, 1H), 7.77 (dd, J₁=8.0 Hz, J₂=1.0 Hz, 1H).

Step N: Resolution of Compound 131 into Enantiomers 124 and 125

Compound 131 was resolved to give two enatiomers by normal phase preparative chiral HPLC under the following conditions:
Column: Normal phase semi preparative CHIRALPAK®IF column, 5 m (particle size), 250×20 mm (L×ID)
Eluent: hexanes/EtOH 100:5+0.1% triethylamine
Gradient: Isocratic
Flow: 10 mL/min
Detector: UV 254 nm
Retention Times: 1ˢᵗ enantiomer: 29.8 min; 2ⁿᵈ enantiomer: 35.4 min Example 1.16: Preparation of 7-cyclopropyl-1,2,3,4,4a,5,6,7-octahydronaphtho[1,8-cd]azepine (Compound 120)

Step A: Preparation of 1-cyclopropyl-1,2,3,4-tetrahydronaphthalene

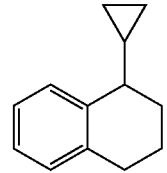 [SMILES: c1ccc2c(c1)CCCC2C1CC1]

A mixture of zinc(II) chloride (131 mg, 0.961 mmol) and lithium chloride (379 mg, 8.940 mmol) in a 50 mL round bottom flask were melt dried under vacuum using a heat gun. The mixture was allowed to cool to room temperature under nitrogen atmosphere and 1 M ((trimethylsilyl)methyl)magnesium chloride in Et₂O (1.5 mL, 1.500 mmol) was added. After stirring at room temperature for 5 min, 1 M cyclopropylmagnesium bromide in 2-methyl-THF (10 mL, 10.000 mmol) was added. After stirring for 1 h, flask was put into an ice/water-bath and a solution of 3,4-dihydronaphthalen-1(2H)-one (1.0 g, 6.841 mmol) in 5 mL THF was added. After stirring at 0° C. for 3 h, the mixture was quenched by the slow addition of 1 M NH₄Cl and extracted with additional 1 M NH₄Cl and CH₂Cl₂. Organic phases were dried over MgSO₄, filtered and concentrated. The residue was dissolved in ca. 10 mL CH₂Cl₂ and ca. 3 mL TFA was added. After stirring at room temperature for 0.5 h, solution was concentrated and residue was purified by biotage column chromatography (SiO₂, hexane/AcOEt gradient). Fractions containing 4-cyclopropyl-1,2-dihydronaphthalene were concentrated, residue was dissolved in 25 mL CH₂Cl₂, triethylsilane (8 mL, 50.16 mmol) and TFA (4 mL, 52.23 mmol) was added. After stirring at room temperature for 0.5 h, solution was concentrated and residue was purified by biotage column chromatography (SiO$_2$, hexane/AcOEt gradient) to give 1-cyclopropyl-1,2,3,4-tetrahydronaphthalene (790 mg, 67%) as a colorless oil. $^1$H NMR (400 MHz, DMSO-d$_6$) δ 0.16-0.24 (m, 1H), 0.44-0.51 (m, 2H), 0.67-0.75 (m, 1H), 0.85-0.93 (m, 1H), 1.68-1.77 (m, 2H), 1.89-1.99 (m, 3H), 2.72-2.85 (m, 2H), 5.05 (s, 1H), 7.06-7.15 (m, 3H), 7.52-7.56 (m, 1H).

Step B: Preparation of 4-cyclopropyl-4-hydroxy-3, 4-dihydronaphthalen-1(2H)-one

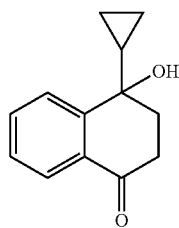 [SMILES: O=C1CCC(O)(C2CC2)c2ccccc21]

To a solution of 1-cyclopropyl-1,2,3,4-tetrahydronaphthalene (782 mg, 4.539 mmol) in 20 mL DCE, sodium bicarbonate (200 mg, 2.381 mmol), Rh$_2$(cap)$_4$ (56 mg, 85.57 μmol), and 5.5 M 2-hydroperoxy-2-methylpropane in decane (5.5 mL, 30.25 mmol) were added. After stirring at 40° C. for 3 h, more Rh$_2$(cap)$_4$ (38 mg) and 5.5 M 2-hydroperoxy-2-methylpropane in decane (5.5 mL) were added. After stirring at 40° C. overnight, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give 4-cyclopropyl-4-hydroxy-3,4-dihydronaphthalen-1(2H)-one (529 mg, 58%). LCMS m/z=201.4 [M+1]. $^1$H NMR (400 MHz, DMSO-d$_6$) δ 0.28-0.47 (m, 4H), 1.16-1.23 (m, 1H), 2.16-2.24 (m, 2H), 2.67-2.84 (m, 2H), 5.05 (s, 1H), 7.38-7.43 (m, 1H), 7.61-7.65 (m, 1H), 7.70-7.72 (m, 1H), 7.81-7.83 (m, 1H).

Step C: Preparation of 2-(4-cyclopropyl-4-hydroxy-3,4-dihydronaphthalen-1(2H)-ylidene)acetonitrile

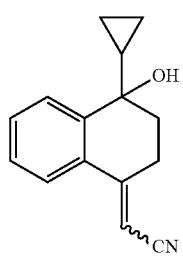 [SMILES: N#CC=C1CCC(O)(C2CC2)c2ccccc21]

To a suspension of 60% sodium hydride dispersion (143 mg, 3.575 mmol) in 5 mL THF, a solution of diethyl (cyanomethyl)phosphonate (649 mg, 3.664 mmol) in 5 mL THF was added slowly (over ca. 5 min). After stirring at room temperature for 5 min, a solution of 4-cyclopropyl-4-hydroxy-3,4-dihydronaphthalen-1(2H)-one (507 mg, 2.507 mmol) in 10 mL THF was added. After stirring at room temperature overnight, the mixture was extracted with CH$_2$Cl$_2$ and water+brine. Organic phases were dried over MgSO$_4$, filtered, and concentrated. The residue was purified by biotage column chromatography (SiO$_2$, hexane/AcOEt gradient) to give 2-(4-cyclopropyl-4-hydroxy-3,4-dihydronaphthalen-1(2H)-ylidene)acetonitrile (465 mg, 82%) as a colorless oil (E:Z=72:28). LCMS m/z=224.3 [M−1]$^+$. $^1$H NMR (400 MHz, CDCl$_3$) δ 0.31-0.63 (m, 4H), 1.10-1.18 (m, 1H), 1.51 (s, 0.28H), 1.60 (s, 0.72H), 2.00-2.20 (m, 2H), 2.72-2.88 (m, 0.56H), 3.03-3.16 (m, 1.44H), 5.33-5.34 (m, 0.28H), 5.77-5.78 (m, 0.72H), 7.29-7.49 (m, 2H), 7.56 (dd, J$_1$=8.0 Hz, J$_2$=1.1 Hz, 1H), 7.71 (dd, J$_1$=7.8 Hz, J$_2$=1.2 Hz, 0.72H), 7.73 (dd, J$_1$=7.8 Hz, J$_2$=1.2 Hz, 0.28H).

Step D: Preparation of 2-(4-cyclopropyl-3,4-dihydronaphthalen-1(2H)-ylidene)acetonitrile

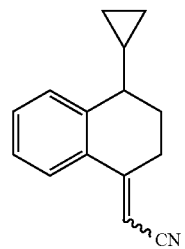 [SMILES: N#CC=C1CCC(C2CC2)c2ccccc21]

To a solution of 2-(4-cyclopropyl-4-hydroxy-3,4-dihydronaphthalen-1 (2H)-ylidene)acetonitrile (418 mg, 1.855 mmol) in 18 mL DCM, triethylsilane (0.296 mL, 1.855 mmol) and TFA (0.142 mL, 1.855 mmol) were added. After stirring at room temperature overnight, solution was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give 2-(4-cyclopropyl-3,4-dihydronaphthalen-1(2H)-ylidene)acetonitrile (328 mg, 85%) as an oil (E:Z=72:28). $^1$H NMR (400 MHz, CDCl$_3$) δ 0.20-0.27 (m, 1H), 0.38-0.59 (m, 2H), 0.68-0.77 (m, 1H), 0.84-0.93 (m, 1H), 1.78-1.90 (m, 1H), 1.98-2.15 (m, 2H), 2.54-2.62 (m, 0.28H), 2.75-2.86 (m, 1H), 3.09-3.16 (m, 0.72H), 5.28-5.30 (m, 0.28H), 5.73-5.74 (m, 0.72H), 7.23-7.42 (m, 2H), 7.56-7.63 (m, 1.72H). 8.25 (dd, J1=7.9 Hz, J2=1.3 Hz, 0.28H).

Step E: Preparation of 2-(4-cyclopropyl-1,2,3,4-tetrahydronaphthalen-1-yl)ethanamine

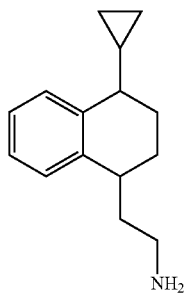 [SMILES: NCCC1CCC(C2CC2)c2ccccc21]

To a mixture of 2-(4-cyclopropyl-3,4-dihydronaphthalen-1 (2H)-ylidene)acetonitrile (330 mg, 1.577 mmol) and cobalt(II) chloride hexahydrate (1.1 g, 4.623 mmol) in 30 mL MeOH, sodium tetrahydroborate (2 g, 52.86 mmol) was added in small portions over ca. 5 h. After stirring at room temperature overnight, di-tert-butyl dicarbonate (720 mg, 3.299 mmol) was added. After stirring at room temperature for 1 h, the mixture was extracted with water and $CH_2Cl_2$. Organic phases were dried over $MgSO_4$, filtered, and concentrated. The residue was purified by biotage column chromatography ($SiO_2$, hexane/AcOEt gradient). Fractions containing Boc-protected product were concentrated. The residue was diluted in 16 mL $CH_2Cl_2$ and 2,2,2-trifluoroacetic acid (4 mL, 52.23 mmol) was added. After stirring at room temperature for 2 h, solution was concentrated and dried under high vacuum to give 2-(4-cyclopropyl-1,2,3,4-tetrahydronaphthalen-1-yl)ethanamine 2,2,2-trifluoroacetate (330 mg, 64%). LCMS m/z=216.0 [M+1]$^+$. $^1$H NMR (400 MHz, $CD_3OD$) δ 0.18-0.26 (m, 1H), 0.44-0.53 (m, 2H), 0.65-0.75 (m, 1H), 0.80-0.89 (m, 1H), 1.57-2.19 (m, 7H), 2.86-3.06 (m, 3H), 7.10-7.19 (m, 3H), 7.50-7.55 (m, 1H).

Step F: Preparation of N-(2-(4-cyclopropyl-1,2,3,4-tetrahydronaphthalen-1-yl)ethyl)-1-(3,4-dichlorophenyl)methanesulfonamide

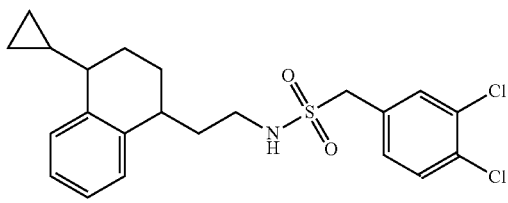 [SMILES: O=S(=O)(Cc1ccc(Cl)c(Cl)c1)NCCC1CCC(C2CC2)c2ccccc21]

To a mixture of 2-(4-cyclopropyl-1,2,3,4-tetrahydronaphthalen-1-yl)ethanamine 2,2,2-trifluoroacetate (326 mg, 0.990 mmol) and triethylamine (0.687 mL, 4.929 mmol) in 8 mL $CH_2Cl_2$, a solution of (3,4-dichlorophenyl)methanesulfonyl chloride (385 mg, 1.483 mmol) in 2 mL $CH_2Cl_2$ was added. After stirring at room temperature overnight, the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give N-(2-(4-cyclopropyl-1,2,3,4-tetrahydronaphthalen-1-yl)ethyl)-1-(3,4-dichlorophenyl)methanesulfonamide (198 mg, 46%). LCMS m/z=436.5 [M−1]$^+$. $^1$H NMR (400 MHz, $CDCl_3$) δ 0.17-0.24 (m, 1H), 0.43-0.54 (m, 2H), 0.67-0.76 (m, 1H), 0.79-0.90 (m, 1H), 1.44-2.09 (m, 7H), 2.78-2.87 (m, 1H), 3.06-3.19 (m, 2H), 4.03-4.19 (m, 3H), 7.07-7.11 (m, 1H), 7.13-7.19 (m, 2H), 7.22-7.26 (m, 1H), 7.44-7.58 (m, 3H).

Step G: Preparation of 7-cyclopropyl-2-((3,4-dichlorobenzyl)sulfonyl)-1,2,3,4,4a,5,6,7-octahydronaphtho[1,8-cd]azepine

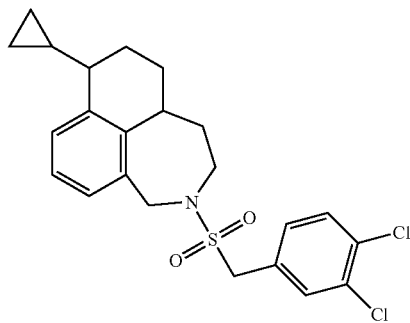 [SMILES: O=S(=O)(Cc1ccc(Cl)c(Cl)c1)N1CCC2CCC(C3CC3)c3cccc(c32)C1]

To a solution of N-(2-(4-cyclopropyl-1,2,3,4-tetrahydronaphthalen-1-yl)ethyl)-1-(3,4-dichlorophenyl)methanesulfonamide (195 mg, 0.445 mmol) in 4 mL DCE, 1,3,5-trioxane (70.7 mg, 0.785 mmol), acetic anhydride (42.1 μl, 0.445 mmol), and methanesulfonic acid (185 μl, 2.853 mmol) were added. After stirring at room temperature for 10 min, the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give 7-cyclopropyl-2-((3,4-dichlorobenzyl)sulfonyl)-1,2,3,4,4a,5,6,7-octahydronaphtho[1,8-cd]azepine (129 mg, 64%) as a white solid. $^1$H NMR (400 MHz, $CDCl_3$) δ 0.19-0.28 (m, 1H), 0.46-0.56 (m, 2H), 0.67-0.91 (m, 2H), 1.04-2.25 (m, 7H), 3.07-3.25 (m, 1H), 3.26-3.35 (m, 1H), 3.73-3.96 (m, 3H), 4.26-4.32 (m, 1H), 4.55-4.65 (m, 1H), 6.80-6.86 (m, 1H), 6.93-7.26 (m, 3H), 7.29-7.32 (m, 1H), 7.53-7.61 (m, 1H).

Step H: Preparation of 7-cyclopropyl-1,2,3,4,4a,5,6,7-octahydronaphtho[1,8-cd]azepine (Compound 120)

To a solution of 7-cyclopropyl-2-((3,4-dichlorobenzyl)sulfonyl)-1,2,3,4,4a,5,6,7-octahydronaphtho[1,8-cd]azepine (124 mg, 0.275 mmol) in 3 mL toluene, 60% bis(2-methoxyethoxy)aluminum(III) sodium hydride in toluene (3 mL, 9.22 mmol) was added and stirred at 80° C. After stirring at 80° C. overnight, quenched by the slow addition of water, concentrated, and residue was purified by HPLC ($CH_3CN$/$H_2O$ gradient+0.1% TFA) to give 7-cyclopropyl-1,2,3,4,4a,5,6,7-octahydronaphtho[1,8-cd]azepine 2,2,2-trifluoroacetate (35.3 mg, 38%). LCMS m/z=228.4 [M+1]$^+$. $^1$H NMR (400 MHz, $CD_3OD$) δ 0.21-0.29 (m, 1H), 0.45-0.55 (m, 2H), 0.66-0.74 (m, 1H), 0.76-0.88 (m, 1H), 1.59-2.37 (m, 7H), 3.24-3.49 (m, 3H), 4.22-4.26 (m, 1H), 4.41-4.46 (m, 1H), 7.17-7.23 (m, 2H), 7.59-7.64 (m, 1H).

Example 1.17: Preparation of 2',3',4',4a',5'-pentahydro-1'H-dispiro[cyclopentane-1,6'-cyclopropane-7',1"-naphtho[1,8-cd]-azepine] (Compound 129)

Step A: Preparation of 3',4'-dihydro-1'H-spiro[cyclopentane-1,2'-naphthalen]-1'-one

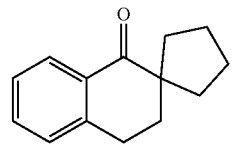 [SMILES: O=C1c2ccccc2CCC12CCCC2]

To a suspension of 60% sodium hydride dispersion (1.4 g, 35.00 mmol) in 90 mL THF, a solution of 3,4-dihydronaphthalen-1(2H)-one (2.0 g, 13.68 mmol) in 10 mL THF was added slowly (over ca. 5 min). After stirring at room temperature for 0.5 h, 1,4-diiodobutane (1.799 mL, 13.68 mmol) was added. After stirring at room temperature overnight, the mixture was quenched by the slow addition of water, partly concentrated and extracted with water and $CH_2Cl_2$. Organic phases were dried over $MgSO_4$, filtered, and concentrated. The residue was purified by biotage column chromatography ($SiO_2$, hexane/AcOEt gradient) to give 3',4'-dihydro-1'H-spiro[cyclopentane-1,2'-naphthalen]-1'-one (2.19 g, 80%) as a colorless liquid. $^1$H NMR (400

MHz, CDCl$_3$) δ 1.51-1.58 (m, 2H), 1.65-1.84 (m, 4H), 2.04-2.16 (m, 4H), 2.99 (t, J=6.2 Hz, 2H), 7.21 (dd, J$_1$=7.6 Hz, J$_2$=0.6 Hz, 1H), 7.27-7.31 (m, 1H), 7.42-7.46 (m, 1H), 8.04 (dd, J$_1$=7.8 Hz, J$_2$=1.2 Hz, 1H).

Step B: Preparation 1'-methylene-3',4'-dihydro-1'H-spiro[cyclopentane-1,2'-naphthalene]

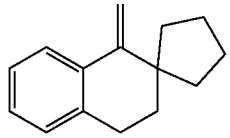

To a suspension of methyltriphenylphosphonium bromide (4.0 g, 11.20 mmol) in 20 mL toluene, 1 M potassium 2-methylpropan-2-olate in THF (15 mL, 15.00 mmol) was added. After stirring at 110° C. (oil bath) for 40 min, a solution of 3',4'-dihydro-1'H-spiro[cyclopentane-1,2'-naphthalen]-1'-one (1.15 g, 5.742 mmol) in 3 mL toluene was added. The mixture was stirred at 110° C. for 10 min, allowed to cool to room temperature, and extracted with water and CH$_2$Cl$_2$. Organic phases were dried over MgSO$_4$, filtered, and concentrated. The residue was purified by biotage column chromatography (SiO$_2$, hexanes) to give 1'-methylene-3',4'-dihydro-1'H-spiro[cyclopentane-1,2'-naphthalene] (823 mg, 72%) as a colorless liquid. $^1$H NMR (400 MHz, CDCl$_3$) δ 1.47-1.55 (m, 2H), 1.66-1.82 (m, 8H), 2.89 (t, J=6.6 Hz, 2H), 5.01 (s, 1H), 5.43 (s, 1H), 7.07-7.19 (m, 3H), 7.54-7.57 (m, 1H).

Step C: Preparation of Compound 62 of FIG. 7, where R$^1$=H

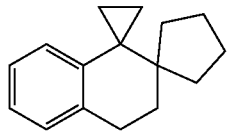 [SMILES: c1ccc2c(c1)CCC1(CCCC1)C21CC1]

To an ice-cooled solution of 1'-methylene-3',4'-dihydro-1'H-spiro[cyclopentane-1,2'-naphthalene] (818 mg, 4.125 mmol) and chloroiodomethane (1.8 mL, 24.80 mmol) in 30 mL DCE, 1 M diethylzinc in hexane (21 mL, 4.125 mmol) was added over ca. 10 min. The mixture was allowed to warm to room temperature. After 5 h, suspension was quenched by the addition of 1 M NH$_4$Cl and ice, and extracted with water and CH$_2$Cl$_2$ (3×). Combined organic phases were dried over MgSO$_4$, filtered, and concentrated. The residue was purified by biotage column chromatography (SiO$_2$, hexane/AcOEt gradient) to give the title compound for this step (608 mg, 69%) as a colorless liquid.

$^1$H NMR (400 MHz, CDCl$_3$) δ 0.79-0.82 (m, 2H), 0.92-0.94 (m, 2H), 1.20-1.29 (m, 2H), 1.34-1.40 (m, 2H), 1.57-1.65 (m, 4H), 1.76 (t, J=6.7 Hz, 2H), 2.92 (t, b=6.7 Hz, 2H), 6.74-6.77 (m, 1H), 7.01-7.09 (m, 3H).

Step D: Preparation of Compound 63 of FIG. 7, where R$^1$=H

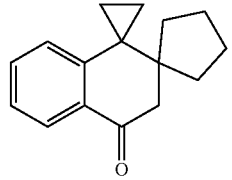 [SMILES: O=C1CC2(CCCC2)C2(CC2)c2ccccc21]

To a solution of the product of Step C (603 mg, 2.840 mmol) in 12 mL DCE, sodium bicarbonate (128 mg, 1.524 mmol), Rh$_2$(cap)$_4$ (40.9 mg, 62.50 µmol), and 5.5 M 2-hydroperoxy-2-methylpropane in decane (3.4 mL, 18.70 mmol) were added. After stirring at 40° C. overnight, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (438 mg, 68%) as a colorless liquid. H NMR (400 MHz, CDCl$_3$) 0.86-1.72 (m, 12H), 2.72 (s, 2H), 6.92 (s, J=7.6 Hz, 1H), 7.22-7.26 (m, 1H), 7.43-7.47 (m, 1H), 8.02 (d, J$_1$=7.8 Hz, J$_2$=1.4 Hz, 1H).

Step E: Preparation of Compound 64 of FIG. 7, where R$^1$=H

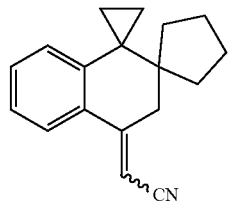 [SMILES: N#CC=C1CC2(CCCC2)C2(CC2)c2ccccc21]

To a suspension of 60% sodium hydride dispersion (176 mg, 4.400 mmol) in 10 mL THF, a solution of diethyl (cyanomethyl)phosphonate (701 mg, 3.957 mmol) in 4 mL THF was added slowly (over ca. 5 min). After stirring at room temperature for 5 min, a solution of the product of Step D (438 mg, 1.935 mmol) in 2 mL THF was added. After stirring at 60° C. (oil bath) overnight, the mixture was extracted with CH$_2$Cl$_2$ and water+brine. Organic phases were concentrated and residue was purified by HPLC (CH$_3$CN/H$_2$O gradient+0.1% TFA). Fractions containing product were partly concentrated and residue was extracted with 1 M NaHCO$_3$ and CH$_2$Cl$_2$. Organic phases were dried over MgSO$_4$, filtered, and concentrated to give the title compound for this step (263 mg, 55%) as a colorless oil (E:Z=77:23). $^1$H NMR (400 MHz, CDCl$_3$) δ 0.88-0.91 (m, 2H), 1.05-1.08 (m, 2H), 1.23-1.40 (m, 5H), 1.58-1.78 (m, 3H), 2.53 (d, J=1.3 Hz, 0.46H), 2.86 (d, J=1.2 Hz, 1.54H), 5.22-5.23 (m, 0.23H), 5.80-5.81 (m, 0.77H), 6.80-6.85 (m, 1H), 7.13-7.24 (m, 1H), 7.29-7.35 (m, 1H), 7.54 (dd, J$_1$=7.9 Hz, J$_2$=1.3 Hz, 0.77H), 8.33 (dd, J$_1$=7.9 Hz, J$_2$=1.3 Hz, 0.23H) Step F: Preparation of Compound 65 of FIG. 7, where R$^1$=H

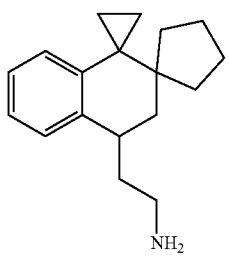 [SMILES: NCCC1CC2(CCCC2)C2(CC2)c2ccccc21]

To a mixture of the product of Step E (260 mg, 1.043 mmol) and cobalt(II) chloride hexahydrate (599 mg, 2.518 mmol) in 20 mL MeOH, sodium tetrahydroborate (1.1 g, 29.08 mmol) was added in small portions over ca. 5 h. After stirring at room temperature overnight, di-tert-butyl dicarbonate (0.5 g, 2.291 mmol) was added. After stirring at room temperature for 0.5 h, the mixture was partly concentrated and residue was extracted with water and CH$_2$Cl$_2$. Organic phases were dried over MgSO$_4$, filtered, and concentrated. The residue was purified by biotage column chromatography (SiOz$_2$, hexane/AcOEt gradient). Fractions containing Boc-protected product were concentrated. The residue was dissolved in 10 mL CH$_2$Cl$_2$ and 2,2,2-trifluoroacetic acid (2.4 mL, 31.34 mmol) was added. After stirring at room temperature for 1 h, solution was concentrated and dried under high vacuum to give the title compound for this step as the TFA salt (267 mg, 69%). LCMS m/z=256.6 [M+1]$^+$. $^1$H NMR (400 MHz, CD$_3$OD) δ 0.41-0.46 (m, 1H), 0.86-0.97 (m, 2H), 1.05-1.12 (m, 1H), 1.20-1.32 (m, 3H), 1.54-1.72 (m, 6H), 1.95-2.05 (m, 2H), 2.16-2.25 (m, 1H), 2.84-2.91 (m, 1H), 2.95-3.02 (m, 1H), 3.18-3.25 (m, 1H), 6.86-6.88 (m, 1H), 7.06-7.13 (m, 2H), 7.24-7.26 (m, 1H).

Step G: Preparation of Compound 66 of FIG. 7, where R$^1$=H and R$^{10}$ is 3,4-dichlorobenzyl

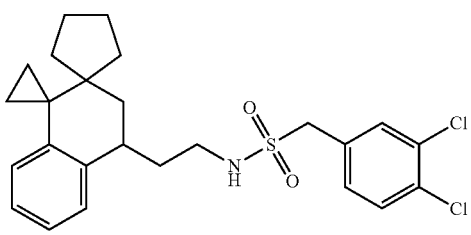 [SMILES: O=S(=O)(Cc1ccc(Cl)c(Cl)c1)NCCC1CC2(CCCC2)C2(CC2)c2ccccc21]

To a solution of the product of Step F (263 mg, 0.712 mmol) and triethylamine (717 µl, 5.144 mmol) in 5 mL CH$_2$Cl$_2$, a solution of (3,4-dichlorophenyl)methanesulfonyl chloride (534 mg, 2.058 mmol) in 5 mL CH$_2$Cl$_2$ was added. After stirring at room temperature overnight, the mixture was extracted with water and CH$_2$Cl$_2$. Organic phases were concentrated and residue was purified by HPLC (CH$_3$CN/H$_2$O gradient+0.1% TFA). Fractions containing product were partly concentrated and residue was extracted with 1 M NaHCO$_3$ and CH$_2$Cl$_2$. Organic phases were dried over MgSO$_4$, filtered, and concentrated to give the title compound for this step (178 mg, 52%). LCMS m/z=476.5 [M−1]$^+$. $^1$H NMR (400 MHz, CDCl$_3$) δ 0.45-0.50 (m, 1H), 0.84-0.93 (m, 2H), 1.01-1.07 (m, 1H), 1.13-1.30 (m, 3H), 1.43-1.66 (m, 6H), 1.80-1.89 (m, 2H), 2.03-2.11 (m, 1H), 2.97-3.14 (m, 3H), 3.99-4.03 (m, 1H), 1.98 (s, 2H), 6.81-6.83 (m, 1H), 7.07-7.16 (m, 3H), 7.23 (dd, J$_1$=8.3 Hz, J$_2$=2.1 Hz, 1H), 7.44-7.49 (m, 2H).

Step H: Preparation of (Compound 67 of FIG. 7, where R$^1$=H and R$^{10}$ is 3,4-dichlorobenzyl

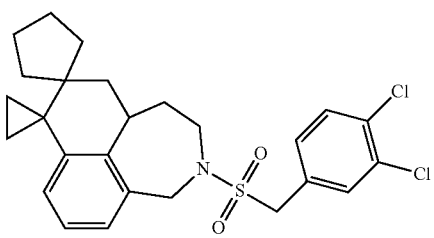 [SMILES: O=S(=O)(Cc1ccc(Cl)c(Cl)c1)N1CCC2CC3(CCCC3)C3(CC3)c3cccc(c32)C1]

To a solution of the product of Step G (174 mg, 0.364 mmol) in 3.5 mL DCE, 1,3,5-trioxane (78 mg, 0.866 mmol), acetic anhydride (35 µl, 0.370 mmol), and methanesulfonic acid (153 µl, 2.359 mmol) were added. After stirring at room temperature for 10 min, the mixture was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (92.3 mg, 52%) as a white solid. $^1$H NMR (400 MHz, CDCl$_3$) 0.60-0.64 (m, 1H), 0.89-0.94 (m, 2H), 1.02-1.28 (m, 5H), 1.53-1.68 (m, 7H), 1.91-1.97 (m, 1H), 3.20-3.32 (m, 2H), 3.88-3.98 (m, 3H), 4.17 (d, J=15.3 Hz, 1H), 4.64 (dd, J$_1$=15.3 Hz, J$_2$=1.8 Hz, 1H), 6.81 (dd, J$_1$=7.9 Hz, J$_2$=1.2 Hz, 1H), 6.90 (dd, J$_1$=8.3 Hz, J$_2$=2.1 Hz, 1H), 7.01-7.12 (m, 3H), 7.30 (d, J=8.2 Hz, 1H).

Step I: Preparation of 2',3',4',4a',5'-pentahydro-1'H-dispiro[cyclopentane-1,6'-cyclopropane-7',1"-naphtho[1,8-cd]-azepine] (Compound 129)

To a solution of the product of Step H (89.6 mg, 0.183 mmol) in 2 mL toluene, 60% bis(2-methoxyethoxy)aluminum(III) sodium hydride in toluene (1.8 mL, 5.535 mmol) was added and stirred at 80° C. After stirring overnight, the mixture was cooled in an ice/water-bath, quenched by the slow addition of water, concentrated, and residue was purified by HPLC (CH$_3$CN/H$_2$O gradient+0.1% TFA) to give the title compound for this example 1.17 as the TFA salt (31.7 mg, 46%). LCMS m/z=268.2 [M+1]$^+$. $^1$H NMR (400 MHz, CD$_3$OD) δ 0.49-0.54 (m, 1H), 0.92-1.01 (m, 2H), 1.08-1.14 (m, 1H), 1.20-1.31 (m, 3H), 1.57-1.77 (m, 7H), 1.98-2.04 (m, 1H), 2.10-2.15 (m, 1H), 3.40-3.56 (m, 3H), 4.25 (dd, J$_1$=14.0 Hz, J$_2$=1.1 Hz, 1H), 4.36 (d, J=14.0 Hz, 1H), 6.92-6.96 (m, 1H), 7.11-7.15 (m, 2H).

Example 1.18: Preparation of (7aS)-5,6,7,7a,8,8a,9,10,11,11a-decahydro-4H-cyclopenta[5,6]naphtho[1,8-cd]azepine (Compound 132) and Preparation of (7aR)-5,6,7,7a,8,8a,9,10,11,11a-decahydro-4H-cyclopenta[5,6]naphtho[1,8-cd]azepine (Compound 118)

Step A: Preparation of methyl 2-oxo-1-phenethylcyclopentanecarboxylate

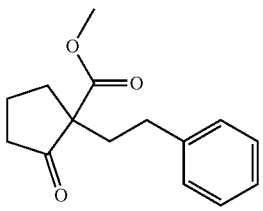 [SMILES: COC(=O)C1(CCc2ccccc2)CCCC1=O]

A mixture of methyl 2-oxocyclopentanecarboxylate (5.0 g, 35.17 mmol) and potassium carbonate (14.8 g, 107.1 mmol) in 50 mL acetone was stirred at room temperature. After 10 min, (2-bromoethyl)benzene (5.3 mL, 38.81 mmol) was added and mixture was heated to 70° C. (oil bath). After stirring overnight at 70° C., solid was filtered off and washed with additional acetone. Filtrate was concentrated and residue was purified by biotage column chromatography (SiO$_2$, hexane/AcOEt gradient) to give methyl 2-oxo-1-phenethylcyclopentanecarboxylate (3.67 g, 42%) as a colorless liquid. LCMS m/z=247.1 [M+1]$^+$. $^1$H NMR (400 MHz, CDCl$_3$) δ 1.78-2.71 (m, 10H), 3.71 (s, 3H), 7.16-7.32 (m, 5H).

Step B: Preparation of 2-phenethylcyclopentanone

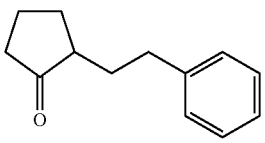 [SMILES: O=C1CCCC1CCc1ccccc1]

A mixture of methyl 2-oxo-1-phenethylcyclopentanecarboxylate (3.68 g, 14.94 mmol) and 6 M hydrogen chloride in water (20 mL, 120.0 mmol) in 40 mL acetic acid was stirred at 100° C. (oil bath) overnight. Solution was concentrated and residue was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give 2-phenethylcyclopentanone (1.42 g, 51%) as a colorless liquid. LCMS m/z=189.4 [M+1]. $^1$H NMR (400 MHz, CDCl$_3$) δ 1.51-1.62 (m, 2H), 1.70-1.82 (m, 1H), 1.97-2.17 (m, 4H), 2.20-2.34 (m, 2H), 2.61-2.77 (m, 2H), 7.16-7.29 (m, 5H).

Step C: Preparation of 2-phenethylcyclopentanol

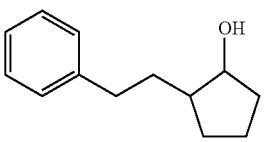 [SMILES: OC1CCCC1CCc1ccccc1]

To a solution of 2-phenethylcyclopentanone (1.41 g, 7.489 mmol) in 40 mL MeOH, sodium borohydride (0.3 g, 7.930 mmol) was added in small portions over ca. 15 min. After stirring at room temperature for 0.5 h, the mixture was concentrated and residue was extracted with 1 M HCl and CH$_2$Cl$_2$. Organic phases were dried over MgSO$_4$, filtered, concentrated, and dried under high vacuum to give 2-phenethylcyclopentanol (1.37 g, 96%) as a colorless liquid. $^1$H NMR (400 MHz, CDCl$_3$) δ 1.20-2.01 (m, 11H), 2.59-2.74 (m, 2H), 7.15-7.29 (m, 5H).

Step D: Preparation of 2,3,3a,4,5,9b-hexahydro-1H-cyclopenta[a]naphthalene

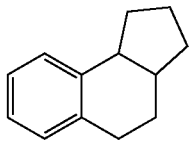 [SMILES: c1ccc2c(c1)CCC1CCCC21]

To a solution of 2-phenethylcyclopentanol (1.28 g, 6.727 mmol) in 100 mL CH$_2$Cl$_2$, 0.33 M trifluoromethanesulfonic acid in DCM (21 mL, 6.930 mmol; prepared by adding 5 g (33.3 mmol) trifluoromethanesulfonic acid into 100 mL CH$_2$Cl$_2$) was added. After stirring at room temperature overnight, the mixture was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give 2,3,3a,4,5,9b-hexahydro-1H-cyclopenta[a]naphthalene (1.08 g, 93%) as a colorless liquid. H NMR (400 MHz, CDCl$_3$) 1.41-1.65 (m, 4H), 1.69-1.78 (m, 2H), 1.94-2.02 (m, 1H), 2.12-2.20 (m, 1H), 2.24-2.33 (m, 1H), 2.63-2.73 (m, 2H), 3.03-3.10 (m, 1H), 7.06-7.19 (m, 4H).

Step E: Preparation of 2,3,3a,4-tetrahydro-1H-cyclopenta[a]naphthalen-5(9bH)-one

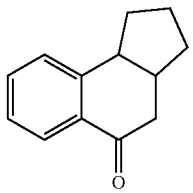 [SMILES: O=C1CC2CCCC2c2ccccc21]

To a solution of 2,3,3a,4,5,9b-hexahydro-1H-cyclopenta[a]naphthalene (769 mg, 4.464 mmol) in 40 mL acetic acid, chromium trioxide (890 mg, 8.901 mmol) was added. After stirring at room temperature for 4 h, the mixture was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give 2,3,3a,4-tetrahydro-1H-cyclopenta[a]naphthalen-5(9bH)-one (48 mg, 6%). LCMS m/z=187.1 [M+1]$^+$. $^1$H NMR (400 MHz, CDCl$_3$) δ 1.48-1.56 (m, 1H), 1.75-2.02 (m, 4H), 2.16-2.25 (m, 1H), 2.53-2.66 (m, 2H), 2.71-2.79 (m, 1H), 3.23-3.29 (m, 1H), 7.28-7.29 (m, 2H), 7.47-7.51 (m, 1H), 7.95-7.97 (m, 1H).

Step F: Preparation of 2-(2,3,3a,4-tetrahydro-1H-cyclopenta[a]naphthalen-5(9bH)-ylidene)acetonitrile

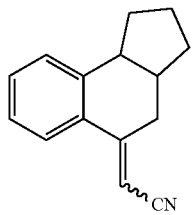 [SMILES: N#CC=C1CC2CCCC2c2ccccc21]

To a suspension of 60% sodium hydride dispersion (23 mg, 0.575 mmol) in 1 mL THF, a solution of diethyl (cyanomethyl)phosphonate (100 mg, 0.565 mmol) in 2 mL THF was added slowly (over ca. 5 min). After stirring at room temperature for 5 min, a solution of 2,3,3a,4-tetrahydro-1H-cyclopenta[a]naphthalen-5(9bH)-one (52 mg, 0.279 mmol) in 1 mL THF was added. After stirring at room temperature for 4 h, the mixture was extracted with $CH_2Cl_2$ and water+brine. Organic phases were dried over $MgSO_4$, filtered, and concentrated. The residue was purified by biotage column chromatography ($SiO_2$, hexane/AcOEt gradient) to give 2-(2,3,3a,4-tetrahydro-1H-cyclopenta[a]naphthalen-5(9bH)-ylidene)acetonitrile (48.4 mg, 83%) as a colorless oil (E:Z=59:41). LCMS m/z=210.3 [M+1]$^+$. $^1$H NMR (400 MHz, CDCl$_3$) δ 1.38-1.79 (m, 4H), 1.93-2.04 (m, 1H), 2.16-2.26 (m, 1H), 2.34-2.88 (m, 3H), 3.20-3.29 (m, 1H), 5.26-5.27 (m, 0.41H), 5.64-5.65 (m, 0.59H), 7.17-7.27 (m, 2H), 7.34-7.39 (m, 1H), 7.43 (dd, J$_1$=7.9 Hz, J$_2$=0.9 Hz, 0.59H), 8.00-8.02 (m, 0.41H).

Step G: Preparation of 1-(3,4-dichlorophenyl)-N-(2-(2,3,3a,4,5,9b-hexahydro-1H-cyclopenta[a]naphthalen-5-yl)ethyl)methanesulfonamide

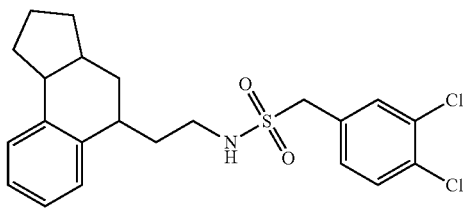 [SMILES: O=S(=O)(Cc1ccc(Cl)c(Cl)c1)NCCC1CC2CCCC2c2ccccc21]

To an undetermined amount of raney nickel (slurry in water; washed three times with MeOH), a solution of 2-(2,3,3a,4-tetrahydro-1H-cyclopenta[a]naphthalen-5(9bH)-ylidene)acetonitrile (48 mg, 0.229 mmol) in ca. 5 mL MeOH and 7 M ammonia in MeOH (1 mL, 7.000 mmol) were added. The mixture was shaken on a Parr-shaker under ca. 60 psi hydrogen pressure for 5 days. Raney nickel was filtered off through celite, washed with additional MeOH, concentrated, and dried under high vacuum. The residue was dissolved in 3 mL $CH_2Cl_2$ and triethylamine (65 µl, 0.466 mmol) and (3,4-dichlorophenyl)methanesulfonyl chloride (78.2 mg, 0.301 mmol) were added. After stirring at room temperature overnight, the mixture was extracted with water and $CH_2Cl_2$. Organic phases were dried over $MgSO_4$, filtered, and concentrated. The residue was purified by biotage column chromatography ($SiO_2$, hexane/AcOEt gradient). Fractions containing product were concentrated and residue was re-purified by HPLC ($CH_3CN/H_2O$ gradient+0.1% TFA). Fractions containing product were partly concentrated and residue was extracted with 1 M $NaHCO_3$ and $CH_2Cl_2$. Organic phases were dried over $MgSO_4$, filtered, and concentrated to give 1-(3,4-dichlorophenyl)-N-(2-(2,3,3a,4,5,9b-hexahydro-1H-cyclopenta[a]naphthalen-5-yl)ethyl)methanesulfonamide (43.7 mg, 44%). LCMS m/z=436.5 [M−1]$^+$. $^1$H NMR (400 MHz, CDCl$_3$) δ 1.31-1.88 (m, 7H), 1.97-2.40 (m, 4H), 2.71-2.82 (m, 1H), 2.97-3.18 (m, 3H), 4.02-4.20 (m, 3H), 6.97-6.99-7,26 (m, 5H), 7.44-7.50 (m, 2H).

Step H: Preparation of (7aS)-5-((3,4-dichlorobenzyl)sulfonyl)-5,6,7,7a,8,8a,9,10,11,11a-decahydro-4H-cyclopenta[5,6]naphtho[1,8-cd]azepine and (7aR)-5-((3,4-dichlorobenzyl)sulfonyl)-5,6,7,7a,8,8a,9,10,11,1 la-decahydro-4H-cyclopenta[5,6]naphtho[1,8-cd]azepine

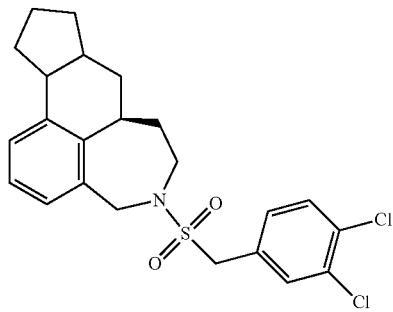

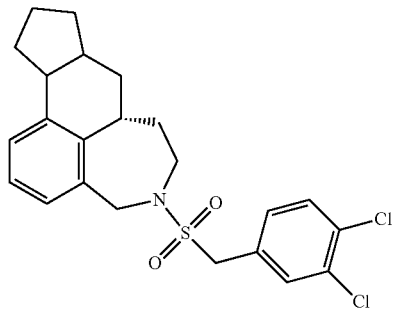

To a mixture of 1-(3,4-dichlorophenyl)-N-(2-(2,3,3a,4,5,9b-hexahydro-1H-cyclopenta[a]naphthalen-5-yl)ethyl)methanesulfonamide (41.4 mg, 94.43 µmol), acetic anhydride (9 µl, 95.21 µmol), and 1,3,5-trioxane (40 mg, 0.444 mmol) in 1 mL DCE, methanesulfonic acid (40 µl, 0.617 mmol) was added. After stirring at room temperature for 10 min, the mixture was extracted with 1 M $NaHCO_3$ and $CH_2Cl_2$. Organic phases were dried over $MgSO_4$, filtered, and concentrated. The residue was purified by biotage column chromatography ($SiO_2$, hexane/AcOEt) followed by re-purification of the mix-fractions by prep TLC (1 mm $SiO_2$, hexane/AcOEt 5:1) to give a first-eluting enantiomer (less polar, first peak coming off biotage column) as a white solid and a second-eluting enantiomer (12.7 mg, 28.20 µmol, 29.9%) (more polar, second peak coming off biotage column) as a viscous, colorless oil. Less polar isomer: $^1$H NMR (400 MHz, CDCl$_3$) δ 1.19-1.84 (m, 8H), 1.98-2.08 (m, 1H), 2.11-2.20 (m, 2H), 3.00-3.11 (m, 2H), 3.28-3.35 (m, 1H), 3.71-3.86 (m, 3H), 4.40 (d, J=15.2 Hz, 1H), 4.60 (d, J=15.2 Hz, 1H), 6.85 (dd, J$_1$=8.2 Hz, J$_2$=2.0 Hz, 1H), 6.91 (d, J=2.0H, 1H), J=7.07 (dd, J$_1$=7.2 Hz, J$_2$=1.1 Hz, 1H), 7.13-

7.17 (m, 1H), 7.22 (d, J=7.6 Hz, 1H), 7.30 (d, J=8.2 Hz, 1H). More polar isomer: $^1$H NMR (400 MHz, CDCl$_3$) δ 1.21-1.88H (m, 8H), 1.91-2.00 (m, 1H), 2.10-2.23 (m, 2H), 2.87-2.98 (m, 2H), 3.29-3.36 (m, 1H), 3.74-3.80 (m, 1H), 3.96-4.04 (m, 2H), 4.19 (d, J=15.8 Hz, 1H), 4.56 (dd, $J_1$=15.8 Hz, $J_2$=1.0 Hz, 1H), 6.94 (dd, $J_1$=8.3 Hz, $J_2$=2.1 Hz, 1H), 6.98 (dd, $J_1$=7.2 Hz, J2=1.2 Hz, 1H), 7.08-7.11 (m, 1H), 7.15 (dd, $J_1$=7.7 Hz, $J_2$=1.2 Hz, 1H), 7.21 (d, J=2.0 Hz, 1H), 7.30 (d, J=8.2 Hz, 1H).

Step I-1 and 1-2: Preparation of (7aS)-5,6,7,7a,8,8a,9,10,11,11a-decahydro-4H-cyclopenta[5,6]naphtho[1,8-cd]azepine (Compound 132) and of (7aR)-5,6,7,7a,8,8a,9,10,11,11a-decahydro-4H-cyclopenta[5,6]naphtho[1,8-cd]azepine (Compound 118)

Step I-1

To the less polar isomer from Step H, 17.2 mg, 38.19 μmol) in 0.5 mL acetic acid, 48% hydrogen bromide in water (0.5 mL, 4.417 mmol) was added. The mixture was stirred at 120° C. for 4 h and then, purified by HPLC (CH$_3$CN/H$_2$O gradient+0.1% TFA) to give the corresponding compound of Formula I. LCMS m/z=228.2 [M+1]$^+$. $^1$H NMR (400 MHz, CD$_3$OD) δ 1.47-1.86 (m, 6H), 1.93-1.98 (m, 2H), 2.03-2.12 (m, 1H), 2.15-2.33 (m, 2H), 3.00-3.07 (m, 1H), 3.25-3.32 (m, 1H), 3.39-3.42 (m, 2H), 4.22 (d, J=14.0 Hz, 1H), 4.55 (d, J=14.0 Hz, 1H), 7.14-7.20 (m, 2H), 7.26-7.31 (m, 1H).

Step 1-2

To the more polar isomer from Step H, 12.6 mg, 27.97 μmol) in 0.5 mL acetic acid, 48% hydrogen bromide in water (0.5 mL, 4.417 mmol) was added. The mixture was stirred at 120° C. for 4 h and then, purified by HPLC (CH$_3$CN/H$_2$O gradient+0.1% TFA) to give the corresponding compound of Formula I. LCMS m/z=228.2 [M+1]$^+$. $^1$H NMR (400 MHz, CD$_3$OD) δ 1.33-1.43 (m, 1H), 1.51-1.91 (m, 6H), 1.95-2.08 (m, 2H), 2.14-2.25 (m, 2H), 2.94-3.01 (m, 1H), 3.16-3.23 (m, 1H), 3.36-3.43 (m, 1H), 3.51-3.56 (m, 1H), 4.25-4.30 (m, 2H), 7.14-7.18 (m, 2H), 7.22-7.28 (m, 1H).

5,6,7,7a,8,8a,9,10,11,11a-decahydro-4H-cyclopenta[5,6]naphtho[1,8-cd]azepine (Compound 140) may be prepared from equal amounts of the two enantiomers 132 and 118, for example by stirring together equal amounts of the two enantiomers in a solvent, followed by solvent removal.

Example 1.19: Preparation of 8'-ethyl-2',3',4',4a',5'-pentahydro-1'H-dispiro[cyclopropane-1,6'-cyclopropane-7',1''-naphtho[1,8-cd]-azepine] (Compound 101)

Step A: Preparation of 8'-bromo-3',4'-dihydro-1'H-spiro[cyclopropane-1,2'-naphthalen]-1'-one

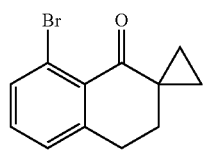 [SMILES: O=C1c2c(Br)cccc2CCC12CC2]

To a solution of 8-bromo-3,4-dihydronaphthalen-1(2H)-one (2.0 g, 8.886 mmol) in 80 mL tBuOH, 1 M potassium 2-methylpropan-2-olate in THF (27 mL, 27.00 mmol) was added. After stirring at room temperature for 0.5 h, (2-chloroethyl)dimethylsulfonium iodide (2.3 g, 9.107 mmol) was added. After stirring at room temperature over-the-weekend, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to 8'-bromo-3',4'-dihydro-1'H-spiro[cyclopropane-1,2'-naphthalen]-1'-one (1.67 g, 75%). LCMS m/z=251.3 [M+1]$^+$. $^1$H NMR (400 MHz, CDCl$_3$) δ 0.85-0.87 (m, 2H), 1.46-1.49 (m, 2H), 1.92 (m, 2H), 2.98-3.01 (m, 2H), 7.19-7.24 (m, 2H), 7.56-7.60 (m, 1H).

Step B: Preparation of 8'-bromo-1'-methylene-3',4'-dihydro-1'H-spiro[cyclopropane-1,2'-naphthalene]

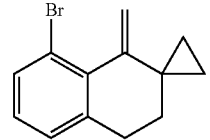

To a suspension of 1 M potassium 2-methylpropan-2-olate in THF (8.7 mL, 8.700 mmol) in 25 mL toluene, 1 M potassium 2-methylpropan-2-olate in THF (8.7 mL, 8.700 mmol) was added. After stirring at 110° C. (oil bath) for 40 min, a solution of 8'-bromo-3',4'-dihydro-1'H-spiro[cyclopropane-1,2'-naphthalen]-1'-one (1.45 g, 5.774 mmol) in 8 mL toluene was added. The mixture was stirred at 110° C. for 20 min, allowed to cool to room temperature, and extracted with water and CH$_2$Cl$_2$. Organic phases were dried over MgSO$_4$, filtered, and concentrated. The residue was purified by biotage column chromatography (SiO$_2$, hexanes) to give 8'-bromo-1'-methylene-3',4'-dihydro-1'H-spiro[cyclopropane-1,2'-naphthalene] (1.41 g, 98%) as a colorless liquid. $^1$H NMR (400 MHz, CDCl$_3$) δ 0.59-0.62 (m, 2H), 0.86-0.88 (m, 2H), 1.73 (t, J=6.6 Hz, 2H), 2.80 (t, J=6.6 Hz, 2H), 5.21 (s, 1H), 5.59 (s, 1H), 6.96-7.00 (m, 1H), 7.07-7.09 (m, 1H), 7.46-7.48 (m, 1H).

Step C: Preparation of the following compound

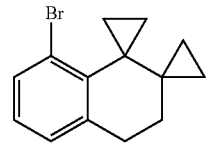

To an ice-cooled solution of 8'-bromo-1'-methylene-3',4'-dihydro-1'H-spiro[cyclopropane-1,2'-naphthalene] (1.41 g, 5.659 mmol) and chloroiodomethane (2.465 mL, 33.96 mmol) in 40 mL DCE, 1 M diethylzinc in hexane (29 mL, 29.00 mmol) was added over ca. 5 min. After stirring at 0° C. for 2 h, the mixture was continued to be stirred at room temperature. After stirring at room temperature for 2 h, the mixture was cooled in an ice-water bath and quenched by the addition of 1 M NH$_4$Cl. The residue was extracted with additional 1 M NH$_4$Cl and CH$_2$Cl$_2$. Combined organic phases were dried over MgSO$_4$, filtered, and concentrated. The residue was purified by biotage column chromatography (SiO$_2$, hexanes) to give the title compound for this step (1.36 g, 91%) as a colorless liquid. $^1$H NMR (400 MHz, CDCl$_3$) δ 0.18-0.20 (m, 2H), 0.42-0.44 (m, 2H), 0.73-0.75 (m, 2H), 1.17-1.20 (m, 2H), 1.79 (t, J=6.8 Hz, 2H), 2.93 (t, J=6.8 Hz, 2H), 6.94-6.98 (m, 1H), 7.10-7.12 (m, 1H), 7.33-7.35 (m, 1H).

Step D: Preparation of the following compound

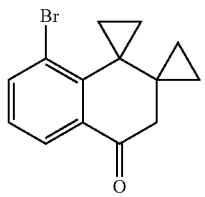 [SMILES: O=C1CC2(CC2)C2(CC2)c2c(Br)cccc21]

To a mixture of the product of step C (1.36 g, 5.168 mmol), sodium bicarbonate (236 mg, 2.809 mmol), and Rh$_2$(cap)$_4$ (71.1 mg, 0.109 mmol) in 20 mL DCE, 5.5 M 2-hydroperoxy-2-methylpropane in decane (4.7 mL, 25.85 mmol) was added. The mixture was stirred at 40° C. (oil bath). After 3 h, more Rh$_2$(cap)$_4$ (75 mg) and 5.5 M 2-hydroperoxy-2-methylpropane in decane (4.7 mL) were added. After stirring for 3 more hours, more Rh$_2$(cap)$_4$ (77 mg) and 5.5 M 2-hydroperoxy-2-methylpropane in decane (4.7 mL) were added. After stirring overnight, more Rh$_2$(cap)$_4$ (77 mg) and 5.5 M 2-hydroperoxy-2-methylpropane in decane (4.7 mL) were added. After stirring for 6 more hours, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (798 mg, 56%) as a colorless oil. LCMS m/z=277.4 [M+1]$^+$. $^1$H NMR (400 MHz, CDCl$_3$) δ 0.35-0.38 (m, 2H), 0.53-0.56 (m, 2H), 0.82-0.84 (m, 2H), 1.78-1.83 (m, 2H), 2.61-2.64 (m, 2H), 7.09-7.13 (m, 1H), 7.67 (dd, J$_1$=7.9 Hz, J$_2$=1.5 Hz, 1H), 8.01 (dd, J$_1$=7.6 Hz, J$_2$=1.5 Hz, 1H).

Step E: Preparation of the following compound

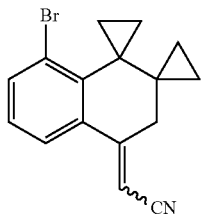 [SMILES: N#CC=C1CC2(CC2)C2(CC2)c2c(Br)cccc21]

To a suspension of 60% sodium hydride dispersion (305 mg, 7.63 mmol) in 20 mL THF, a solution of diethyl (cyanomethyl)phosphonate (1.35 g, 7.621 mmol) in 20 mL THF was added slowly (over ca. 5 min). After stirring at room temperature for 5 min, a solution of the product of Step D (795 mg, 2.868 mmol) in 20 mL THF was added. After stirring at 60° C. (oil bath) for 40 min, the mixture was partly concentrated and residue was extracted with CH$_2$Cl$_2$ and water. Organic phases were dried over MgSO$_4$, filtered, and concentrated. The residue was purified by biotage column chromatography (SiO$_2$, hexane/AcOEt gradient) to give the title compound for this step (838 mg, 97%) as a colorless oil (E:Z=56:44). H NMR (400 MHz, CDCl$_3$) δ 0.29-0.32 (m, 1H), 0.36-0.39 (m, 1H), 0.51-0.55 (m, 2H), 0.75-0.82 (m, 2H), 1.20-1.38 (m, 2H), 2.69 (d, J=1.8 Hz, 0.88H), 2.9 (d, J=2.0 Hz, 1.12H), 5.34-5.35 (m, 0.44H), 5.68-5.69 (m, 0.56H), 7.04-7.08 (m, 0.56H), 7.13-7.16 (m, 0.44H), 7.37 (dd, J$_1$=7.6 Hz, J$_2$=1.2 Hz, 0.56H), 7.53-7.56 (m, 1H), 7.78 (dd, J$_1$=7.6 Hz, J$_2$=1.2 Hz, 0.44H).

Step F: Preparation of Compound 16 of FIG. 4, where R$^1$ is ethyl

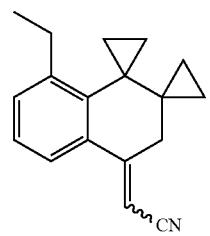 [SMILES: CCc1cccc2c1C1(CC1)C1(CC1)CC2=CC#N]

A mixture of the product of Step E (307 mg, 1.023 mmol), bis(tri-t-butylphosphine)palladium (25 mg, 48.73 μmol), and 1 M diethylzinc in hexanes (3 mL, 3.000 mmol) in 10 mL THF was stirred at 60° C. (oil bath). After 2.5 h, the mixture was cooled in an ice/water-bath and quenched by the dropwise addition of 2 M NH$_4$Cl. The residue was extracted with 2 M NH$_4$Cl and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (216 mg, 85%). $^1$H NMR (400 MHz, CDCl$_3$) δ 0.29-0.32 (m, 1H), 0.35-0.38 (m, 1H), 0.46-0.49 (m, 2H), 0.70-0.73 (m, 1H), 0.78-0.82 (m, 1H), 0.85-0.92 (m, 2H), 1.15-1.20 (m, 3H), 2.65-2.72 (m, 3H), 2.89-2.90 (m, 1H), 5.29-5.30 (m, 0.56H), 5.65-5.66 (m, 0.44H), 7.14-7.28 (m, 2.56H), 7.66 (dd, J$_1$=7.2 Hz, J$_2$=1.6 Hz, 0.44H).

Step G: Preparation of Compound 17 of FIG. 4, where R$^1$ is ethyl

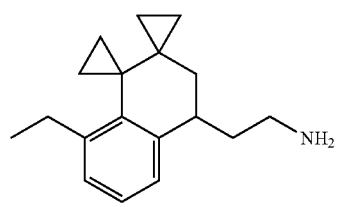 [SMILES: CCc1cccc2c1C1(CC1)C1(CC1)CC2CCN]

To a mixture of the product of step F (215 mg, 0.862 mmol) and cobalt(II) chloride hexahydrate (650 mg, 2.732 mmol) in 20 mL MeOH, sodium tetrahydroborate (1 g, 26.43 mmol) was added in small portions over 6 h. After stirring at room temperature overnight, (BOC)$_2$O (1 g, 4.582 mmol) was added. After stirring at room temperature for 0.5 h, the mixture was partly concentrated. The residue was diluted with water and CH$_2$Cl$_2$ and shaken in a separatory funnel. Phases were filtered through celite and separated. Aqueous phase was washed twice more with CH$_2$Cl$_2$. Organic phases were dried over MgSO$_4$, filtered, and concentrated. The residue was purified by biotage column chromatography (SiO$_2$, hexane/AcOEt gradient). Fractions containing Boc-protected product were concentrated. The residue was dissolved in 10 mL $CH_2Cl_2$, cooled in an ice/water-bath, and TFA (2 mL, 26.12 mmol) was added. After stirring at 0° C. for 2.5 h, solution was concentrated and dried under high vacuum to give the title compound for this step (191 mg, 60%). LCMS m/z=256.4 [M+1]$^+$. $^1$H NMR (400 MHz, $CD_3OD$) δ 0.13-0.18 (m, 1H), 0.24-0.29 (m, 1H), 0.39-0.48 (m, 3H), 0.65-0.70 (m, 1H), 0.88-0.93 (m, 1H), 1.11-1.33 (m, 6H), 1.85-1.94 (m, 1H), 2.04-2.09 (m, 1H), 2.32-2.41 (m, 1H), 2.62-2.82 (m, 2H), 3.10-3.14 (m, 2H), 7.02-7.06 (m, 2H), 7.11-7.14 (m, 1H).

Step H: Preparation of Compound 18 of FIG. 4, where $R^1$ is ethyl and $R^{10}$ is 3,4-dichlorobenzyl

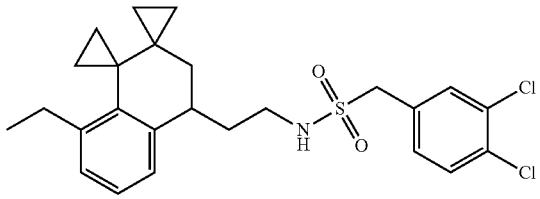 [SMILES: CCc1cccc2c1C1(CC1)C1(CC1)CC2CCNS(=O)(=O)Cc1ccc(Cl)c(Cl)c1]

To an ice-cooled solution of the product of step G (189 mg, 0.512 mmol) and N-ethyl-N-isopropylpropan-2-amine (267 μl, 1.533 mmol) in 5 mL $CH_2Cl_2$, a solution of (3,4-dichlorophenyl)methanesulfonyl chloride (199 mg, 0.767 mmol) dissolved in 2 mL $CH_2Cl_2$ was added slowly by a syringe pump (over ca. 15 min). After stirring at 0° C. for 0.5 h, the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give the title compound for this step (172 mg, 70%). LCMS m/z=476.5 [M−1]. $^1$H NMR (400 MHz, $CDCl_3$) δ 0.15-0.18 (m, 1H), 0.20-0.23 (m, 1H), 0.32-0.37 (m, 1H), 0.40-0.46 (m, 2H), 0.57-0.62 (m, 1H), 0.81-0.86 (m, 1H), 1.10-1.28 (m, 5H), 1.70-1.79 (m, 1H), 1.94-1.98 (m, 1H), 2.19-2.28 (m, 1H), 2.61-2.81 (m, 1H), 3.18-3.28 (m, 3H), 4.13-4.21 (m, 3H), 6.98 (d, J=7.7 Hz, 1H), 7.05 (d, J=7.3 Hz, 1H), 7.14-7.18 (m, 1H), 7.24-7.27 (m, 1H), 7.46 (d, J=8.2H, 1H), 7.52 (d, =2.1 Hz, 1H).

Step I: Preparation of Compound 19 of FIG. 4, where $R^1$ is ethyl and $R^{10}$ is 3,4-dichlorobenzyl

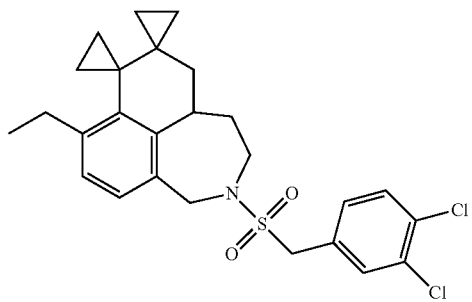 [SMILES: CCc1ccc2c3c1C1(CC1)C1(CC1)CC3CCN(S(=O)(=O)Cc1ccc(Cl)c(Cl)c1)C2]

To a solution of the product of Step H (171 mg, 0.357 mmol) in 4 mL DCE, 1,3,5-trioxane (80 mg, 0.888 mmol), acetic anhydride (34 μl, 0.360 mmol), and methanesulfonic acid (147 μl, 2.267 mmol) were added. After stirring at room temperature for 10 min, the mixture was extracted with 1 M $NaHCO_3$ and $CH_2Cl_2$. Organic phases were dried over $MgSO_4$, filtered, and concentrated. The residue was purified by biotage column chromatography ($SiO_2$, hexane/AcOEt gradient) to give the title compound for this step (110 mg, 63%). $^1$H NMR (400 MHz, $CDCl_3$) δ 0.181-0.276 (m, 2H), 0.30-0.35 (m, 1H), 0.44-0.54 (m, 2H), 0.60-0.65 (m, 1H), 0.81-0.86 (m, 1H), 1.02-1.07 (m, 1H), 1.20 (t, J=7.5 Hz, 3H), 1.57-1.63 (m, 1H), 1.86-1.99 (m, 3H), 2.60-2.75 (m, 2H), 3.43-3.62 (m, 3H), 3.82 (d, J=13.8 Hz, 1H), 3.94 (d, J=13.8 Hz, 1H), 4.41 (d, J=16.2 Hz, 1H), 4.59 (d, J=16.2 Hz, 1H), 6.86 (d, J=7.8 Hz, 1H), 6.94-6.99 (m, 2H), 7.24-7.29 (m, 2H).

Step J: Preparation of 8'-ethyl-2',3',4',4a',5'-pentahydro-1'H-dispiro[cyclopropane-1,6'-cyclopropane-7',1''-naphtho[1,8-cd]-azepine] (Compound 101)

To a solution of Reactant 7 (107.7 mg, 0.220 mmol) in 3 mL toluene, 60% bis(2-methoxyethoxy)aluminum(III) sodium hydride in toluene (1.5 mL, 4.612 mmol) was added. The mixture was stirred at 80° C. (oil bath). After 3 h, more 60% bis(2-methoxyethoxy)aluminum(III) sodium hydride in toluene (1.5 mL) was added and continued to be stirred at 80° C. After another 3 h, the mixture was diluted with toluene (ca. 10 mL), cooled in an ice-water bath, and quenched by the dropwise addition of 1 M $NH_4Cl$. After stirring for 0.5 h, di-tert-butyl dicarbonate (265 mg, 1.214 mmol) was added. The mixture was allowed to warm to room temperature. After 1 h, the mixture was extracted with 1 M NaOH and $CH_2Cl_2$. Organic phases were dried over $MgSO_4$, filtered, and concentrated. The residue was purified by biotage column chromatography ($SiO_2$, hexane/AcOEt gradient). Fractions containing Boc-protected product were concentrated. The residue was dissolved in 3 mL $CH_2Cl_2$, cooled in an ice-water bath, and TFA (551 μl, 7.195 mmol) was added. After stirring at 0° C. for 1.5 h, the mixture was concentrated and residue was purified by HPLC ($CH_3CN$/$H_2O$ gradient+0.1% TFA) to give the title compound for this example 1.19 (40.3 mg, 48%) as a white solid. LCMS m/z=268.2 [M+1]$^+$. $^1$H NMR (400 MHz, $CD_3OD$) δ 0.21-0.26 (m, 1H), 0.29-0.40 (m, 2H), 0.47-0.52 (m, 1H), 0.69-0.75 (m, 2H), 0.85-0.92 (m, 1H), 0.96-1.03 (m, 1H), 1.16 (t, J=7.5 Hz, 3H), 1.71-1.76 (m, 1H), 1.93-1.98 (m, 1H), 2.02-2.08 (m, 1H), 2.15-2.26 (m, 1H), 2.62-2.76 (m, 2H), 3.41-3.44 (m, 2H), 3.58-3.66 (m, 1H), 4.29 (d, J=14.7 Hz, 1H), 4.48 (d, J=14.7 Hz, 1H), 7.02-7.06 (m, 2H).

Example 1.20: Preparation of 8'-methyl-2',3',4',4a',5'-pentahydro-1'H-dispiro[cyclopropane-1,6'-cyclopropane-7',1''-naphtho[1,8-cd]-azepine]Compound 116)

Step A: Preparation of Compound 16 of FIG. 4, where $R^1$ is methyl

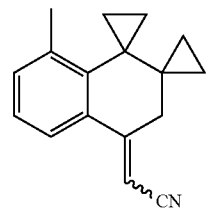 [SMILES: Cc1cccc2c1C1(CC1)C1(CC1)CC2=CC#N]

A mixture of the product of Step E in Example 1.19 (298 mg, 0.993 mmol), bis(tri-tert-butylphosphoranyl)palladium (25 mg, 48.73 µmol), and 1 M dimethylzinc in heptane (3 mL, 3.000 mmol) in 10 mL THF was stirred at 60° C. (oil bath). After 4 h, the mixture was cooled in an ice/water-bath and quenched by the dropwise addition of 2 M NH$_4$Cl. The residue was extracted with 2 M NH$_4$Cl and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (219 mg, 94%) as an off-white solid. LCMS m/z=236.3 [M+1]$^+$. $^1$H NMR (400 MHz, CDCl$_3$) δ 0.29-0.31 (m, 1H), 0.35-0.38 (m, 1H), 0.44-0.47 (m, 2H), 0.69-0.72 (m, 1H), 0.76-0.79 (m, 1H), 0.87-0.90 (m, 1H), 0.92-0.95 (m, 1H), 2.32 (s, 1.68H), 2.33 (s, 1.32H), 2.69 (d, J=1.8 Hz, 0.88H), 2.90 (d, J=2.2 Hz, 1.12H), 5.28-5.30 (m, 0.44H), 5.66-5.67 (m, 0.56H), 7.09-7.21 (m, 2H), 7.27-7.30 (m, 0.56H), 7.68 (dd, J$_1$=7.4 Hz, J$_2$=1.1 Hz, 0.44H).

Step B: Preparation of Compound 17 of FIG. 4, where R$^1$ is methyl

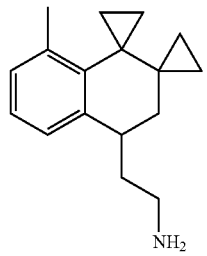 [SMILES: Cc1cccc2c1C1(CC1)C1(CC1)CC2CCN]

To a mixture of the product of Step A (215 mg, 0.914 mmol) and cobalt(II) chloride hexahydrate (660 mg, 2.774 mmol) in 20 mL MeOH, sodium tetrahydroborate (1 g, 26.43 mmol) was added in small portions over 6 h. After stirring at room temperature overnight, di-tert-butyl dicarbonate (1 g, 4.582 mmol) was added. After stirring at room temperature for 0.5 h, the mixture was partly concentrated. The residue was diluted with water and CH$_2$Cl$_2$ and shaken in a separatory funnel. Phases were filtered through celite and separated. Aqueous phase was washed twice more with CH$_2$Cl$_2$. Organic phases were dried over MgSO$_4$, filtered, and concentrated. The residue was purified by biotage column chromatography (SiO$_2$, hexane/AcOEt gradient). Fractions containing Boc-protected product were concentrated. The residue was dissolved in 10 mL CH$_2$Cl$_2$, cooled in an ice-water bath, and 2,2,2-trifluoroacetic acid (2.1 mL, 27.42 mmol) was added. After stirring at 0° C. for 1.5 h, solution was concentrated and dried under high vacuum to give the title compound for this step (191 mg, 60%) as an off-white solid. LCMS m/z=242.0 [M+1]$^+$. $^1$H NMR (400 MHz, CD$_3$OD) δ 0.15-0.18 (m, 1H), 0.24-0.28 (m, 1H), 0.37-0.49 (m, 3H), 0.64-0.69 (m, 1H), 0.86-0.91 (m, 1H), 1.12-1.17 (m, 1H), 1.29-1.34 (m, 1H), 1.85-1.94 (m, 1H), 2.05-2.10 (m, 1H), 2.32-2.40 (m, 4H), 3.09-3.13 (m, 2H), 3.26-3.33 (m, 1H), 6.96-6.98 (m, 1H), 7.03-7.09 (m, 2H).

Step C: Preparation of Compound 18 of FIG. 4, where R$^1$ is methyl and R$^{10}$ is 3,4-dichlorobenzyl

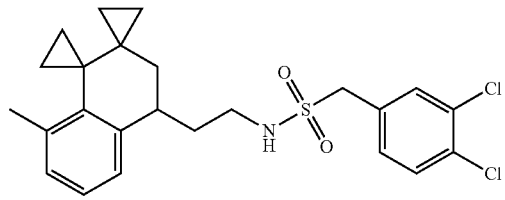 [SMILES: Cc1cccc2c1C1(CC1)C1(CC1)CC2CCNS(=O)(=O)Cc1ccc(Cl)c(Cl)c1]

To an ice-cooled solution of the product of Step B (255 mg, 0.567 mmol) and N-ethyl-N-isopropylpropan-2-amine (375 µl, 2.167 mmol) in 7 mL CH$_2$Cl$_2$, a solution of (3,4-dichlorophenyl)methanesulfonyl chloride (220 mg, 0.848 mmol) dissolved in 5 mL CH$_2$Cl$_2$ was added slowly by a syringe pump (over ca. 15 min). After stirring at 0° C. for 0.5 h, the mixture was extracted with water and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (213 mg, 81%). LCMS m/z=462.5 [M−1]$^+$. $^1$H NMR (400 MHz, CDCl$_3$) δ 0.15-0.18 (m, 1H), 0.20-0.25 (m, 1H), 0.30-0.35 (m, 1H), 0.40-0.48 (m, 2H), 0.57-0.62 (m, 1H), 0.80-0.84 (m, 1H), 1.09-1.13 (m, 1H), 1.23-1.29 (m, 2H), 1.70-1.79 (m, 1H), 1.94-1.99 (m, 1H), 2.19-2.28 (m, 1H), 2.33 (s, 3H), 3.16-3.25 (m, 3H), 4.13-4.17 (m, 1H), 4.21 (s, 2H), 6.99 (d, J=7.6 Hz, 1H), 7.08-7.12 (m, 1H), 7.25-7.27 (m, 1H), 7.46 (d, J=8.2 Hz, 1H), 7.51 (d, J=2.1 Hz, 1H).

Step D: Preparation of Compound 19 of FIG. 4, where R$^1$ is methyl and R$^{10}$ is 3,4-dichlorobenzyl

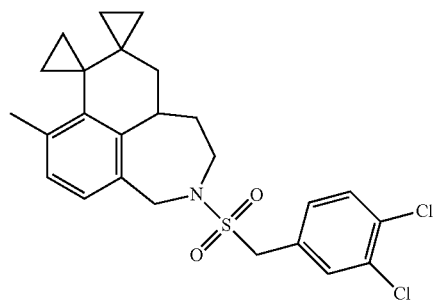 [SMILES: Cc1ccc2c3c1C1(CC1)C1(CC1)CC3CCN(S(=O)(=O)Cc1ccc(Cl)c(Cl)c1)C2]

To a solution of the product of Step C (210 mg, 0.452 mmol) in 5 mL DCE, 1,3,5-trioxane (110 mg, 1.221 mmol), acetic anhydride (43 µl, 0.455 mmol), and methanesulfonic acid (182 µl, 2.807 mmol) were added. After stirring at room temperature for 5 min, the mixture was extracted with 1 M NaHCO$_3$ and CH$_2$Cl$_2$. Organic phases were dried over MgSO$_4$, filtered, and concentrated. The residue was purified by biotage column chromatography (SiO$_2$, hexane/AcOEt gradient) to give the title compound for this step (165 mg, 77%). $^1$H NMR (400 MHz, CDCl$_3$) δ 0.18-0.27 (m, 2H), 0.29-0.33 (m, 1H), 0.43-0.47 (m, 1H), 0.57-0.66 (m, 2H), 0.76-0.82 (m, 1H), 1.10-1.15 (m, 1H), 1.56-1.62 (m, 1H), 1.84-1.95 (m, 3H), 2.32 (s, 3H), 3.40-3.54 (m, 2H), 3.60-3.66 (m, 1H), 3.81 (d, J=13.8 Hz, 1H), 3.93 (d, J=13.8 Hz, 1H), 4.39 (d, J=16.1 Hz, 1H), 4.60 (d, J=16.1 Hz, 1H), 6.81

(d, J=7.7 Hz, 1H), 6.89 (d, J=7.7 Hz, 1H), 7.00 (dd, J₁=8.2 Hz, J₂=2.1 Hz, 1H), 7.17 (d, J=2.1 Hz, 1H), 7.29 (d, J=8.2 Hz, 1H).

Step E: Preparation of 8'-methyl-2',3',4',4a',5'-pentahydro-1'H-dispiro[cyclopropane-1,6'-cyclopropane-7',1"-naphtho[1,8-cd]-azepine] (Compound 116)

To a solution of the product of Step C (163 mg, 0.342 mmol) in 3 mL toluene, 60% bis(2-methoxyethoxy)aluminum(III) sodium hydride in toluene (3 mL, 9.22 mmol) was added. After stirring at 80° C. (oil bath) for 4 h, more 60% bis(2-methoxyethoxy)aluminum(III) sodium hydride in toluene (3 mL) was added and continued to be stirred at 80° C. After another 2 h, the mixture was diluted with toluene, cooled in an ice/water-bath, and quenched by the dropwise addition of 1 M NH₄Cl. After stirring for 0.5 h, di-tert-butyl dicarbonate (746 mg, 3.418 mmol) was added. After stirring for ca. 0.5 h, the mixture was extracted with 1 M NaOH and CH₂Cl₂. Combined organic phases were dried over MgSO₄, filtered, and concentrated. The residue was purified by biotage column chromatography (SiO₂, hexane/AcOEt gradient). Fractions containing Boc-protected product were concentrated. The residue was dissolved in 3 mL CH₂Cl₂, cooled in an ice/water-bath, and 2,2,2-trifluoroacetic acid (786 µl, 10.26 mmol) was added. After stirring at 0° C. for 1 h, the mixture was concentrated to give the title compound for this Example 1.20 (63.4 mg, 50%). LCMS m/z=254.4 [M+1]⁺. ¹H NMR (400 MHz, CD₃OD) δ 0.22-0.26 (m, 1H), 0.29-0.37 (m, 2H), 0.46-0.50 (m, 1H), 0.66-0.72 (m, 1H), 0.81-0.89 (m, 2H), 1.04-1.09 (m, 1H), 1.73-1.78 (m, 1H), 1.93-1.99 (m, 1H), 2.02-2,07 (m, 1H), 2.12-2.22 (m, 1H), 2.32 (s, 3H), 3.37-3.48 (m, 2H), 3.55-3.63 (m, 1H), 4.30 (d, J=14.6 Hz, 1H), 4.44 (d, J=14.6 Hz, 1H), 6.96-7.01 (m, 2H).

Example 1.21: Preparation of 2',3',4',4a',5'-pentahydro-1'H-dispiro[cyclobutane-1,6'-cyclopropane-7',1"-naphtho[1,8-cd]-azepine] (Compound 108)

Step A: Preparation of ethyl 1-phenethylcyclobutanecarboxylate

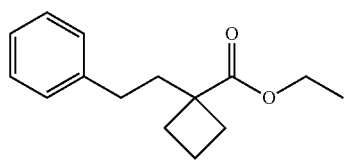 [SMILES: CCOC(=O)C1(CCc2ccccc2)CCC1]

To a solution of diisopropylamine (2.84 mL, 20.26 mmol) in 40 mL THF, cooled in a acetonitrile/dry-ice bath, 2.5 M butyllithium in hexanes (9 mL, 22.50 mmol) was added slowly (over ca. 5 min). After stirring at ca. −30° C. for 15 min, flask was put into an acetone/dry-ice bath and ethyl cyclobutanecarboxylate (2.16 mL, 15.64 mmol) in 6 mL THF was added slowly by a syringe pump (over ca. 20 min). Flask was put into an acetonitrile/dry-ice bath. After stirring for 15 min, flask was put back into an acetone/dry-ice bath and a solution of (2-bromoethyl)benzene (3.2 mL, 23.43 mmol) in 8 mL THF was added slowly by a syringe pump (over ca. 30 min). The mixture was allowed to slowly warm to room temperature (over ca. 4 h). After stirring at room temperature overnight, the mixture was quenched with 2 M NH₄Cl and extracted with additional 2 M NH₄Cl and CH₂Cl₂. Organic phases were dried over MgSO₄, filtered, and concentrated. The residue was purified by biotage column chromatography (SiO₂, hexane/AcOEt gradient). Fractions containing product were concentrated and residue was re-purified by HPLC (CH₃CN/H₂O gradient+0.1% TFA). Fractions congaing product were partly concentrated and residue was extracted with 1 M NaHCO₃ and CH₂Cl₂. Organic phases were dried over MgSO₄, filtered, and concentrated to give ethyl 1-phenethylcyclobutanecarboxylate (1.75 g, 48%) as a colorless liquid. LCMS m/z=233.4 [M+1]⁺. ¹H NMR (400 MHz, CDCl₃) δ 1.28 (t, J=7.2 Hz, 3H), 1.87-1.98 (m, 4H), 2.06-2.11 (m, 2H), 2.42-2.52 (m, 4H), 4.15 (q, J=7.2 Hz, 2H), 7.16-7.19 (m, 3H), 7.26-7.29 (m, 2H).

Step B: Preparation of 1-phenethylcyclobutanecarboxylic acid

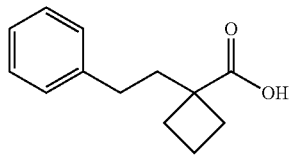 [SMILES: O=C(O)C1(CCc2ccccc2)CCC1]

A mixture of ethyl 1-phenethylcyclobutanecarboxylate (1.74 g, 7.490 mmol) and lithium hydroxide hydrate (1.03 g, 24.55 mmol) in 75 mL THF/MeOH/H₂O (3:1:1) was stirred at 60° C. (oil bath). After stirring overnight, the mixture was partly concentrated and residue was extracted with 2 M HCl and CH₂Cl₂. Organic phases were dried over MgSO₄, filtered, and concentrated to give 1-phenethylcyclobutanecarboxylic acid (1.51 g, 99%) as a white solid. LCMS m/z=203.4 [M−1]⁺. ¹H NMR (400 MHz, DMSO-d₆) δ 1.75-1.99 (m, 6H), 2.29 (m, 2H), 2.42-2.46 (m, 2H), 7.15-7.20 (m, 3H), 7.25-7.29 (m, 2H), 12.17 (s, 1H).

Step C: Preparation of 3',4'-dihydro-1'H-spiro[cyclobutane-1,2'-naphthalen]-1'-one

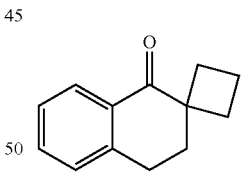

To a solution of 1-phenethylcyclobutanecarboxylic acid (1.378 g, 6.746 mmol) in 70 mL CH₂Cl₂, oxalyl chloride (1.2 mL, 13.76 mmol) was added. After stirring at room temperature overnight, solution was concentrated and dried under high vacuum. The residue was dissolved in 70 mL DCE and aluminum trichloride (1.75 g, 13.12 mmol) was added. The mixture was stirred at 40° C. (oil bath). After 0.5 h, black mixture was poured onto ice and extracted with CH₂Cl₂. Organic phases were dried over MgSO₄, filtered, and concentrated. The residue was purified by biotage column chromatography (SiO₂, hexane/AcOEt gradient) to give 3',4'-dihydro-1'H-spiro[cyclobutane-1,2'-naphthalen]-1'-one (940 mg, 75%) as a dark yellow liquid. LCMS m/z=187.1[M+1]⁺. ¹H NMR (400 MHz, CDCl₃) δ 1.87-2.07 (m, 4H), 2.22 (t, J=6.3 Hz, 2H), 2.45-2.52 (m, 2H), 2.95 (t, J=6.3 Hz, 2H), 7.20 (d, J=7.7 Hz, 1H), 7.29 (m, 1H), 7.41-7.45 (m, 1H), 8.07 (dd, J1=7.8 Hz, J2=1.1 Hz, 1H).

Step D: Preparation of 1'-methylene-3',4'-dihydro-1'H-spiro[cyclobutane-1,2'-naphthalene]

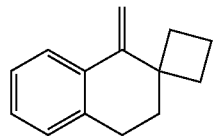

To a suspension of methyltriphenylphosphonium bromide (3.87 g, 10.83 mmol) in 20 mL toluene, 1 M potassium 2-methylpropan-2-olate in THF (11 mL, 11.00 mmol) was added. After stirring at 110° C. (oil bath) for 40 min, a solution of 3',4'-dihydro-1'H-spiro[cyclobutane-1,2'-naphthalen]-1'-one (988 mg, 5.305 mmol) in 4 mL toluene was added. The mixture was stirred at 110° C. for 20 min, allowed to cool to room temperature, and extracted with water and $CH_2Cl_2$. Organic phases were dried over $MgSO_4$, filtered, and concentrated. The residue was purified by biotage column chromatography ($SiO_2$, hexanes) to give 1'-methylene-3',4'-dihydro-1'H-spiro[cyclobutane-1,2'-naphthalene] (730 mg, 75%) as a colorless liquid. $^1$H NMR (400 MHz, $CDCl_3$) δ 1.84-1.99 (m, 6H), 2.10-2.18 (m, 2H), 2.88 (t, J=6.5 Hz, 2H), 5.14 (s, 1H), 5.48 (s, 1H), 7.06-7.18 (m, 3H), 7.56-7.60 (m, 1H), Step E: Preparation of Compound 26 of FIG. 3, where $R^1$=H

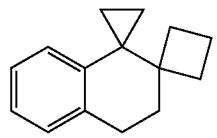 [SMILES: c1ccc2c(c1)CCC1(CCC1)C21CC1]

To an ice-cooled solution of 1'-methylene-3',4'-dihydro-1'H-spiro[cyclobutane-1,2'-naphthalene] (724 mg, 3.929 mmol) and chloroiodomethane (1.715 mL, 23.63 mmol) in 25 mL DCE, 1 M diethylzinc in hexanes (20 mL, 20.00 mmol) was added over ca. 10 min. The mixture was allowed to slowly warm to room temperature. After stirring overnight, suspension was quenched by the addition of 1 M $NH_4Cl$ and extracted with water and $CH_2Cl_2$. Combined organic phases were dried over $MgSO_4$, filtered, and concentrated. The residue was purified by biotage column chromatography ($SiO_2$, hexane) to give the title compound for this step (650 mg, 83.4%) as a colorless liquid. $^1$H NMR (400 MHz, $CDCl_3$) δ 0.83-0.86 (m, 2H), 0.97-1.01 (m, 2H), 1.61-1.77 (m, 5H), 1.85-2.00 (m, 3H), 2.94 (t, J=6.5 Hz, 2H), 6.74 (d, J=7.6 Hz, 1H), 7.00-7.09 (m, 3H).

Step F: Preparation of Compound 27 of FIG. 3, where $R^1$=H

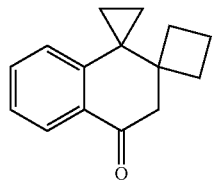 [SMILES: O=C1CC2(CCC2)C2(CC2)c2ccccc21]

To a solution of the product of Step E (647 mg, 3.263 mmol) in 25 mL DCE, sodium bicarbonate (140 mg, 1.667 mmol), $Rh_2(cap)_4$ (52.5 mg, 80.22 μmol), and 5.5 M 2-hydroperoxy-2-methylpropane in decane (4 mL, 22.00 mmol) were added. After stirring at 40° C. (oil bath) overnight, more $Rh_2(cap)_4$ (48 mg) and 5.5 M 2-hydroperoxy-2-methylpropane in decane (4 mL) were added. After stirring for another 6 h, the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give the title compound for this step (430 mg, 62%) as a colorless liquid. LCMS m/z=213.1 $[M+1]^+$. $^1$H NMR (400 MHz, $CDCl_3$) δ 1.01-1.04 (m, 2H), 1.16-1.18 (m, 2H), 1.64-1.85 (m, 5H), 1.91-2.01 (m, 1H), 2.92 (s, 2H), 6.94 (d, J=7.9 Hz, 1H), 7.22-7.26 (m, 1H), 7.44-7.49 (m, 1H), 8.00 (dd, $J_1$=7.8 Hz, $J_2$=1.4 Hz, 1H).

Step G: Preparation of Compound 28 of FIG. 3, where $R^1$=H

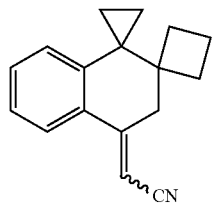 [SMILES: N#CC=C1CC2(CCC2)C2(CC2)c2ccccc21]

To a suspension of 60% sodium hydride dispersion (393 mg, 9.83 mmol) in 20 mL THF, a solution of diethyl (cyanomethyl)phosphonate (1.5 g, 8.468 mmol) in 30 mL THF was added slowly (over ca. 5 min). After stirring at room temperature for 5 min, a solution of the product of Step F (429 mg, 2.021 mmol) in 15 mL THF was added. After stirring at 60° C. (oil bath) overnight, the mixture was concentrated and residue was extracted with $CH_2Cl_2$ and water+brine. Organic phases were dried over $MgSO_4$, filtered, and concentrated. The residue was purified by biotage column chromatography ($SiO_2$, hexane/AcOEt gradient) to give the title compound for this step (393 mg, 83%) as a colorless oil (E:Z=66:34). LCMS m/z=236.3 $[M+1]^+$. $^1$H NMR (400 MHz, $CDCl_3$) δ 0.91-0.06 (m, 2H), 1.10-1.14 (m, 2H), 1.61-2.08 (m, 6H), 2.74 (d, J=1.2 Hz, 0.64H), 3.06 (d, J=1.2 Hz, 1.32H), 5.31-5.32 (m, 0.34H), 5.81-5.82 (m, 0.66H), 6.78-6.85 (m, 1H), 7.12-7.23 (m, 1H), 7.29-7.34 (m, 1H), 7.51 (dd, $J_1$=8.0 Hz, $J_2$=1.2 Hz, 0.64H), 8.26 (dd, $J_1$=8.0 Hz, $J_2$=1.2 Hz, 0.34H).

Step H: Preparation of Compound 29 of FIG. 3, where R¹=H

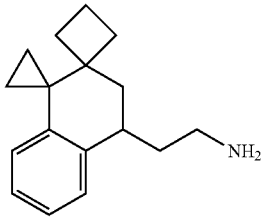 [SMILES: NCCC1CC2(CCC2)C2(CC2)c2ccccc21]

To a mixture of the product of Step G (390 mg, 1.657 mmol) and cobalt(II) chloride hexahydrate (1.2 g, 5.043 mmol) in 30 mL MeOH, sodium tetrahydroborate (2 g, 52.86 mmol) was added in small portions over 3.5 h. After stirring overnight, the mixture was extracted with water and $CH_2Cl_2$. Phases were filtered through celite and washed with $CH_2Cl_2$. Phases were separated and aqueous phase was extracted three more times with $CH_2Cl_2$. Combined organic phases were dried over $MgSO_4$, filtered, and concentrated. The residue was purified by biotage column chromatography ($SiO_2$, hexane/AcOEt gradient first and then $CH_2Cl_2$/MeOH/7M $NH_3$ in MeOH 80:18:2) to give the title compound for this step (262 mg, 66%). LCMS m/z=242.0 $[M+1]^+$. H NMR (400 MHz, $CDCl_3$) δ 0.51-0.56 (m, 1H), 0.71-0.76 (m, 1H), 1.11-1.46 (m, 5H), 1.60-1.93 (m, 7H), 2.05-2.14 (m, 1H), 2.19-2.24 (m, 1H), 2.79-2.86 (m, 2H), 3.12-3.20 (m, 1H), 6.77-6.82 (m, 1H), 7.04-7.11 (m, 2H), 7.24-7.28 (m, 1H).

Step I: Preparation of Compound 30 of FIG. 3, where R¹=H and R¹⁰ is 3,4-dichlorobenzyl

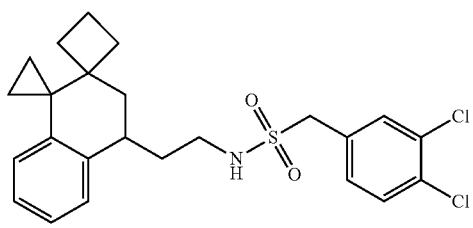 [SMILES: O=S(=O)(Cc1ccc(Cl)c(Cl)c1)NCCC1CC2(CCC2)C2(CC2)c2ccccc21]

To an ice-cooled solution of the product of Step H (258 mg, 1.069 mmol) and N-ethyl-N-isopropylpropan-2-amine (0.280 mL, 1.608 mmol) in 10 mL $CH_2Cl_2$, a solution of (3,4-dichlorophenyl)methanesulfonyl chloride (333 mg, 1.283 mmol) dissolved in 5 mL $CH_2Cl_2$ was added slowly by a syringe pump (over ca. 15 min). After stirring at 0° C. for 15 min, the mixture was extracted with water and $CH_2Cl_2$. Organic phases were dried over $MgSO_4$, filtered, and concentrated. The residue was purified by biotage column chromatography ($SiO_2$, hexane/AcOEt gradient) to give the title compound for this step (436 mg, 88%). LCMS m/z=462.5 $[M-1]+$. H NMR (400 MHz, $CDCl_3$) δ 0.50-0.55 (m, 1H), 0.71-0.76 (m, 1H), 1.13-1.27 (m, 2H), 1.38-1.45 (m, 1H), 1.52-1.94 (m, 7H), 2.06-2.18 (m, 2H), 3.01-3.20 (m, 3H), 4.02-4.05 (m, 1H), 4.17 (s, 2H), 6.78-6.82 (m, 1H), 7.07-7.16 (m, 3H), 7.22-7.25 (m, 1H), 7.46 (d, J=8.2 Hz, 1H), 7.50 d, J=1.8 Hz, 1H).

Step J: Preparation of Compound 31 of FIG. 3, where R¹=H and R¹⁰ is 3,4-dichlorobenzyl

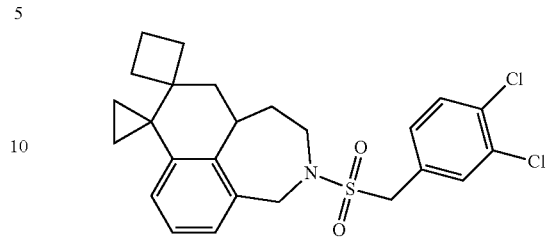

To a solution of the product of Step I (430 mg, 0.926 mmol) in 10 mL DCE, 1,3,5-trioxane (194 mg, 2.154 mmol), acetic anhydride (89 μl, 0.942 mmol), and methanesulfonic acid (383 μl, 5.906 mmol) were added. After stirring at room temperature for 5 min, the mixture was extracted with 1 M $NaHCO_3$ and $CH_2Cl_2$. Organic phases were dried over $MgSO_4$, filtered, and concentrated. The residue was purified by biotage column chromatography ($SiO_2$, hexane/AcOEt gradient) to give the title compound for this step (177 mg, 40%) as a white solid. $^1H$ NMR (400 MHz, $CDCl_3$) δ 0.70-0.76 (m, 1H), 0.78-0.83 (m, 1H), 1.11-1.28 (m, 3H), 1.40-1.47 (m, 1H), 1.63-1.93 (m, 7H), 2.21-2.26 (m, 1H), 3.26-3.34 (m, 2H), 3.88-3.99 (m, 3H), 4.16 (d, J=15.3 Hz, 1H), 4.63 (dd, $J_1$=15.3 Hz, $J_2$=1.8 Hz, 1H), 6.82 (dd, $J_1$=8.0 Hz, $J_2$=1.2 Hz, 1H), 6.90 (dd, $J_1$=8.2 Hz, $J_2$=2.1 Hz, 1H), 7.02 (dd, $J_1$=7.3 Hz, $J_2$=1.3 Hz, 1H), 7.07-7.11 (m, 2H), 7.30 (d, J=8.2 Hz, 1H).

Step K: Preparation of 2',3',4',4a',5'-pentahydro-1'H-dispiro[cyclobutane-1,6'-cyclopropane-7',1"-naphtho[1,8-cd]-azepine] (Compound 108)

To a solution of the product of Step J (171 mg, 0.359 mmol) in 2 mL toluene, 60% bis(2-methoxyethoxy)aluminum(III) sodium hydride in toluene (2 mL, 6.15 mmol) was added. After stirring at 80° C. (oil bath) for 7 h, the mixture was diluted with additional toluene, cooled in an ice-bath, and quenched by the slow addition of 2 M $NH_4Cl$. The mixture was extracted with 1 M NaOH and $CH_2Cl_2$. Organic phases were concentrated and residue was purified by HPLC ($CH_3CN/H_2O$ gradient+0.1% TFA) to give the title compound for this Example 1.21 (80.3 mg, 61%). LCMS m/z=254.4 $[M+1]^+$. $^1H$ NMR (400 MHz, $CDCl_3$) δ 0.60-0.65 (m, 1H), 0.78-0.84 (m, 1H), 1.18-1.26 (m, 2H), 1.48-1.56 (m, 1H), 1.64-1.78 (m, 5H), 1.87-2.09 (m, 3H), 2.40-2.45 (m, 1H), 3.41-3.58 (m, 3H), 4.24 (dd, $J_1$=14.0 Hz, $J_2$=1.2 Hz, 1H), 4.34 (d, J=14.0 Hz, 1H), 6.93-6.97 (m, 1H), 7.12-7.16 (m, 2H).

Example 1.22: Preparation of 8-methoxy-1,2,3,4,4a,5,6,7-octahydronaphtho[1,8-cd]azepine (Compound 126)

Step A: Preparation of 2-(5-methoxy-3,4-dihydronaphthalen-1(2H)-ylidene)acetonitrile To a suspension of sodium hydride (0.908 g, 22.70 mmol) in anhydrous THF (15 mL) under $N_2$ was added diethyl (cyanomethyl)phosphonate (4.021 g, 22.70 mmol) dropwise. The mixture was stirred at 23° C. for 2 h. a solution of 5-methoxy-3,4-dihydronaphthalen-1(2H)-one (2.0 g, 11.35 mmol) in THF (5 mL) was added. The reaction was stirred at 23° C. for 2 h. The mixture was concentrated. The residue was dissolved in EtOAc and washed with H$_2$O. The organic extract was purified by column chromatography (0-80% EtOAc/Hex) to give the title compound. LCMS m/z=200.2 [M+1]$^+$.

Step B: Preparation of 2-(5-methoxy-1,2,3,4-tetrahydronaphthalen-1-yl)ethanamine To a suspension of Raney-Nickel 2800 (1.2 g, 20.45 mmol) washed 3 time with methanol were added MeOH (15 mL), (E)-2-(5-methoxy-3,4-dihydronaphthalen-1(2H)-ylidene)acetonitrile (0.5 g, 2.509 mmol), and 7M ammonia in methanol (7.170 mL, 50.19 mmol). The reaction was shaken under 80 psi of H$_2$ at 23° C. for 72 h. The mixture was filtered over celite and washed with MeOH. The filtrate was concentrated. The residue was purified by HPLC to give the title compound (248 mg). LCMS m/z=206.2 [M+1]$^+$; $^1$H NMR (400 MHz, CD$_3$OD) δ 1.64-1.79 (m, 2H), 1.79-1.88 (m, 2H), 1.88-2.07 (m, 2H), 2.52-2.73 (m, 2H), 2.84-2.93 (m, 1H), 2.94-3.07 (m, 2H), 6.72 (d, J=8.1 Hz, 1H), 6.77 (d, J=7.8 Hz, 1H), 7.09 (t, J=7.9 Hz, 1H).

Step C: Preparation of 8-methoxy-1,2,3,4,4a,5,6,7-octahydronaphtho[1,8-cd]azepine To a solution of 2-(5-methoxy-1,2,3,4-tetrahydronaphthalen-1-yl)ethanamine.trifluoroacetic acid (47 mg, 0.147 mmol) and Formaldehyde (5.303 mg, 0.177 mmol) in MeOH (3 mL) was added TFA (13.53 μL, 0.177 mmol). The reaction was stirred at 80° C. for 1 h. The mixture was concentrated. The residue was purified by HPLC to give the title compound (3.4 mg). LCMS m/z=218.4 [M+1]$^+$; $^1$H NMR (400 MHz, CD$_3$OD) δ 1.67-1.78 (m, 3H), 1.80-2.07 (m, 3H), 2.52-2.63 (m, 1H), 2.64-2.74 (m, 1H), 3.19-3.27 (m, 1H), 3.35-3.46 (m, 2H), 4.18 (d, J=4.0 Hz, 1H), 4.38 (d, J=4.0 Hz, 1H), 6.77 (d, J=8.3 Hz, 1H), 7.17 (t, J=8.3 Hz, 1H).

Example 1.23: Preparation of 1,1-dimethyl-3,3a,4,5,6,7-hexahydro-1H-isochromeno[5,4-cd]azepine 2,2,2-trifluoroacetate (Compound 139)

Step A: Preparation of 2-(1,1-dimethylisochroman-4-ylidene)acetonitrile

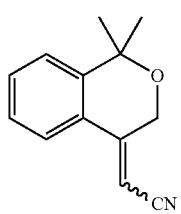

To a suspension of 60% sodium hydride dispersion (0.545 g, 13.62 mmol) in THF (20 mL), a solution of diethyl (cyanomethyl)phosphonate (2.203 mL, 13.62 mmol) in THF (40 mL) was added slowly. After stirring at room temperature for 5 min, a solution of 1,1-dimethylisochroman-4-one (1 g, 5.675 mmol) in THF (20 mL) was added. After stirring at room temperature overnight, the mixture was extracted with AcOEt and water. Organic phase was dried over MgSO$_4$, filtered, and concentrated. The residue was purified by biotage column chromatography (SiO2, hexane/AcOEt gradient) to give 2-(1,1-dimethylisochroman-4-ylidene)acetonitrile (871.5 mg, 77%) (E:Z=57:43). LCMS m/z=200.2 [M+1]$^+$. $^1$H NMR (400 MHz, CDCl$_3$) δ 1.56 (d, J=3.28 Hz, 6H), 4.41 (d, J=1.16 Hz, 1.12H), 4.80 (d, J=1.64 Hz, 0.88H), 5.29 (m, 0.57H), 5.77 (m, 0.43H), 7.20-7.24 (m, 1H), 7.26-7.30 (m, 0.43H), 7.32-7.36 (m, 0.57H), 7.40-7.46 (m, 1H), 7.57 (m, 1.06 Hz, 0.43H), 8.37 (m, 0.57H).

Step B: Preparation of 2-(1,1-dimethylisochroman-4-yl)ethanamine

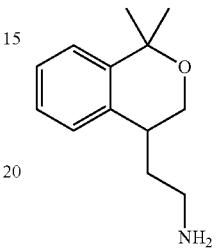

To an undetermined amount of raney nickel (slurry in water; washed three times with MeOH), a solution of 2-(1,1-dimethylisochroman-4-ylidene)acetonitrile (871 mg, 4.371 mmol) in MeOH (ca. 95 mL) and 7 M ammonia in MeOH (2 mL, 14.00 mmol) were added. The mixture was shaken on a Parr-shaker under ca. 60 psi hydrogen pressure for 5 days. Raney nickel was filtered off through celite, washed with additional MeOH, concentrated, and dried under high vacuum. The residue was purified by HPLC (CH$_3$CN/H$_2$O gradient+0.1% TFA) to give 2-(1,1-dimethylisochroman-4-yl)ethanamine (448.6 mg, 50%). LCMS m/z=205.6 [M+1]$^+$. $^1$H NMR (400 MHz, CDCl$_3$) δ 1.52 (d, J=12.8 Hz, 6H), 2.15-2.22 (m, 2H), 2.71 (br s, 1H), 2.89-2.92 (m, 1H), 2.97 (br s, 1H), 3.06 (br s, 2H), 3.86 (d, J=12.4 Hz, 1H), 4.09 (dd, J=3.5, 12.5 Hz, 1H), 7.06-7.12 (m, 2H), 7.17-7.25 (m, 2H).

Step C: Preparation of 1-(3,4-dichlorophenyl)-N-(2-(1,1-dimethylisochroman-4-yl)ethyl)methanesulfonamide

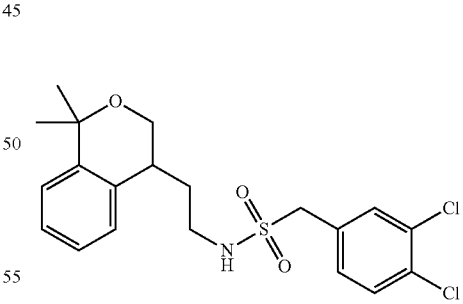

To an ice-cooled solution of 2-(1,1-dimethylisochroman-4-yl)ethanamine 2,2,2-trifluoroacetate (448 mg, 1.403 mmol) and N-ethyl-N-isopropylpropan-2-amine (0.733 mL, 4.209 mmol) in CH$_2$Cl$_2$ (14 mL), a solution of (3,4-dichlorophenyl)methanesulfonyl chloride (0.546 g, 2.104 mmol) dissolved in CH$_2$Cl$_2$ (6 mL) was added slowly by a syringe pump (over ca. 15 min). After stirring at 0° C. for 0.5 h, the mixture was extracted with water and CH$_2$Cl$_2$. Organic phases were dried over MgSO$_4$, filtered, and concentrated. The residue was purified by biotage column chromatography (SiO2, hexane/AcOEt gradient) to give 1-(3,4-dichlorophenyl)-N-(2-(1,1-dimethylisochroman-4-yl)ethyl)methanesulfonamide (460.28 mg, 77%). LCMS m/z=428.0 [M+1]+. 1H NMR (400 MHz, CDCl3) δ 1.48 (d, J=3.92 Hz, 6H), 1.91-2.04 (m, 2H), 2.72-2.75 (m, 1H), 2.92-2.99 (m, 1H), 3.03-3.09 (m, 1H), 3.81 (dd, J=12.04, 1.28 Hz, 1H), 4.00 (dd, J=12.0, 3.36 Hz, 1H), 4.14 (s, 2H), 4.95-4.98 (m, 1H), 7.03 (dd, J=7.38, 1.62 Hz, 1H), 7.08-7.11 (m, 1H), 7.15-7.23 (m, 3H), 7.43 (d, J=8.24 Hz, 1H), 7.46 (d, J=2.04 Hz, 1H).

Step D: Preparation of 6-((3,4-dichlorobenzyl)sulfonyl)-1,1-dimethyl-3,3a,4,5,6,7-hexahydro-1H-isochromeno[5,4-cd]azepine

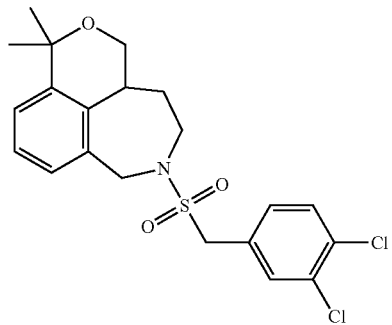 [SMILES: CC1(C)OCC2CCN(S(=O)(=O)Cc3ccc(Cl)c(Cl)c3)Cc3cccc1c32]

To a solution of 1-(3,4-dichlorophenyl)-N-(2-(1,1-dimethylisochroman-4-yl)ethyl)methanesulfonamide (230 mg, 0.537 mmol) in DCE (6 mL), 1,3,5-trioxane (0.120 g, 1.334 mmol), acetic anhydride (51.06 µl, 0.540 mmol), and methanesulfonic acid (0.220 mL, 3.395 mmol) were added. After stirring at room temperature for 10 min. LCMS showed small amount of product formed with major amount of starting material left. The reaction was continued to stir under room temperature for 2.5 hours. According to LCMS, reaction was not completed. The mixture was extracted with 1 M NaHCO3 and CH2Cl2. Organic phases were dried over MgSO4, filtered, and concentrated. The residue was purified by biotage column chromatography (SiO2, hexane/AcOEt gradient) to give 6-((3,4-dichlorobenzyl)sulfonyl)-1,1-dimethyl-3,3a,4,5,6,7-hexahydro-1H-isochromeno[5,4-cd]azepine (118.5 mg, 50%). LCMS m/z=440.5 [M+1]+. 1H NMR (400 MHz, CD3OD) δ 1.50 (d, J=5.48 Hz, 6H), 1.62-1.80 (m, 2H), 3.00-3.06 (m, 1H), 3.35-3.42 (m, 1H), 3.70 (dd, J=12.00, 4.08 Hz, 1H), 3.74-3.79 (m, 1H), 4.03-4.08 (m, 2H), 4.23 (d, J=13.85 Hz, 1H), 4.37 (d, J=15.16 Hz, 1H), 4.46-4.50 (m, 1H), 7.02 (dd, J=8.66, 4.44 Hz, 1H), 7.14-7.18 (m, 3H), 7.44 (d, J=8.28 Hz, 1H), 7.46 (d, J=2.00 Hz, 1H).

Step E: Preparation of 1,1-dimethyl-3,3a,4,5,6,7-hexahydro-1H-isochromeno[5,4-cd]azepine 2,2,2-trifluoroacetate (Compound 139 as the TFA salt)

To a solution of 6-((3,4-dichlorobenzyl)sulfonyl)-1,1-dimethyl-3,3a,4,5,6,7-hexahydro-1H-isochromeno[5,4-cd]azepine (118 mg, 0.268 mmol) in toluene (3 mL), 60% bis(2-methoxyethoxy)aluminum(III) sodium hydride in toluene (1.569 mL, 4.823 mmol) was added. The mixture was stirred at 80° C. After 3 hours, more 60% bis(2-methoxyethoxy)aluminum(III) sodium hydride in toluene (1.5 mL) was added and continued to be stirred at 80° C. After another 3 hours, the mixture was diluted with toluene (ca. 10 mL), cooled in an ice-water bath, and quenched by the dropwise addition of 1 M NH4Cl. After stirring for 0.5 h, di-tert-butyl dicarbonate (0.322 g, 1.474 mmol) was added. The mixture was allowed to warm to room temperature. After 1 hour, the mixture was extracted with 1 M NaOH and CH2Cl2. Organic phases were dried over MgSO4, filtered, and concentrated. The residue was purified by biotage column chromatography (SiO2, hexane/AcOEt gradient to give tert-butyl 1,1-dimethyl-3,3a,4,5-tetrahydro-1H-isochromeno[5,4-cd]azepine-6(7H)-carboxylate. Tert-butyl 1,1-dimethyl-3,3a,4,5-tetrahydro-1H-isochromeno[5,4-cd]azepine-6(7H)-carboxylate was dissolved in CH2Cl2 (3 mL), cooled in an ice-water bath, and TFA (0.616 mL, 8.038 mmol) was added. After stirring at 0° C. for 1.5 hour, the mixture was concentrated and residue was purified by HPLC (CH3CN/H2O gradient+0.1% TFA) to give 1,1-dimethyl-3,3a,4,5,6,7-hexahydro-1H-isochromeno[5,4-cd]azepine 2,2,2-trifluoroacetate (22.3 mg, 25%). LCMS m/z=218.4 [M+1]+. 1H NMR (400 MHz, CD3OD) δ 1.52 (d, J=8.00 Hz, 6H), 1.93-2.07 (m, 2H), 3.11-3.16 (m, 1H), 3.43-3.52 (m, 2H), 3.76 (dd, J=12.14, 3.70 Hz, 1H), 4.13 (dd, J=12.12, 4.72 Hz, 1H), 4.29 (d, J=14.2 Hz, 1H), 4.50 (d, J=14.2 Hz, 1H), 7.23-7.32 (m, 3H).

Example 1.24: Preparation of 8'-fluoro-6',6'-dimethyl-2',3',4',4a',5',6'-hexahydro-1'H-spiro[cyclopropane-1,7'-naphtho[1,8-cd]azepine] 2,2,2-trifluoroacetate (Compound 119)

Step A: Preparation of 8-fluoro-2,2-dimethyl-3,4-dihydronaphthalen-1(2H)-one

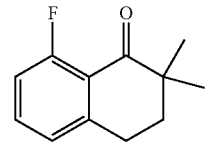

To a suspension of 60% sodium hydride dispersion (0.82 g, 20.5 mmol) in THF (28 mL), a solution of 8-fluoro-3,4-dihydronaphthalen-1(2H)-one (1.53 g, 9.3 mmol) in THF (14 mL) was added (over ca. 5 min). After stirring at room temperature for 20 min, iodomethane (1.16 mL, 18.6 mmol) was added. After stirring at room temperature for 50 min, the mixture was extracted with water and AcOEt. Organic phase was dried over MgSO4, filtered, and concentrated. The residue was purified by biotage column chromatography (SiO2, hexane/AcOEt gradient) to give 8-fluoro-2,2-dimethyl-3,4-dihydronaphthalen-1(2H)-one (1.3003 g, 73%). LCMS m/z=192.4 [M+1]+. 1H NMR (400 MHz, CDCl3) δ 1.22 (s, 6H), 1.96 (t, J=12.8 Hz, 2H), 2.99 (t, J=6.4 Hz, 2H), 6.93-7.01 (m, 2H), 7.39 (td, J=15.9, 5.12 Hz, 1H).

Step B: Preparation of 8-fluoro-2,2-dimethyl-1-methylene-1,2,3,4-tetrahydronaphthalene

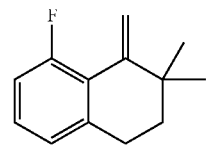

To a suspension of methyltriphenylphosphonium bromide (4.107 g, 11.50 mmol) in Toluene (25 mL), 1M potassium 2-methylpropan-2-olate in THF (20.29 mL, 20.29 mmol) was added. After stirring at 110° C. for 40 min, a solution of 8-fluoro-2,2-dimethyl-3,4-dihydronaphthalen-1(2H)-one (1.3 g, 6.763 mmol) in Toluene (5 mL) was added. The mixture was stirred at 110° C. for 20 min, allowed to cool to room temperature, and extracted with water and CH$_2$Cl$_2$. Organic phases were dried over MgSO4, filtered, and concentrated. The residue was purified by biotage column chromatography (SiO2, hexanes) to give 8-fluoro-2,2-dimethyl-1-methylene-1,2,3,4-tetrahydronaphthalene (429 mg, 33%). $^1$H NMR (400 MHz, CDCl$_3$) δ 1.15 (s, 6H), 1.67 (t, J=13.48 Hz, 2H), 2.87 (t, J=6.74 Hz, 2H), 5.38-5.39 (m, 1H), 5.70 (d, J=1.64 Hz, 1H), 6.86-6.91 (m, 2H), 7.05-7.10 (m, 1H).

Step C: Preparation of 8'-fluoro-2',2'-dimethyl-3',4'-dihydro-2'H-spiro[cyclopropane-1,1'-naphthalene]

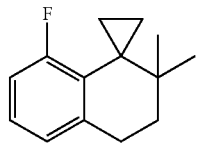

To an ice-cooled solution of 8-fluoro-2,2-dimethyl-1-methylene-1,2,3,4-tetrahydronaphthalene (429 mg, 2.255 mmol) and chloroiodomethane (0.982 mL, 13.53 mmol) in Dichloroethane (15 mL), 1 M diethylzinc in hexanes (11.27 mL, 11.27 mmol) was added over ca. 10 min. The mixture was allowed to warm to room temperature. The reaction was stirred under room temperature overnight, suspension was quenched by the addition of 2 M NH$_4$Cl and extracted with water and CH$_2$Cl$_2$. Combined organic phases were dried over MgSO$_4$, filtered, and concentrated. The residue was purified by biotage column chromatography (SIO2, hexane/AcOEt gradient) to give 8'-fluoro-2',2'-dimethyl-3',4'-dihydro-2'H-spiro[cyclopropane-1,1'-naphthalene] (382.93 mg, 83%). $^1$H NMR (400 MHz, CDCl$_3$) δ 0.827 (s, 6H), 0.85-0.88 (m, 2H), 1.32 (q, J=10.96, 1.68 Hz, 2H), 1.65 (t, J=13.52 Hz, 2H), 2.88 (t, J=6.78 Hz, 2H), 6.70-6.75 (m, 1H), 6.85-6.87 (m, 1H), 6.94-6.99 (m, 1H).

Step D: Preparation of 8'-fluoro-2',2'-dimethyl-2'H-spiro[cyclopropane-1,1'-naphthalen]-4'(3'H) one

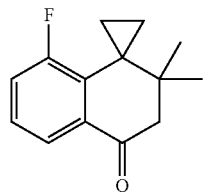 [SMILES: CC1(C)CC(=O)c2cccc(F)c2C12CC2]

To a solution of 8'-fluoro-2',2'-dimethyl-3',4'-dihydro-2'H-spiro[cyclopropane-1,1'-naphthalene](447 mg, 2.188 mmol) in DCE (17 mL), sodium bicarbonate (0.121 g, 1.435 mmol), Rh2(cap)4 (14.32 mg, 21.88 μmol), and 5.5 M 2-hydroperoxy-2-methylpropane in decane (2.514 mL, 13.82 mmol) were added. After stirring at 40° C. for 3 hours, more Rh2(cap)4 (14.32 mg) and 5.5 M 2-hydroperoxy-2-methylpropane in decane (1.3 mL, 7.15 mmol) were added. After stirring at 40° C. overnight, the mixture was extracted with water and CH$_2$Cl$_2$. Organic phases were dried over MgSO$_4$, filtered, and concentrated. The residue was purified by biotage column chromatography (SiO2, hexane/AcOEt gradient) to give 8'-fluoro-2',2'-dimethyl-2'H-spiro[cyclopropane-1,1'-naphthalen]-4'(3'H)-one (440.19 mg, 92%). LCMS m/z=219.2 [M+1]$^+$. $^1$H NMR (400 MHz, CDCl$_3$) δ 2.05-2.12 (s, 6H), 3.79 (t, J=6.4 Hz, 2H), 4.13 (t, J=6.4 Hz, 2H).

Step E: Preparation of 2-(8'-fluoro-2',2'-dimethyl-2'H-spiro[cyclopropane-1,1'-naphthalen]-4'(3'H)-ylidene)acetonitrile

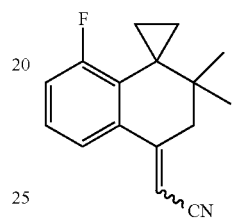

To a suspension of 60% sodium hydride dispersion (0.194 g, 4.838 mmol) in 20 mL THF, a solution of diethyl (cyanomethyl)phosphonate (0.783 mL, 4.838 mmol) in 30 mL THF was added slowly. After stirring at room temperature for 10 min, a solution of 8'-fluoro-2',2'-dimethyl-2'H-spiro[cyclopropane-1,1'-naphthalen]-4'(3'H)-one (440 mg, 2.016 mmol) in 15 mL THF was added. After stirring at room temperature overnight, the mixture was extracted with AcOEt and water. Organic phase was dried over MgSO$_4$, filtered, and concentrated. The residue was purified by biotage column chromatography (SiO2, hexane/AcOEt gradient) to give 2-(8'-fluoro-2',2'-dimethyl-2'H-spiro[cyclopropane-1,1'-naphthalen]-4'(3'H)-ylidene)acetonitrile (445.2 mg, 75%), (E:Z=60:40). LCMS m/z=242.4 [M+1]$^+$. $^1$H NMR (400 MHz, CDCl$_3$) δ 0.85 (s, 3H), 0.88 (s, 3H), 0.93-1.00 (m, 2H), 1.44-1.50 (m, 2H), 2.44 (d, J=Hz, 0.82H), 2.75 (d, J=Hz, 1.18H), 5.25-5.27 (m, 0.4H), 5.76-5.77 (m, 0.6H), 6.96-7.04 (m, 1H), 7.11 (m, 0.6H), 7.18 (m, 0.4H), 7.33 (dd, J=7.9, 1.1 Hz, 0.6H), 8.01 (dd, J=7.9, 0.8 Hz, 0.4H).

Step F: Preparation of 2-(8'-fluoro-2',2'-dimethyl-3',4'-dihydro-2'H-spiro[cyclopropane-1,1'-naphthalen]-4'-yl)ethanamine 2,2,2-trifluoroacetate

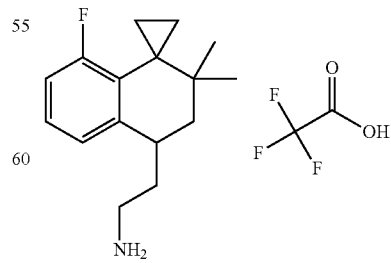

To a mixture of 2-(8'-fluoro-2',2'-dimethyl-2'H-spiro[cyclopropane-1,1'-naphthalen]-4'(3'H)-ylidene)acetonitrile (445 mg, 1.501 mmol) and cobalt(II) chloride hexahydrate (1.179 g, 4.954 mmol) in MeOH (27 mL), sodium tetrahydroborate (1.840 g, 48.64 mmol) was added in small portions over 2 hours. After stirring at room temperature overnight, di-tert-butyl dicarbonate (0.754 g, 3.453 mmol) was added. After stirring at room temperature for 1 hour, the mixture was filtered through celite. Filtrate was extracted with $CH_2Cl_2$/water. Organic phases were dried over MgSO4, filtered, and concentrated. The residue was purified by biotage column chromatography (SiO2, hexane/AcOEt gradient) to give tert-butyl (2-(8'-fluoro-2'-methyl-3',4'-dihydro-2'H-spiro[cyclopropane-1,1'-naphthalen]-4'-yl)ethyl)carbamate. tert-butyl (2-(8'-fluoro-2'-methyl-3',4'-dihydro-2'H-spiro[cyclopropane-1,1'-naphthalen]-4'-yl)ethyl) carbamate was dissolved in $CH_2Cl_2$ with TFA (3.449 mL, 45.03 mmol) added under 0° C. and stirred for 1 hour. The mixture was concentrated and purified by HPLC ($CH_3CN$/$H_2O$ gradient+0.1% TFA) to give 2-(8'-fluoro-2',2'-dimethyl-3',4'-dihydro-2'H-spiro[cyclopropane-1,1'-naphthalen]-4'-yl)ethanamine 2,2,2-trifluoroacetate (471.76 mg, 87%). LCMS m/z=248.4 [M+1]$^+$. $^1$H NMR (400 MHz, $CD_3OD$) δ 0.77 (s, 3H), 0.89 (s, 3H), 0.91-1.05 (m, 3H), 1.33-1.37 (m, 1H), 1.42 (dd, J=13.06, 11.06 Hz, 1H), 1.82 (dd, J=13.08, 6.56 Hz, 1H), 1.89-1.99 (m, 1H), 2.21-2.27 (m, 1H), 2.91-3.05 (m, 2H), 3.09-3.17 (m, 1H), 6.79-6.84 (m, 1H), 7.07-7.15 (m, 2H), Step G: Preparation of 1-(3,4-dichlorophenyl)-N-(2-(8'-fluoro-2',2'-dimethyl-3',4'-dihydro-2'H-spiro[cyclopropane-1,1'-naphthalen]-4'-yl)ethyl)methanesulfonamide

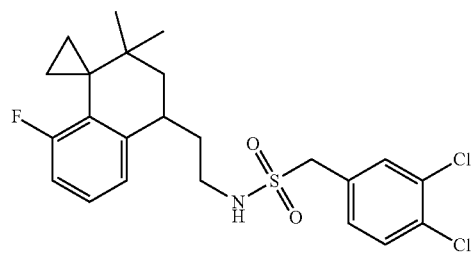 [SMILES: CC1(C)CC(CCNS(=O)(=O)Cc2ccc(Cl)c(Cl)c2)c2cccc(F)c2C12CC2]

To an ice-cooled solution of 2-(8'-fluoro-2',2'-dimethyl-3',4'-dihydro-2'H-spiro[cyclopropane-1,1'-naphthalen]-4'-yl)ethanamine 2,2,2-trifluoroacetate (468 mg, 1.295 mmol) and N-ethyl-N-isopropylpropan-2-amine (0.677 mL, 3.885 mmol) in $CH_2Cl_2$ (12 mL), a solution of (3,4-dichlorophenyl)methanesulfonyl chloride (0.504 g, 1.943 mmol) dissolved in $CH_2Cl_2$ (6 mL) was added slowly by a syringe pump (over ca. 15 min). After stirring at 0° C. for 1 hour, the mixture was extracted with water and $CH_2Cl_2$. Organic phases were dried over $MgSO_4$, filtered, and concentrated. The residue was purified by biotage column chromatography (SiO2, hexane/AcOEt gradient) to give 1-(3,4-dichlorophenyl)-N-(2-(8'-fluoro-2',2'-dimethyl-3',4'-dihydro-2'H-spiro[cyclopropane-1,1'-naphthalen]-4'-yl)ethyl)methanesulfonamide (228.68 mg, 38%). LCMS m/z=470.8 [M+1]$^+$. $^1$H NMR (400 MHz, CDCl$_3$) δ 0.74 (s, 3H), 0.86 (s, 3H), 0.82-0.95 (m, 2H), 1.06-1.11 (m, 1H), 1.31-1.37 (m, 2H), 1.69 (dd, 1H), 1.73-1.82 (m, 1H), 2.05-2.13 (m, 1H), 2.97-3.15 (m, 3H), 4.10 (t, 1H), 4.19 (s, 2H), 6.79 (dd, 1H), 6.93 (d, 1H), 7.04-7.09 (m, 1H), 7.23-7.26 (m, 1H), 7.46 (d, 1H), 7.50 (d, 1H).

Step H: Preparation of 2'-((3,4-dichlorobenzyl)sulfonyl)-8'-fluoro-6',6'-dimethyl-2',3',4',4a',5',6'-hexahydro-1'H-spiro[cyclopropane-1,7'-naphtho[1,8-cd]azepine]

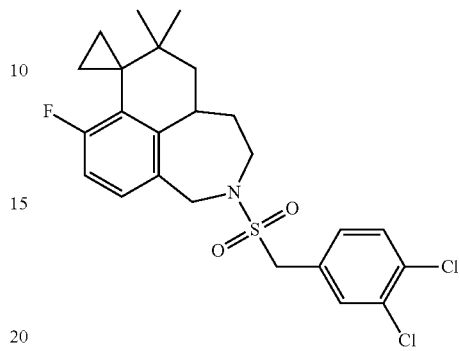

To a solution of 1-(3,4-dichlorophenyl)-N-(2-(8'-fluoro-2',2'-dimethyl-3',4'-dihydro-2'H-spiro[cyclopropane-1,1'-naphthalen]-4'-yl)ethyl)methanesulfonamide (228 mg, 0.485 mmol) in Dichloroethane (0.5 mL), 1,3,5-trioxane (0.118 g, 1.309 mmol), acetic anhydride (46.09 μl, 0.488 mmol), and methanesulfonic acid (0.195 mL, 3.005 mmol) were added. After stirring at room temperature for 10 min, the mixture was extracted with 1 M $NaHCO_3$ and $CH_2Cl_2$. Organic phases were dried over $MgSO_4$, filtered, and concentrated. Residue was purified by biotage column chromatography (SiO2, hexane/AcOEt gradient) to give 2'-((3,4-dichlorobenzyl)sulfonyl)-8'-fluoro-6',6'-dimethyl-2',3',4',4a',5',6'-hexahydro-1'H-spiro[cyclopropane-1,7'-naphtho[1,8-cd]azepine] (220.2 mg, 82%). LCMS m/z=482.0 [M+1]$^+$. $^1$H NMR (400 MHz, CDCl$_3$) δ 0.70-0.77 (m, 1H), 0.722 (s, 3H), 0.863 (s, 3H), 0.95-1.00 (m, 1H), 1.19-1.14 (m, 1H), 1.22-1.32 (m, 1H), 1.50-1.56 (m, 1H), 1.63-1.78 (m, 3H), 3.16-3.23 (m, 1H), 3.24-3.31 (m, 1H), 3.82-3.87 (m, 1H), 3.96 (q, J=4.8 Hz, 2H), 4.09-4.15 (m, 1H), 4.57 (dd, J=15.4, 1.76 Hz, 1H), 6.74 (dd, 13.7, 8.1 Hz, 1H), 6.95 (dd, J=8.2, 5.0 Hz, 1H), 7.03 (dd, 10.3, 6.2 Hz, 1H), 7.11 (d, J=1.96 Hz, 1H), 7.36 (d, J=8.2 Hz, 1H).

Step I: Preparation of 8'-fluoro-6',6'-dimethyl-2',3',4',4a',5',6'-hexahydro-1'H-spiro[cyclopropane-1,7'-naphtho[1,8-cd]azepine] 2,2,2-trifluoroacetate (Compound 119 as the TFA salt)

To a solution of 2'-((3,4-dichlorobenzyl)sulfonyl)-8'-fluoro-6',6'-dimethyl-2',3',4',4a',5',6'-hexahydro-1'H-spiro[cyclopropane-1,7'-naphtho[1,8-cd]azepine] (110 mg, 0.199 mmol) in toluene (5 mL), 60% bis(2-methoxyethoxy)aluminum(III) sodium hydride in toluene (1.163 mL, 3.575 mmol) was added. The mixture was stirred at 80° C. After 3 hours, more 60% bis(2-methoxyethoxy)aluminum(III) sodium hydride in toluene (2.44 mL) was added and continued to be stirred at 80° C. After another 3 hours, the mixture was diluted with toluene (10 mL), cooled in an ice-water bath, and quenched by the dropwise addition of 1 M $NH_4Cl$. After stirring for 0.5 h, di-tert-butyl dicarbonate (0.238 g, 1.092 mmol) was added. The mixture was allowed to warm to room temperature. After 1 hour, the mixture was extracted with 1 M NaOH and $CH_2Cl_2$. Organic phases were dried over $MgSO_4$, filtered, and concentrated. The residue was purified by biotage column chromatography (SiO2, hexane/

AcOEt gradient) to give tert-butyl 8'-fluoro-6',6'-dimethyl-4',4a',5',6'-tetrahydro-1'H-spiro[cyclopropane-1,7'-naphtho[1,8-cd]azepine]-2'(3'H)-carboxylate. tert-butyl 8'-fluoro-6',6'-dimethyl-4',4a',5',6'-tetrahydro-1'H-spiro[cyclopropane-1,7'-naphtho[1,8-cd]azepine]-2'(3'H)-carboxylate was dissolved in $CH_2Cl_2$ (3 mL), cooled in an ice-water bath, and TFA (0.456 mL, 5.958 mmol) was added. After stirring at 0° C. for 1.5 hour, the mixture was concentrated and residue was purified by HPLC ($CH_3CN/H_2O$ gradient+0.1% TFA) to give 8'-fluoro-6',6'-dimethyl-2',3',4',4a',5',6'-hexahydro-1'H-spiro[cyclopropane-1,7'-naphtho[1,8-cd]azepine] 2,2,2-trifluoroacetate (40.48 mg, 55%) LCMS m/z=260.3 $[M+1]^+$. $^1H$ NMR (400 MHz, $CD_3OD$) δ 0.77 (s 3H), 0.78-0.85 (m, 1H), 0.92 (S, 3H), 0.99-1.07 (m, 2H), 1.59-1.65 (m, 1H), 1.67-1.78 (m, 2H), 1.92 (dd, J=13.3, 7.3 Hz, 1H), 1.98-2.01 (m, 1H), 3.40-3.53 (m, 3H), 4.30 (q, J=16.6 Hz, 2H), 6.86 (dd, J=13.9, 8.3 Hz, 1H), 7.17 (dd, J=8.3, 5.0 Hz, 1H).

Example 2—Generation of Stable Cell Lines

Plasmid DNA coding for a receptor of interest is produced using standard molecular biology tools. The plasmid typically contains a multi-cloning site where the coding sequence for the receptor of interest is inserted, a promoter to drive expression of the receptor when introduced into a host cell, and a resistance gene sequence that causes the host cell to produce a protein that confers antibiotic resistance. A commonly used promoter is the cytomegalovirus promoter (CMV), and a commonly used resistance gene is the neo gene that confers resistance to neomycin. The plasmid DNA is introduced into parental cells (commonly used cell lines include CHO-K1 and HEK293) using methods such as lipofection or electroporation. Cells are then allowed to recover in culture for 1-2 days. At this point, a selection agent (e.g., neomycin if the expression plasmid contained the neo gene) is added to the cell culture media at a concentration sufficient to kill any cells that did not uptake the plasmid DNA and therefore have not become neomycin resistant.

Since transient transfection is an efficient method to introduce plasmid DNA into cells, many cells in the culture will initially display neomycin resistance. Over the course of a few cell divisions, expression of proteins encoded by the plasmid is typically lost and most cells will eventually be killed by the antibiotic. However, in a small number of cells, the plasmid DNA may become randomly integrated into the chromosomal DNA. If the plasmid DNA becomes integrated in a way that allows continued expression of the neo gene, these cells become permanently resistant to neomycin. Typically, after culturing the transfected cells for two weeks, most of the remaining cells are those that have integrated the plasmid in this manner.

The resulting stable pool of cells is highly heterogeneous, and may express vastly different levels of receptor (or no receptor at all). While these types of cell populations may provide functional responses when stimulated with appropriate agonists to the receptor of interest, they are typically not suitable for careful pharmacological studies in view of receptor reserve effects caused by high expression levels.

Clonal cell lines are therefore derived from this cell population. The cells are plated in multi-well plates at a density of one cell per well. After cell plating, the plates are inspected and wells containing more than one cell are rejected. The cells are then cultured for a period of time and those that continue to divide in the presence of neomycin are eventually expanded into larger culture vessels until there are sufficient cells for evaluation.

Evaluation of Cells

Numerous methods can be used to evaluate the cells. Characterization in functional assays may reveal that some cells exaggerate the potencies and efficacies of agonists, likely indicating the presence of a receptor reserve. The preparation of cell membranes for evaluation in radioligand binding assays allows for quantitative determination of membrane receptor densities. Evaluation of cell surface receptor density may also be performed by flow cytometry using antibodies to the receptor or an epitope tag that can be engineered into the receptor, typically at the N-terminus for GPCRs. The flow cytometry method allows one to determine if the clonal cell population expresses the receptor in a homogenous manner (which would be expected) and quantitate relative expression levels between each clonal cell population. However, it does not provide absolute receptor expression levels.

If the cell line is intended to be free of receptor reserve effects, receptor expression should be low (relative to other clones evaluated) and homogeneous (if flow cytometry evaluation is possible). In functional assays, a suitable clone will produce agonist potencies that are lower than other clones (i.e., higher $EC_{50}$ values). If partial agonists are available, the absence of receptor reserve will be reflected in low efficacies relative to full agonists, whereas cells with higher receptor expression levels will exaggerate partial agonist efficacies. In cells expressing high receptor levels, partial agonists may no longer display efficacies lower than full agonists.

If agents that irreversibly bind to or covalently interact with the receptor of interest are available, treatment of cell lines that contain no receptor reserve should reduce the available receptor density measured by radioligand binding and may reduce the magnitude of functional responses to agonists. However, the reduction of receptor density should occur without producing reductions in agonist potencies or partial agonist efficacies.

Example 3: Membrane Preparations for Radioligand Binding Assays

For the compounds of Table A, the following procedure was used. HEK293 cells stably expressing recombinant 5-$HT_2$ receptors were harvested, suspended in ice-cold phosphate buffered saline, pH 7.4 (PBS), and then centrifuged at 48,000 g for 20 min at 4° C. The resulting cell pellet was then re-suspended in wash buffer containing 20 mM HEPES, pH 7.4 and 0.1 mM EDTA, homogenized on ice using a Brinkman Polytron, and centrifuged (48,000 g for 20 min at 4° C.). The pellet was then resuspended in 20 mM HEPES, pH 7.4, homogenized on ice, and centrifuged (48,000 g for 20 min at 4° C.). Crude membrane pellets were stored at −80° C. until used for radioligand binding assays.

Example 4: Radioligand Binding Assay

For the compounds of Table A, the following procedure was used. Radioligand binding assays were performed using the commercially available 5-$HT_2$ receptor agonist $[^{125}I]$ DOI as the radioligand and nonspecific binding was determined in the presence of unlabeled DOI at a saturating concentration of 10 µM. Competition experiments utilized 5-$HT_2$ receptor expressing HEK293 cell membranes obtained as described in Example 3 (15-25 µg membrane protein/well) and radioligand at final assay concentrations of 0.4 to 0.6 nM. Experiments comprised addition of 95 µL of assay buffer (20 mM HEPES, pH 7.4, 10 mM $MgCl_2$), 50 µL of membranes, 50 μL of radioligand stock, and 5 μL of test compound diluted in assay buffer to 96-well microtiter plates, which were then incubated for 1 h at room temperature. Assay incubations were terminated by rapid filtration through PerkinElmer F/C filtration plates under reduced pressure using a 96-well Packard filtration apparatus, followed by washing three times with ice cold assay buffer. Plates were then dried at 45° C. for a minimum of 2 h. Finally, 25 μL of BetaScint™ scintillation cocktail was added to each well and the plates were counted in a Packard TopCount® scintillation counter. In each competition study, test compounds were dosed at ten concentrations with triplicate determinations at each test concentration.

The observed DOI Binding Ki values for several compounds of Table A at $5\text{-HT}_{2C}$ c, $5\text{-HT}_{2B}$, and $5\text{-HT}_{2A}$ receptors are listed in Table B.

TABLE B

| | DOI Binding Ki (nM) | | |
|---|---|---|---|
| Compound Number | 2C | 2A | 2B |
| 102 | 10.3 | 236 | 255 |
| $2^{nd}$ eluting enantiomer in example 1.2 | 3.85 | 104 | 130 |
| 106 | 105 | 244 | 125 |
| $2^{nd}$ eluting enantiomer in example 1.14 | 29.6 | 427 | 647 |
| 121 | 27.6 | 423 | 634 |
| 130 | 1.96 | 34.4 | 75.7 |
| $2^{nd}$ eluting enantiomer in example 1.1 | 0.708 | 20.9 | 53.3 |
| 135 | 69.6 | 458 | 395 |

The compounds of Table A that were tested had DOI Binding Ki values ranging from about 0.71 nM to about 105 nM in this assay.

Example 5: IP Accumulation Assays

HEK293 cells expressing recombinant $5\text{-HT}_2$ receptors were added to sterile poly-D-lysine-coated 96-well microtiter plates (35,000 cells/well) and labeled with 0.6 μCi/well of [$^3$H]inositol in myoinositol-free DMEM for 18 h. Unincorporated [$^3$H]inositol was removed by aspiration and replaced with fresh myoinositol-free DMEM supplemented with LiCl (10 mM final) and pargyline (10 μM final). Serially diluted test compounds were then added and incubation was conducted for 2 h at 37° C. Incubations were then terminated by lysing cells with the addition of ice-cold 0.1 M formic acid followed by freezing at −80° C. After thawing, total [$^3$H]inositol phosphates were resolved from [$^3$H]inositol using AG1-X8 ion exchange resin (Bio-Rad) and [$^3$H]inositol phosphates were measured by scintillation counting using a Perkin Elmer TopCount® scintillation counter. All $EC_{50}$ determinations were performed using 10 different concentrations and triplicate determinations were made at each test concentration. The observed IP Accumulation $EC_{50}$ values for several compounds of Table A at $5\text{-HT}_2$ receptors are listed in Table C.

TABLE C

| | IP Accumulation $EC_{50}$ (nM) | | |
|---|---|---|---|
| Compound Number | 2C | 2A | 2B |
| 101 | 2040 | >100000 | >100000 |
| 1st eluting enantiomer in example 1.8 | >100000 | >100000 | >100000 |
| 119 | 391 | >100000 | >100000 |
| 121 | 222 | >100000 | >100000 |
| $1^{st}$ eluting enantiomer in example 1.9 | 4860 | >100000 | >100000 |

TABLE C-continued

| | IP Accumulation $EC_{50}$ (nM) | | |
|---|---|---|---|
| Compound Number | 2C | 2A | 2B |
| 128 | 108 | >100000 | 284 |
| 130 | 5.21 | 465 | 967 |
| 131 | 83.5 | >100000 | >100000 |
| $2^{nd}$ eluting enantiomer in example 1.1 | 7.6 | 12400 | 1600 |

The compounds of Table A that were tested had IP Accumulation $EC_{50}$ values at the $5\text{-HT}_{2C}$ receptor ranging from about 5.2 nM to about 44 μM (with the exception of the 1st eluting enantiomer in example 1.8 in Table C) in this assay.

Example 6: Effect of Compounds on Food Intake in the Male Sprague Dawley Rat

Male Sprague Dawley rats (225-300 g) were housed three per cage in a temperature and humidity controlled environment (12 h: 12 h light:dark cycle, lights on at 0600 h). At 1600 h on the day before the test, rats were placed in fresh cages and food was removed. On test day, rats were placed into individual cages with grid floors at 1000 h with no access to food. At 1130 h, rats (n=8) were administered either vehicle (20% hydroxypropyl-β-cyclodextrin) or test compound via oral gavage (PO, 1 mL/kg, with an amount of 2 mg/Kg or 10 mg/Kg of test compound) 30 min prior to food presentation. Food intake was measured at 60 min after drug administration (30 min after food presentation).

As shown in FIG. 1, cumulative food intake significantly decreased relative to placebo 1 hour following administration of the $2^{nd}$ eluting enantiomer in example 1.1 at 2 mg/kg, 5 mg/kg, and 10 mg/kg.

Other uses of the disclosed methods will become apparent to those in the art based upon, inter alia, a review of this patent document.

What is claimed is:

1. A process for preparing a compound selected from compounds of Formula I, and pharmaceutically acceptable salts, solvates, and hydrates thereof:

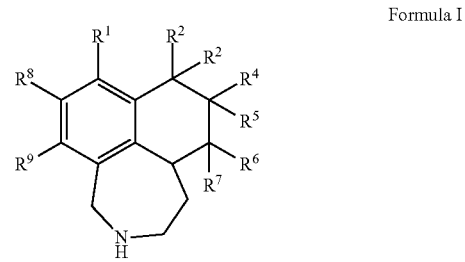

Formula I wherein:
$R^1$ is selected from: H, $C_1\text{-}C_6$ alkyl optionally substituted with one or more halogens, halogen, O—$C_1\text{-}C_6$ alkyl optionally substituted with one or more halogens, and $C_3\text{-}C_8$ cycloalkyl;
$R^2$ and $R^3$ are each independently H, $C_1\text{-}C_6$ alkyl optionally substituted with one or more halogens, or $C_3\text{-}C_8$ cycloalkyl; or $R^2$ and $R^3$ taken together with the carbon connecting them form a 3- to 6-membered spirocyclic carbocyclic ring;
$R^4$ and $R^5$ are each independently H, $C_1\text{-}C_6$ alkyl optionally substituted with one or more halogens, or $C_3\text{-}C_8$ cycloalkyl; or R⁴ and R⁵ taken together with the carbon connecting them form a 3- to 6-membered spirocyclic carbocyclic ring;

or R² and R⁵ are each H and R³ and R⁴ taken together with the carbons connecting them form a 3- to 6-membered carbocyclic ring;

R⁶ and R⁷ are each independently H, $C_1$-$C_6$ alkyl optionally substituted with one or more halogens, or $C_3$-$C_8$ cycloalkyl; or R⁶ and R⁷ taken together with the carbon connecting them form a 3- to 6-membered spirocyclic carbocyclic ring;

and

R⁸ and R⁹ are each independently H, $C_1$-$C_6$ alkyl optionally substituted with one or more halogens, or halogen, wherein the process comprises reacting a compound of the formula

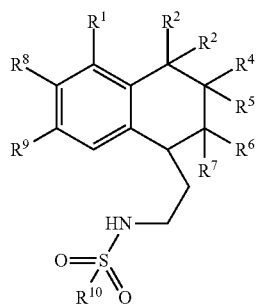

wherein $R^{10}$ is benzyl optionally substituted with one or more halogens with a compound of the formula

to form a compound of the formula

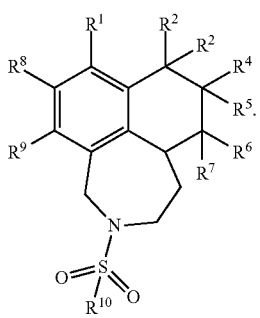

2. The process of claim 1, wherein $R^{10}$ is 3,4-dichlorobenzyl.

3. The process of claim 1, wherein the compound of the formula

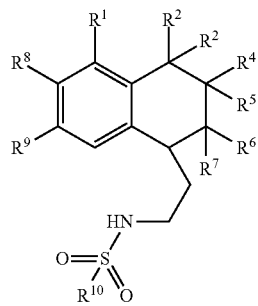

is reacted with a compound of the formula

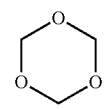

in the presence of an acid.

4. The process of claim 1, further comprising removing the group

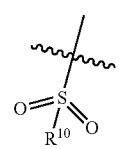

in the compound of the formula

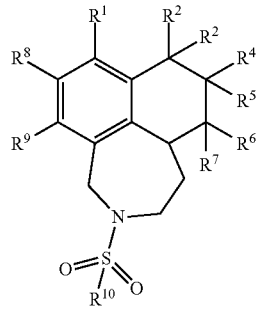

to form the compound selected from compounds of Formula I, and pharmaceutically acceptable salts, solvates, and hydrates thereof.

5. The process of claim 4, wherein removing the group

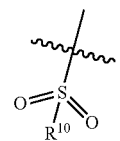

comprises treating the compound of the formula

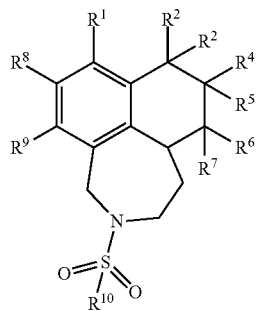

with a reducing agent.

6. The process of claim 5, wherein the reducing agent comprises aluminum.

7. The process of claim 2, further comprising admixing the compound selected from compounds of Formula I, and pharmaceutically acceptable salts, solvates, and hydrates thereof compound with a pharmaceutically acceptable carrier, to form a pharmaceutical composition.

8. The process of claim 1, wherein $R^1$ is H, $C_1$-$C_6$ alkyl, halogen, O—$C_1$-$C_6$ alkyl, or $C_3$-$C_8$ cycloalkyl.

9. The process of claim 1, wherein $R^1$ is $C_1$-$C_6$ alkyl substituted with one or more halogens.

10. The process of claim 1, wherein $R^1$ is H, methyl, ethyl, fluorine, chlorine, bromine, methoxy, or cyclopropyl.

11. The process of claim 1, wherein $R^2$ and $R^3$ are each independently H, $C_1$-$C_6$ alkyl optionally substituted with one or more halogens, or $C_3$-$C_5$ cycloalkyl.

12. The process of claim 11, wherein $R^2$ and $R^3$ are each H.

13. The process of claim 11, wherein $R^2$ and $R^3$ are each methyl.

14. The process of claim 1, wherein $R^2$ and $R^3$ taken together with the carbon connecting them form a 3- to 6-membered spirocyclic carbocyclic ring.

15. The process of claim 14, wherein $R^2$ and $R^3$ taken together with the carbon connecting them form a 3-membered spirocyclic carbocyclic ring.

16. The process of claim 1, wherein $R^4$ and $R^5$ are each independently H, $C_1$-$C_6$ alkyl optionally substituted with one or more halogens, or $C_3$-$C_8$ cycloalkyl.

17. The process of claim 16, wherein $R^4$ and $R^5$ are each methyl.

18. The process of claim 1, wherein $R^4$ and $R^5$ taken together with the carbon connecting them form a 3- to 6-membered spirocyclic carbocyclic ring.

19. The process of claim 18, wherein $R^4$ and $R^5$ taken together with the carbon connecting them form a 3-membered spirocyclic carbocyclic ring.

20. The process of claim 1, wherein $R^2$ and $R^5$ are each H, and $R^3$ and $R^4$ taken together with the carbons connecting them form a 3- to 6-membered carbocyclic ring.

21. The process of claim 1, wherein $R^2$ and $R^5$ are each H, and $R^3$ and $R^4$ taken together with the carbons connecting them form a 5-membered carbocyclic ring.

22. The process of claim 1, wherein $R^6$ and $R^7$ are each H.

23. The process of claim 1, wherein $R^6$ and $R^7$ taken together with the carbon connecting them form a 3- to 6-membered spirocyclic carbocyclic ring.

24. The process of claim 1, wherein $R^8$ and $R^9$ are each independently H or halogen.

25. The process of claim 1, wherein $R^8$ and $R^9$ are each H.

* * * * *

UNITED STATES PATENT AND TRADEMARK OFFICE
CERTIFICATE OF CORRECTION

PATENT NO. : 10,624,900 B2  
APPLICATION NO. : 16/299880  
DATED : April 21, 2020  
INVENTOR(S) : Juerg Lehmann et al.

Page 1 of 2

It is certified that error appears in the above-identified patent and that said Letters Patent is hereby corrected as shown below:

On the Title Page

Item (54), Line 1, delete "5-HT$_{2C}$" and insert -- 5-HT2C --;

Item (56), Column 2, Line 10, delete "Seris" and insert -- Series --;

Item (56), Column 2, Line 23, delete "psuedopeptide" and insert -- pseudopeptide --;

In the Specification

Column 1, Line 1, delete "5-HT$_{2C}$" and insert -- 5-HT2C --;

In the Claims

Column 180, Lines 45-54, Claim 1, delete ": 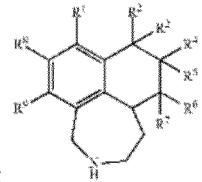 " and insert -- 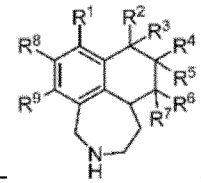 --;

Column 181, Lines 21-32, Claim 1, delete " 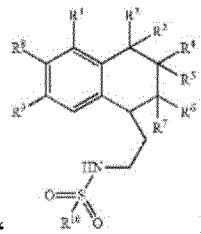 ;" and insert -- 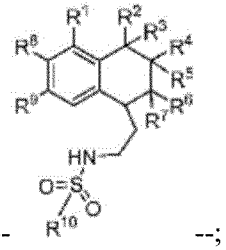 --;

Signed and Sealed this  
Twenty-eighth Day of July, 2020

Andrei Iancu  
*Director of the United States Patent and Trademark Office*

CERTIFICATE OF CORRECTION (continued)
U.S. Pat. No. 10,624,900 B2

Column 181, Lines 48-60, Claim 1, delete ": 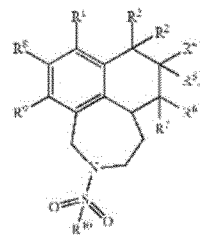 " and insert -- 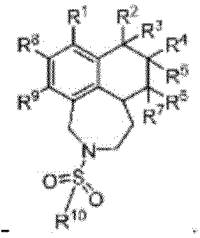 --;

Column 182, Lines 2-13, Claim 3, delete ": 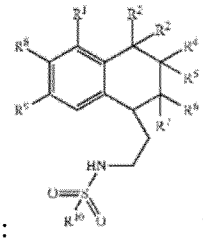 " and insert -- 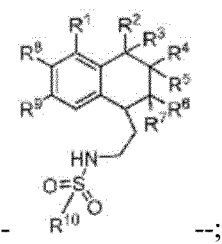 --;

Column 182, Lines 40-51, Claim 4, delete ": 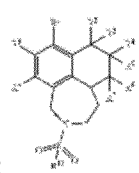 " and insert -- 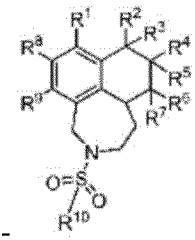 --;

Column 183, Lines 4-15, Claim 5, delete ": 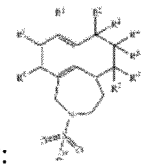 " and insert -- 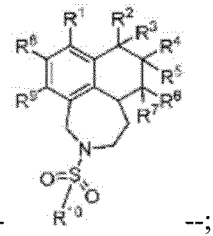 --;

Column 183, Line 32, Claim 11, delete "$C_3$-$C_5$" and insert -- $C_3$-$C_8$ --.